US011524005B2

(12) United States Patent
Dalton et al.

(10) Patent No.: US 11,524,005 B2
(45) Date of Patent: Dec. 13, 2022

(54) SOLID FORMS OF FXR AGONISTS

(71) Applicant: Gilead Sciences, Inc., Foster City, CA (US)

(72) Inventors: Derek M. Dalton, Berkeley, CA (US); Peter C. Fung, San Mateo, CA (US); Nolan Griggs, San Mateo, CA (US); Jeffrey N. Hemenway, San Mateo, CA (US); Olga V. Lapina, Newark, CA (US); Matthew M. Logan, San Mateo, CA (US); Sean T. Neville, San Mateo, CA (US); Bryan J. Reynolds, Mountain View, CA (US); Hui-Wen Shih, San Mateo, CA (US); Anna M. Wagner, Hayward, CA (US)

(73) Assignee: Gilead Sciences, Inc., Foster City, CA (US)

(*) Notice: Subject to any disclaimer, the term of this patent is extended or adjusted under 35 U.S.C. 154(b) by 36 days.

(21) Appl. No.: 16/791,974

(22) Filed: Feb. 14, 2020

(65) Prior Publication Data

US 2020/0281911 A1    Sep. 10, 2020

Related U.S. Application Data

(60) Provisional application No. 62/807,542, filed on Feb. 19, 2019.

(51) Int. Cl.
*A61K 31/4439* (2006.01)
*C07D 401/14* (2006.01)
*C07D 413/14* (2006.01)

(52) U.S. Cl.
CPC ........ *A61K 31/4439* (2013.01); *C07D 401/14* (2013.01); *C07D 413/14* (2013.01)

(58) Field of Classification Search
CPC ............................ C07D 401/14; C07D 413/14
See application file for complete search history.

(56) References Cited

U.S. PATENT DOCUMENTS

| | | | |
|---|---|---|---|
| 4,943,584 A | 7/1990 | Theobald et al. |
| 5,256,666 A | 10/1993 | Mueller et al. |
| 5,258,551 A | 11/1993 | Murabayashi et al. |
| 5,502,252 A | 3/1996 | Takase et al. |
| 5,633,272 A | 5/1997 | Talley et al. |
| 5,849,746 A | 12/1998 | Chambers et al. |
| 5,854,268 A | 12/1998 | Baker et al. |
| 5,912,243 A | 6/1999 | Dowling et al. |
| 6,407,140 B1 | 6/2002 | Gregory et al. |
| 6,974,830 B2 | 12/2005 | Bauer et al. |
| 7,034,046 B2 | 4/2006 | Bauer et al. |
| 7,098,336 B2 | 8/2006 | Bauer et al. |
| 7,560,551 B2 | 7/2009 | Cee et al. |
| 8,188,080 B2 | 5/2012 | Mustelin et al. |
| 8,193,192 B2 | 6/2012 | Kremoser et al. |
| 8,222,256 B2 | 7/2012 | Zhang |
| 8,952,042 B2 | 2/2015 | Kremoser et al. |
| 9,139,539 B2 | 9/2015 | Kinzel et al. |
| 9,539,244 B2 | 1/2017 | Kinzel et al. |
| 9,751,874 B2 | 9/2017 | Gege et al. |
| 9,820,979 B2 | 11/2017 | Kinzel et al. |
| 9,855,249 B2 | 1/2018 | Cole et al. |
| 9,932,332 B2 | 4/2018 | Gege |
| 9,938,278 B2 | 4/2018 | Gege et al. |
| 10,220,027 B2 | 3/2019 | Kinzel et al. |
| 10,485,795 B2 | 11/2019 | Kinzel et al. |
| 10,981,881 B2 | 4/2021 | Blomgren et al. |
| 2003/0130296 A1 | 7/2003 | Bauer et al. |
| 2003/0149087 A1 | 8/2003 | Bauer et al. |
| 2003/0187042 A1 | 10/2003 | Bauer et al. |
| 2004/0048908 A1 | 3/2004 | Momose et al. |
| 2004/0105883 A1 | 6/2004 | Gao et al. |
| 2004/0105884 A1 | 6/2004 | Gao et al. |
| 2004/0105885 A1 | 6/2004 | Gao |
| 2004/0106607 A1 | 6/2004 | Arora et al. |
| 2004/0131670 A1 | 7/2004 | Gao |
| 2004/0152699 A1 | 8/2004 | Arora et al. |
| 2004/0157881 A1 | 8/2004 | Maekawa et al. |
| 2005/0272779 A1 | 12/2005 | Edwards et al. |
| 2006/0063772 A1 | 3/2006 | Arora et al. |
| 2007/0010562 A1 | 1/2007 | Bauer et al. |
| 2008/0032990 A1 | 2/2008 | Khalifah et al. |
| 2008/0114044 A1 | 5/2008 | Epple et al. |
| 2008/0182837 A1 | 7/2008 | Steurer et al. |
| 2008/0194634 A1 | 8/2008 | Arndt et al. |

(Continued)

FOREIGN PATENT DOCUMENTS

| | | |
|---|---|---|
| CA | 1145344 | 4/1983 |
| CN | 104045635 | 9/2014 |

(Continued)

OTHER PUBLICATIONS

Yu; Advanced Drug Delivery Reviews, 2001, 48, 27-42. doi: 10.1016/S0169-409X(01)00098-9 (Year: 2001).*
Abel et al., (2010) "Synthesis and pharmacological validation of a novel series of non-steroidal FXR agonists", Bioorganic & Medicinal Chemistry Letters 20: 4911-4917.
Abu-Hayyeh et al., (2010) "Sulphated progesterone metabolites attenuate FXR function", 61st Annual Meeting of the American Association for the Study of Liver Diseases (Abstract).
ADAMS et al., (2012) "In vitro and in vivo regulation of FGF21 by FXR", 2012 Genetic and Molecular Basis of Obesity and Body Weight Regulation (J7) held jointly with 2012 Pathogenesis of Diabetes: Emerging Insights into Molecular Mechanisms (J8), (Abstract).
Adorini, (2008) "Clinical Translation of FXR agonists for the Treatment of Liver and Metabolic Disorders", 2008 Nuclear Receptors: Orphan Brothers (Z1), (Abstract).

(Continued)

*Primary Examiner* — Daniel R Carcanague
(74) *Attorney, Agent, or Firm* — Sheppard Mullin Richter & Hampton LLP

(57) ABSTRACT

Disclosed herein are novel solid forms of FXR agonists. The disclosure also relates to pharmaceutical compositions containing one or more of the solid forms disclosed herein, as well as methods of using the solid forms in the treatment of conditions mediated by FXR. The disclosure also relates to methods for obtaining such solid forms.

36 Claims, 48 Drawing Sheets

(56) References Cited

U.S. PATENT DOCUMENTS

| | | |
|---|---|---|
| 2008/0207910 A1 | 8/2008 | Podhorez et al. |
| 2009/0074717 A1 | 3/2009 | Leivers et al. |
| 2009/0076103 A1 | 3/2009 | Olson et al. |
| 2009/0105251 A1 | 4/2009 | Jones et al. |
| 2009/0143451 A1 | 6/2009 | Andrews et al. |
| 2009/0197880 A1 | 8/2009 | Leivers et al. |
| 2009/0286782 A1 | 11/2009 | Ibrahim et al. |
| 2009/0286806 A1 | 11/2009 | Pajouhesh et al. |
| 2009/0306086 A1 | 12/2009 | Ibrahim et al. |
| 2010/0016313 A1 | 1/2010 | Millan et al. |
| 2010/0029655 A1 | 2/2010 | Leivers et al. |
| 2010/0048910 A1 | 2/2010 | Godschalx et al. |
| 2010/0093751 A1 | 4/2010 | Hynd et al. |
| 2010/0184809 A1 | 7/2010 | Kremoser et al. |
| 2010/0197662 A1 | 8/2010 | Ogawa et al. |
| 2010/0210660 A1 | 8/2010 | Kremoser et al. |
| 2010/0216827 A1 | 8/2010 | Ma et al. |
| 2010/0234347 A1 | 9/2010 | Dollinger et al. |
| 2010/0240657 A1 | 9/2010 | Sapountzis et al. |
| 2010/0256145 A1 | 10/2010 | Bak-Jensen et al. |
| 2011/0044943 A1 | 2/2011 | Leivers et al. |
| 2011/0212975 A1 | 9/2011 | Kao et al. |
| 2011/0220880 A1 | 9/2011 | Cheng et al. |
| 2011/0257196 A1 | 10/2011 | Lu et al. |
| 2011/0306493 A1 | 12/2011 | Paulini et al. |
| 2011/0312950 A1 | 12/2011 | Eckhardt et al. |
| 2012/0015988 A1 | 1/2012 | Hickey et al. |
| 2012/0021519 A1 | 1/2012 | Ichida et al. |
| 2012/0022067 A1 | 1/2012 | Chen et al. |
| 2012/0029027 A1 | 2/2012 | Estenne-Bouhtou et al. |
| 2012/0071524 A1 | 3/2012 | Lu et al. |
| 2012/0110705 A1 | 5/2012 | Le Vezouet et al. |
| 2012/0122681 A1 | 5/2012 | Le Vezouet et al. |
| 2012/0220603 A1 | 8/2012 | Pajouhesh et al. |
| 2012/0232116 A1 | 9/2012 | Kremoser et al. |
| 2012/0245166 A1 | 9/2012 | Grimaldi et al. |
| 2013/0231348 A1 | 9/2013 | Campbell et al. |
| 2013/0261108 A1 | 10/2013 | Tully et al. |
| 2013/0281503 A1 | 10/2013 | Melander et al. |
| 2014/0039007 A1 | 2/2014 | Tully et al. |
| 2014/0249100 A1 | 9/2014 | Shalwitz et al. |
| 2015/0082981 A1 | 3/2015 | Shiflett |
| 2015/0291572 A1 | 10/2015 | Schunk et al. |
| 2016/0376279 A1 | 12/2016 | Evans et al. |
| 2017/0073635 A1 | 3/2017 | Zhang |
| 2017/0204073 A1 | 7/2017 | Almstead et al. |
| 2017/0204096 A1 | 7/2017 | Gelin et al. |
| 2017/0279055 A1 | 9/2017 | Jang et al. |
| 2017/0304270 A1 | 10/2017 | Or et al. |
| 2017/0304271 A1 | 10/2017 | Or et al. |
| 2017/0304272 A1 | 10/2017 | Or et al. |
| 2017/0333399 A1 | 11/2017 | Or et al. |
| 2017/0334893 A1 | 11/2017 | Or et al. |
| 2017/0334894 A1 | 11/2017 | Or et al. |
| 2017/0355685 A1 | 12/2017 | Blomgren et al. |
| 2017/0355693 A1 | 12/2017 | Blomgren et al. |
| 2017/0355694 A1 | 12/2017 | Gege et al. |
| 2017/0368038 A1 | 12/2017 | Badman et al. |
| 2018/0009754 A1 | 1/2018 | Long et al. |
| 2018/0030003 A1 | 2/2018 | Wang et al. |
| 2018/0051258 A1 | 2/2018 | Zhang et al. |
| 2018/0099957 A1 | 4/2018 | Ma et al. |
| 2018/0123052 A1 | 5/2018 | Zysman-Colman et al. |
| 2018/0280394 A1 | 10/2018 | Bates et al. |
| 2019/0308962 A1 | 10/2019 | Blomgren et al. |
| 2019/0315729 A1 | 10/2019 | Blomgren et al. |
| 2020/0071282 A1 | 3/2020 | Blomgren et al. |
| 2020/0165248 A1 | 5/2020 | Blomgren et al. |
| 2020/0255418 A1 | 8/2020 | Blomgren et al. |
| 2020/0315972 A1 | 10/2020 | Kirby et al. |

FOREIGN PATENT DOCUMENTS

| | | |
|---|---|---|
| CN | 104513213 | 4/2015 |
| CN | 106146483 | 11/2016 |
| CN | 106588804 | 4/2017 |
| CN | 106632294 | 5/2017 |
| CN | 106748922 | 5/2017 |
| CN | 107021957 | 8/2017 |
| CN | 107021958 | 8/2017 |
| EP | 1894924 | 3/2008 |
| EP | 2128158 | 12/2009 |
| EP | 2289883 | 3/2011 |
| EP | 3257847 | 12/2017 |
| JP | 2008308448 | 12/2008 |
| WO | WO-199417059 | 8/1994 |
| WO | WO-199424095 | 10/1994 |
| WO | WO-199712883 | 4/1997 |
| WO | WO-200037077 | 6/2000 |
| WO | WO-200077011 | 12/2000 |
| WO | WO-2003015771 | 2/2003 |
| WO | WO-2003015777 | 2/2003 |
| WO | WO-2003016280 | 2/2003 |
| WO | WO-2003016288 | 2/2003 |
| WO | WO-2003080803 | 10/2003 |
| WO | WO-2004024162 | 3/2004 |
| WO | WO-2004045511 | 6/2004 |
| WO | WO-2004046068 | 6/2004 |
| WO | WO-2004046162 | 6/2004 |
| WO | WO-2004048349 | 6/2004 |
| WO | WO-2004087076 | 10/2004 |
| WO | WO-2005056554 | 6/2005 |
| WO | WO-2005077345 | 8/2005 |
| WO | WO-2005077373 | 8/2005 |
| WO | WO-2005123731 | 12/2005 |
| WO | WO-2006101052 | 9/2006 |
| WO | WO-2007070796 | 6/2007 |
| WO | WO-2007076260 | 7/2007 |
| WO | WO-2007092751 | 8/2007 |
| WO | WO-2007095174 | 8/2007 |
| WO | WO-2007110237 | 10/2007 |
| WO | WO-2007140174 | 12/2007 |
| WO | WO-2007140183 | 12/2007 |
| WO | WO-2007140200 | 12/2007 |
| WO | WO-2008002573 | 1/2008 |
| WO | WO-2008025539 | 3/2008 |
| WO | WO-2008025540 | 3/2008 |
| WO | WO-2008051942 | 5/2008 |
| WO | WO-2008073825 | 6/2008 |
| WO | WO-2008097235 | 8/2008 |
| WO | WO-2008155054 | 12/2008 |
| WO | WO-2008157270 | 12/2008 |
| WO | WO-2009005998 | 1/2009 |
| WO | WO-2009012125 | 1/2009 |
| WO | WO-2009081197 | 7/2009 |
| WO | WO-2009127321 | 10/2009 |
| WO | WO-2009149795 | 12/2009 |
| WO | WO-2010034649 | 4/2010 |
| WO | WO-2010034657 | 4/2010 |
| WO | WO-2010036362 | 4/2010 |
| WO | WO-2010052253 | 5/2010 |
| WO | WO-2010093191 | 8/2010 |
| WO | WO-2011020615 | 2/2011 |
| WO | WO-2011109059 | 9/2011 |
| WO | WO-2012076063 | 6/2012 |
| WO | WO-2012087519 | 6/2012 |
| WO | WO-2012087521 | 6/2012 |
| WO | WO-2013001030 | 1/2013 |
| WO | WO-2013007387 | 1/2013 |
| WO | WO-2013037482 | 3/2013 |
| WO | WO-2013192097 | 12/2013 |
| WO | WO-2014181287 | 11/2014 |
| WO | WO-2014184271 | 11/2014 |
| WO | WO-2015017813 | 2/2015 |
| WO | WO-2015036442 | 3/2015 |
| WO | WO-2015065983 | 5/2015 |
| WO | WO-2015069666 | 5/2015 |
| WO | WO-2015116856 | 8/2015 |
| WO | WO-2015138969 | 9/2015 |
| WO | WO-2015138986 | 9/2015 |
| WO | WO-2015162244 | 10/2015 |
| WO | WO-2015162538 | 10/2015 |
| WO | WO-2015165960 | 11/2015 |
| WO | WO-2015181275 | 12/2015 |

(56) References Cited

FOREIGN PATENT DOCUMENTS

| | | |
|---|---|---|
| WO | WO-2016055441 | 4/2016 |
| WO | WO-2016073767 | 5/2016 |
| WO | WO-2016081918 | 5/2016 |
| WO | WO-2016086115 | 6/2016 |
| WO | WO-2016086134 | 6/2016 |
| WO | WO-2016086169 | 6/2016 |
| WO | WO-2016086218 | 6/2016 |
| WO | WO-2016096115 | 6/2016 |
| WO | WO-2016096116 | 6/2016 |
| WO | WO-2016112305 | 7/2016 |
| WO | WO-2017011466 | 1/2017 |
| WO | WO-2017096130 | 6/2017 |
| WO | WO-2017097870 | 6/2017 |
| WO | WO-2017117687 | 7/2017 |
| WO | WO-2017118294 | 7/2017 |
| WO | WO-2017118762 | 7/2017 |
| WO | WO-2017122209 | 7/2017 |
| WO | WO-2017128896 | 8/2017 |
| WO | WO-2017133521 | 8/2017 |
| WO | WO-2017147047 | 8/2017 |
| WO | WO-2017162211 | 9/2017 |
| WO | WO-2017210526 | 12/2017 |
| WO | WO-2017216727 | 12/2017 |
| WO | WO-2017218330 | 12/2017 |
| WO | WO-2017218337 | 12/2017 |
| WO | WO-2018024224 | 2/2018 |
| WO | WO-2018039384 | 3/2018 |
| WO | WO-2018039386 | 3/2018 |
| WO | WO-2018059314 | 4/2018 |
| WO | WO-2018060075 | 4/2018 |
| WO | WO-2018075207 | 4/2018 |
| WO | WO-2018075650 | 4/2018 |
| WO | WO-2018087599 | 5/2018 |
| WO | WO-2018089212 | 5/2018 |
| WO | WO-2018183193 | 10/2018 |
| WO | WO-2018190643 | 10/2018 |
| WO | WO-2018191393 | 10/2018 |
| WO | WO-2020150136 | 7/2020 |
| WO | WO-2020185686 | 9/2020 |

OTHER PUBLICATIONS

Akwabi-Ameyaw et al., (2009) "FXR agonist activity of conformationally constrained analogs of GW 4064", Bioorganic & Medicinal Chemistry Letters 19: 4733-4739.

Alasmael et al., (2014) "The regulatory role of Farsenoid X Receptor on Matrix Metalloproteinases -2 and -9 in advanced Breast Cancer", The European Association for Cancer Research Conference Series on Goodbye Flat Biology: 3D Models and the Tumour Microenvironment (Abstract).

Ali et al., (2014) "Recent advances in the development of Farsenoid X Receptor agonists", Annals of Translational Medicine 3(1): 1-16.

Alrashid et al,. (2007) "FXR plays a key role in the anti-proliferative and apoptotic responses of bile acids in coloncarcinoma cell lines", 98th Annual Meeting of the American Association for Cancer Research, (Abstract).

Alvarez et al., "Reduced hepatic expression of Farsenoid X Receptor in hereditary cholestasis associated to mutation in ATP8B1", Human Molecular Genetics,13(20): 2451-2460, 2004.

Amiri-Kordestani et al., (2012) "Why Do Phase III Clinical Trials in Oncology Fail So Often?", JNCI, vol. 104, Issue 8, pp. 568-569.

Ananthanarayanan et al., "Human Bile Salt Export Pump Promoter is Transactivated by the Farsenoid X Receptor/Bile Acid Receptor", The Journal of Biological Chemistry, 276(31): 28857-28865, Aug. 3, 2001.

Andreone et al., (2014) "The FXR Agonist Obeticholic Acid (OCA) Improves Liver Biochemistry Parameters Correlated With Clinical Benefit Across a Range of Patient Characteristics", 65th Annual Meeting and Postgraduate Course of the American Association for the Study of Liver Diseases (AASLD), (Abstract).

Aparecida et al., (2012) "Alcoholic liver steatosis in mice is aggravated by low-protein diet and reversed by FXR agonist", 1st Conference on Metabolism, Diet and Disease (Abstract).

Aranda et al., "Nuclear Hormone Receptors and Gene Expression", Physiological Reviews 81(3): 1269-1304, Jul. 2001.

Auwerx, (2006) "Turning Up the Heat with Bile Acids", Nuclear Receptors: Steroid Sisters (X4), (Abstract).

Baghdasaryan et al., (2010) "Therapeutic Effects of FXR and TGR5 Activation in the MDR2 (ABCB4)Mouse Model of Sclerosing Cholangitis", 45th Annual Meeting of the European Association for the Study of the Liver (EASL), (Abstract).

Baghdasaryan et al., (2010) "Therapeutic Targeting of Nuclear and Membrane Bile Acid Receptors in a Mouse Model of Chronic Cholestasis", 61st Annual Meeting of the American Association for the Study of Liver Diseases (AASLD), (Abstract).

Baghdasaryan et al., (2011) "FXR but not Tgr5 activation stimulates $HCO_3$—rich bile secretion and ameliorates liver damage in Mdr2-/-(Abcb4-/-) mouse model of chronic liver injury", 62nd Annual Meeting of the American Association for the Study of Liver Diseases (AASLD), (Abstract).

Balasubramaniyan et al., (2005) "Human Organic Solute Transporter Alpha (OST-ALPHA) is Transactivated by FXR, HNF-4 Alpha and FTF/LRH-1: Implications for Basolateral Bile Acid Transport in Human Liver", 56th Annual Meeting of the American Association for the Study of Liver Diseases (AASLD), (Abstract).

Ballatori et al., (2010) "Ost alpha-Ost beta: A key membrane transporter of bile acids and conjugated steroids", Front Biosci 14: 2829-2844.

BART et al., (2004) "Perspective targets in the treatment of the metabolic syndrome", 13th European Congress on Obesity (European Association for the Study of Obesity, (Abstract).

Bass et al., (2011) "Conformationally constrained Farsenoid X Receptor (FXR) agonists: Heteroaryl replacements of the naphthalene", Bioorganic & Medicinal Chemistry Letters 21: 1206-1213.

Bechmann et al., (2011) "Free fatty acids repress SHP activation and adiponectin counteracts bile acid induced liver injury: New target options for NASH treatment?", 62nd Annual Meeting of the American Association for the Study of Liver Diseases (AASLD), (Abstract).

Beth et al., "Soy Lipid-Derived Phytosterols are FXR Antagonists-Potential Role in Total Parenteral Nutrition-Associated Cholestasis (TPNAC)", Digestive Disease Week 2004: American Association for the Study of Liver Diseases, American Gastroenterological Association, American Society for Gastrointestinal Endoscopy, Society for Surgery of the Alimentary Tract, (Abstract).

Beuers et al., (2014) "FXR Agonist Obeticholic Acid: Pruritus, A Common Side Effect Ameliorated by Dose Titration", 65th Annual Meeting and Postgraduate Course of the American Association for the Study of Liver Diseases (AASLD), (Abstract).

Bianchi et al., (2011) "Farnesoid-X-receptor (FXR) agonist INT-747 restores hepatic DDAH activity after ischemia/reperfusion injury", 35 ° Congresso Nazionale della Società Italiana di Farmacologia (SIF) /35th National Congress of the Italian Society of Pharmacology, (Abstract).

Bilz et al., "Activation of the Farsenoid X Receptor improves lipid metabolism in combined hyperlipidemic hamsters", Am. J. Physiol. Endocrinol. Metab., 290(4) E716-722, 2006, doi: 10.1152/aipendo. 00355.2005.

Boesjes et al., (2014) "Hepatic Farnesoid X-Receptor Isoforms a2 and a4 Differentially Modulate Bile Salt and Lipoprotein Metabolism in Mice", PLOS ONE 9: 1-19.

Bowlus et al., (2014) "Obeticholic Acid in PBC Patients: The Utility of Titration Based on Therapeutic Response and Tolerability", 65th Annual Meeting and Postgraduate Course of the American Association for the Study of Liver Diseases (AASLD), (Abstract).

Brzozowski et al., "Molecular basis of agonism and antagonism in the oestrogen receptor", Nature, 389:753-758, Oct. 16, 1997.

Buttar et al., (2007) "Role of Farnesoid-X-receptor in Esophageal Carcinogenesis"Digestive Disease Week 2007 (DDW): American Association for the Study of Liver Diseases (AASLD), American Gastroenterological Association (AGA), American Society for Gastrointestinal Endoscopy (ASGE), Society for Surgery of the Alimentary Tract (SSAT), (Abstract).

Cai et al., "FXR: a target for cholestatic syndromes?", Expert Opin. Ther. Targets, 10(3): 409-421, 2006.

(56) References Cited

OTHER PUBLICATIONS

Cariou et al., "The Farsenoid X Receptor Modulates Adiposity and Peripheral Insulin Sensitivity in Mice", The Journal of Biological Chemistry, vol. 281, pp. 11039-11049, Apr. 21, 2006.
Cariou et al., (2005) "Farsenoid X Receptor (FXR) regulates peripheral insulin sensitivity", 41st Annual Meeting of the European Association for the Study of Diabetes (EASD), (Abstract).
Carotti et al., (2014) "Beyond Bile Acids: Targeting Farnesoid X Receptor (FXR) with Natural and Synthetic Ligands", Current Topics in Medicinal Chemistry 14: 2129-2142.
Carr et al., (2015) "FXR Agonists as Therapeutic Agents for Non-Alcoholic Fatty Liver Disease", Curr Atheroscler Rep, vol. 17, No. 4, pp. 1-14.
Cha et al., (2009) "Farsenoid X Receptor (FXR) Agonist Improves Insulin Resistance and Ameliorates Diabetic Nephropathy in db/db Mice", 42nd Annual Meeting and Exposition of the American Society of Nephrology (ASN), (Abstract).
Changming et al., (2009) "Ileal bile acid binding protein mediates the chemopreventative effect of ursodeoxycholic acid by activating nuclear receptor FXR in colorectal cancer cells", 100th Annual Meeting of the American Association for Cancer Research (AACR), (Abstract).
Chen et al., "Progressive Familial Intrahepatic Cholestasis: Type I, Is Associated With Decreased Farsenoid X Receptor Activity", Gastroenterology, 126, 756-764, Mar. 2004.
Cheng et al., (2011) "Farsenoid X Receptor (FXR) controls expression of Fibroblast Growth Factor 21 (FGF21) in liver cells", 4th International Congress on Prediabetes and the Metabolic Syndrome, (Abstract).
Chennamsetty et al., (2010) "Role of Farsenoid X Receptor Agonists in the In Vivo and In Vitro Expression of Apolipoprotein(a)", 78th European Atherosclerosis Society Congress (EAS), (Abstract).
Chiang et al., (2004) "Mechanisms of bile acid inhibition of genes in bile acid synthesis", Falk Symposium No. 141, Bile Acids and Cholesterol Metabolism and its Therapeutical Implications, (Abstract).
Chignard et al., (2003) "The VILP receptor VPAC-1 in highly expressed and regulated by FXR and RXR alpha nuclear receptors in the human gallbladder epithelium", 54th Annual Meeting of the American Association for the Study of Liver Diseases (AASLD), (Abstract).
Cho et al., (2011) "Guggulsterone Inhibits LXRa Mediated SREBP-1C-Dependent Hepatic Steatosis through PKC Dependent Pathway", 46th Annual Meeting of the European Association for the Study of the Liver (EASL), (Abstract).
Chouinard et al., (2007) "Bile Acid 7a-Hydroxylase and 12s-Hydroxylase Indices Convey Target Pharmacology, Predict Preclinical Endpoint Efficacy and Offer Utility as Clinical Translational Markers of FXR Agonist Activity", Nuclear Receptors and Metabolism (Z1) held jointly with Metabolic Syndrome and Cardiovascular Risk (Z2), (Abstract).
Chu et al., (2013) "Bile Acids Induce COX-2 Expression in Human Esophagus via Activation of Farsenoid X Receptor (FXR) and NfB", 54th Annual Meeting at Digestive Disease Week (DDW 2013): American Association for the Study of Liver Diseases (AASLD), American Gastroenterological Association (AGA), American Society for Gastrointestinal Endoscopy (ASGE), Society for Surgery of the Alimentary Tract (SSAT), (Abstract).
Claudel et al., (2005) "Constitutive Androstane Receptor Negatively Regulates Human Apolipoprotein A-1 Expression", 78th Annual Scientific Sessions of the American Heart Association (AHA), (Abstract).
Claudel et al., "The Farsenoid X Receptor: A Molecular Link Between Bile Acid and Lipid and Glucose Metabolism", Arteriosclerosis, Thrombosis, and Vascular Biology, 25, 2020-2031, 2005, obtained from URL=http://atvb.ahaioumals.org, download date Jan. 19, 2012.
Cortés et al., (2005) "Recombinant Adenovirus-Mediated Functional Expression and Heterodimeric Nuclear Receptor—Dependent Regulation Of Syndecan-1 in the Murine Liver: Implications in Cholesterol Metabolism", Digestive Disease Week 2005 (DDW): American Association for the Study of Liver Diseases, American Gastroenterological Association, American Society for Gastrointestinal Endoscopy, Society for Surgery of the Alimentary Tract, (Abstract).
D'Amore et al., (2014) "Design, Synthesis, and Biological Evaluation of Potent Dual Agonists of Nuclear and Membrane Bile Acid Receptors", Journal of Medicinal Chemistry 57: 937-954.
Das et al., (2007) "Farsenoid X Receptor Dependent Regulation of MMP9 in Blood Outgrowth Endothelial Cells Contributes to Cell Migration and Homing Through A Pathway involving SHP and KLF repressor proteins", Digestive Disease Week 2007 (DDW): American Association for the Study of Liver Diseases (AASLD), American Gastroenterological Association (AGA), American Society for Gastrointestinal Endoscopy (ASGE), Society for Surgery of the Alimentary Tract (SSAT), (Abstract).
Das et al., (2007) "FXR bile acid receptor activates focal adhesion kinase and stress fiber-mediated motility in endothelial cells", 58th Annual Meeting of the American Association for the Study of Liver Diseases (AASLD), (Abstract).
Das et al., (2009) "FXR Promotes Endothelial Cell Motility through Reciprocal Regulation of FAK and MMP-9", 2009 Experimental Biology Annual Meeting (FASEB) held jointly with the the American Association of Anatomists (AAA), the American Physiological Society (APS), American Society for Biochemistry and Molecular Biology (ASBMB), American Society for Investigative Pathology (ASIP), American Society for Nutrition (ASN), and the American Society for Pharmacology and Experimental Therapeutics (ASPET), (Abstract).
De Oliveira et al., (2012) "Bile acid receptor agonists INT-747 and INT-777 decrease estrogen deficiency-related postmenopausal obesity and hepatic steatosis", 63rd Annual Meeting and Postgraduate Course of the American Association for the Study of Liver Diseases (AASLD), (Abstract).
Demars et al., (2005) "Farnesoid-X-receptor and carcinogenesis in Barrett's esophagus", 96th American Association for Cancer Research Annual Meeting, (Abstract).
Deuschle et al., (2012) "FXR directly controls the tumor suppressor NDRG2 and FXR agonists reduce tumor growth and metastasis in an orthotopic xenograft mouse model", 47th Annual Meeting of the European Association for the Study of the Liver (EASL), (Abstract).
Deuschle et al., (2014) "The nuclear bile acid receptor FXR controls the liver derived tumor suppressor histidine-rich glycoprotein", International Journal of Cancer, 00: 00-00.
Dodson et al., (2005) "Concerted Control of Lipids and Insulin Sensitization by FXR", 87th Annual Meeting of the Endocrine Society (ENDO), (Abstract).
Dodson et al., (2007) "Concerted control of insulin sensitization through lipid and carbohydrate metabolism by FXR", Nuclear Receptors and Metabolism (Z1) held jointly with Metabolic Syndrome and Cardiovascular Risk (Z2), (Abstract).
Doggrell, "New targets in and potential treatments for cholesterol gallstone disease", Current Opinion in Investigational Drugs 7(4): 344-348, 2006.
Dossa et al., (2014) "Bile Acids Differentially Control Intestinal Cell Proliferation via Src Kinase", 2014 Clinical Congress of the American College of Surgeons (ACS), (Abstract).
Dossa et al., (2014) "Intestinal bile acids differentially control intestinal cell proliferation", 34th Annual Meeting of the Surgical Infection Society (SIS), (Abstract).
Duran-Sandoval et al., "Potential regulatory role of the Farsenoid X Receptor in the metabolic syndrome", Biochimie 87:93-98, 2005.
Edwards et al., (2007) "FXR Modulates Lipid and Glucose Metabolism", Nuclear Receptors and Metabolism (Z1) held jointly with Metabolic Syndrome and Cardiovascular Risk (Z2), (Abstract).
Eloranta et al., (2005) "Coordinate transcriptional regulation of bile acid homeostasis and drug metabolism", Archives of Biochemistry and Biophysics 433: 397-412.
Eloranta et al., (2005) "Human organic solute transporter-alpha (OSTalpha) and-beta (OSTbeta) genes are transactivated by the nuclear bile acid receptor/Farsenoid X Receptor (FXR)", 56th Annual Meeting of the American Association for the Study of Liver Diseases (AASLD), (Abstract).

(56) References Cited

OTHER PUBLICATIONS

European Search Report for EP11005722, completed Sep. 13, 2011, 4 pages.
European Search Report for EP15002478.4, completed Nov. 17, 2015, 8 pages.
Extended European Search Report for EP17175336.1 dated Jul. 19, 2017, 8 pages.
Extended European Search Report for EP19188723.1 dated Oct. 24, 2019, 8 pages.
Evans, "The Nuclear Receptor Superfamily: A Rosetta Stone for Physiology", Molecular Endocrinology 19(6): 1429-1438, Jun. 2005.
Evans et al., (2007) "Activation of Farsenoid X Receptor (FXR) in the treatment of dyslipidemia", Nuclear Receptors and Metabolism (Z1) held jointly with Metabolic Syndrome and Cardiovascular Risk (Z2), (Abstract).
Evans et al., (2007) "Activation of Farsenoid X Receptor (FXR) protects against diet-induced dyslipidemia", 76th European Atherosclerosis Society Congress (EAS), (Abstract).
Falk et al., (2006) "Primary biliary cirrhosis: From ursodeoxycholic acid towards targeting strategies for therapy", Falk Symposium No. 155: XIX International Bile Acid Meeting—Bile Acids: Biological Actions and Clinical Relevance (Abstract).
Fang et al., (2008) "The acetylase p300 and deacetylase SIRT1 are critical in vivo FXR cofactors in regulation of liver metabolism", 2008 Nuclear Receptors: Orphan Brothers (Z1), (Abstract).
Feng et al., (2009) "Identification of an N-oxide pyridine GW4064 analog as a potent FXR agonist", Bioorganic & Medicinal Chemistry Letters 19: 2595-2598.
Figge et al., "Hepatic Overexpression of Murine Abcb11 Increases Hepatobiliary Lipid Secretion and Reduces Hepatic Steatosis", The Journal of Biological Chemistry 279(4): 2790-2799, Jan. 23, 2004.
Fiorucci et al., (2005), "A Farsenoid X Receptor-Small Heterodimer Partner Regulatory Cascade Modulates Tissue Metalloproteinase Inhibitor-1 and Matrix Metalloprotease Expression in Hepatic Stellate Cells and Promotes Resolution of Liver Fibrosis", TheJournal of Pharmacology and Experimental Therapeutics, 314: 584-595.
Fiorucci et al., "Protective Effects of 6-Ethyl Chenodeoxycholic Acid, a Farsenoid X Receptor Ligand, in Estrogen-Induced Cholestasis", The Journal of Pharmacology and Experimental Therapeutics 313(2): 604-612,2005.
Fiorucci et al., "The Nuclear Receptor SHP Mediates Inhibition of Hepatic Stellate Cells by FXR and Protects Against Liver Fibrosis", Gastroenterology 127(5): 1497-1512, Nov. 2004.
Fiorucci et al., (2003) "The FXR-agonist, 6-Ethyl-Chenodeoxycholic Acid (6-ECDCA), protects against estrogen-induced cholestasis in rats"; Pellicciari R, Digestive Disease Week 2003 (DDW): American Association for the Study of Liver Diseases, American astroenterological Association, American Society for Gastrointestinal Endoscopy, Society for Surgery of the Alimentary Tract (Abstract).
Fiorucci et al., (2010) "The Bile Acid Sensor FXR Modulates Hydrogen Sulfide Generation in the Gastric Mucosa and Protects Against Injury Caused by Aspirin", Digestive Disease Week 2010 (DDW), (Abstract).
Fiorucci et al., (2014) "Targeting FXR in cholestasis: hype or hope", Expert Opinion 18 (12).
Flatt et al., (2005) "SAR of highly potent full-range modulators of the Farsenoid X Receptor", 229th National Meeting of the American Chemical Society (Abstract).
Flesch et al., (2014) "Screening, synthesis and characterization of novel ligands for Farsenoid X Receptor (FXR)", 2014 Annual Meeting on Trends and Perspectives in Pharmaceutical Sciences (DPhG ) Annual Meeting of the German Pharmaceutical Society (DPhG), (Abstract).
Flesch et al., (2014) "Screening, Synthesis and Characterization of Novel Ligands for Farsenoid X Receptor (FXR)", 23rd International Symposium on Medicinal Chemistry (ISMC) held Jointly with the European Federation for Medicinal Chemistry (EFMC), (Abstract).
Flesch et al., (2015) "Fragmentation of GW4064 led to a highly potent partial Farsenoid X Receptor agonist with improved drug-like properties", Bioorganic& Medicinal Chemistry 13: 3490-8.

Forman et al., "Identification of a Nuclear Receptor That is Activated by Farnesol Metabolites", Cell 81:687-693, Jun. 2, 1995.
Fuchs et al., (2012) "Changes in hepatic bile acid composition protect Bsep (ABCB11) KO mice from hepatic inflammation in methionine choline deficient (MCD)-diet induced NASH", 63rd Annual Meeting and Postgraduate Course of the American Association for the Study of Liver Diseases (AASLD), (Abstract).
Fuchs et al., (2012) "FXR is a key player in NAFLD development by controlling chop expression", 47th Annual Meeting of the European Association for the Study of the Liver (EASL), (Abstract).
Fuchs et al., (2013) "FXR controlled CHOP as novel key player in NAFLD progression", 64th Annual Meeting and Postgraduate Course of the American Association for the Study of Liver Diseases (AASLD), (Abstract).
Fuchs et al., (2014) "Intrahepatic Changes in Bile Acid Composition Protects Bsep (ABCB11) KO Mice From Hepatic Injury in Methionine Choline-Deficient Diet Induced NASH", 55th Annual Meeting at Digestive Disease Week (DDW 2014 ): American Association for the Study of Liver Diseases (AASLD), American Gastroenterological Association (AGA), American Society for Gastrointestinal Endoscopy (ASGE), Society for Surgery of the Alimentary Tract (SSAT), (Abstract).
Gadaleta et al., (2009) "FXR activation represses TNFa-induced NF-?B signalling", 2009 Spring Meeting of the Dutch Society for Gastroenterology/2009 Voorjaarsvergadering Nederlandse Vereniging voor Gastroenterologie (Abstract).
Gadaleta et al., (2010) "Intestinal Bile Salt Nuclear Receptor FXR Protects From Inflammatory Bowel Disease: Potential Therapeutic Implications", Digestive Disease Week 2010 (DDW), (Abstract).
Gadaleta et al., (2011) "Farsenoid X Receptor activation inhibits inflammation and preserves the intestinal barrier in inflammatory bowel disease", Inflammatory bowel disease 60: 463-472.
Gautier et al., (2011) "Farsenoid X Receptor Activation Induces Cholesteryl Ester Transfer Protein Expression in Humans and Transgenic Mice", 12th Annual Conference on Arteriosclerosis, Thrombosis and Vascular Biology (ATVB) in collaboration with the Council on Peripheral Vascular Disease (Abstract).
Gautier et al., (2011) "Farsenoid X Receptor Activation Induces Cholesteryl Ester Transfer Protein Expression in Humans and Transgenic Mice", 79th European Atherosclerosis Society Congress (EAS), (Abstract).
Gege et al., (2014) "Knocking on FXR's Door: The "Hammerhead"-Structure Series of FXR Agonists—Amphiphilic Isoxazoles with Potent In Vitro and In Vivo Activities", Current Topics in Medicinal Chemistry 14: 1-16.
Gioiello et al., (2014) "Bile Acid Derivatives as Ligands of the Farsenoid X Receptor: Molecular Determinants for Bile Acid Binding and Receptor Modulation", Current Topics in Medicinal Chemistry 14: 2159-2174.
Giordano et al., (2010) "Activated Farsenoid X Receptor Inhibits Growth of Tamoxifen-Resistant MCF-7 Breast Cancer Cells, through Down-Regulation of HER2 Expression", 92nd Annual Meeting of the Endocrine Society (ENDO), (Abstract).
Giordano et al., (2010) "Activated Farsenoid X Receptor inhibits growth of tamoxifen-resistant breast cancer cells", 2010 Experimental Biology Annual Meeting (FASEB) held jointly with the the American Association of Anatomists (AAA), the American Physiological Society (APS), American Society for Biochemistry and Molecular Biology (ASBMB), American Society for Investigative Pathology (ASIP), American Society for Nutrition (ASN) and the American Society for Pharmacology and Experimental Therapeutics (ASPET), (Abstract).
Giordano et al., (2014) "FXR Ligands, by Interfering with Tumor/Microenvironment Crosstalk, Inhibit Breast Tumor Growth and Progression", 2nd Joint Meeting of Pathology and Laboratory Diagnostics, 32.Congress of the Società Italiana di Patologia e Medicina Traslazionale, 64.National Congress of the Associazione Italiana di Patologia Clinica e Medicina Molecolare/32nd Congress of the Italian Society of Pathology and Translational Medicine and 64th National Congress of the Italian Association of Clinical Pathology and Molecular Medicine (Abstract).
Glastras et al., (2013) "The role of FXR in maternal obesity related renal injury in mother and offspring", 2013 Annual Scientific

(56) References Cited

OTHER PUBLICATIONS

Meeting of the Australian Diabetes Educators Association (ADEA) and the Australian Diabetes Society (ADS), (Abstract).
Gnerre et al., (2004) "CYP3A4 and CYP3A11 are regulated by the nuclear receptor FXR and primary bile acids in cell cultures and in mice", 15th International Symposium on Microsomes and Drug Oxidations: Chemical Biology in the Postgenomic Era—New Approaches and Applications (Abstract).
Goodwin et al., "A Regulatory Cascade of the Nuclear Receptors FXR, SHP-1, and LRH-I Represses Bile Acid Biosynthesis", Molecular Cell 6: 517-526, Sep. 2000.
Grefhorst et al., (2004) "The role of nuclear hormone receptors in hepatic insulin resistance", 3rd Dutch Endo-Neuro-Psycho Meeting 2004 (Abstract).
Guan et al., (2008) "Nuclear receptors and metabolic syndrome", 2008 Beijing Conference of Physiological Sciences jointly supported by the American Physiological Society, Australian Physiological Society, Canadian Physiological Society, Chinese Association for Physiological Sciences, and the Physiological Society (UK), (Abstract).
Guo-Ning et al., (2014) "Synthesis and Bioactivity of Chalcones and Related Compounds as Farsenoid X Receptor (FXR) Antagonists", 34th National Medicinal Chemistry Symposium (NMCS), (Abstract).
Habegger et al., (2012) "Fibroblast Growth Factor 21 and Farsenoid X Receptor Mediate Chronic Glucagon Action", 72nd Annual Meeting and Scientific Sessions of the American Diabetes Association (ADA), (Abstract).
Hambruch, et al, (2013) "FXR agonist Px-102 improves hepatic steatosis in NAFLD mouse models", Phenex (Poster).
Hambruch et al., (2012) "Synthetic Farsenoid X Receptor agonist PX20606 demonstrates anti-atherosclerotic effects and lowers cholesterol in HDL2 but not in HDL3 subfractions", Poster.
Hambruch et al., (2013) "FXR Agonist Px-102 Improves Hepatic Steatosis in NAFLD Rodent Models", 23rd Conference of the Asia Pacific Associaton for the Study of the Liver (APASL 2013): Transforming Science to Clinical Practice (Abstract).
Hanniman et al., "Loss of functional Farsenoid X Receptor increases atherosclerotic lesions in apolipoprotein E-deficient mice", Journal of Lipid Research, 46:2595-2604, 2005.
Hansen et al., (2014) "The FXR agonist obeticholic acid improves alkaline phospatase/bilirubin response criterion associated with transplant-free survival in primary biliary cirrhosis", 2014 European Association for the Study of the Liver (EASL) Monothematic Conference: Primary Biliary Cirrhosis (PBC), (Abstract).
Harnish, (2007) "A Synthetic Farsenoid X Receptor Agonist Protects Against Diet-Induced Dyslipidemia", 80th Annual Scientific Sessions of the American Heart Association (AHA), (Abstract).
Harnish et al., (2007) "A synthetic Farsenoid X Receptor (FXR) agonist protects against diet-induced dyslipidemia", 16th International Symposium on Drugs Affecting Lipid Metabolism (Abstract).
Harnish et al., (2007) "The Farsenoid X Receptor (FXR) Antagonizes Oxidized LDL Receptor, LOX-1, Activation", 80th Annual Scientific Sessions of the American Heart Association (AHA), (Abstract).
Harriman et al., (2015) "Acetyl-CoA Carboxylase Inhibition by ND-630 Reduces Hepatic Steatosis, Improves Insulin Sensitivity, and Modulates Dyslipidemia in Rats", PNAS, pp. E1796-1805.
Hartman et al., (2007) "Farsenoid X Receptor (FXR) Regulates RECK Expression", 58th Annual Meeting of the American Association for the Study of Liver Diseases (AASLD), (Abstract).
Hawksworth, (2010) "Hepatic transporters—Regulation, induction and potential for drug-drug interactions", 8th Southeast European Congress on Xenobiotic Metabolism and Toxicity (XEMET 2010), (Abstract).
He et al., "Downregulation of Endothelin-1 by Farsenoid X Receptor in Vascular Endothelial Cells", Circulation Research 98(2): 192-199,2006, plus online supplement, obtained from URL=http://circres.ahaiournals.org, download date Jun. 11, 2012, 14pages.
Heery et al., "A signature motif in transcriptional co-activators mediates binding to nuclear receptors", Nature 387:733-736, Jun. 12, 1997.
Heinzel et al., "A complex containing N-CoR, mSin3 and histone deacetylase mediates transcriptional repression", Nature, 387:43-48, May 1, 1997.
Henry et al., (2009) "Farsenoid X ReceptorAgonists: A New Therapeutic Class for Diabetes and Fatty Liver Disease? The First FXR Therapeutic Study in Diabetes", 69th Annual Meeting and Scientific Sessions of the American Diabetes Association (ADA), (Abstract).
Hirschfield et al., (2014) "Efficacy of Obeticholic Acid in Patients with Primary Biliary Cirrhosis and Inadequate Response to Ursodeoxycholic Acid", Gastroenterology 148: 751-761.
Hoegenauer et al., (2014) "G-Protein-coupled Bile Acid Receptor 1 (GPBAR1,TGR5) agonists reduce the production of proinflammatory cytokines and stabilize the alternative macrophage phenotype", Journal of Medicinal Chemistry 57: 10343-54.
Holt et al., "Definition of a novel growth factor-dependent signal cascade for the suppression of bile acid biosynthesis", Genes & Development 17:1581-1591, 2003.
Horth et al., (2009) "Influence of bile acids on stimulus-secretion coupling in pancreatic beta cells", Frühjahrstagung der Deutschen Gesellschaft für Experimentelle und Klinische Pharmakologie und Toxikologie/50th Spring Meeting of the German Society for Experimental and Clinical Pharmacology and Toxicology (Abstract).
Horth et al., (2010) "The function of murine pancreatic beta cells is affected by bile acids", Frühjahrstagung der Deutschen Gesellschaft für Experimentelle und Klinische Pharmakologie und Toxikologie/51st Spring Meeting of the German Society for Experimental and Clinical Pharmacology and Toxicology (Abstract).
Horth et al., (2011) "Bile acids affect the function of murine pancreatic beta cells", 47th Annual Meeting of the European Association for the Study of Diabetes (EASD), (Abstract).
Horth et al., (2011) "Link between the nuclear farnesoid receptor and KATP channel activity in beta-cells", 90th Annual Meeting of the German Physiological Society/Deutsche Physiologische Gesellschaft (DPG), (Abstract).
Houssin et al., (2010) "The FXR activators, chenodeoxycholic acid and GW4064 inhibit the proliferation of prostate cancer LNCaP and LAPC-4 cells", 2010 Nuclear Receptors: Signaling, Gene Regulation and Cancer (X7), (Abstract).
Howarth et al., (2007) "Is the Farsenoid X Receptor in Japanese medaka (Oryzias latipes) a target for exogenous compounds?", 46th Annual Meeting of the Society of Toxicology (Abstract).
Hsu et al., (2014) "Quantitative Profiling of Environmental Chemicals and Drugs for Farsenoid X Receptor Activity", 53rd Annual Meeting of the Society of Toxicology (SOT 2014), (Abstract).
Huang et al., "Design, Synthesis, and Biological Evaluation of Novel Nonsteriodal Farnesoid X Receptor (FXR) Antagonists: Molecular Basis of FXR Antagonism", Chem Med Chem, 2015, vol. 10, pp. 1184-1199.
Huang et al., "Farsenoid X Receptor Activates Transcription of the Phospholipid Pump MDR3", The Journal of Biological Chemistry 278(51): 51085-51090. Dec. 19, 2003.
Huang et al., "Nuclear Receptor-Dependent Bile Acid Signaling Is Required for Normal Liver Regeneration", Science 312:233-236, Apr. 14, 2006.
Huang et al., (2014) "Recent Advances in Non-Steroidal FXR Antagonists Development for Therapeutic Applications", Current Topics in Medicinal Chemistry 14: 2175-2187.
Hulzebos et al., (2005) "Pharmacological FXR Activation and the Enterohepatic Circulation of Bile Salts in Rats: Inhibition of Cholate Synthesis Rate and Reduced Cholate Pool Size", 115th Annual Meeting of the American Pediatric Society and 74th Annual Meeting of the Society for Pediatric Research together with the American Society of Pediatric Hematology/Oncology (ASPHO), the American Society of Pediatric Nephrology, the Lawson Wilkins Pediatric Endocrine Society and the Pediatric Infectious Disease Society (Abstract).
Hwang et al., (2004) "The Cellular Distribution of FXR and RXRa Expression in Developing Rat Ileal Mucosa", Digestive Disease Week 2004 (DDW): American Association for the Study of Liver

(56) References Cited

OTHER PUBLICATIONS

Diseases, American Gastroenterological Association, American Society for Gastrointestinal Endoscopy, Society for Surgery of the Alimentary Tract (Abstract).
Idelman et al., (2012) "Activation of the farnesoid X-receptor (FXR) suppresses cyclin D1 expression and decreases proliferation of colon and breast cancer cells", 63rd Annual Meeting and Postgraduate Course of the American Association for the Study of Liver Diseases (AASLD), (Abstract).
Idelman et al., (2014) "Activation of the farnesoid X-receptor suppresses cyclin D1 expression and decreases proliferation", 2014 Experimental Biology Annual Meeting (FASEB) held jointly with the American Association of Anatomists (AAA), the American Physiological Society (APS), American Society for Biochemistry and Molecular Biology (ASBMB), American Society for Investigative Pathology (ASIP), American Society for Nutrition (ASN),Chinese Pharmacological Society (CPS) and the American Society for Pharmacology and Experimental Therapeutics (ASPET), (Abstract).
Ikpa et al., (2014) "Impaired FXR Signaling in the CF Intestine", 28th Annual North American Cystic Fibrosis Conference (NACFC), (Abstract).
Inagaki et al., (2004) "Bile acid receptor, FXR, regulates host defense in intestine", 18th International Bile Acid Meeting: Bile Acid and Cholesterol Metabolism and its Therapeutic Implications (Abstract).
Inagaki et al., (2004) "Bile acid receptor, FXR, regulates host defense in intestine", Falk Symposium No. 141 Bile Acids and Cholesterol Metabolism and its Therapeutical Implications (Abstract).
Inagaki et al., "Regulation of antibacterial defense in the small intestine by the nuclear bile acid receptor", Proc. Natl. Acad. Sci USA, 103, 3920-3925, 2006, doi:10.1073/pnas.0509592103.
Inagaki et al., (2006) "Regulation of Mucosal Defense in Intestine by the Nuclear Bile Acid Receptor", Nuclear Receptors: Orphan Brothers (X3), (Abstract).
Inagaki et al., "Fibroblast growth factor 15 functions as an enterohepatic signal to regulate bile acid homeostasis", Cell Metabolism, 2, 217-225, Oct. 2005.
International Search Report and Written Opinion for International Application No. PCT/US2017/036743 dated Jul. 25, 2017. (10 pages).
International Search Report and Written Opinion for International Application No. PCT/EP2012/002941 dated Aug. 7, 2012. (9 pages).
International Search Report and Written Opinion for PCT/US2017/036727 dated Sep. 12, 2017, 11 pages.
Ishii, (2010) "Bile acids and their pathophysiological role in metabolic disorders", 83rd Annual Meeting of the Japanese Society for Pharmacology (Abstract).
Jae et al., (2009) "Antidiabetic effects of novel ligands for the orphan nuclear receptor LRH-1", 2009 Type 2 Diabetes and Insulin Resistance (J3), (Abstract).
Jain et al., (2009) "Enteral bile acids improve TPN related cholestasis and gut mucosal atrophy: potential role of FXR and FGF19", 22nd Annual Meeting of the North American Society for Pediatric Gastroenterology, Hepatology and Nutrition (NASPGHAN), (Abstract).
Jeong et al., (2005) "Expression of All 48 Nuclear Hormone Receptors in Lung Cancer", Molecular Pathogenesis of Lung Cancer: Opportunities for Translation to the Clinic, (Abstract).
Jiang et al., (2006) "Protective Role of FXR Activation in Diabetic Nephropathy", 39th Annual Meeting and Exposition of the American Society of Nephrology (ASN): Renal Week 2006 (Abstract).
Jiang et al., (2007) "FXR Modulates Renal Lipid Metabolism, Fibrosis, and Inflammation", 40th Annual Meeting and Exposition of the American Society of Nephrology (ASN): Renal Week 2007 (Abstract).
Jiang et al., (2009) "A Novel Bile Acid Receptor Agonist Prevents Diabetic Nephropathy", 42nd Annual Meeting and Exposition of the American Society of Nephrology (ASN): Renal Week 2009 (Abstract).
Jiang et al., (2014) "Intestinal Farsenoid X Receptor signaling promotes nonalcoholic fatty liver disease", The Journal of Clinical Investigation 125: 386-402.

Johansson, (2004) "Effects of the thyroid receptor-beta agonist, GC-1, on bile acid in intact male mice", 18th International Bile Acid Meeting: Bile Acid and Cholesterol Metabolism and its Therapeutic Implications (Abstract).
John et al., (2004) Mechanisms of bile acid inhibition of genes in bile acid synthesis. 18th International Bile Acid Meeting: Bile Acid and Cholesterol Metabolism and its Therapeutic Implications (Abstract).
Johnson et al., (2001) "Relationships Between Drug Activity in NCI Preclinical In Vitro and In Vivo Models and Early Clinical Trials", British Journal of Cancer, 84(10), pp. 1424-1431.
Johnston. et al., (2013) "A New Therapy for Chronic Diarrhea? a Proof of Concept Study of the FXR Agonist Obeticholic Acid in Patients With Primary Bile Acid Diarrhea", 54th Annual Meeting at Digestive Disease Week (DDW 2013): American Association for the Study of Liver Diseases (AASLD), American Gastroenterological Association (AGA), American Society for Gastrointestinal Endoscopy (ASGE), Society for Surgery of the Alimentary Tract (SSAT), (Abstract).
Journe et al., "Association between Farsenoid X Receptor expression and cell proliferation in estrogen receptor-positive luminal-like breast cancer from postmenopausal patients", Breast Cancer Res. Treat. 115(3): 523-535, 2009, doi: 10.1007/s10549-008-0094-2.
Journe et al., (2006) "Bone-Derived Lipid Stimulates MCF-7 Breast Cancer Cell Growth through Farsenoid X Receptor—Mediated Estrogen Receptor Activation", 28th Annual Meeting of the American Society for Bone and Mineral Research (ASBMR), (Abstract).
Journe et al., (2006) "Crosstalk between Farsenoid X Receptor and estrogen receptor might account for mitogenic effect of bone-derived lipids in bone metastasis from breast cancer", 6th International Meeting on Cancer Induced Bone Disease (CABS), (Abstract).
Journe et al., (2006) "Farsenoid X Receptor: a new marker of poor prognosis in luminal subtype of breast carcinomas?", 29th Annual San Antonio Breast Cancer Symposium (SABCS), (Abstract).
Journe et al., (2006) "Farnesol, an intermediate of the mevalonate pathway, stimulates MCF-7 breast cancer cell growth: evidence for a positive crosstalk between Farsenoid X Receptor and estrogen receptor", 29th Annual San Antonio Breast Cancer Symposium (SABCS), (Abstract).
Journe et al., (2007) "Activation of Farsenoid X Receptor in Breast Cancer Cell Lines by Bone-Derived Lipid", 29th Annual Meeting of the American Society for Bone and Mineral Research (ASBMR), (Abstract).
Journe et al., (2007) "Bone-derived lipids stimulate breast cancer cell growth through a crosstalk between Farsenoid X Receptor and estrogen receptor: in vitro and clinical data", 34th European Symposium on Calcified Tissues (ECTS), (Abstract).
Jung et al., (2004) "Reverse cholesterol transport in cholangiocytes is regulated by LXR", 55th Annual Meeting of the American Association for the Study of Liver Diseases (AASLD), (Abstract).
Jung et al., (2006) "PXR is a target of FXR", 16th International Symposium on Microsomes and Drug Oxidations (MDO), (Abstract).
Kainuma, M. et al., "Design, synthesis, and evaluation of non-steroidal Farsenoid X Receptor (FXR) antagonist", 2007, Bioorg. Med. Chem., 15, 2587-2600.
Kansy et al., "Physicochemical high throughput screening: parallel artificial membrane permeation assay in the description of passive absorption processes", J. Med. Chem. 41(7), 1007-1010, Mar. 26, 1998.
Kast et al., "Farnesoid X-Activated Receptor Induces Apolipoprotein C-II Transcription: a Molecular Mechanism Linking Plasma Triglyceride Levels to Bile Acids", Molecular Endocrinology, 5(10): 1720-1728, 2001.
Kast et al., "Regulation of Multidrug Resistance-associated Protein 2 (ABCC2) by the Nuclear Receptors Pregnane X Receptor, Farnesoid X-activated Receptor, and Constitutive Androstane Receptor", The Journal of Biological Chemistry, 277(4):2908-2915, 2002.
Katona et al., (2006) "Synthesis and Nuclear Receptor Agonistic/Antagonistic Profiles of Enantiomeric Bile Acids", 97th Annual Meeting and Expo of the American Oil Chemists Society Joint Symposium on Biosciences: A Global Business Forum on Fats, Oils, Surfactants, Lipids, and Related Materials (Abstract).

(56) References Cited

OTHER PUBLICATIONS

Kawamura, et al., (2012) "Functional Analysis of the Farsenoid X Receptor in Colorectal Cancer Cells", 35th Annual Meeting of Molecular Biology Society of Japan (MBSJ), (Abstract).
Keating et al., (2009) "Farsenoid X Receptor Activation Downregulates Chloride Secretion in Colonic Epithelial Cells", Digestive Disease Week 2009 (DDW), (Abstract).
Keating et al., (2010) "Farnesoid X-receptor Agonists Inhibit Colonic Secretion In Vitro and In Vivo", Digestive Disease Week 2010 (DDW), (Abstract).
Keitel et al., (2014) "TGR5: Pathogenetic Role and/or Therapeutic Target in Fibrosing Cholangitis?", Clinic Rev Allerg Immunol 48: 218-25.
Kennie et al., (2013) "Relative Potencies of Bile Acids in Inducing Fibroblast Growth Factor 19 in the Human Ileum", 54th Annual Meeting at Digestive Disease Week (DDW 2013): American Association for the Study of Liver Diseases (AASLD), American Gastroenterological Association (AGA), American Society for Gastrointestinal Endoscopy (ASGE), Society for Surgery of the Alimentary Tract (SSAT), (Abstract).
Kerr et al., (2012) "Cysteine Sulfinic Acid Decarboxylase Regulation by Bile Acids: A Role for FXR and SHP in Hepatic Taurine Metabolism", 53rd Annual Meeting at Digestive Disease Week (DDW 2012): American Association for the Study of Liver Diseases (AASLD), American Gastroenterological Association (AGA), American Society for Gastrointestinal Endoscopy (ASGE), Society for Surgery of the Alimentary Tract (SSAT), (Abstract).
Kim et al., "Spontaneous hepatocarcinogenesis in Farsenoid X Receptor-null mice", Carcinogenesis 28(5): 940-946, 2007.
Kim et al., (2014) "Therapeutic Targets and Management of Non-Alcoholic Steatohepatitis", 20th Annual Meeting of the Korean Association for the Study of the Liver (KASL) and Postgraduate Course—Liver Week (Abstract).
Kir et al., (2011) "FGF19 as a Postprandial, Insulin-Independent Activator of Hepatic Protein and Glycogen Synthesis", Science 331: 1621-1624.
Klaman et al., (2007) "Potent FXR Agonist Decreases Triglyceride and Cholesterol Levels in Dyslipidemic Mice, but Does Not Lower Glycemia in Insulin Resistant Mouse Models", 67th Annual Meeting and Scientific Sessions of the American Diabetes Association (ADA), (Abstract).
Kliewer, (2006) "Coordinate Regulation of Bile Acid Homeostasis & Innate Immunity by the Nuclear Bile Acid Receptor", 88th Annual Meeting of the Endocrine Society (ENDO), (Abstract).
Komichi et al., (2004) "A Nuclear Receptor Ligand Down-Regulates Cytosolic Phospholipase A2 (cPLA2) Expression to Reduce bile Acid-Induced Cyclooxygenase 2 (COX-2) Activity in Cholangiocytes: Implication of Anti-Carcinogenic Action of Farsenoid X Receptor (FXR) Agonist", Digestive Disease Week 2004 (DDW): American Association for the Study of Liver Diseases, American Gastroenterological Association, American Society for Gastrointestinal Endoscopy, Society for Surgery of the Alimentary Tract (Abstract).
Kong et al., (2009) "Suppression of cyp7a1 gene transcription by FXR in mice is mediated through the intestine-initiated FGF15/FGFR4 pathway rather than the liver-initiated SHP/LRH1 pathway", 60th Annual Meeting of the American Association for the Study of Liver Diseases (AASLD), (Abstract).
Kong et al., (2011) "Differential Roles of Intestinal Fgf15 and Hepatic Shp in Feed-back Suppression of Cyp7a1 and Cyp8b1 Gene Transcription in Mice", 62nd Annual Meeting of the American Association for the Study of Liver Diseases (AASLD), (Abstract).
Kowdley et al., (2011) "An international study evaluating the Farsenoid X Receptor agonist obeticholic acid as monotherapy in PBC", 46th Annual Meeting of the European Association for the Study of the Liver (EASL), (Abstract).
Kowdley et al., (2014) "FXR Agonist Obeticholic Acid: Sustained Improvement in Markers of Cholestasis and Long-Term Safety in Patients with Primary Biliary Cirrhosis through 4 Years", 65th Annual Meeting and Postgraduate Course of the American Association for the Study of Liver Diseases (AASLD), (Abstract).
Kremoser et al., (2010) "FXR agonists as novel medication for metabolic syndrome and NASH", 16th World Congress of Basic and Clinical Pharmacology (WorldPharma 2010) of the International Union of Pharmacology (IUPHAR), (Abstract).
Kremoser et al., (2010) Strong anti-steatotic and anti-fibrotic effects of novel FXR agonists in a murine NASH model that resembles human NASH, "Phenex Pharmaceuticals AG", Poster.
Kremoser et al., (2012) "FXR agonists prevent steatosis, hepatocyte death and progression of NASH towards hcc in a hypoinsulinaemic mouse model of progressive liver disease", 47th Annual Meeting of the European Association for the Study of the Liver (EASL), (Abstract).
Kremoser et al., (2012) "Synthetic FXR agonists improve liver histopathology and reduce liver tumor formation in mouse models of NASH and liver cancer", 22nd Conference of the Asian Pacific Association for the Study of the Liver (APASL), (Abstract).
Kumar et al., (2009) "Farsenoid X ReceptorAgonist (GW4064) Protects the Kidney from Ischemic Acute Kidney Injury", 42nd Annual Meeting and Exposition of the American Society of Nephrology (ASN): Renal Week 2009 (Abstract).
Kunne et al., (2011) "Hepatic steatosis in mice lacking hepatic cytochrome p450 activity is bile salt dependent", 62nd Annual Meeting of the American Association for the Study of Liver Diseases (AASLD), (Abstract).
Kurata et al., (2011) Pathophysiological Role of Chenodeoxycholic Acid on Hepatic Disposition of Metformin via Organic Cation Transporter 1 in Acute Cholestasis, 2011 Annual Meeting of the American Association of Pharmaceutical Scientists (AAPS), (Abstract).
Lambert et al., "The Farnesoid X-receptor is an Essential Regulator of Cholesterol Homeostasis", The Journal of Biological Chemistry, 278, 2563-2570, 2003.
Lamers et al., (2012) "Structure and Ligand-Based Identification of Novel Synthetic Ligands for Farsenoid X Receptor", 22nd Biennial International Symposium on Medicinal Chemistry (EFMC-ISMC 2012), (Abstract).
Lamers et al., (2014) "Medicinal Chemistry and Pharmacological Effects of Farsenoid X Receptor (FXR) Antagonists", Current Topics in Medicinal Chemistry 14: 2188-2205.
Lamers et al., (2014) "Pyridinol/Pyridinon Tautomerism Determining Activity at Farsenoid X Receptor (FXR): New Agonistic or Antagonistic Ligands of FXR", 23rd International Symposium on Medicinal Chemistry (ISMC) held Jointly with the European Federation for Medicinal Chemistry (EFMC), (Abstract).
Lamers et al., (2014) "Pyridinol/Pyridinon-tautomerism determining activity at Farsenoid X Receptor: new agonistic or antagonistic ligands of FXR", 2014 Annual Meeting on Trends and Perspectives in Pharmaceutical Sciences (DPhG ) Annual Meeting of the German Pharmaceutical Society (DPhG), (Abstract).
Lavine et al., (2014) "Association of Hepatic Nuclear Hormone Receptor Expression Profiles with Features of Hepatic Histology in Children with Nonalcoholic Fatty Liver Disease", 65th Annual Meeting and Postgraduate Course of the American Association for the Study of Liver Diseases (AASLD), (Abstract).
Lawson, J. et al., "Diarylcyclobutane analogs of diethylstilbestrol", 1974, J. Med. Chem., 17, 383-386.
Leckie et al., (2009) "Modulation of the DDAH-ADMA pathway with the Farnesoid receptor (FXR) agonist INT-747 restores hepatic eNOS activity and lowers portal pressure in cirrhotic rats", 2009 Annual Meeting of the British Association for the Study of the Liver (BASL), (Abstract).
Leclercq, (2009) "Experimental therapies in NASH", 2009 European Association for the Study of Liver Special Conference: Non Alcoholic Fatty Liver Disease/Non Alcoholic Steato-Hepatitis (NAFLD/NASH) and Related Metabolic Disease (Abstract).
Lee et al., (2010) "FXR Positively Regulates Hepatic SIRT1 Levels Via MicroRNA-34a Inhibition", 92nd Annual Meeting of the Endocrine Society (ENDO), (Abstract).
Li et al., (2010) "Transgenic expression of CYP7A1 in mouse livers promotes biliary cholesterol secretion via FXRdependent induction

(56) References Cited

OTHER PUBLICATIONS of hepatic ABCG5 and ABCG8 expression", 61st Annual Meeting of the American Association for the Study of Liver Diseases (AASLD), (Abstract).
Li et al., (2015) "Bile acids as metabolic regulators", Curr Opin Gastroenterol 31: 000-000.
Lian et al., (2011) "Hepatoprotective effect of Farsenoid X Receptor on liver injury in systemic lupus erythematosus", 12th Annual European League Against Rheumatism (EULAR 2011), (Abstract).
Liebman et al., (2004) "PPAR-y Agonists Modulate Renal Lipid Metabolism and Prevent the Development of Glomerulosclerosis in Zucker Diabetic Fatty Rats", 37th Annual Meeting and Exposition of the American Society of Nephrology (ASN), (Abstract).
Lien et al., (2010) "Regulation of FXR transcriptional activity by AMPK", 2010 Nuclear Receptors: Signaling, Gene Regulation and Cancer (X7), (Abstract).
Lihong et al., American Diabetes Association (ADA) 66th annual scientific sessions, Jun. 2006, Abstract No. 856-P.
Lihong et al., (2006) "FXR Agonist, GW4064, Reverses Metabolic Defects in High-Fat Diet Fed Mice", 66th Annual Meeting and Scientific Sessions of the American Diabetes Association (ADA), (Abstract).
Lin, (2008) "Study of role of Farsenoid X Receptor in hepatocarcinoma cells", Biennial Shanghai—Hong Kong International Liver Congress 2008 (Abstract).
Liu et al., "Hepatoprotection by the Farsenoid X Receptor agonist GW4064 in rat models of intra-and extrahepatic cholestasis", The Journal of Clinical Investigation, 112, 1678-1687, 2003, doi: 10.1172/JCI200318945.
Liu et al., (2004) "Protection against cclinduced hepatic fibrosis by the Farsenoid X Receptor agonist GW4064 in rat", 55th Annual Meeting of the American Association for the Study of Liver Diseases (AASLD), (Abstract).
Loomba et al., (2015) "Polyunsaturated fatty acid metabolites as novel lipidomic biomarkers for noninvasive diagnosis of nonalcoholic steatohepatitis", Journal of Lipid Research 56: 2015.
Lu et al., "Molecular Basis for Feedback Regulation of Bile Acid Synthesis by Nuclear Receptors", Molecular Cell, 6, 507-515, 2000.
Luketic et al., (2014) "Efficacy of Obeticholic Acid In Primary Biliary Cirrhosis as Assessed by Response Criteria Associated With Clinical Outcome: A Poise Analysis", 65th Annual Meeting and Postgraduate Course of the American Association for the Study of Liver Diseases (AASLD), (Abstract).
Lundquist et al., (2010), "Improvement of Physiochemical Properties of the Tetrahydroazepinoindole Series of Farsenoid X Receptor (FXR) Agonists: Beneficial Modulation of Lipids in Primates", J. Med. Chem., 53:1774-1787.
Ma et al., "Farsenoid X Receptor is essential for normal glucose homeostasis", The Journal of Clinical Investigation, 116, 1102-1109, 2006, doi: 10.1172/JCI25604.
Ma et al., (2004) "The Role of Farsenoid X Receptor (FXR) in Glucose Metabolism", 86th Annual Meeting of the Endocrine Society (ENDO), (Abstract).
Makishima et al., "Identification of a Nuclear Receptor for Bile Acids", Science, 284,:1362-1365, 1999.
Maloney et al., "Identification of a Chemical Tool for the Orphan Nuclear Receptor FXR", Journal of Medicinal Chemistry, Supporting Info Page, 6 pages, 2000.
Maloney et al., "Identification of a Chemical Tool for the Orphan Nuclear Receptor FXR", Journal of Medicinal Chemistry, 43, 2971-2974, 2000.
Maneschi et al., (2013) "The FXR agonist obeticholic acid normalizes lipid droplet and triglyceride handling in visceral adipose tissue preadipocytes from a non-genomic rabbit model of metabolic syndrome", 16th European Congress of Endocrinology (ECE), (Abstract).
Mangelsdorf et al., "The Nuclear Receptor Superfamily: The Second Decade", Cell, 83, 835-839, 1995.
Mangelsdorf, (2005) "The Contrasting Roles of LXRs and FXR in Lipid Metabolism", Bioactive Lipids, Lipidomics and their Targets (Z1), (Abstract).
Mangelsdorf, (2006) "Nuclear receptors and transcriptional control of lipid metabolism", 197th Annual Meeting of the Society for Endocrinology (Abstract).
Maran et al., "FXR Deficiency in Mice Leads to Increased Intestinal Epithelial Cell Proliferation and Tumor Development", American Society for Pharmacology and Experimental Therapeutics, Published on Nov. 3, 2008 as DOI: 10.1124/jpet.108.145409, 35 pages.
Marinozzi et al., (2014) "Medicinal Chemistry of Farsenoid X Receptor (FXR) Modulators: The-State-of-the-Art"Current Topics in Medicinal Chemistry 14 (19): 2127-2128.
Martinez-Fernandez et al., (2008) "Specific down-regulation of the bile acid sensor FXR by silencing ATP8B1 in HepG2 cells. Effect of the FXR agonist GW4064", 3rd World Congress of Pediatric Gastroenterology, Hepatology and Nutrition (WCPGHAN) held jointly with the 41st Annual Meeting of the European Society for Paediatric Gastroenterology, Hepatology and Nutrition (ESPGHAN), (Abstract).
Maruyama et al., (2010) "Selective anti-androgens with a 3,3-diphenylpentane skeleton", 2010 International Chemical Congress of Pacific Basin Societies (PACIFICHEM 2010), (Abstract).
Marzolini et al., (2004) "Unexpected Complexity in Nuclear Receptor Activation by HIV Protease Inhibitors and Induction of CYP Enzymes and Transporters", 2004 Annual Meeting and Science Innovation Exposition of The American Association for the Advancement of Science (Abstract).
Mason et al., (2010) "Farnesoid-X Receptor Agonists: a New Class of Drugs for the Treatment of PBC? An International Study Evaluating the Addition of Obeticholic Acid (INT-747) to Ursodeoxycholic Acid", 61st Annual Meeting of the American Association for the Study of Liver Diseases (AASLD), (Abstract).
Matsumura et al., "Palladium-Catalyzed Asymmetric Arylation, Vinylation, and Allenylation of Tert-cyclobutanols via Enantioselective C—C Bond Cleavage", 2003, J. Am. Chem. Soc., 125, 8862-8869.
Matsuzaki et al., (2012) "FXR Activation Promotes CDX2 Degradation via the Ubiquitin-Proteosome System with Upregulation of microRNA-221/222 in Human Esophageal Cells", 5th Annual International Gastrointestinal Consensus Symposium (IGICS), (Abstract).
McMahan et al., (2009) "FXR and TGR5 activation improves nonalcoholic fatty liver disease (nafld) and increases intrahepatic myeloid suppressor cells", 60th Annual Meeting of the American Association for the Study of Liver Diseases (AASLD), (Abstract).
McMahan et al., (2011) "Bile-Acid Receptor Activation Shifts Hepatic Monocytes/Macrophages Towards an Anti-Inflammatory Phenotype and Improves Non-Alcoholic Fatty Liver Disease", 62nd Annual Meeting of the American Association for the Study of Liver Diseases (AASLD), (Abstract).
McMahan et al., (2014) "Downregulation of pro-fibrotic and pro-inflammatory genes in liver sinusoidal endothelial cells following activation of the bile acid receptors FXR and TGR5", 65th Annual Meeting and Postgraduate Course of the American Association for the Study of Liver Diseases (AASLD), (Abstract).
McMillin et al., (2014) "Central expression of the hypothalamic neuropeptide galanin is upregulated in rodent models of primary sclerosing cholangitis", 65th Annual Meeting and Postgraduate Course of the American Association for the Study of Liver Diseases (AASLD), (Abstract).
McNulty et al., (2007) "FXR Plays A Major Role In Cholic Acid Mediated Effects In High-fat Diet Fed Mice", 67th Annual Meeting and Scientific Sessions of the American Diabetes Association (ADA), (Abstract).
Meech et al., (2014) "UDP-glycosyltransferase 8 (UGT8) galactosidates bile acids and modulates FXR signalling", 2014 Joint Scientific Meeting of the Australasian Society of Clinical and Experimental Pharmacologists and Toxicologists (ASCEPT) and the Molecular Pharmacology of GPCRs (MPGPCR), (Abstract).
Mencarelli et al., (2009) "FXR Activation Corrects Immune-Dysfunction and Attenuates Inflammation in a Rodent Model of Hepatitis", Digestive Disease Week 2009 (DDW), (Abstract).

(56) References Cited

OTHER PUBLICATIONS

Menendez et al., (2014) "The effects of bile acids on intestinal antimicrobial peptides expression", 2014 Annual Meeting of the Canadian Association of Gastroenterology (CAG) held jointly with the Canadian Association for the Study of the Liver (CASL): Canadian Digestive Disease Week (CDDW), (Abstract).

Merk et al., (2014) "Development of partial Farsenoid X Receptor (FXR) agonists", 2014 Annual Meeting on Trends and Perspectives in Pharmaceutical Sciences (DPhG) Annual Meeting of the German Pharmaceutical Society (DPhG), (Abstract).

Merk et al., (2014) "Development of Partial Farsenoid X Receptor (FXR) Agonists", 23rd International Symposium on Medicinal Chemistry (ISMC) held Jointly with the European Federation for Medicinal Chemistry (EFMC), (Abstract).

Merk, et al., (2012) "Medicinal chemistry of Farsenoid X Receptor ligands: from agonists and antagonists to modulators", Future Med. Chem. 4(8), 1015-1036.

Miyata et al., "Role of Farsenoid X Receptor in the Enhancement of Canalicular Bile Acid Output and Excretion of Unconjugated Bile Acids: A Mechanism for Protection against Cholic Acid-Induced Liver Toxicity", The Journal of Pharmacology andExperimental Therapeutics, 312,: 759-766, 2005.

Miyazaki et al., (2013) "Deoxycholic Acid Contributes to Chronic Kidney Disease-Dependent Vascular Calcification", 86th Annual Scientific Sessions of the American Heart Association (AHA 2013) and 2013 ReSuscitation Science Symposium (RSS), (Abstract).

Modica et al., Nuclear Bile Acid Receptor FXR Protects against Intestinal Tumorigenesis, Cancer Res, 68, 9589-9594, Dec. 1, 2008.

Mohan et al., (2014) "Mechanism of FXR Mediated Apoptosis in Breast Cancer", 2014 Surrey Postgraduate Research Conference of the University of Surrey (Abstract).

Moloney et al., (2009) "The Effect of the Farsenoid X Receptor (FXR) and It'S Agonist—GSK488062B—On Experimental Models of Colitis and Cytokine Production from IBD Tissue", Digestive Disease Week 2009 (DDW), (Abstract).

Mookerjee et al., (2014) "Effects of the FXR agonist obeticholic acid on hepatic venous pressure gradient (HVPG) in alcoholic cirrhosis: a proof of concept phase 2a study", 2014 International Liver Congress (ILC) and 49th annual meeting of the European Association for the Study of the Liver (EASL), (Abstract).

Moraes et al., (2009) "The nuclear receptor FXR as a novel regulator of platelet function", 22nd Biennial Congress of the International Society on Thrombosis and Haemostasis (ISTH) held jointly with the 55th Scientific and Standardisation Committee (SSC), (Abstract).

Moschetta et al., "Prevention of cholesterol gallstone disease by FXR agonists in a mouse model", Nature Medicine, 10, 1352-1358, 2004.

Moschetta et al., (2005) "The Role of LXRs and FXR in Enterohepatic Lipid Metabolism", Tissue-Selective Nuclear Receptors (D4), (Abstract).

Moscovitz et al., (2014) "Activation of the Farsenoid X Receptor Restores Hepatic and Intestinal Bile Acid Synthetic Enzyme and Transporter Expression in Pregnant Mice", 53rd Annual Meeting of the Society of Toxicology (SOT 2014), (Abstract).

Moussa et al., (2014) "Activation of Bile Acid Receptor (FXR) Attenuates Osteoclast Differentiation, Survival and Function", 60th Annual Meeting of the Orthopaedic Research Society (ORS 2014), (Abstract).

Moya et al., (2009) "Role of nuclear receptor ligands in fatty acid-induced hepatic steatosis", 2009 Joint Meeting of the European Association for the Study of the Liver (EASL) and the American Association for the Study of Liver Diseases (AASLD) Monothematic Conference: Nuclear Receptors and Liver Disease (Abstract).

Mroz et al., (2011) "The nuclear bile acid receptor, Farsenoid X Receptor, inhibits CFTR expression and Clsecretion in colonic epithelial cells", 2011 Annual Conference of the Physiological Society (Abstract).

Mroz et al., (2013) "Activation of the nuclear bile acid receptor, Farsenoid X Receptor, acutely regulates cAMPstimulated Cl-secretion in colonic epithelial cells", 2013 Physiological Society Joint Themed Meeting on Epithelia and Smooth Muscle Interactions in Health and Disease (Abstract).

Mroz et al., (2014) "Agonists of the nuclear bile acid receptor, FXR, prevent secretory diarrhoea by a novel mechanism involving repression of CFTR promoter activity", 2014 Conference on Physiology—Physiological Society (Abstract).

Mudaliar et al., (2009) "Farnesoid-X receptor agonists—a new therapeutic class for diabetes and NAFLD—first clinical data", 45th Annual Meeting of the European Association for the Study of Diabetes (EASD), (Abstract).

Nejak-Bowen et al., (2013) "Novel therapeutic implications of modulating β-Catenin during intrahepatic cholestasis", 64th Annual Meeting and Postgraduate Course of the American Association for the Study of Liver Diseases (AASLD), (Abstract).

Nettles et al., "Ligand Control of Coregulator Recruitment to Nuclear Receptors", Annu. Rev. Physiol. 67, 309-333, 2005.

Neuschwander-Tetri, (2015) "Targeting the FXR Nuclear Receptor to Treat Liver Disease", Division of Gastroenterology and Hepatology.

Neuschwander-Tetri et al., (2014) "Farnesoid X nuclear receptor ligand obeticholic acid for non-cirrhotic, non-alcoholic steatohepatitis (FLINT): a multicentre, randomised, placebo-controlled trial", Supplementary appendix, The Lancet; published online Nov. 7. http://dx.doi.org/10.1016/S0140-6736(14)61933-4.

Neuschwander-Tetri et al., (2014) "Farnesoid X nuclear receptor ligand obeticholic acid for no-ncirrhotic, non-alcoholic steatohepatitis (FLINT): a multicentre, randomised, placebo-controlled trial", Articles, The Lancet; published online Nov. 7. http://dx.doi.org/10.1016/S0140-6736(14)61933-4.

Nevens et al., (2014) "An International Phase 3 Study of the FXR Agonist Obeticholic Acid in PBC Patients: Effects on Markers of Cholestasis Associated with Clinical Outcomes and Hepatocellular Damage", 65th Annual Meeting and Postgraduate Course of the American Association for the Study of Liver Diseases (AASLD), (Abstract).

Nevens et al., (2014) "The first primary biliary cirrhosis (PBC) phase 3 trial in two decades—an international study of the FXR agonist obeticholic acid in PBC patients", 2014 International Liver Congress (ILC) and 49th annual meeting of the European Association for the Study of the Liver (EASL), (Abstract).

Nijmeijer et al., (2009) "Genetic Variants of Farsenoid X Receptor (FXR) Predispose to Mortality and Infectious Complications in Acute Pancreatitis", Digestive Disease Week 2009 (DDW), (Abstract).

Nolan et al., (2012) "The induction of FGF19 in human ileum by bile acids reflects their relative potencies as FXR-binding ligands", 20th Annual Meeting of the United European Gastroenterology Week (UEGW), (Abstract).

Nolan et al., (2014) "The Effects of Obeticholic Acid, a Farsenoid X Receptor Agonist, in Patients With Chronic Diarrhea Secondary to Crohn's Ileal Disease", 55th Annual Meeting at Digestive Disease Week (DDW 2014 ): American Association for the Study of Liver Diseases (AASLD), American Gastroenterological Association (AGA), American Society for Gastrointestinal Endoscopy (ASGE), Society for Surgery of the Alimentary Tract (SSAT), (Abstract).

Parks et al., "Bile Acids: Natural Ligands for an Orphan Nuclear Receptor", Science, 284, 1365-1368, May 21, 1999.

Patani et al., "Bioisosteriem: A Rational Approach to Drug Design", Chem. Rev. 1996, vol. 96, pp. 3147-3176.

Patman et al., (2014) "A variant of FGF19 protects the liver from cholestatic injury without inducing cancer", Nature Reviews Gastroenterology & Hepatology.

Payer et al., (2014) "The synthetic FXR agonist PX20606 attenuates bacterial translocation, intestinal inflammation, and reduces splanchnic blood flow in portal hypertensive mice", 47. Jahrestagung der Österreichischen Gesellschaft für Gastroenterologie und Hepatologie (ÖGGH) start gemeinsam mit der 25. Lehrgang der Österreichischen Gesellschaft für Gastroenterologie und Hepatologie / 47th Annual Meeting of the Austrian Society for Gastroenterology and Hepatology held jointly with the 25th training course of the Austrian Society of Gastroenterology and Hepatology (Abstract).

Pedraz et al., (2012) "Transcription elongation factor TFIIS.1 gene is regulated by Farsenoid X Receptor", 37th Congress of Federation

(56) References Cited

OTHER PUBLICATIONS of the European Biochemical Societies (FEBS) held jointly with the 22nd Conference of the International Union of Biochemistry and Molecular Biology (IUBMB) and the Spanish Society of Biochemistry and Molecular Biology (SEBBM), (Abstract).
Pellicciari et al., "6a-Ethyl-Chenodeoxycholic Acid (6-ECDCA), a Potent and Selective FXR Agonist Endowed with Anticholestatic Activity", Journal of Medicinal Chemistry, 45. 3569-3572, Aug. 15, 2002.
Pellicciari, (2008) "Novel targets for metabolic diseases", Metabolic Disorders: From Bench to Bedside (Abstract).
Pellicciari, (2009) "Genomic and nongenomic bile acid receptors as novel targets for the treatment of metabolic disorders", 6th Biennial Joint Meeting of the European Federation for Medicinal Chemistry (EFMC), (Abstract).
Peng et al., (2012) "SRC-Mediated Cross-Talk Between Farnesoid X and Epidermal Growth Factor Receptors Inhibits Human Intestinal Cell Proliferation and Tumorigenesis", 53rd Annual Meeting at Digestive Disease Week (DDW 2012): American Association for the Study of Liver Diseases (AASLD), American Gastroenterological Association (AGA), American Society for Gastrointestinal Endoscopy (ASGE), Society for Surgery of the Alimentary Tract (SSAT), (Abstract).
Penna et al., (2009) "Inhibition of experimental colitis by Farnesoid X Receptor agonists", 2009 European Congress of Immunology (ECI): 2nd Joint Meeting of European National Societies of Immunology under the Auspices of EFIS (Abstract).
Perttilä et al., (2010) "Adiponutrin, a lipid droplet surface enzyme—evidence for regulation by ChREBP, SREBPlc and FXR in human hepatocytes", 46th Annual Meeting of the European Association for the Study of Diabetes (EASD), (Abstract).
Plass et al., "Farsenoid X Receptor and Bile Salts are Involved in Transcriptional Regulation of the Gene Encoding the Human Bile Salt Export Pump", Hepatology, 35, 589-596, Mar. 2002.
Poupon, (2007) "Targeting cholestasis", European Association for the Study of the Liver Monothematic Conference: Primary Biliary Cirrhosis (PBC), (Abstract).
Prentiss et al., (2008) "Characterization of transporter expression in primary cultures of human hepatocytes", 10th European Meeting of the International Society for the Study of Xenobiotics (ISSX), (Abstract).
Prough et al., (2014) "PCB regulation of hepatic nuclear receptors: Implications for hepatic steatosis", 5th Asia Pacific Regional Meeting of the International Society for the Study of Xenobiotics (ISSX 2014), (Abstract).
Qin et al., (2006) "Bile acids induces hypercholesterolemia through a FXR-independent mechanism in LDLR Knockout mice", Nuclear Receptors: Orphan Brothers (X3), (Abstract).
Qin et al., (2006) "Bile acis induce hypercholesterolemia through a FXR-independent mechanism in Idlr knockout mice", 14th International Symposium on Atherosclerosis (ISA), (Abstract).
Quiroga et al., (2012) "Deficiency of Carboxylesterase 1/Esterase-x Results in Obesity, Hepatic Steatosis, and Hyperlipidemia", Hepatology, 56 (6): 2188-2198.
Radreau et al., (2014) "Bile acids receptor FXR agonists repress HBV replication in HepaRG cell", 65th Annual Meeting and Postgraduate Course of the American Association for the Study of Liver Diseases (AASLD), (Abstract).
Ratziu et al., (2014) "Starting the battle to control non-alcoholic steatohepatitis", Institute for Cardiometabolism and Nutrition, Universite Pierre et Marie Curie, Assistance Publique Hopitauxde Paris.
Renga et al., (2009) "A Dark Side of FXR Activation in Cholestasis. FXR Is a Negative Regulator of MRP4", Digestive Disease Week 2009 (DDW), (Abstract).
Renga et al., (2012) "A Farnesoid-X-receptor (FXR)- Glucocorticoid Receptor (GR) Cascade Regulates Intestinal Innate Immunity in Response to FXR Activation", 53rd Annual Meeting at Digestive Disease Week (DDW 2012): American Association for the Study of Liver Diseases (AASLD), American Gastroenterological Association (AGA), American Society for Gastrointestinal Endoscopy (ASGE), Society for Surgery of the Alimentary Tract (SSAT), (Abstract).
Renga et al., (2012) "Theonellasterol: a highly selective FXR antagonist that protects against liver injury in cholestasis", 34th National Conference of the Division of Organic Chemistry—Italian Chemical Society/34 Convegno Nazionale della Divisione di Chimica Organica—Società Chimica Italiana (SCI), (Abstract).
Richter et al., (2011) "Discovery of novel and orally active FXR agonists for the potential treatment of dyslipidemia & diabetes", Bioorganic & Medicinal Chemistry Letters 21: 191-194.
Richter et al., (2011) "Optimization of a novel class of benzimidazole-based Farsenoid X Receptor (FXR) agonists to improve physicochemical and ADME properties", Bioorganic & Medicinal Chemistry Letters 21: 1134-1140.
Ricketts et al., (2006) "The coffee diterpene, cafestol requlates cholesterol homeostasis from the intestine via FXR and FGF15", Nuclear Receptors: Orphan Brothers (X3), (Abstract).
Rizzo et al., "Role of FXR in Regulating Bile Acid Homeostasis and Relevance for Human Diseases", Current Drug Targets—Immune, Endocrine & Metabolic Disorders, 5, 289-303, 2005.
Rizzo et al., (2009) "INT-747: a Potent and Selective FXR Agonist Regulating Glucose Metabolism and Enhancing Insulin Secretion", 60th Annual Meeting of the American Association for the Study of Liver Diseases (AASLD), (Abstract).
Rizzo et al., (2009) "The Farsenoid X Receptor agonist int-747 enhances glucose-induced insulin secretion", 2009 Joint Meeting of the European Association for the Study of the Liver (EASL) and the American Association for the Study of Liver Diseases (AASLD) Monothematic Conference: Nuclear Receptors and Liver Disease (Abstract).
Rizzo et al., (2010) "Functional characterization of the semi-synthetic bile acid derivative INT-767, a dual FXR and TGR5 agonist", 16th World Congress of Basic and Clinical Pharmacology (WorldPharma 2010) of the International Union of Pharmacology (IUPHAR), (Abstract).
Rizzo et al., (2010) "Functional characterization of the semi-synthetic bile acid derivative INT-767, a dual FXR and TGR5 agonist", 45th Annual Meeting of the European Association for the Study of the Liver (EASL), (Abstract).
Rizzo et al., (2010) "Functional characterization of the semi-synthetic bile acid derivative INT-767, a dual FXR and TGR5 agonist", 61st Annual Meeting of the American Association for the Study of Liver Diseases (AASLD), (Abstract).
Rizzo et al., (2011) "Functional Characterization of the Semi-synthetic Bile Acid Derivative Int-767, a Dual FXR and TGR5 Agonist", 21st Conference of the Asian Pacific Association for the Study of the Liver (APASL), (Abstract).
Robitaille et al., (2008) "Role of the Farsenoid X Receptor (FXR) in intestinal epithelial cell growth and differentiation", 2008 Annual Meeting of the Canadian Digestive Disease Week (CDDW), (Abstract).
Sanyal, (2011) "Emerging Treatments of NASH", 21st Conference of the Asian Pacific Association for the Study of the Liver (APASL), (Abstract).
Sanyal et al., (2009) "A New Therapy for Nonalcoholic Fatty Liver Disease and Diabetes? INT-747—the First FXR Hepatic Therapeutic Study", 60th Annual Meeting of the American Association for the Study of Liver Diseases (AASLD), (Abstract).
Sanyal et al., (2013). "Novel therapeutic targets for alcoholic hepatitis", 14th Biennial Congress of the European Society for Biomedical Research on Alcoholism (ESBRA), (Abstract).
Sanz Ortega et al., (2012) "Effect of treatment with glucocorticoids FXR-mediated signaling pathway and bile acid homeostasis", 37th Congress of Federation of the European Biochemical Societies (FEBS) held jointly with the 22nd Conference of the International Union of Biochemistry and Molecular Biology (IUBMB) and the Spanish Society of Biochemistry and Molecular Biology (SEBBM), (Abstract).
Savkur et al., (2005) "Regulation of Pyruvate Dehydrogenase Kinase Expression by the Farsenoid X Receptor", Bioactive Lipids, Lipidomics and their Targets (Z1), (Abstract).

(56) References Cited

OTHER PUBLICATIONS

Schaap et al., (2006) "Evidence for regulation of human FGF19 gene expression by ileal FXR", 57th Annual Meeting of the American Association for the Study of Liver Diseases (AASLD), (Abstract).
Schaap et al., (2009) "FGF19 represses CYP7A1 through an ERK1/2-dependent pathway", 2009 Joint Meeting of the European Association for the Study of the Liver (EASL) and the American Association for the Study of Liver Diseases (AASLD) Monothematic Conference: Nuclear Receptors and Liver Disease (Abstract).
Schaap et al., (2014) "Bile acid receptors as targets fordrug development", Nat. Rev. Gastroenterol. Hepatol. 11, 55-67.
Schena et al., "Mammalian Glucocorticoid Receptor Derivatives Enhance Transcription in Yeast", Science 241, 965-967, Aug. 19, 1988.
Schittenhelm et al., (2013) "Bile acids affect beta-cell function and glucose homeostasis by interference with the Farsenoid X Receptor (FXR)", 92nd Annual Meeting of the German Physiological Society/Deutsche Physiologische Gesellschaft (DPG), (Abstract).
Schonewille et al., (2014) "Combination treatment of the novel pharmacological FXR-compound PX20606 and ezetimibe leads to massively increased neutral sterols excretion in mice", 82nd European Atherosclerosis Society Congress (EAS), (Abstract).
Schubert-Zsilavecz, (2014) "Medicinal chemistry of Farsenoid X Receptor ligands", 134th Annual Meeting of the Pharmaceutical Society of Japan (PSJ), (Abstract).
Schwabl et al., (2014) "The synthetic FXR agonist PX20606 attenuates bacterial translocation, intestinal inflammation, and reduces splanchnic blood flow in portal hypertensive mice", 2014 International Liver Congress (ILC) and 49th annual meeting of the European Association for the Study of the Liver (EASL), (Abstract).
Sepe et al., (2012) "Conicasterol E, a small heterodimer partner sparing farnesoid-X-receptor modulator endowed with a pregnane-X-receptor agonistic activity, from the marine sponge Theonella swinhoei", 34th National Conference of the Division of Organic Chemistry—Italian Chemical Society/ 34 Convegno Nazionale della Divisione di Chimica Organica—Società Chimica Italiana (SCI), (Abstract).
Shapiro et al., (2009) "First human experience with a synthetic Farsenoid X Receptor (FXR) agonist—INT-747 (6-ethylchenodeoxycholic acid)", 2009 Joint Meeting of the European Association for the Study of the Liver (EASL) and the American Association for the Study of Liver Diseases (AASLD) Monothematic Conference: Nuclear Receptors and Liver Disease (Abstract).
Shapiro et al., (2009) "First Human Experience With A Synthetic Farsenoid X Receptor (FXR) Agonist-INT-747 (6a-Ethylchenodeoxycholic Acid)", 60th Annual Meeting of the American Association for the Study of Liver Diseases (AASLD), (Abstract).
Sinal et al., "Targeted Disruption of the Nuclear Receptor FXR/BAR Impairs Bile Acid and Lipid Homeostasis", Cell 102:731-744, Sep. 15, 2000.
Smalley Jr. et al., (2015) "Novel heterocyclic scaffolds of GW4064 as Farsenoid X Receptor agonists", Bioorganic & Medicinal Chemistry Letters 25: 280-284.
Song et al., (2008) "Bile Acids Activate Farsenoid X Receptor and Fibroblast Growth Factor 19 Signaling To Inhibit Cholesterol 7a-Hydroxylase Gene Expression in Human Hepatocytes", 90th Annual Meeting of the Endocrine Society (ENDO), (Abstract).
Soo Shin et al., (2013) "Positive regulation of osteogenesis by bile acid through FXR", 40th Annual Congress of the European Calcified Tissue Society (ECTS 2013), (Abstract).
Staels, (2006) "Nuclear receptors as therapeutic targets to modulate the metabolic syndrome", 31st International Meeting of the Federation of the European Biochemical Societies (FEBS), (Abstract).
Staels, (2009) "Bile acids : from simple detergents to complex signalling molecules controlling lipid and glucose homeostasis", 6th Annual Congress on Metabolic Syndrome, Type II Diabetes and Atherosclerosis (Abstract).
Stayrook et al., Regulation of Carbohydrate Metabolism by the Farsenoid X Receptor, Endocrinology, 146, 984-991, 2005.
Stayrook et al., (2005) "Regulation of Carbohydrate Metabolism by the Farsenoid X Receptor", Bioactive Lipids, Lipidomics and their Targets (Z1), (Abstract).
Suzuki et al., (2008) "Mechanism of regulation of bile acid transport in the small intestine", Falk Symposium 165: 20th International Bile Acid Meeting (Abstract).
Swales et al., "The Farsenoid X Receptor is Expressed in Breast Cancer and Regulates Apoptosis and Aromatase Expression", Cancer Res., 66, 10120-10126, Oct. 15, 2006.
Takada et al., (2006) "Transcriptional regulation of mouse organic solute transporter alpha and beta by FXR and LXR alpha", Falk Symposium No. 155: XIX International Bile Acid Meeting—Bile Acids: Biological Actions and Clinical Relevance (Abstract).
Taiwanese Search Report for TW101123785, completed Jan. 16, 2013, 1 page.
Tazuma, (2004) "A nuclear receptor ligand down-regulates cytosolic phosphollpaseA2(cPLA2)expression to reduce bile acid-Induced cyclooxygenase 2 (COX-2) activity in cholanglocytes: Implication of antlcarcinogenic action of farnesold X receptor (FXR) agonist", 18th International Bile Acid Meeting: Bile Acid and Cholesterol Metabolism and its Therapeutic Implications. (Abstract).
Tazuma et al., (2004) "A nuclear receptor ligand down-regulates cytosolic phospholipase AcPLA expression to reduce bile acid-induced cyclooxygenase 2 (COX-2) activity in cholangiocytes: Implication of anticarcinogenic action of Farsenoid X Receptor (FXR) agonist", Falk Symposium No. 141 Bile Acids and Cholesterol Metabolism and its Therapeutical Implications (Abstract).
Tomlinson et al., "Transgenic Mice Expressing Human Fibroblast Growth Factor-19 Display Increased Metabolic Rate and Decreased Adiposity", Endocrinology, 143, 1741-1747, May 2002.
Trauner (2010) "Nuclear hormone receptors—biliary diseases", 2010 European Association for the Study of the Liver (EASL) Monothematic Conference: Signaling in the Liver, (Abstract).
Trauner (2014) "Bile acids as regulators of hepatic transport and metabolism in cholestatic and metabolic liver diseases", 20th International Symposium on MIcrosomes and Drug Oxidations, (Abstract).
Trauner (2014) "FXR VS PPAR Agonists: Competitors or fellow-combatants", 2014 European Association for the Study of the Liver (EASL) Monothematic Conference: Primary Biliary Cirrhosis (PBC), (Abstract).
Unsworth et al., (2014) "Non-genomic effects of nuclear receptors: Different mechanisms of regulation of outside—in signalling in platelets", 2nd European Platelet Group Conference (EUPLAN), (Abstract).
Uriarte et al., (2014) "Ileal FGF15 contributes to fibrosis-associated hepatocellular carcinoma development", International Journal of Cancer.
Urizar et al., "A Natural Product That Lowers Cholesterol as an Antagonist Ligand for FXR", Science, 296, 1703-1706, May 31, 2002.
Urizar et al., "The Farnesoid X-activated Receptor Mediates Bile Acid Activation of Phospholipid Transfer Protein Gene Expression", The Journal of Biological Chemistry, 275, 39313-39317, Dec. 15, 2000.
Vairappan et al., (2009) "Modulation of the DDAH-ADMA pathway with the Farnesoid receptor (FXR) agonist INT-747 restores hepatic eNOS activity and lowers portal pressure in cirrhotic rats", 2009 Annual Meeting of the British Association for the Study of the Liver, (Abstract).
Vairappan et al., (2009) "Modulation of the DDAH-ADMA pathway with the Farsenoid X Receptor (FXR) agonist INT-747 restores hepatic eNOS activity and lowers portal pressure in cirrhotic rats", 60th Annual Meeting of the American Association for the Study of Liver Diseases, (Abstract).
Vaquero et al., (2012) "Role of BCRP in FXR-induced chemoresistance in liver and intestinal cancer cells", 37th Congress of Federation of the European Biochemical Societies (FEBS) held jointly with the 22nd Conference of the International Union of Biochemistry and Molecular Biology (IUBMB) and the Spanish Society of Biochemistry and Molecular Biology, (Abstract).
Vassie et al., (2014) "Obeticholic Acid, a Farsenoid X Receptor Agonist, Reduces Bile Acid Synthesis in Patients With Primary Bile Acid Diarrhea", 55th Annual Meeting at Digestive Disease Week

(56) References Cited

OTHER PUBLICATIONS (DDW 2014 ): American Association for the Study of Liver Diseases (AASLD), American Gastroenterological Association (AGA), American Society for Gastrointestinal Endoscopy (ASGE), Society for Surgery of the Alimentary Tract (SSAT), (Abstract).
Verbeke et al., (2013) "Obeticholic acid, a farnesoid-X receptor agonist, improves portal hypertension by two distinct pathways in cirrhotic rats", 64th Annual Meeting and Postgraduate Course of the American Association for the Study of Liver Diseases, (Abstract).
Verbeke et al., (2014) "Obeticholic acid, a Farnesoid-X receptor agonist, improves portal hypertension in cirrhotic rats", 26th Belgian Week of Gastroenterology, (Abstract).
Verbeke et al., (2014) "Obeticholic acid, a Farnesoid-X receptor agonist, reduces bacterial translocation and restores intestinal permeability in a rat model of cholestatic liver disease", 2014 International Liver Congress (ILC) and 49th annual meeting of the European Association for the Study of the Liver, (Abstract).
Verbeke et al., (2014) "Obeticholic acid, an FXR agonist, reduces bacterial translocation in experimental cholestasis", 26th Belgian Week of Gastroenterology, (Abstract).
Visschers et al., (2011) "FXR stimulation with INT-747 in a rat biliary drainage model protects from hepatocellular injury after loss of enterohepatic circulation", 2011 Annual Meeting of the British Association for the Study of the Liver, (Abstract).
Visschers et al., (2012) "Cholangiopathy is the trigger for intestinal failure associated liver disease through failure of cyp7a1 inhibition resulting from lack of FXR stimulation after biliary drainage in rats", 34th Annual Congress of the European Society for Clinical Nutrition and Metabolism, (Abstract).
Visschers et al., (2012) "FXR stimulation with INT-747 in a rat biliary drainage model protects from hepatocellular injury after loss of enterohepatic circulation", 47th Annual Meeting of the European Association for the Study of the Liver, (Abstract).
Vlasuk et al., (2007) "Introduction to mechanistic approaches to increasing high density lipoprotein cholesterol", 233rd National Meeting of the American Chemical Society (Abstract).
Voskoglou-Nomikos et al., (2003) "Clinical Predictive Value of the In Vitro Cell Line, Human Xenograft, and Mouse Allograft Preclinical Cancer Models", Clinical Cancer Research, vol. 9, pp. 4227-4239.
Wagner et al., (2007) "Absence of FXR Protects Mice from Bile-infarcts in Biliary Obstruction by Reduction of Bile Acid-Independent Bile Flow: Implications for Targeting FXR in Treatment of Cholestasis?", 42nd Annual Meeting of the European Association for the Study of the Liver, (Abstract).
Wagner et al., (2007) "Ursodeoxycholic acid (UDCA) stimulates intestinal fibroblast growth factor 15 (Fgf-15) expression independent of the Farsenoid X Receptor (FXR)", Digestive Disease Week 2007 (DDW): American Association for the Study of Liver Diseases (AASLD), American Gastroenterological Association (AGA), American Society for Gastrointestinal Endoscopy (ASGE), Society for Surgery of the Alimentary Tract (SSAT), (Abstract).
Wang et al., "FXR: a metabolic regulator and cell protector", Cell Research advance online publication Sep. 30, 2008; doi: 10.1038/cr.2008.289, pp. 1-9.
Wang et al., (2007) "FXR Modulates Renal Lipid Metabolism and Fibrosis in Diabetic Nephropathy", 2007 Experimental Biology Annual Meeting (FASEB) held jointly with the 2007 Annual Meeting of the American Society for Investigative Pathology, (Abstract).
Wang et al., (2008) "FXR Agonist Modulates Renal Lipid Metabolism, Inflammation, Oxidative Stress and Fibrosis in Diet-induced Obesity and Renal Disease", 2008 Nuclear Receptors: Orphan Brothers, (Abstract).
Wang et al., (2009) "Farsenoid X Receptor Deficiency Accelerates Diabetic Nephropathy in Nephropathy-Resistant C57BL/6 Mice", 42nd Annual Meeting and Exposition of the American Society of Nephrology, (Abstract).
Wang et al., (2010) "Dual Bile Acid Receptors Agonist INT-767 Prevents Diabetic Nephropathy through Multiple Mechanisms", 43rd Annual Meeting and Exposition of the American Society of Nephrology, (Abstract).
Wang et al., (2014) "Treatment with the FXR-TGR5 dual agonist INT-767 decreases NAFLD-NASH in mice fed a Western diet", 65th Annual Meeting and Postgraduate Course of the American Association for the Study of Liver Diseases, (Abstract).
Watanabe et al., "Bile acids lower triglyceride levels via a pathway involving FXR, SHP, and SREBP-1c", The Journal of Clinical Investigation, 113, 1408-1418, May 2004.
Watanabe et al., (2006) "Bile acids induce energy expenditure by promoting intracellular thyroid hormone activation", Nature Publishing Group 439 (26): 484-489.
Watanabe et al., (2010) "Lowering bile acid pool size with an FXR aqonist induces obesity and diabetes through the decrease of energy expenditure", 2010 Nuclear Receptors: Development, Physiology and Disease, (Abstract).
Watts, (2013) "Hepatic Steatosis, Dyslipoproteinaemia and Cardiometabolic Disease", 2013 Annual Scientific Meeting of the Australian Diabetes Educators Association (ADEA) and the Australian Diabetes Society (ADS), (Abstract).
Willson et al., "Chemical Genomics: Functional Analysis of Orphan Nuclear Receptors in the Regulation of Bile Acid Metabolism", Medicinal Research Reviews, 21, 513-522, 2001.
Winkler et al., (2012) "Transcriptional regulation of hepatic and extrahepatic glucuronidation in tgUGT1A WT mice in obstructive cholestasis (BDL) and by FXR agonist GW4064", 63rd Annual Meeting and Postgraduate Course of the American Association for the Study of Liver Diseases, (Abstract).
Wittenburg et al., "FXR and ABCG5/ABCG8 as Determinants of Cholesterol Gallstone Formation From Quantitative Trait Locus Mapping in Mice", Gastroenterology, 125, 868-881, Sep. 2003.
Xie et al., (2014) "Metabolites profiling identifies a key role of Farsenoid X Receptor for glucose metabolism in proliferating cells", 5th Asia Pacific Regional Meeting of the International Society for the Study of Xenobiotics (Abstract).
Xing et al., (2007) "Adrenal Expression of 3s-Hydroxysteroid Dehydrogenase Type II Is Regulated by the Farsenoid X Receptor (FXR, NR1H4)", 89th Annual Meeting of the Endocrine Society, (Abstract).
Xing et al., (2008) "FXR Induces Liver Hypertrophy Through the Homeobox Factor Hex", Digestive Disease Week 2008, (Abstract).
Xu et al., (2014) "The Role of Bile Acid Receptor FXR Activation on NHE8 Expression Regulation", 55th Annual Meeting at Digestive Disease Week, (Abstract).
Yamada et al., (2008) "Bile Acids Induce CDX2 Expression via Farsenoid X Receptor (FXR) in Barrett's Oesophagus", 16th Annual Meeting of the United European Gastroenterology Week, (Abstract).
Yang et al., "Spontaneous Development of Liver Tumors in the Absence of the Bile Acid Receptor Farsenoid X Receptor", Cancer Res, 67, 863-867, Feb. 1, 2007.
Yingji et al., (2009) "Bile Acids Induce Expression of CDx2 and MUC2 in Normal Rat Gastric Epithelial Cells via Activation of Nuclear Receptor FXR—a Possible Mechanism of Intestinal Metaplasia in the Stomach", Digestive Disease Week 2009, (Abstract).
Yu et al., (2014) "A Novel Treatment for Liver Injury in Western Diet Mouse Models", 1st Annual In Silico Drug Discovery Conference, (Abstract).
Yu et al., (2014) "A novel treatment for liver injury in Western diet mouse models", 70th Annual Southwest Regional Meeting of the American Chemical Society, (Abstract).
Zhan et al., (2013) "Genome-wide binding and transcriptome analysis of human Farsenoid X Receptor in the liver", 2013 Experimental Biology Annual Meeting, (Abstract).
Zhan et al., (2014) "Genome-Wide Binding and Transcriptome Analysis of Human Farsenoid X Receptor in Primary Human Hepatocytes", PLOS One 9(9).
Zhang et al., "Activation of the nuclear receptor FXR improves hyperglycemia and hyperlipidemia in diabetic mice", PNAS 103(a): 1006-1011, Jan. 24, 2006.
Zhang et al., (2007) "FXR signaling in metabolic disease", FEBS Letters 582: 10-18.

(56) References Cited

OTHER PUBLICATIONS

Zhang et al., (2009) "Farsenoid X Receptor agonist WAY-362450 attenuatesliver inflammation and fibrosis in murine model of non-alcoholic steatohepatitis", Journal of Hepatology, 51: 380-388.
Zhang et al., (2010) "Identification of Novel Pathways That Control FXR-mediated Hypocholesterolemia", 2010 Nuclear Receptors: Development, Physiology and Disease (X8), (Abstract).
Zhang et al., (2010) "Identification of Novel Pathways that Control FXR-Regulated Cholesterol Homeostasis", 11th Annual Conference on Arteriosclerosis, Thrombosis and Vascular Biology, (Abstract).
Zhang et al., (2015) "GW4064, an agonist of Farsenoid X Receptor (FXR), represses CYP3A4 expression in human hepatocytes by inducing small heterodimer partner (SHP) expression", downloaded from dmd.aspetjournals.org at ASPET Journals on Mar. 10, 2015, 23 pages.
Zollner et al., "Role of Nuclear Receptors in the Adaptive Response to Bile Acids and Cholestasis: Pathogenetic and Therapeutic Considerations", Molecular Pharmaceutics 3(3): 231-251,2006.
Anonymous: Cilofexor. Internet Citation 2018, XP002781675, retrieved from the internet: probechem.com/products_Cilofexor.aspx, retrieved on Jul. 7, 2020. 2 pages.
Anonymous: Safety, Tolerability, and Efficacy of Cilofexor in Adults With Primary Sclerosing Cholangitis Without Cirrhosis. ClinicalTrials.gov 2016, XP055703962, retrieved from the internet: clinicaltrials.gov/ct2/show/NCT02943460, retrieved on Jul. 9, 2020. 8 pages.
Ashland; Pharmaceutical Technology Report: PTR-096. Utility of PolyplasdoneTM crospovidone as a Solubilizer; 2014; ashland.com/file_source/Ashland/Product/Documents/Pharmaceutical_1/PTR_096_Polyplasdone_crospovidone_Solubilizer.pdf; accessed Aug. 14, 2021 (Year: 2014). 5 pages.
Caira, M.R., Crystalline Polymorphism of Organic Compounds. Topics in Current Chemistry 1998, vol. 198, pp. 163-208, XP001156954.
ClinicalTrials.gov; NCT02781584 (Year: 2016). 7 pages.
ClinicalTrials.gov; NCT02854605 (Year: 2016). 5 pages.
Extended European Search Report for European Patent Application No. 17000383.4 dated Oct. 4, 2017. 8 pages.
Extended European Search Report for European Patent Application No. 20179813.9 dated Aug. 3, 2020. 7 pages.
Healy et al., Pharmaceutical solvates, hydrates and amorphous forms: A special emphasis on cocrystals. Advanced Drug Delivery Reviews 2017, vol. 117, pp. 25-46, XP085279593.
International Search Report and Written Opinion for International Application No. PCT/US2020/018403 dated Jun. 18, 2020. 19 pages.
International Search Report and Written Opinion for International Application No. PCT/US2020/021722 dated Jun. 19, 2020. 10 pages.
International Search Report and Written Opinion International Application No. PCT/US2020/013319 dated May 6, 2020. 11 pages.
Li et al., Bile Acids and Farnesoid X Receptor: Novel Target for the Treatment of Diabetic Cardiomyopathy. Current Protein & Peptide Science 2019, 20(10): 976-983.
Li et al., Farnesoid X Receptor Agonists as Therapeutic Target for Cardiometabolic Diseases. Frontiers in Pharmacology 2020, vol. 11, Article 1247, pp. 1-15.
Ning et al., Nuclear Receptors in the Pathogenesis and Management of Inflammatory Bowel Disease. Hindawi, Mediators of Inflammation 2019, Article ID 2624941, 1-13.
Porez et al., Bile acid receptors as targets for the treatment of dyslipidemia and cardiovascular disease. Journal of Lipid Research 2012, 53, pp. 1723-1737.
PubChem CID 132234195, retrieved from internet on Feb. 19, 2021. 8 pages.
PubChem CID 140823897, retrieved from internet on Feb. 19, 2021. 8 pages.
Saal et al., Pharmaceutical salts: A summary on doses of salt formers from the Orange Book. European Journal of Pharmaceutical Sciences 2013, vol. 49, No. 4, pp. 614-623, XP028676562.
Shah et al., Emerging drugs for the treatment of non-alcoholic steatohepatitis: a focused review of farnesoid X receptor agonists. Expert Opinion on Emerging Drugs 2020, 25(3), pp. 251-260.
Stojancevic et al., The impact of farnesoid X receptor activation on intestinal permeability in inflammatory bowel disease. Can J Gastroenterol. 2012; 26(9):631-637.
Tanaka, A., Emerging novel treatments for autoimmune liver diseases. Hepatology Research 2019, 49:489-499.
Trauner et al., The Nonsteroidal Farnesoid X Receptor Agonist Cilofexor (GS-9674) Improves Markers of Cholestasis and Liver Injury in Patients With Primary Sclerosing Cholangitis. Hepatology 2019; vol. 70, No. 3, pp. 788-801.
Yan et al., The pathophysiological function of non-gastrointestinal farnesoid X receptor. Pharmacology & Therapeutics 2021, vol. 226, 107867, pp. 1-16.
Communication Pursuant to Rule 114(2) EPC, observations by an anonymous third party, for European Patent Application No. 20708721.4 dated Sep. 20, 2021. 8 pages.
Crawley, M.L., "Farnesoid X receptor modulators: a patent review", Expert Opinion on Therapeutic Patents, 2010, vol. 20, No. 8, doi:10.1517/13543776.2010.496777, ISSN 1354-3776, pp. 1047-1057, XP055401832.
Examination Report for Indian Patent Application No. 202117034809 dated Dec. 6, 2021. 6 pages.
Gokhale and Mantri, Chapter 4 API Solid-Form Screening and Selection. Developing Solid Oral Dosage Forms: Pharmaceutical Theory and Practice, 2017 Elsevier Inc. 28 pages.
Opposition filed by Laboratorios Legrand S.A. for Colombian Patent Application No. NC2021/0009240 dated Nov. 19, 2021. 29 pages.
Zhou et al., PPARα-UGT axis activation represses intestinal FXR-FGF15 feedback signalling and exacerbates experimental colitis. Nature Communications 2014, pp. 1-15.
Balbach et al., Pharmaceutical evaluation of early development candidates "the 100 mg-approach", International Journal of Pharmaceutics 275 (2004) 1-12.
Patel et al., Cilofexor, a Nonsteroidal FXR Agonist, in Non-Cirrhotic Patients with Nonalcoholic Steatohepatitis: A Phase 2 Randomized Controlled Trial, first published Mar. 2020, doi/10.1002/hep.31205. 31 pages.
Singhal et al., Drug polymorphism and dosage form design: a practical perspective. Advanced Drug Delivery Reviews 56 (2004), pp. 335-347.

\* cited by examiner

SOLID FORMS OF FXR AGONISTS

CROSS-REFERENCE TO RELATED APPLICATIONS

This application claims the benefit of priority to U.S. Provisional Patent Application No. 62/807,542, filed 19 Feb. 2019, the contents of which are incorporated herein by reference in their entirety.

FIELD

The present disclosure relates to novel solid forms of FXR agonists, and the pharmaceutical formulations and therapeutic uses thereof.

BACKGROUND

The present disclosure relates to solid forms of compounds that bind to the NR1H4 receptor (FXR) and act as agonists or modulators of FXR. The disclosure further relates to the use of the solid forms of such compounds for the treatment and/or prophylaxis of diseases and/or conditions through binding of said nuclear receptor by said compounds.

Compounds that bind to the NR1H4 receptor (FXR) can act as agonists or modulators of FXR. FXR agonists are useful for the treatment and/or prophylaxis of diseases and conditions through binding of the NR1H4 receptor. One such FXR agonist is the compound of Formula I:

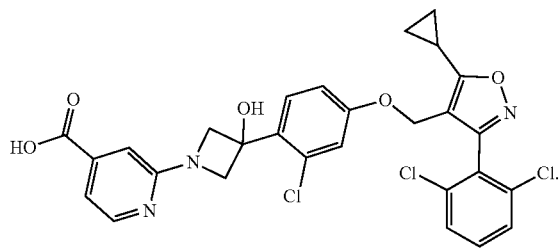

I

Although numerous FXR agonists are known, what is desired in the art are physically stable forms of the compound of Formula I, or pharmaceutically acceptable salt thereof, with desired properties such as good physical and chemical stability, good aqueous solubility and good bioavailability. For example, pharmaceutical compositions are desired that address challenges of stability, variable pharmacodynamics responses, drug-drug interactions, pH effect, food effects, and oral bioavailability.

Accordingly, there is a need for stable forms of the compound of Formula I with suitable chemical and physical stability for the formulation, therapeutic use, manufacturing, and storage of the compound.

Moreover, it is desirable to develop a solid form of Formula I that may be useful in the synthesis of Formula I. A solid form, such as a crystalline form of a compound of Formula I may be an intermediate to the synthesis of Formula I. A solid form may have properties such as bioavailability, stability, purity, and/or manufacturability at certain conditions that may be suitable for medical or pharmaceutical uses.

SUMMARY

In some embodiments, the present disclosure is directed to novel solid forms of a compound of Formula I:

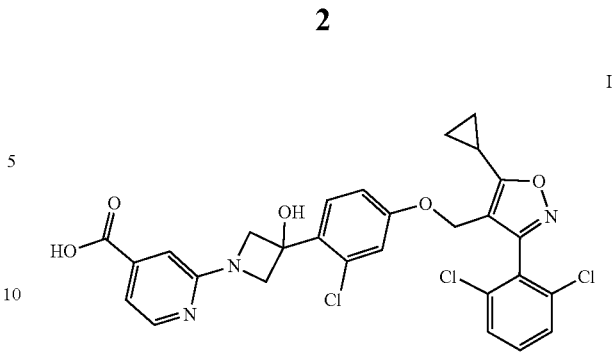

I and pharmaceutically acceptable salts, solvates and hydrates thereof.

These novel forms are useful, for example, for treating human patients suffering from a liver disease, such as nonalcoholic steatohepatitis ("NASH"). The novel solid forms of the present disclosure can be useful for preparing a medicament for treating a liver disease. The novel solid forms of the present disclosure can be used as FXR agonists.

In some embodiments, the present disclosure is directed to solid forms of a zwitterionic form of Formula I

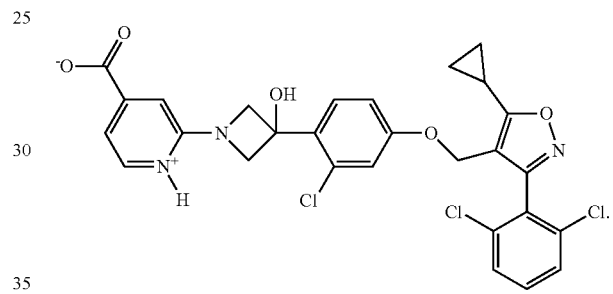

In some embodiments, the present disclosure is directed to zwitterion Form I.

In some embodiments, the present disclosure is directed to zwitterion Form II.

In some embodiments, the present disclosure is directed to zwitterion hydrate.

In some embodiments, the present disclosure is directed to zwitterion amorphous form.

In some embodiments, the present disclosure is directed to solid forms of a tromethamine salt of Formula I. In some embodiments, the tromethamine salt of Formula I has the structure:

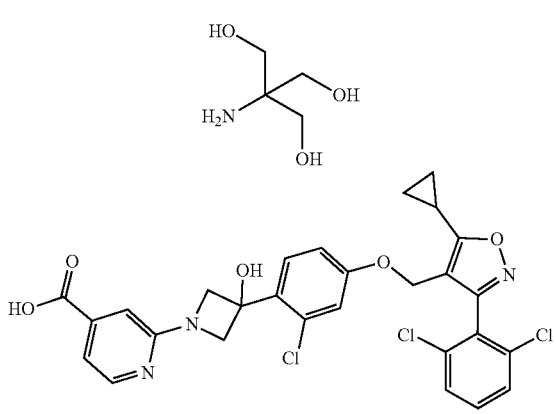

In some embodiments, the present disclosure is directed to tromethamine salt Form I.

In some embodiments, the present disclosure is directed to tromethamine salt Form II.

In some embodiments, the present disclosure is directed to tromethamine salt hydrate I.

In some embodiments, the present disclosure is directed to tromethamine salt hydrate II.

In some embodiments, the present disclosure is directed to tromethamine salt hydrate III.

In some embodiments, the present disclosure is directed to tromethamine salt hydrate IV.

In some embodiments, the present disclosure is directed to tromethamine salt methanol solvate I.

In some embodiments, the present disclosure is directed to tromethamine salt methanol solvate II.

In some embodiments, the present disclosure is directed to tromethamine salt methanol solvate III.

In some embodiments, the present disclosure is directed to tromethamine salt methyl t-butyl ether ("MTBE") solvate.

In some embodiments, the present disclosure is directed to tromethamine salt amorphous form.

In some embodiments, the present disclosure is directed to tromethamine salt ethanol solvate.

In some embodiments, the present disclosure is directed to solid forms of ap-toluenesulfonic acid salt of Formula I.

In some embodiments, the present disclosure is directed to p-toluenesulfonic acid salt Form I.

In some embodiments, the present disclosure is directed to p-toluenesulfonic acid salt Form II.

In some embodiments, the present disclosure is directed to p-toluenesulfonic acid salt Form III.

In some embodiments, the present disclosure is directed to p-toluenesulfonic acid salt hydrate.

In some embodiments, a pharmaceutical composition comprises a therapeutically effective amount of a solid form of Formula I.

DETAILED DESCRIPTION

Figure 1:
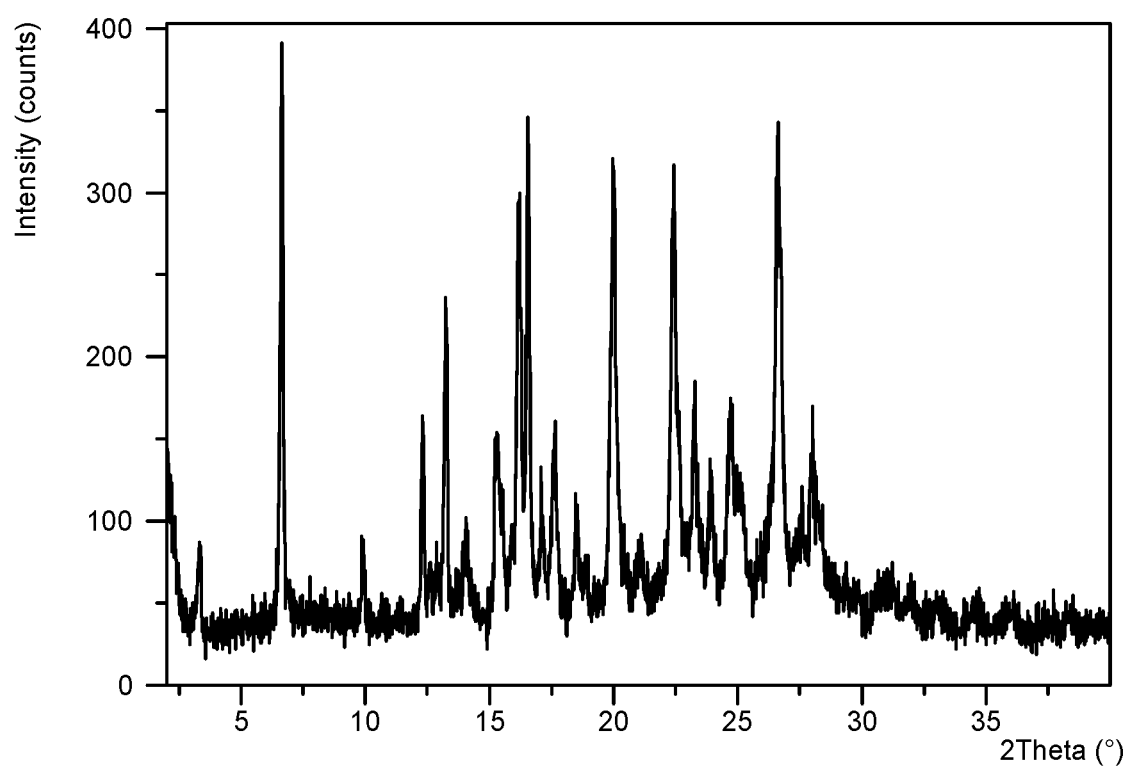
FIG. 1 shows an XRPD pattern of the zwitterionic compound of Formula I Form I.

In the following description, certain specific details are set forth in order to provide a thorough understanding of various embodiments of the disclosure. However, one skilled in the art will understand that the disclosure may be practiced without these details. The description below of several embodiments is made with the understanding that the present disclosure is to be considered as an exemplification of the claimed subject matter, and is not intended to limit the appended claims to the specific embodiments illustrated. The headings used throughout this disclosure are provided for convenience only and are not to be construed to limit the claims in any way. Embodiments illustrated under any heading may be combined with embodiments illustrated under any other heading.

Definitions

Unless the context requires otherwise, throughout the present specification and claims, the word "comprise" and variations thereof, such as, "comprises" and "comprising" are to be construed in an open, inclusive sense, that is as "including, but not limited to."

Reference throughout this specification to "one embodiment" or "an embodiment" means that a particular feature, structure or characteristic described in connection with the embodiment is included in at least one embodiment of the present disclosure. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

Embodiments that reference throughout this specification to "a compound" include the crystalline, salt, co-crystal, zwitterion, hydrate, solvate, and/or amorphous forms of the formulas and/or compounds disclosed herein. Thus, the appearance or the phrase "a compound of Formula I" can include Formula I zwitterion Form I; Formula I zwitterion Form II; Formula I hydrate; Formula I zwitterion amorphous; Formula I tromethamine salt Form I; Formula I tromethamine salt Form II; Formula I tromethamine salt hydrate I; Formula I tromethamine salt hydrate II; Formula I tromethamine salt hydrate III; Formula I tromethamine salt hydrate IV; Formula I tromethamine salt methanol solvate I; Formula I tromethamine salt methanol solvate II; Formula I tromethamine salt methanol solvate III; Formula I tromethamine salt MTBE solvate; Formula I tromethamine salt amorphous form; Formula I tromethamine salt ethanol solvate; Formula I p-toluenesulfonic acid salt Form I; Formula I p-toluenesulfonic acid salt Form II; Formula I p-toluenesulfonic acid salt Form III; and/or Formula I p-toluenesulfonic acid salt hydrate.

The disclosure disclosed herein is also meant to encompass all pharmaceutically acceptable compounds of Formula I being isotopically-labeled by having one or more atoms replaced by an atom having a different atomic mass or mass number. Examples of isotopes that can be incorporated into the disclosed compounds include isotopes of hydrogen, carbon, nitrogen, oxygen, phosphorous, fluorine, chlorine, and iodine, such as $^{2}H$, $^{3}H$, $^{11}C$, $^{13}C$, $^{14}C$, $^{13}N$, $^{15}N$, $^{15}O$, $^{17}O$, $^{18}O$, $^{31}P$, $^{32}P$, $^{35}S$, $^{18}F$, $^{36}Cl$, $^{123}I$, and 125I, respectively. These radiolabeled compounds could be useful to help determine or measure the effectiveness of the compounds, by characterizing, for example, the site or mode of action, or binding affinity to pharmacologically important site of action. Certain isotopically labeled compounds of Formula I, for example, those incorporating a radioactive isotope, are useful in drug and/or substrate tissue distribution studies. The radioactive isotopes tritium, i.e. $^{3}H$, and carbon-14, i.e., $^{14}C$, are particularly useful for this purpose in view of their ease of incorporation and ready means of detection.

Substitution with heavier isotopes such as deuterium, i.e., $^{2}H$, may afford certain therapeutic advantages resulting from greater metabolic stability. For example, in vivo half-life may increase or dosage requirements may be reduced. Thus, heavier isotopes may be preferred in some circumstances.

Substitution with positron emitting isotopes, such as $^{11}C$, $^{18}F$, $^{15}O$ and $^{13}N$, can be useful in Positron Emission Topography (PET) studies for examining substrate receptor occupancy. Isotopically labeled compounds of Formula I can generally be prepared by conventional techniques known to those skilled in the art or by processes analogous to those described in the Examples as set out below using an appropriate isotopically labeled reagent in place of the non-labeled reagent previously employed.

"Stable compound" and "stable structure" are meant to indicate a compound that is sufficiently robust to survive isolation to a useful degree of purity from a reaction mixture, and formulation into an efficacious therapeutic agent.

"Optional" or "optionally" means that the subsequently described event or circumstances may or may not occur, and that the description includes instances where said event or circumstance occurs and instances in which it does not. For example, "optionally substituted aryl" means that the aryl radical may or may not be substituted and that the description includes both substituted aryl radicals and aryl radicals having no substitution.

"Pharmaceutically acceptable excipient" includes without limitation any adjuvant, carrier, excipient, glidant, sweetening agent, diluent, preservative, dye/colorant, flavor enhancer, surfactant, wetting agent, dispersing agent, suspending agent, stabilizer, isotonic agent, solvent, and/or emulsifier, or a combination of one or more of the above which has been approved by the United States Food and Drug Administration as being acceptable for use in humans or domestic animals.

A "pharmaceutical composition" refers to a formulation of a compound of the disclosure (e.g., a compound of Formula I) and a medium generally accepted in the art for the delivery of the biologically active compound to mammals, e.g., humans. Such a medium includes all pharmaceutically acceptable excipients therefor.

"Effective amount" or "therapeutically effective amount" refers to an amount of a compound according to the disclosure, which when administered to a patient in need thereof, is sufficient to effect treatment for disease-states, conditions, or disorders for which the compounds have utility. Such an amount would be sufficient to elicit the biological or medical response of a tissue system, or patient that is sought by a researcher or clinician. The amount of a compound according to the disclosure which constitutes a therapeutically effective amount will vary depending on such factors as the compound and its biological activity, the composition used for administration, the time of administration, the route of administration, the rate of excretion of the compound, the duration of the treatment, the type of disease-state or disorder being treated and its severity, drugs used in combination with or coincidentally with the compounds of the disclosure, and the age, body weight, general health, sex and diet of the patient. Such a therapeutically effective amount can be determined routinely by one of ordinary skill in the art having regard to their own knowledge, the state of the art, and this disclosure.

"Prevention" or "preventing" or "prophylaxis" means any treatment of a disease or condition that causes the clinical symptoms of the disease or condition not to develop. Compounds may, in some embodiments, be administered to a subject (including a human) who is at risk or has a family history of the disease or condition.

"Treating" and "treatment" of a disease include the following:
(1) preventing or reducing the risk of developing the disease, i.e., causing the clinical symptoms of the disease not to develop in a subject that may be exposed to or predisposed to the disease but does not yet experience or display symptoms of the disease,
(2) inhibiting the disease, i.e., arresting or reducing the development of the disease or its clinical symptoms, and
(3) relieving the disease, i.e., causing regression of the disease or its clinical symptoms.

The terms "subject" or "patient" refer to an animal, such as a mammal (including a human), that has been or will be the object of treatment, observation or experiment. The methods described herein may be useful in human therapy and/or veterinary applications. In some embodiments, the subject is a mammal (or the patient). In some embodiments the subject (or the patient) is human, domestic animals (e.g., dogs and cats), farm animals (e.g., cattle, horses, sheep, goats, and pigs), and/or laboratory animals (e.g., mice, rats, hamsters, guinea pigs, pigs, rabbits, dogs, and monkeys). In some embodiments, the subject (or the patient) is a human. "Human (or patient) in need thereof" refers to a human who may have or is suspect to have diseases or conditions that would benefit from certain treatment; for example, being treated with the compounds disclosed herein according to the present application.

Reference to "about" a value or parameter herein includes (and describes) embodiments that are directed to that value or parameter per se. For example, description referring to "about X" includes description of "X." Also, the singular forms "a" and "the" include plural references unless the context clearly dictates otherwise. Thus, e.g., reference to "the compound" includes a plurality of such compounds and reference to "the assay" includes reference to one or more assays and equivalents thereof known to those skilled in the art.

"Pharmaceutically acceptable" or "physiologically acceptable" refer to compounds, salts, compositions, dosage forms and other materials which are useful in preparing a pharmaceutical composition that is suitable for veterinary or human pharmaceutical use.

"Unit dosage forms" are physically discrete units suitable as unitary dosages for subjects (e.g., human subjects and other mammals), each unit containing a predetermined quantity of active material calculated to produce the desired therapeutic effect, in association with a suitable pharmaceutical excipient.

The term "substantially as shown in" when referring, for example, to an XRPD pattern, a DSC thermogram, a DVS isotherm, or a TGA thermogram includes a pattern, thermogram or spectrum that is not necessarily identical to those depicted herein, but that falls within the limits of experimental error or deviations when considered by one of ordinary skill in the art.

In some embodiments, the term "substantially pure" or "substantially free" with respect to a particular crystalline form of a compound means that the composition comprising the crystalline form contains less than 99%, less than 95%, less than 90%, less than 85%, less than 80%, less than 75%, less than 70%, less than 65%, less than 60%, less than 55%, less than 50%, less than 40%, less than 30%, less than 20%, less than 15%, less than 10%, less than 5%, or less than 1% by weight of other substances, including other crystalline forms and/or impurities. In certain embodiments, "substantially pure" or "substantially free of" refers to a substance free of other substances, including other crystalline forms and/or impurities. Impurities may, for example, include by-products or left-over reagents from chemical reactions, contaminants, degradation products, other crystalline forms, water, and solvents.

The term "pharmaceutically acceptable salts" refers to salts prepared from pharmaceutically acceptable non-toxic bases or acids, including inorganic bases or acids and organic bases or acids. In case the compounds of the present disclosure contain one or more acidic or basic groups, the disclosure also comprises their corresponding pharmaceutically or toxicologically acceptable salts, in particular their pharmaceutically utilizable salts. Thus, the compounds of the present disclosure which contain acidic groups can be present on these groups and can be used according to the disclosure, for example, as alkali metal salts, alkaline earth metal salts or ammonium salts. More precise examples of such salts include sodium salts, potassium salts, calcium salts, magnesium salts or salts with ammonia or organic amines such as, for example, ethylamine, ethanolamine, triethanolamine or amino acids. The compounds of the present disclosure which contain one or more basic groups, i.e. groups which can be protonated, can be present and can be used according to the disclosure in the form of their addition salts with inorganic or organic acids. Examples of suitable acids include hydrogen chloride, hydrogen bromide, phosphoric acid, sulfuric acid, nitric acid, methanesulfonic acid, p-toluenesulfonic acid, naphthalenedisulfonic acids, oxalic acid, acetic acid, tartaric acid, lactic acid, salicylic acid, benzoic acid, formic acid, propionic acid, pivalic acid, diethylacetic acid, malonic acid, succinic acid, pimelic acid, fumaric acid, maleic acid, malic acid, sulfaminic acid, phenylpropionic acid, gluconic acid, ascorbic acid, isonicotinic acid, citric acid, adipic acid, and other acids known to the person skilled in the art. If the compounds of the present disclosure simultaneously contain acidic and basic groups in the molecule, the disclosure also includes, in addition to the salt forms mentioned, inner salts or betaines (zwitterions). The respective salts can be obtained by customary methods which are known to the person skilled in the art like, for example, by contacting these with an organic or inorganic acid or base in a solvent or dispersant, or by anion exchange or cation exchange with other salts. The present disclosure also includes all salts of the compounds of the present disclosure which, owing to low physiological compatibility, are not directly suitable for use in pharmaceuticals but which can be used, for example, as intermediates for chemical reactions or for the preparation of pharmaceutically acceptable salts.

Further the compounds of the present disclosure may be present in the form of solvates, such as those which include as solvate water, or pharmaceutically acceptable solvates, such as alcohols, in particular ethanol. A "solvate" is formed by the interaction of a solvent and a compound. When the solvent is water, the "solvate" is a "hydrate."

In certain embodiments, provided are optical isomers, racemates, or other mixtures thereof of the compounds described herein or a pharmaceutically acceptable salt or a mixture thereof. If desired, isomers can be separated by methods well known in the art, e.g. by liquid chromatography. In those situations, the single enantiomer or diastereomer, i.e., optically active form, can be obtained by asymmetric synthesis or by resolution. Resolution can be accomplished, for example, by conventional methods such as crystallization in the presence of a resolving agent, or chromatography, using for example, a chiral high-pressure liquid chromatography (HPLC) column.

A "stereoisomer" refers to a compound made up of the same atoms bonded by the same bonds but having different three-dimensional structures, which are not interchangeable. The present invention contemplates various stereoisomers and mixtures thereof and includes "enantiomers," which refers to two stereoisomers whose molecules are nonsuperimposeable mirror images of one another. "Diastereomers" are stereoisomers that have at least two asymmetric atoms, but which are not mirror-images of each other.

The compounds disclosed herein and their pharmaceutically acceptable salts may include an asymmetric center and may thus give rise to enantiomers, diastereomers, and other stereoisomeric forms that may be defined, in terms of absolute stereochemistry, as (R)- or (S)- or, as (D)- or (L)- for amino acids. The present invention is meant to include all such possible isomers, as well as their racemic and optically pure forms. Optically active (+) and (−), (R)- and (S)-, or (D)- and (L)-isomers may be prepared using chiral synthons or chiral reagents, or resolved using conventional techniques, for example, chromatography and fractional crystallization. Conventional techniques for the preparation/isolation of individual enantiomers include chiral synthesis from a suitable optically pure precursor or resolution of the racemate (or the racemate of a salt or derivative) using, for example, chiral high-pressure liquid chromatography (HPLC). When the compounds described herein contain olefinic double bonds or other centres of geometric asymmetry, and unless specified otherwise, it is intended that the compounds include both E and Z geometric isomers.

Compositions provided herein that include a compound described herein or pharmaceutically acceptable salts, isomer, or a mixture thereof may include racemic mixtures, or mixtures containing an enantiomeric excess of one enantiomer or single diastereomers or diastereomeric mixtures. All such isomeric forms of these compounds are expressly included herein the same as if each and every isomeric form were specifically and individually listed.

A "tautomer" is an isomer of a compound which exists together, in equilibrium, with another isomer where the two isomers are interchangeable by migration of an atom or a group within the molecule.

Solid Forms of Formula I

Solid forms of Formula I, including crystalline forms and substantially pure forms, may provide the advantage of bioavailability and stability, suitable for use as an active ingredient in a pharmaceutical composition. Formula I tromethamine salt Form I, for example, exhibits advantageous physical properties such as good physical and chemical stability, good aqueous solubility and good bioavailability. Variations in the crystal structure of a pharmaceutical drug substance or active ingredient may affect the dissolution rate (which may affect bioavailability, etc.), manufacturability (e.g., ease of handling, ability to consistently prepare doses of known strength), and stability (e.g., thermal stability, shelf life, etc.) of a pharmaceutical drug product or active ingredient. Such variations may affect the preparation or formulation of pharmaceutical compositions in different dosage or delivery forms, such as solutions or solid oral dosage form including tablets and capsules. Compared to other forms such as non-crystalline or amorphous forms, crystalline forms may provide desired or suitable hygroscopicity, particle size controls, dissolution rate, solubility, purity, physical and chemical stability, manufacturability, yield, and/or process control. Thus, solid forms of the compound of Formula I may provide advantages such as improving: the manufacturing process of the compound, the stability or storability of a drug product form of the compound, the stability or storability of a drug substance of the compound and/or the bioavailability and/or stability of the compound as an active agent.

The use of certain solvents and/or processes have been found to produce different solid forms of the compound Formula I described herein which may exhibit one or more favorable characteristics described above. The processes for the preparation of the solid forms described herein and characterization of these solid forms are described in detail below.

In particular embodiments, novel solid forms, such as crystalline forms of Formula I are disclosed. In some embodiments, zwitterionic solid forms of a compound of Formula I are disclosed. In some embodiments, solid forms of a tromethamine salt of Formula I are disclosed. In some embodiments, solid forms of a p-toluene sulfonic acid salt of Formula I are disclosed.

Formula I Zwitterion Form I

Figure 2:
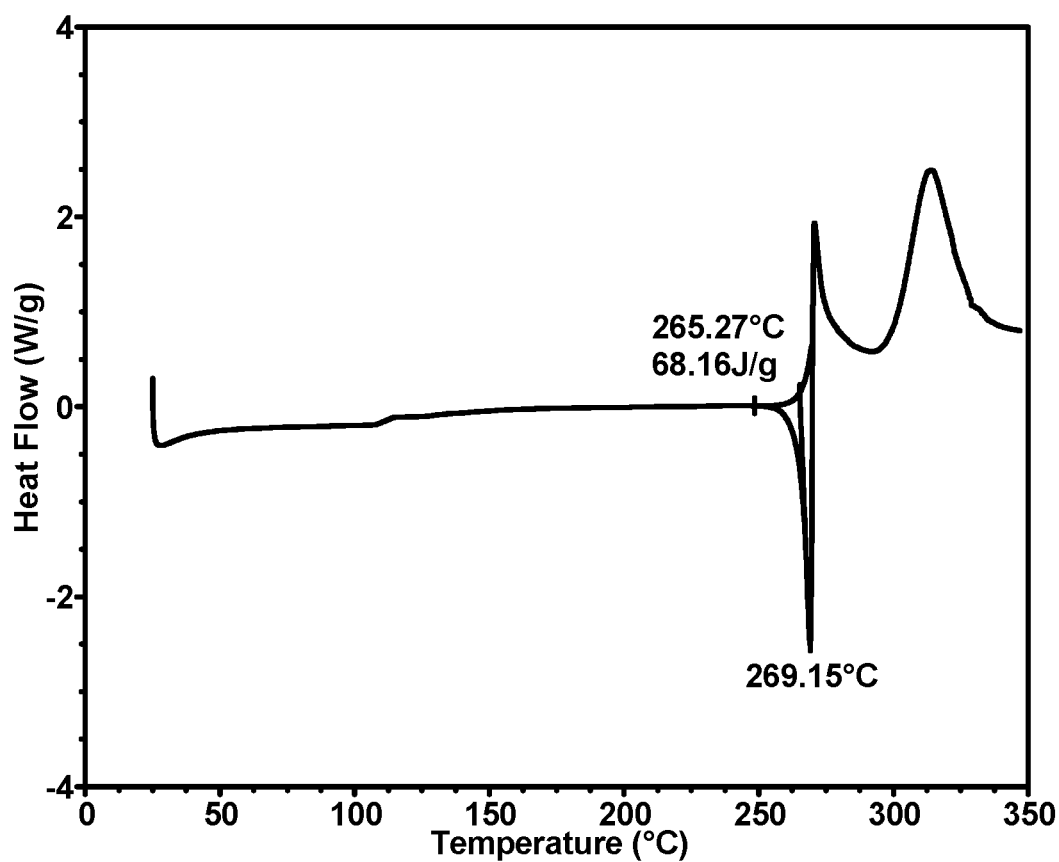
FIG. 2 shows a DSC thermogram of the zwitterionic compound of Formula I Form I.

In some embodiments, provided herein is a zwitterionic solid compound of Formula I (Formula I Form I), wherein the solid form exhibits an X-ray powder diffraction (XRPD) pattern substantially as shown in FIG. 1. Zwitterionic crystalline Formula I Form I may exhibit a differential scanning calorimetry (DSC) thermogram substantially as shown in FIG. 2. Crystalline Formula I Form I may exhibit a thermogravimetric analysis (TGA) thermogram substantially as shown in FIG. 3.

In some embodiments of crystalline Formula I Form I, at least one, at least two, or all of the following (a)-(c) apply: (a) crystalline Formula I Form I has an XRPD pattern substantially as shown in FIG. 1; (b) crystalline Formula I Form I has a DSC thermogram substantially as shown in FIG. 2; (c) crystalline Formula I Form I has a TGA thermogram substantially as shown in FIG. 3.

Figure 3:
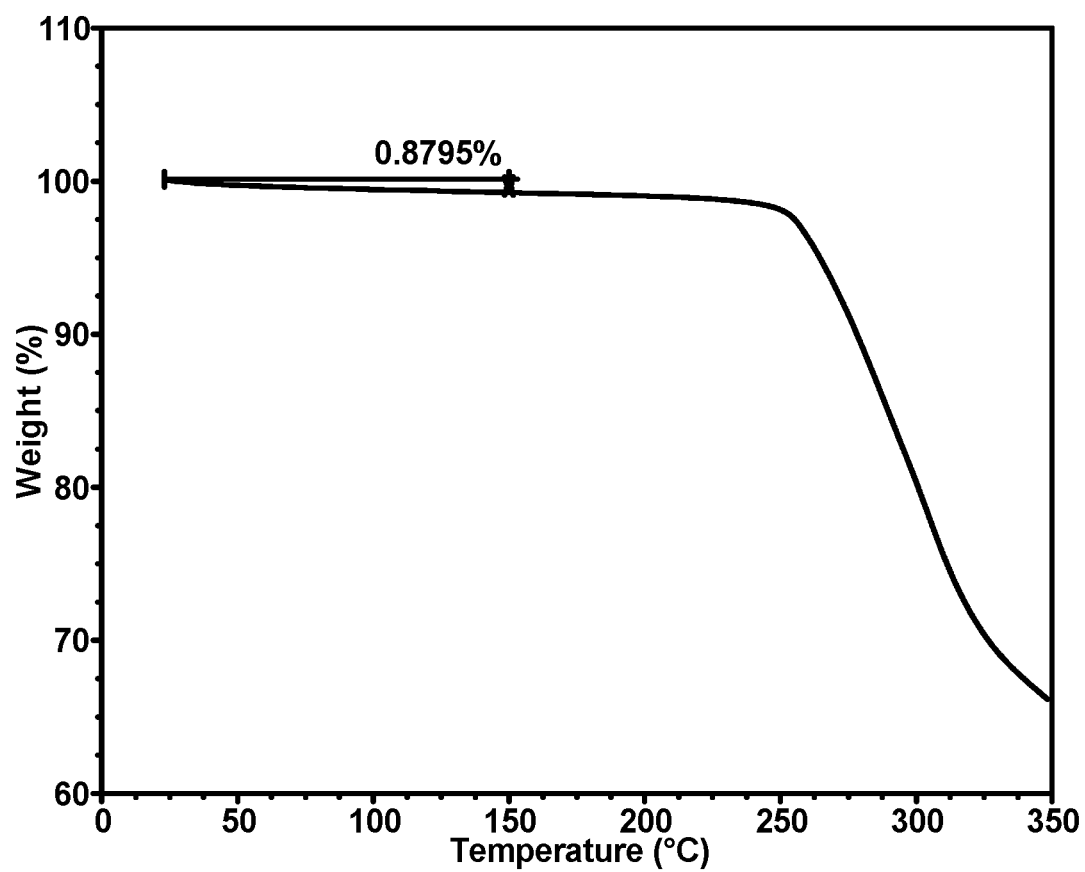
FIG. 3 shows a TGA thermogram of the zwitterionic compound of Formula I Form I.

In some embodiments, crystalline Formula I Form I has at least one, at least two, or at least three of the following properties:

(a) an XRPD pattern substantially as shown in FIG. 1
(b) a DSC thermogram substantially as shown in FIG. 2
(c) a TGA thermogram substantially as shown in FIG. 3.

In some embodiments, crystalline Formula I Form I has an XRPD pattern displaying at least two, at least three, at least four, at least five, at least six, at least seven, at least eight, or at least nine of the degree 2θ-reflections with the greatest intensity as the XRPD pattern substantially as shown in FIG. 1.

In certain embodiments, zwitterionic crystalline Formula I Form I has an XRPD pattern comprising degree 2θ-reflections (±0.2 degrees 2θ) at 6.7, 13.3, and 16.6 degrees. In some embodiments, zwitterionic Formula I Form I has an XRPD pattern comprising degree 2θ-reflections (±0.2 degrees 2θ) at 6.7, 13.3, and 16.6 degrees and one, two or three of the degree 2θ-reflections (±0.2 degrees 2θ) at 12.3, 16.2, and 20.0 degrees. In some embodiments, zwitterionic Formula I Form I has an XRPD pattern comprising degree 2θ-reflections (±0.2 degrees 2θ) at 6.7, 13.3, and 16.6 degrees and one, two or three of the degree 2θ-reflections (±0.2 degrees 2θ) at 15.3, 22.4, and 26.6 degrees. In some embodiments, zwitterionic Formula I Form I has an XRPD pattern comprising degree 2θ-reflections (±0.2 degrees 2θ) at 6.7, 13.3, 16.6, 12.3, 16.2, 20.0, 15.3, 22.4, and 26.6 degrees.

In some embodiments, zwitterionic Formula I Form I has a differential scanning calorimetry thermogram comprising, an endotherm with an onset at about 265° C.

Formula I Zwitterion Form II

Figure 4:
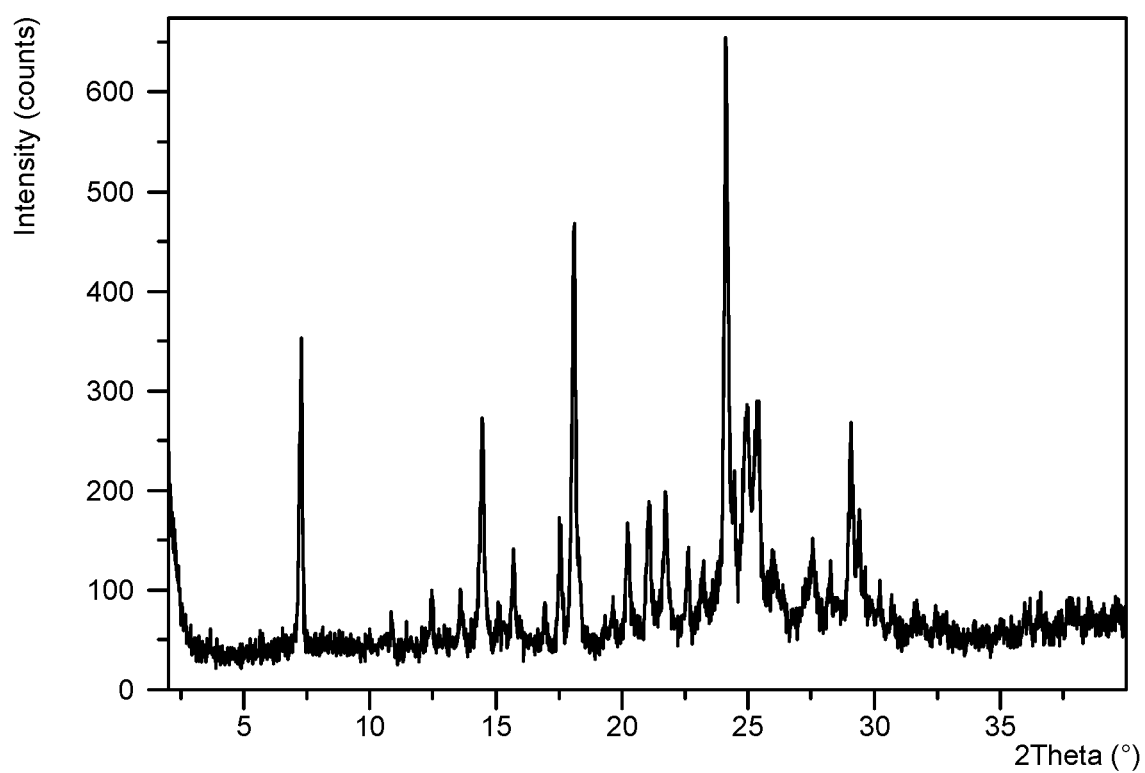
FIG. 4 shows an XRPD pattern of the zwitterionic compound of Formula I Form II.
Figure 5:
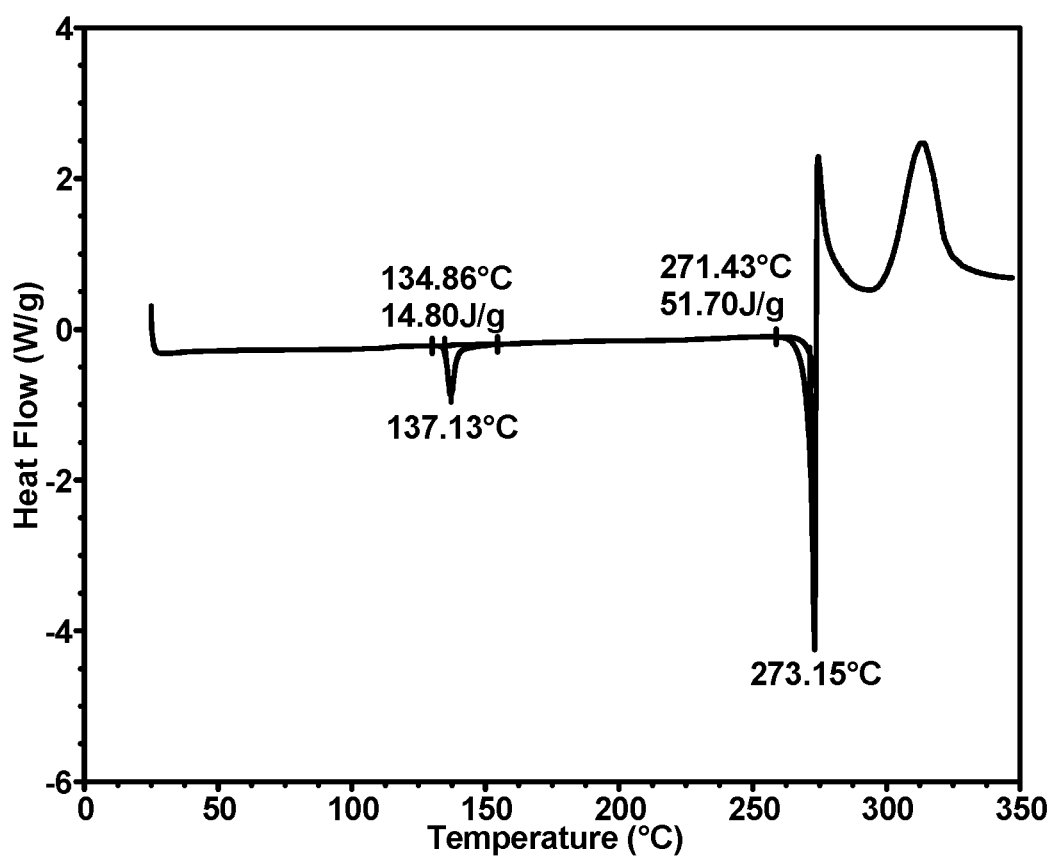
FIG. 5 shows a DSC thermogram of the zwitterionic compound of Formula I Form II.
Figure 6:
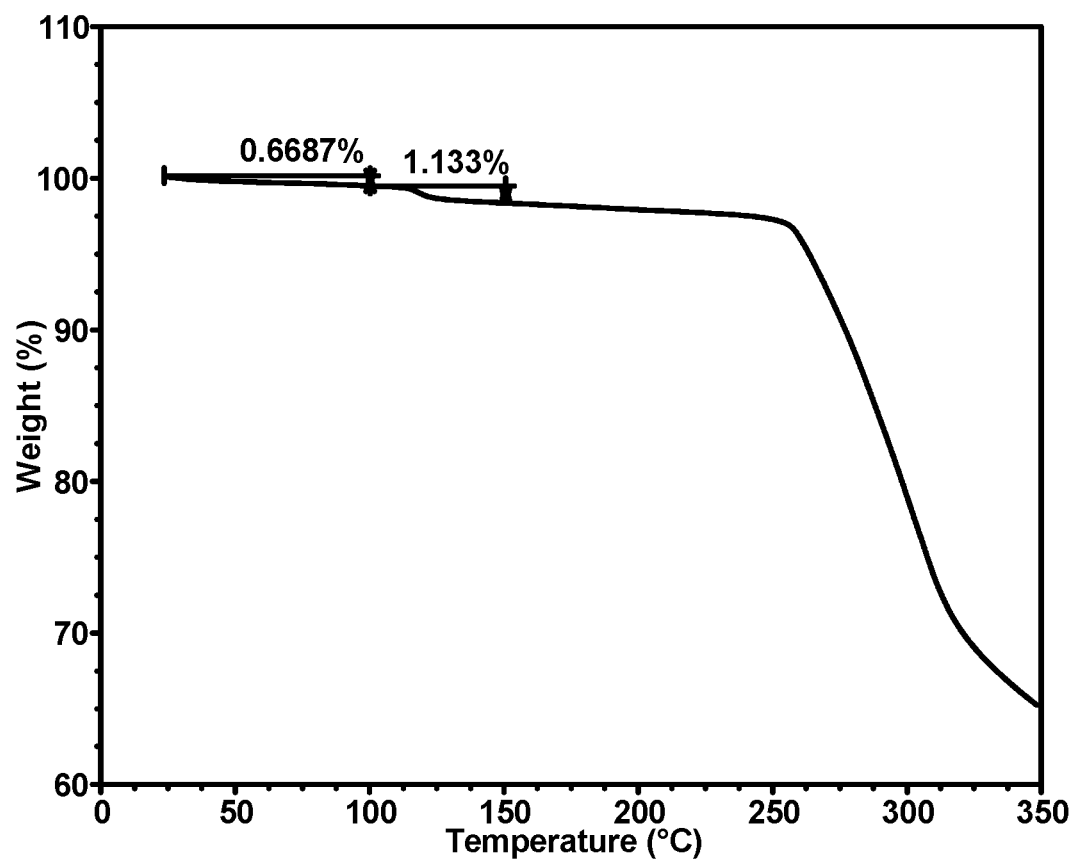
FIG. 6 shows a TGA thermogram of the zwitterionic compound of Formula I Form II.

In some embodiments, provided herein is a zwitterionic crystalline compound of Formula I (Formula I Form II), wherein the crystal structure exhibits an X-ray powder diffraction (XRPD) pattern substantially as shown in FIG. 4. Zwitterionic crystalline Formula I Form II may exhibit a differential scanning calorimetry (DSC) thermogram substantially as shown in FIG. 5. Crystalline Formula I Form I may exhibit a thermogravimetric analysis (TGA) thermogram substantially as shown in FIG. 6.

In some embodiments of crystalline Formula I Form II, at least one, at least two, or all of the following (a)-(c) apply: (a) crystalline Formula I Form II has an XRPD pattern substantially as shown in FIG. 4; (b) crystalline Formula I Form II has a DSC thermogram substantially as shown in FIG. 5; (c) crystalline Formula I Form II has a TGA thermogram substantially as shown in FIG. 6.

In some embodiments, crystalline Formula I Form II has at least one, at least two, or at least three of the following properties:
    (a) an XRPD pattern substantially as shown in FIG. 4
    (b) a DSC thermogram substantially as shown in FIG. 5
    (c) a TGA thermogram substantially as shown in FIG. 6.

In some embodiments, crystalline Formula I Form II has an XRPD pattern displaying at least two, at least three, at least four, at least five, at least six, at least seven, at least eight, or at least nine of the degree 2θ-reflections with the greatest intensity as the XRPD pattern substantially as shown in FIG. 4.

In certain embodiments, zwitterionic crystalline Formula I Form II has an XRPD pattern comprising degree 2θ-reflections (±0.2 degrees 2θ) at 7.3, 18.1, and 24.1 degrees. In some embodiments, zwitterionic Formula I Form II has an XRPD pattern comprising degree 2θ-reflections (±0.2 degrees 2θ) at 7.3, 18.1, and 24.1 degrees and one, two, three, or four of the degree 2θ-reflections (±0.2 degrees 2θ) at 14.5, 25.0, 25.4, and 29.1 degrees. In some embodiments, zwitterionic Formula I Form II has an XRPD pattern comprising degree 2θ-reflections (±0.2 degrees 2θ) at 7.3, 18.1, 24.1, 14.5, 25.0, 25.4, and 29.1 degrees.

In some embodiments, zwitterionic Formula I Form II has a differential scanning calorimetry thermogram having an endotherm with onset at about 135° C. In some embodiments, zwitterionic Formula I Form II has a differential scanning calorimetry thermogram having an endotherm with onset at about 271° C.

Formula I Zwitterion Hydrate

Figure 7:
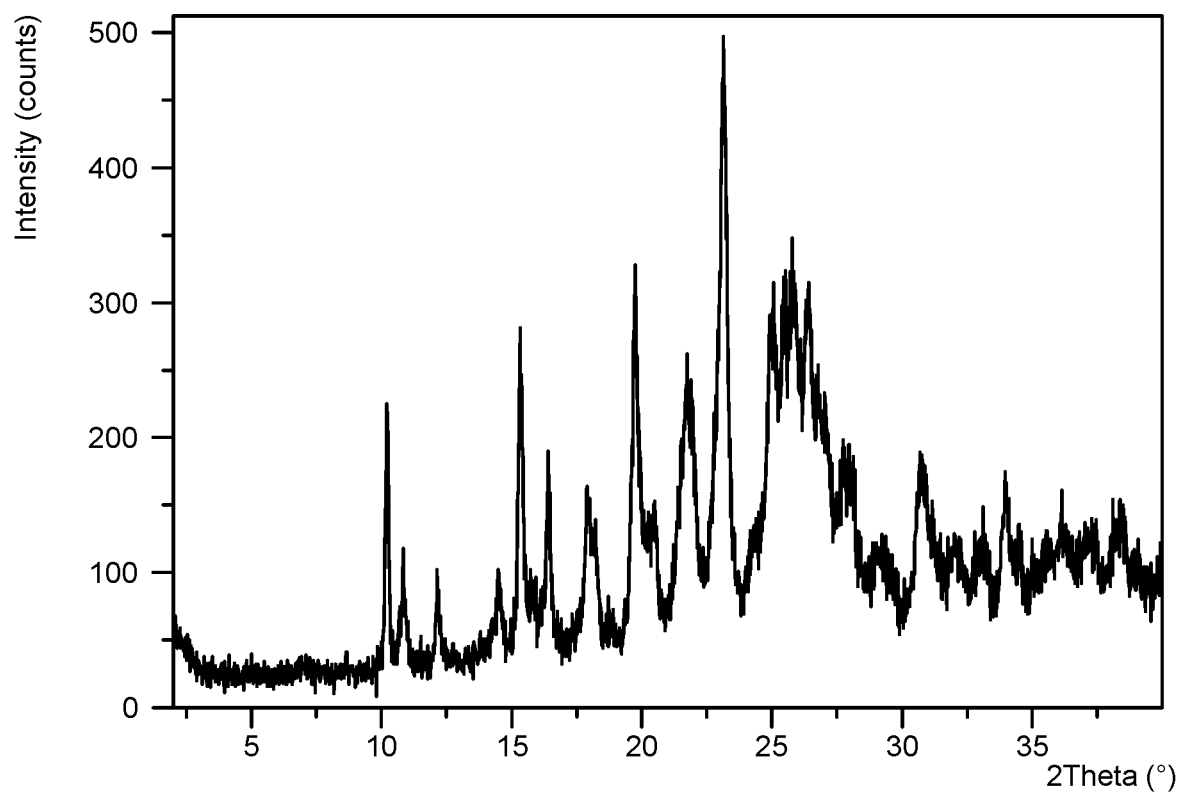
FIG. 7 shows an XRPD pattern of the zwitterionic compound of Formula I hydrate.
Figure 8:
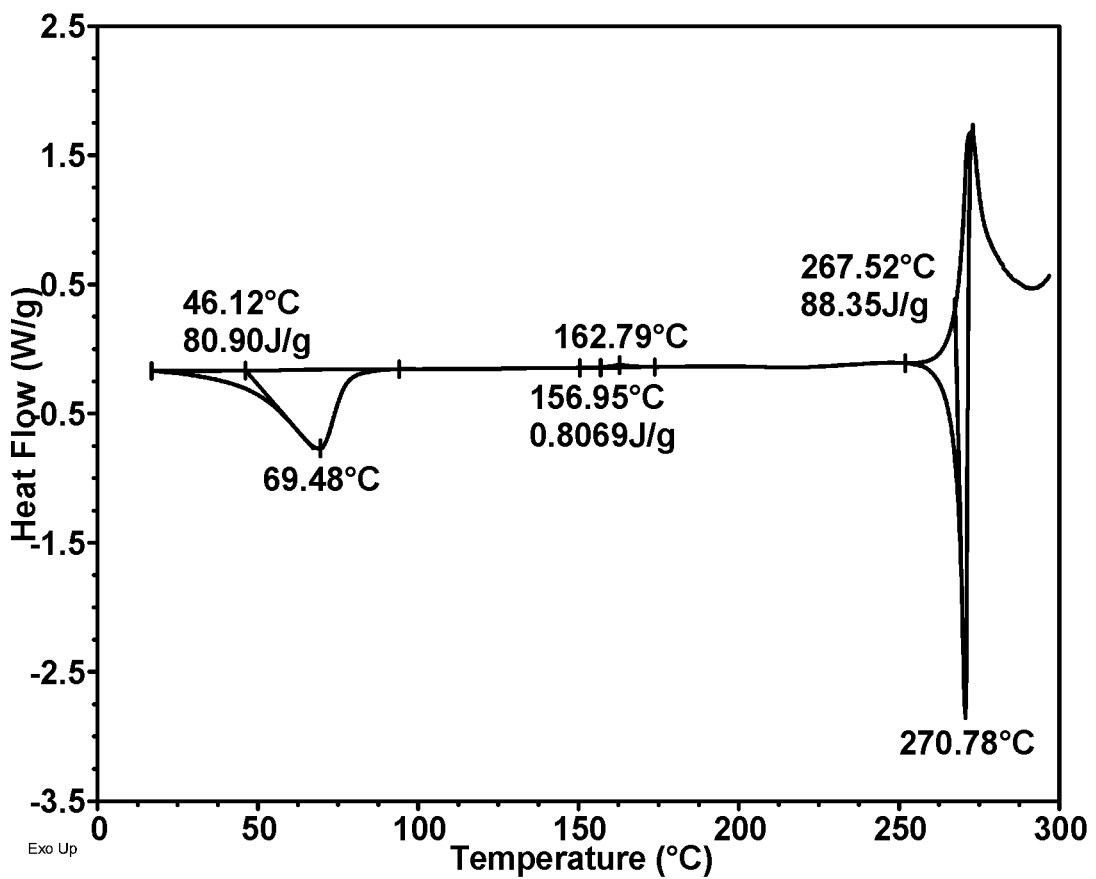
FIG. 8 shows a DSC thermogram of the zwitterionic compound of Formula I hydrate.
Figure 9:
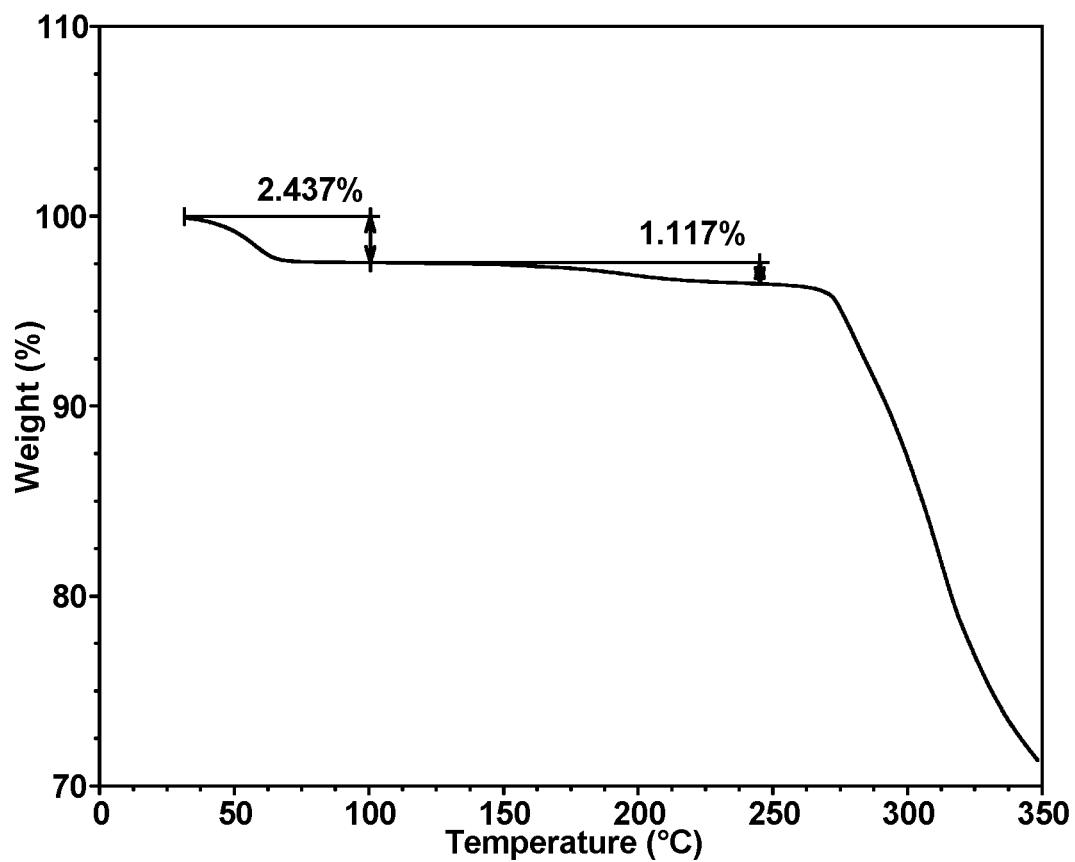
FIG. 9 shows a TGA thermogram of the zwitterionic compound of Formula I hydrate.

In some embodiments, provided herein is a zwitterionic crystalline compound of Formula I (Formula I hydrate), wherein the crystal structure exhibits an X-ray powder diffraction (XRPD) pattern substantially as shown in FIG. 7. Zwitterionic crystalline Formula I hydrate may exhibit a differential scanning calorimetry (DSC) thermogram substantially as shown in FIG. 8. Crystalline Formula I hydrate may exhibit a thermogravimetric analysis (TGA) thermogram substantially as shown in FIG. 9.

In some embodiments of crystalline Formula I hydrate, at least one, at least two, or all of the following (a)-(c) apply: (a) crystalline Formula I hydrate has an XRPD pattern substantially as shown in FIG. 7; (b) crystalline Formula I hydrate has a DSC thermogram substantially as shown in FIG. 8; (c) crystalline Formula I hydrate has a TGA thermogram substantially as shown in FIG. 9.

In some embodiments, crystalline Formula I hydrate has at least one, at least two, or at least three of the following properties:
    (a) an XRPD pattern substantially as shown in FIG. 7
    (b) a DSC thermogram substantially as shown in FIG. 8
    (c) a TGA thermogram substantially as shown in FIG. 9.

In some embodiments, crystalline Formula I hydrate has an XRPD pattern displaying at least two, at least three, at least four, at least five, at least six, at least seven, at least eight, or at least nine of the degree 2θ-reflections with the greatest intensity as the XRPD pattern substantially as shown in FIG. 7.

In certain embodiments, zwitterionic crystalline Formula I hydrate has an XRPD pattern comprising degree 2θ-reflections (±0.2 degrees 2θ) at 10.2, 15.4, 19.7, and 23.1 degrees. In some embodiments, zwitterionic Formula I hydrate has an XRPD pattern comprising degree 2θ-reflections (±0.2 degrees 2θ) at 10.2, 15.4, 19.7, and 23.1 degrees and one, two, three, or four of the degree 2θ-reflections (±0.2 degrees 2θ) at 16.4, 17.9, 21.7, and 25.8 degrees. In some embodiments, zwitterionic Formula I hydrate has an XRPD pattern comprising degree 2θ-reflections (±0.2 degrees 2θ) at 10.2, 15.4, 19.7, and 23.1 degrees and one, two, or three of the degree 2θ-reflections (±0.2 degrees 2θ) at 10.8, 25.0, and 26.4 degrees. In some embodiments, zwitterionic Formula I hydrate has an XRPD pattern comprising degree 2θ-reflections (±0.2 degrees 2θ) at 10.2, 15.4, 19.7, 23.1, 16.4, 17.9, 21.7, 25.8, 10.8, 25.0, and 26.4 degrees.

In some embodiments, zwitterionic Formula I hydrate has a differential scanning calorimetry thermogram having a broad endotherm with onset at about 46° C. In some embodiments, zwitterionic Formula I hydrate has a differential scanning calorimetry thermogram having an exotherm with onset at about 157° C. In some embodiments, zwitterionic Formula I hydrate has a differential scanning calorimetry thermogram having an endotherm with onset at about 268° C.

Formula I Zwitterion Amorphous

Figure 10:
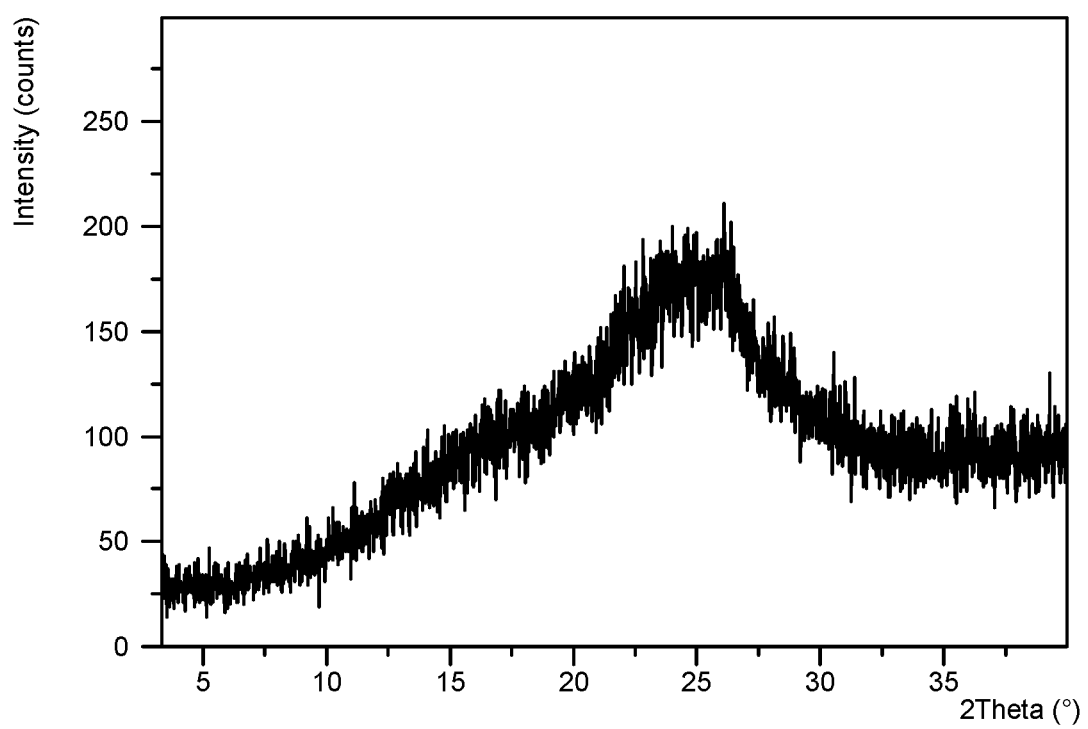
FIG. 10 shows an XRPD pattern of the amorphous zwitterionic compound of Formula I.

In some embodiments, provided herein is a solid zwitterionic compound of Formula I (Formula I amorphous), wherein the solid form exhibits an X-ray powder diffraction (XRPD) pattern substantially as shown in FIG. 10.

Formula I Tromethamine Salt Form I

Figure 11:
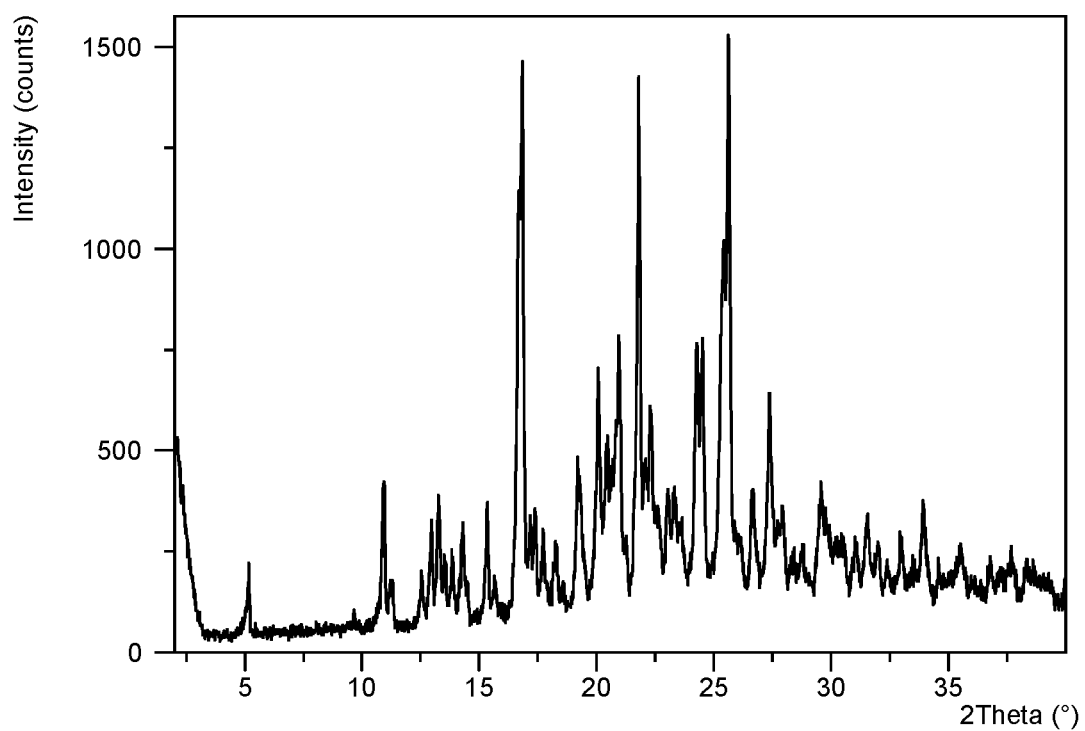
FIG. 11 shows an XRPD pattern of Formula I tromethamine salt Form I.
Figure 12:
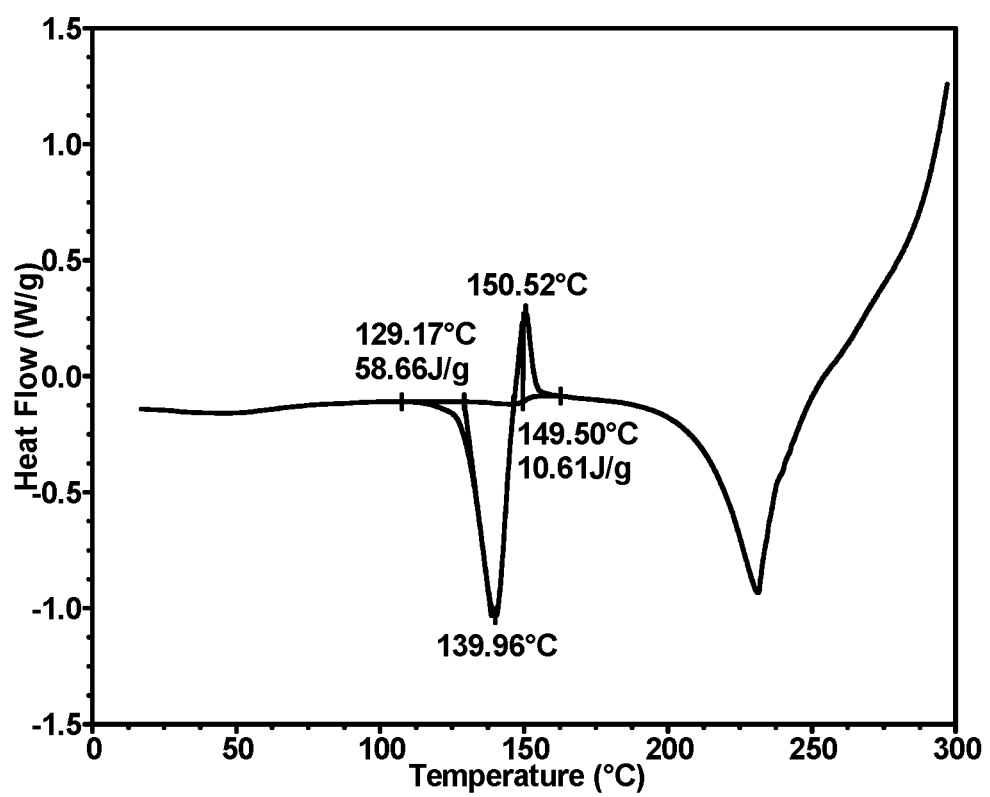
FIG. 12 shows a DSC thermogram of the Formula I tromethamine salt Form I.

In some embodiments, provided herein is a crystalline compound of Formula I tromethamine salt Form I (Formula I tromethamine salt Form I), wherein the crystal structure exhibits an X-ray powder diffraction (XRPD) pattern substantially as shown in FIG. 11. Formula I tromethamine salt Form I may exhibit a differential scanning calorimetry (DSC) thermogram substantially as shown in FIG. 12. Crystalline Formula I tromethamine salt Form I may exhibit a thermogravimetric analysis (TGA) thermogram substantially as shown in FIG. 13.

In some embodiments of crystalline Formula I tromethamine salt Form I, at least one, at least two, or all of the following (a)-(c) apply: (a) crystalline Formula I tromethamine salt Form I has an XRPD pattern substantially as shown in FIG. 11; (b) crystalline Formula I tromethamine salt Form I has a DSC thermogram substantially as shown in FIG. 12; (c) crystalline Formula I tromethamine salt Form I has a TGA thermogram substantially as shown in FIG. 13.

Figure 13:
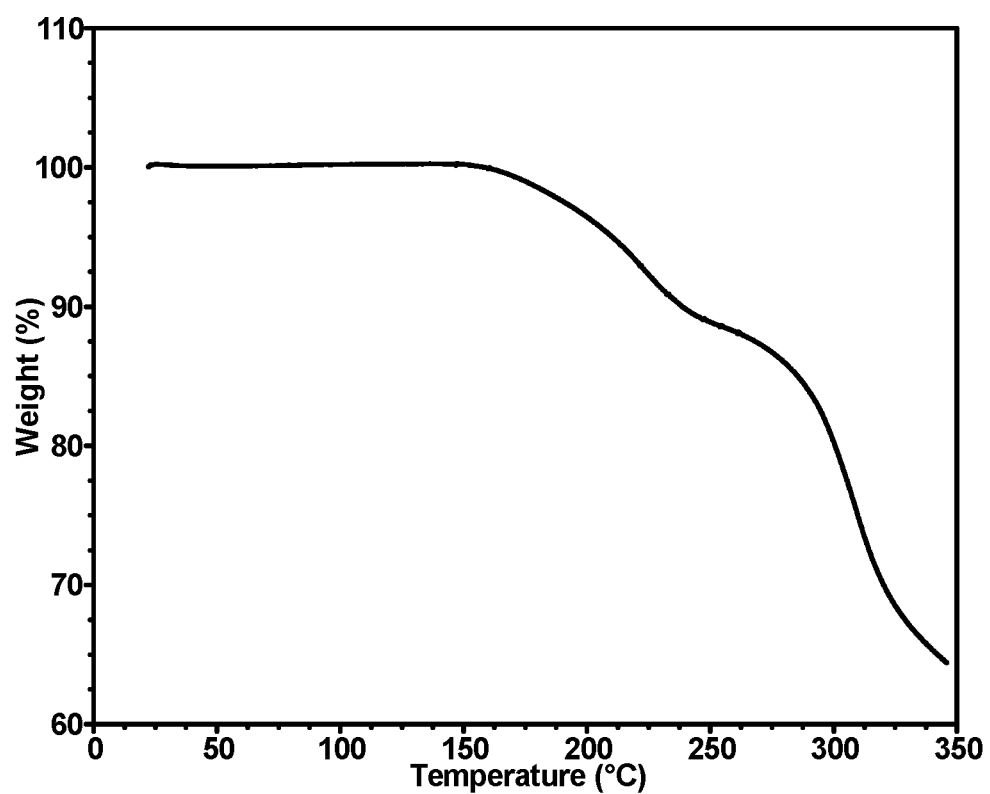
FIG. 13 shows a TGA thermogram of the Formula I tromethamine salt Form I.

In some embodiments, crystalline Formula I tromethamine salt Form I has at least one, at least two, or at least three of the following properties:

(a) an XRPD pattern substantially as shown in FIG. 11
(b) a DSC thermogram substantially as shown in FIG. 12
(c) a TGA thermogram substantially as shown in FIG. 13.

In some embodiments, crystalline Formula I tromethamine salt Form I has an XRPD pattern displaying at least two, at least three, at least four, at least five, at least six, at least seven, at least eight, or at least nine of the degree 2θ-reflections with the greatest intensity as the XRPD pattern substantially as shown in FIG. 11.

In certain embodiments, crystalline Formula I tromethamine salt Form I has an XRPD pattern comprising degree 2θ-reflections (±0.2 degrees 2θ) at 5.2, 16.8, and 25.6 degrees.

In some embodiments, Formula I tromethamine salt Form I has an XRPD pattern comprising degree 2θ-reflections (±0.2 degrees 2θ) at 5.2, 16.8, and 25.6 degrees and one, two, or three of the degree 2θ-reflections (±0.2 degrees 2θ) at 10.9, 15.3, and 21.8 degrees.

In some embodiments, Formula I tromethamine salt Form I has an XRPD pattern comprising degree 2θ-reflections (±0.2 degrees 2θ) at 5.2, 16.8, and 25.6 degrees and one, two, three, four, or five of the degree 2θ-reflections (±0.2 degrees 2θ) at 13.3, 20.1, 20.4, 21.0, and 24.3 degrees.

In some embodiments, Formula I tromethamine salt Form I has an XRPD pattern comprising degree 2θ-reflections (±0.2 degrees 2θ) at 5.2, 16.8, 25.6, 10.9, 15.3, 21.8, and 13.3, 20.1, 20.4, 21.0, and 24.3.

In some embodiments, Formula I tromethamine salt Form I has a differential scanning calorimetry thermogram having an endotherm with onset at about 129° C. In some embodiments, Formula I tromethamine salt Form I has a differential scanning calorimetry thermogram having an exotherm with onset at about 150° C.

Formula I Tromethamine Salt Form II

Figure 14:
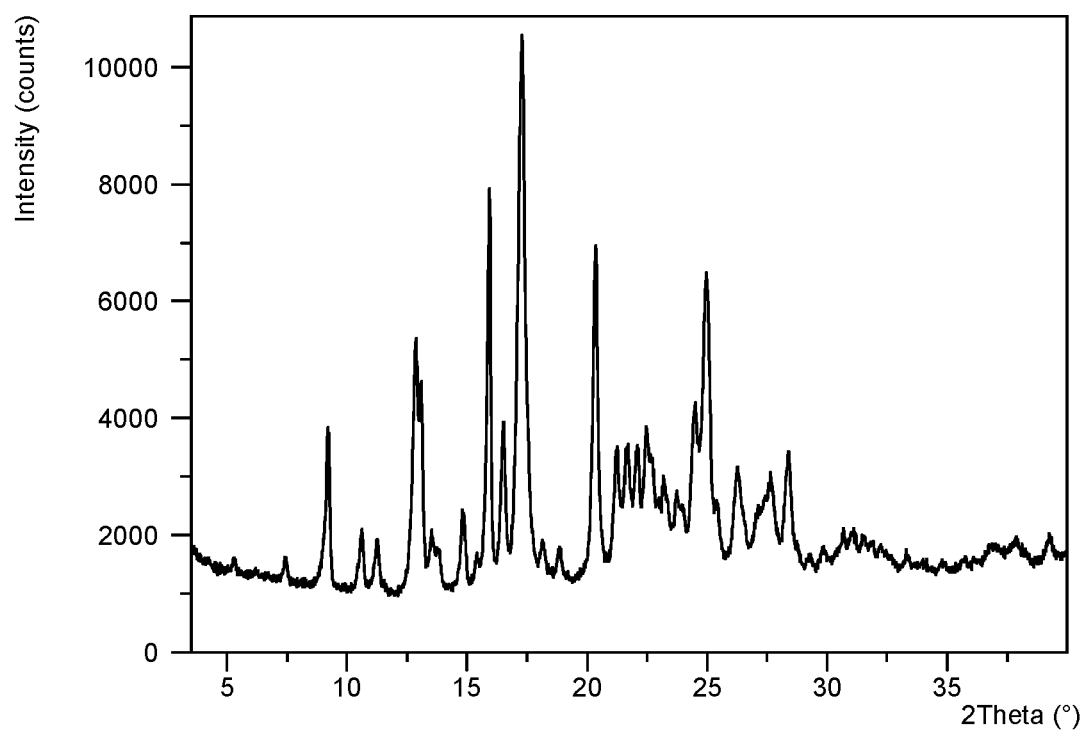
FIG. 14 shows an XRPD pattern of Formula I tromethamine salt Form II.

In some embodiments, provided herein is a crystalline compound of Formula I tromethamine salt Form II (Formula I tromethamine salt Form II), wherein the crystal structure exhibits an X-ray powder diffraction (XRPD) pattern substantially as shown in FIG. 14.

In some embodiments, crystalline Formula I tromethamine salt Form II has an XRPD pattern displaying at least two, at least three, at least four, at least five, at least six, at least seven, at least eight, or at least nine of the degree 2θ-reflections with the greatest intensity as the XRPD pattern substantially as shown in FIG. 14.

In certain embodiments, crystalline Formula I tromethamine salt Form II has an XRPD pattern comprising degree 2θ-reflections (±0.2 degrees 2θ) at 9.2, 15.9, and 17.3 degrees. In some embodiments, Formula I tromethamine salt Form II has an XRPD pattern comprising degree 2θ-reflections (±0.2 degrees 2θ) at 9.2, 15.9, and 17.3 degrees and one, two, three, or four of the degree 2θ-reflections (±0.2 degrees 2θ) at 12.9, 20.4, 24.5, and 25.1 degrees. In some embodiments, Formula I tromethamine salt Form II has an XRPD pattern comprising degree 2θ-reflections (±0.2 degrees 2θ) at 9.2, 15.9, 17.3, 12.9, 20.4, 24.5, and 25.1 degrees.

Formula I Tromethamine Salt Hydrate I

Figure 15:
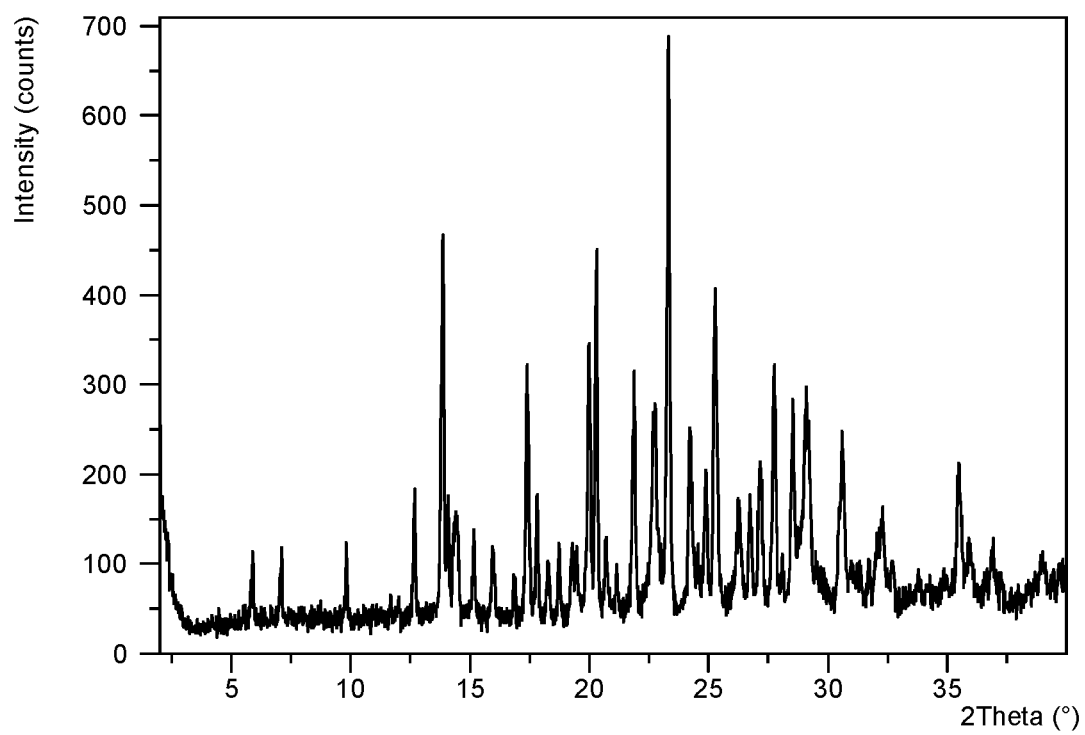
FIG. 15 shows an XRPD pattern of the Formula I tromethamine salt hydrate I.
Figure 16:
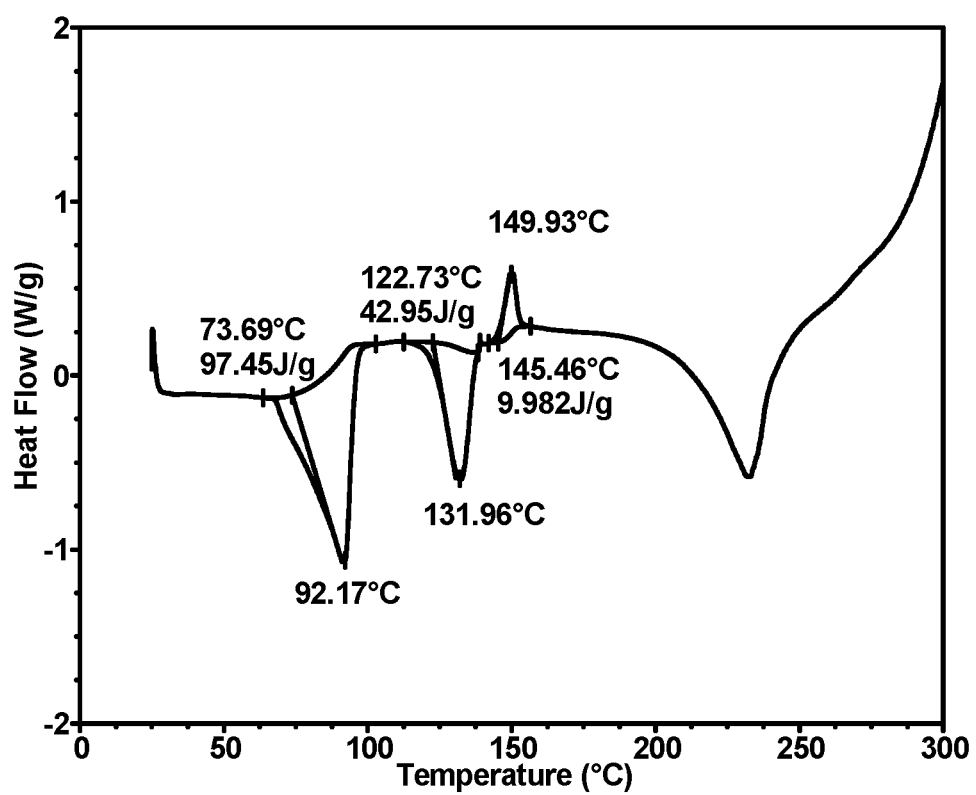
FIG. 16 shows a DSC thermogram of the Formula I tromethamine salt hydrate I.

In some embodiments, provided herein is a crystalline compound of Formula I tromethamine salt hydrate I (Formula I tromethamine salt hydrate I), wherein the crystal structure exhibits an X-ray powder diffraction (XRPD) pattern substantially as shown in FIG. 15. Formula I tromethamine salt hydrate I may exhibit a differential scanning calorimetry (DSC) thermogram substantially as shown in FIG. 16. Crystalline Formula I tromethamine salt hydrate I may exhibit a thermogravimetric analysis (TGA) thermogram substantially as shown in FIG. 17.

In some embodiments of crystalline Formula I tromethamine salt hydrate I, at least one, at least two, or all of the following (a)-(c) apply: (a) crystalline Formula I tromethamine salt hydrate I has an XRPD pattern substantially as shown in FIG. 15; (b) crystalline Formula I tromethamine salt hydrate I has a DSC thermogram substantially as shown in FIG. 16; (c) crystalline Formula I tromethamine salt hydrate I has a TGA thermogram substantially as shown in FIG. 17.

Figure 17:
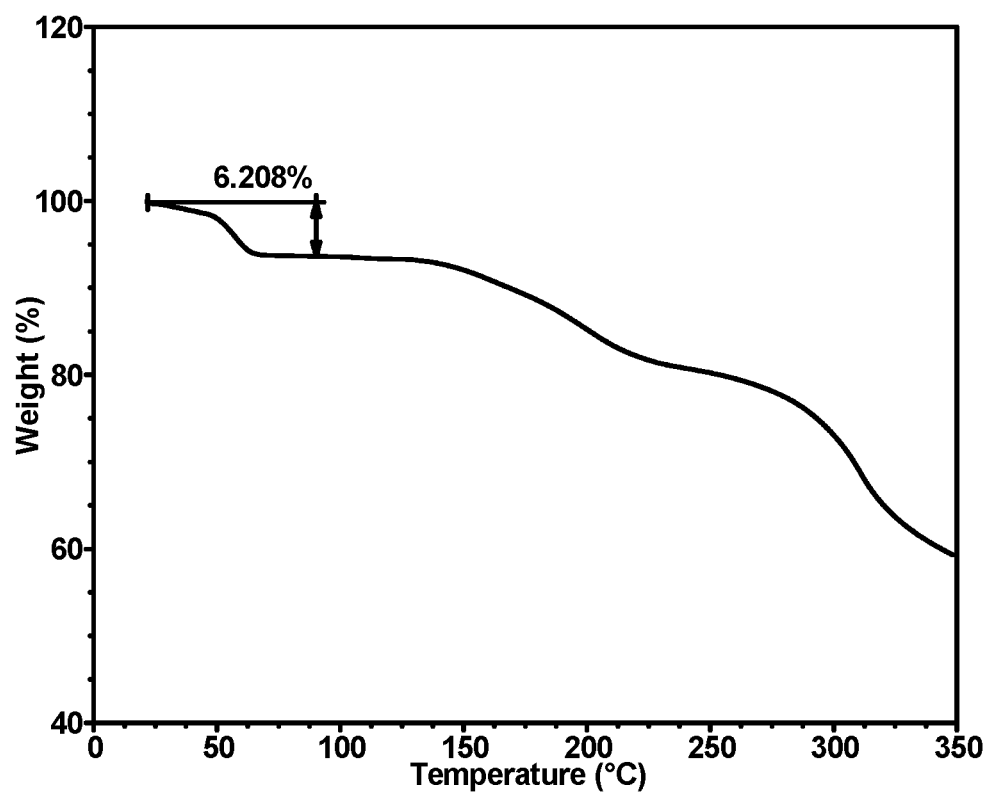
FIG. 17 shows a TGA thermogram of the Formula I tromethamine salt hydrate I.

In some embodiments, crystalline Formula I tromethamine salt hydrate I has at least one, at least two, or at least three of the following properties:

(a) an XRPD pattern substantially as shown in FIG. 15
(b) a DSC thermogram substantially as shown in FIG. 16
(c) a TGA thermogram substantially as shown in FIG. 17.

In some embodiments, crystalline Formula I tromethamine salt hydrate I has an XRPD pattern displaying at least two, at least three, at least four, at least five, at least six, at least seven, at least eight, or at least nine of the degree 2θ-reflections with the greatest intensity as the XRPD pattern substantially as shown in FIG. 15.

In certain embodiments, crystalline Formula I tromethamine salt hydrate I has an XRPD pattern comprising degree 2θ-reflections (±0.2 degrees 2θ) at 5.9, 13.9, and 23.3 degrees. In some embodiments, Formula I tromethamine salt hydrate I has an XRPD pattern comprising degree 2θ-reflections (±0.2 degrees 2θ) at 5.9, 13.9, and 23.3 degrees and one, two, or three of the degree 2θ-reflections (±0.2 degrees 2θ) at 7.1, 12.7, and 20.3 degrees. In some embodiments, Formula I tromethamine salt hydrate I has an XRPD pattern comprising degree 2θ-reflections (±0.2 degrees 2θ) at 5.9, 13.9, and 23.3 degrees and one, two, three, or four of the degree 2θ-reflections (±0.2 degrees 2θ) at 9.8, 17.4, 22.7, and 25.3 degrees. In some embodiments, Formula I tromethamine salt hydrate I has an XRPD pattern comprising degree 2θ-reflections (±0.2 degrees 2θ) at 5.9, 13.9, 23.3, 7.1, 12.7, 20.3, 9.8, 17.4, 22.7, and 25.3 degrees.

In some embodiments, Formula I tromethamine salt hydrate I has a differential scanning calorimetry thermogram having an endotherm with onset at about 74° C. In some embodiments, Formula I tromethamine salt hydrate I having endotherm with onset at about 123° C. In some embodiments, Formula I tromethamine salt hydrate I has a differential scanning calorimetry thermogram having an exotherm with onset at about 145° C.

Formula I Tromethamine Salt Hydrate II

Figure 18:
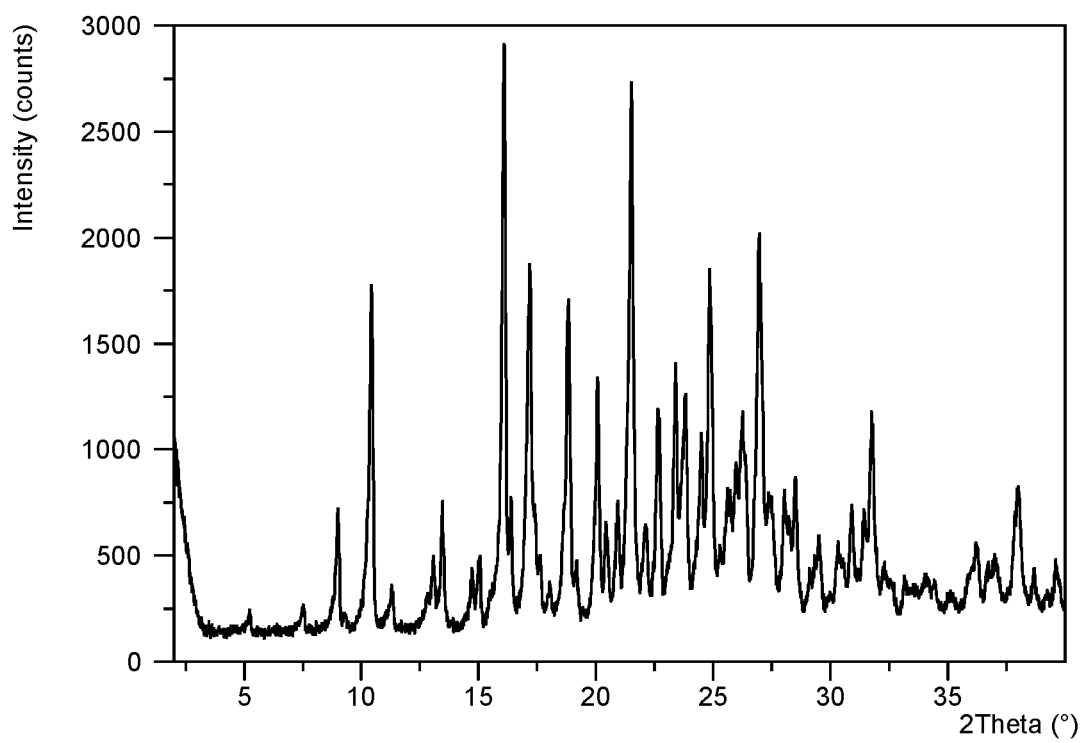
FIG. 18 shows an XRPD pattern of the Formula I tromethamine salt hydrate II.
Figure 19:
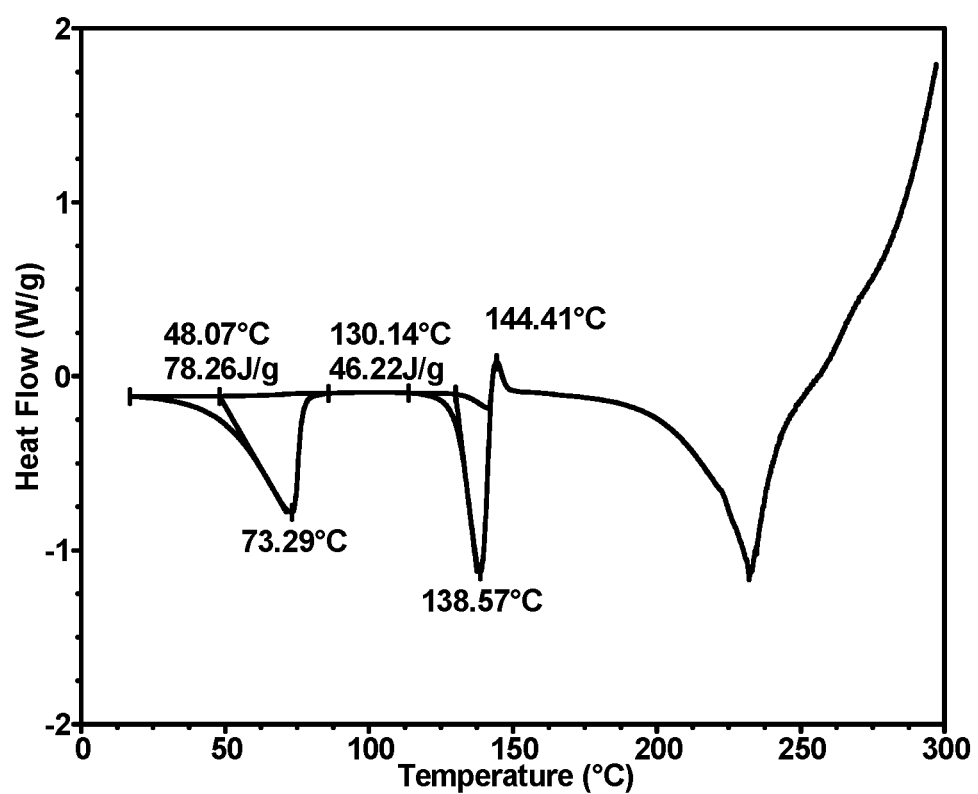
FIG. 19 shows a DSC thermogram of the Formula I tromethamine salt hydrate II.

In some embodiments, provided herein is a crystalline compound of Formula I tromethamine salt hydrate II (Formula I tromethamine salt hydrate II), wherein the crystal structure exhibits an X-ray powder diffraction (XRPD) pattern substantially as shown in FIG. 18. Formula I tromethamine salt hydrate II may exhibit a differential scanning calorimetry (DSC) thermogram substantially as shown in FIG. 19. Crystalline Formula I tromethamine salt hydrate II may exhibit a thermogravimetric analysis (TGA) thermogram substantially as shown in FIG. 20.

In some embodiments of crystalline Formula I tromethamine salt hydrate II, at least one, at least two, or all of the following (a)-(c) apply: (a) crystalline Formula I tromethamine salt hydrate II has an XRPD pattern substantially as shown in FIG. 18; (b) crystalline Formula I tromethamine salt hydrate II has a DSC thermogram substantially as shown in FIG. 19; (c) crystalline Formula I tromethamine salt hydrate II has a TGA thermogram substantially as shown in FIG. 20.

Figure 20:
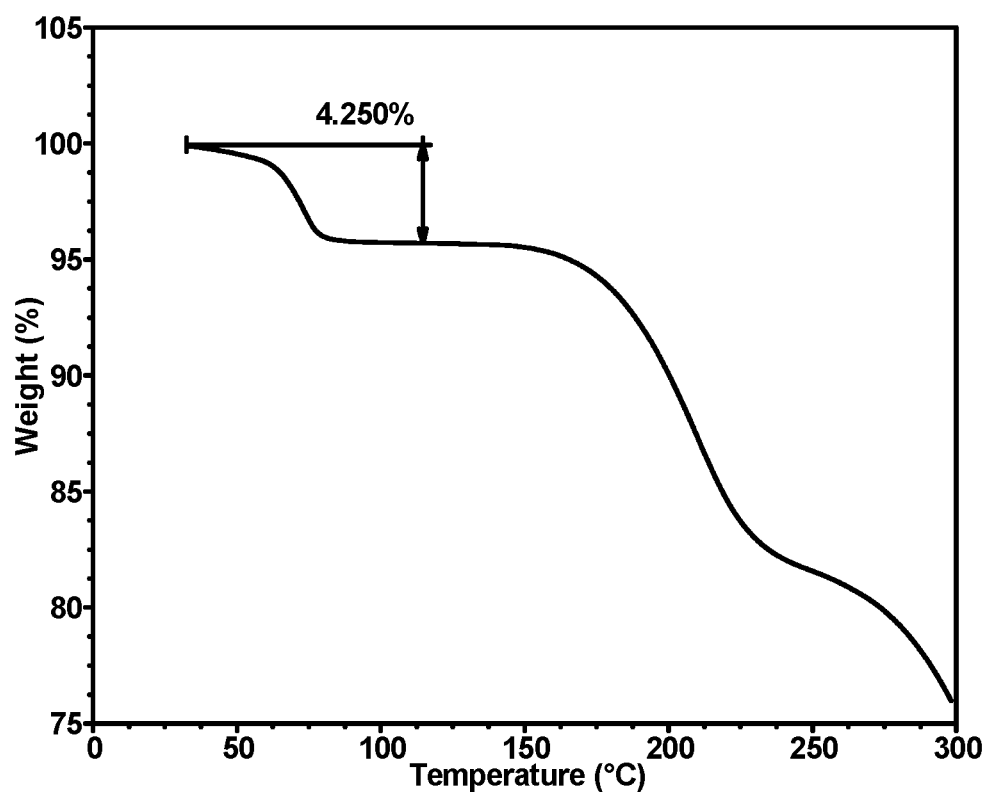
FIG. 20 shows a TGA thermogram of the Formula I tromethamine salt hydrate II.

In some embodiments, crystalline Formula I tromethamine salt hydrate II has at least one, at least two, or at least three of the following properties:

(a) an XRPD pattern substantially as shown in FIG. 18
(b) a DSC thermogram substantially as shown in FIG. 19
(c) a TGA thermogram substantially as shown in FIG. 20.

In some embodiments, crystalline Formula I tromethamine salt hydrate II has an XRPD pattern displaying at least two, at least three, at least four, at least five, at least six, at least seven, at least eight, or at least nine of the degree 2θ-reflections with the greatest intensity as the XRPD pattern substantially as shown in FIG. 18.

In certain embodiments, crystalline Formula I tromethamine salt hydrate II has an XRPD pattern comprising degree 2θ-reflections (±0.2 degrees 2θ) at 10.5, 16.1, and 21.5 degrees. In some embodiments, Formula I tromethamine salt hydrate II has an XRPD pattern comprising degree 2θ-reflections (±0.2 degrees 2θ) at 10.5, 16.1, and 21.5 degrees and one, two, or three of the degree 2θ-reflections (±0.2 degrees 2θ) at 9.0, 17.2, and 18.8 degrees. In some embodiments, Formula I tromethamine salt hydrate II has an XRPD pattern comprising degree 2θ-reflections (±0.2 degrees 2θ) at 10.5, 16.1, and 21.5 degrees and one, two, three, or four of the degree 2θ-reflections (±0.2 degrees 2θ) at 13.4, 20.1, 24.9, and 26.9 degrees. In some embodiments, Formula I tromethamine salt hydrate II has an XRPD pattern comprising degree 2θ-reflections (±0.2 degrees 2θ) at 10.5, 16.1, 21.5, 9.0, 17.2, 18.8, 13.4, 20.1, 24.9, and 26.9 degrees.

In some embodiments, Formula I tromethamine salt hydrate II has a differential scanning calorimetry thermogram having a broad endotherm with onset at about 48° C. In some embodiments, Formula I tromethamine salt hydrate II has a differential scanning calorimetry thermogram having an endotherm with onset at about 130° C.

Formula I Tromethamine Salt Hydrate III

Figure 21:
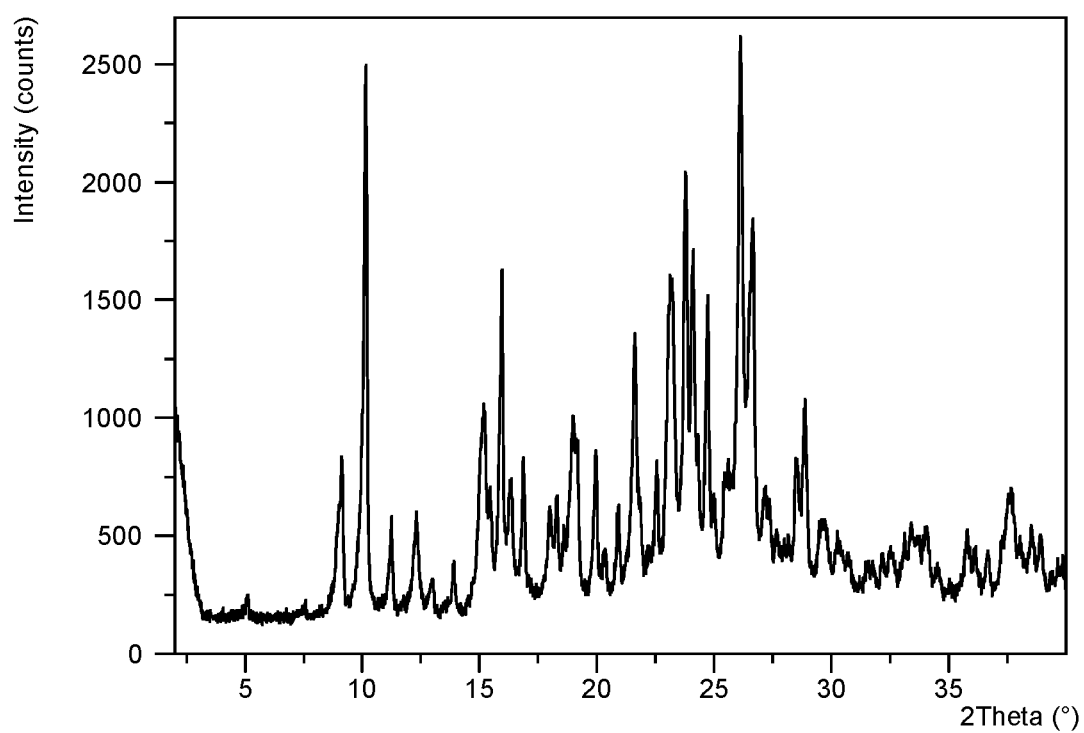
FIG. 21 shows an XRPD pattern of the Formula I tromethamine salt hydrate III.
Figure 22:
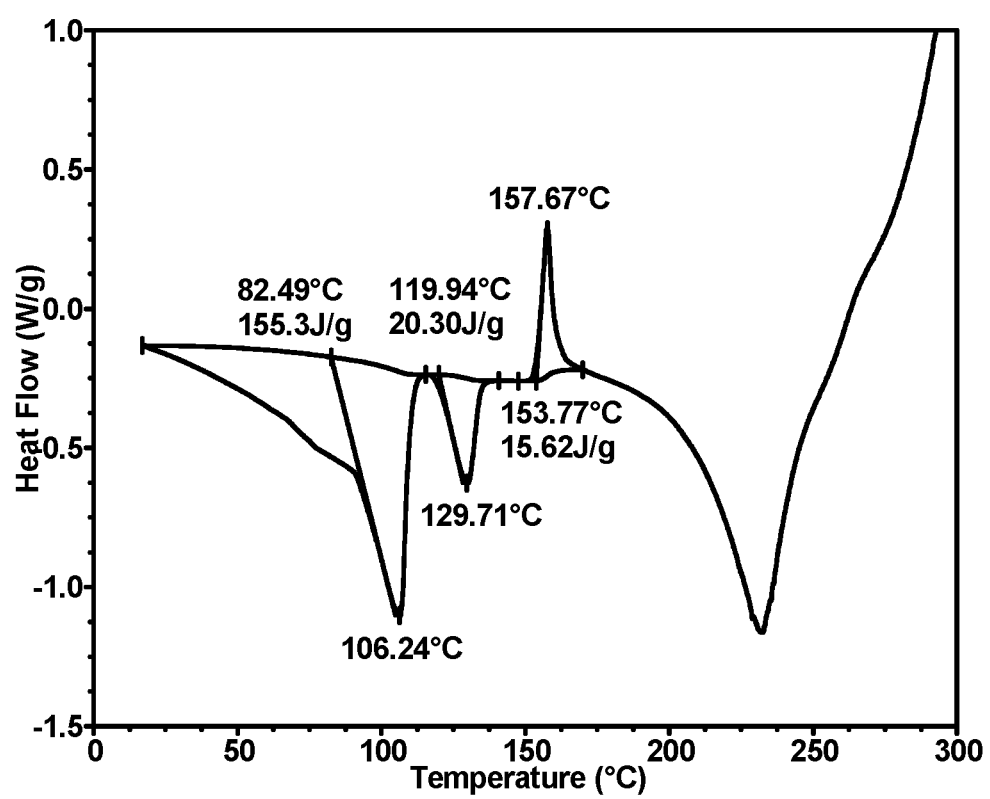
FIG. 22 shows a DSC thermogram of the Formula I tromethamine salt hydrate III.

In some embodiments, provided herein is a crystalline compound of Formula I tromethamine salt hydrate III (Formula I tromethamine salt hydrate III), wherein the crystal structure exhibits an X-ray powder diffraction (XRPD) pattern substantially as shown in FIG. 21. Formula I tromethamine salt hydrate III may exhibit a differential scanning calorimetry (DSC) thermogram substantially as shown in FIG. 22. Crystalline Formula I tromethamine salt hydrate III may exhibit a thermogravimetric analysis (TGA) thermogram substantially as shown in FIG. 23.

In some embodiments of crystalline Formula I tromethamine salt hydrate III, at least one, at least two, or all of the following (a)-(c) apply: (a) crystalline Formula I tromethamine salt hydrate III has an XRPD pattern substantially as shown in FIG. 21; (b) crystalline Formula I tromethamine salt hydrate III has a DSC thermogram substantially as shown in FIG. 22; (c) crystalline Formula I tromethamine salt hydrate III has a TGA thermogram substantially as shown in FIG. 23.

Figure 23:
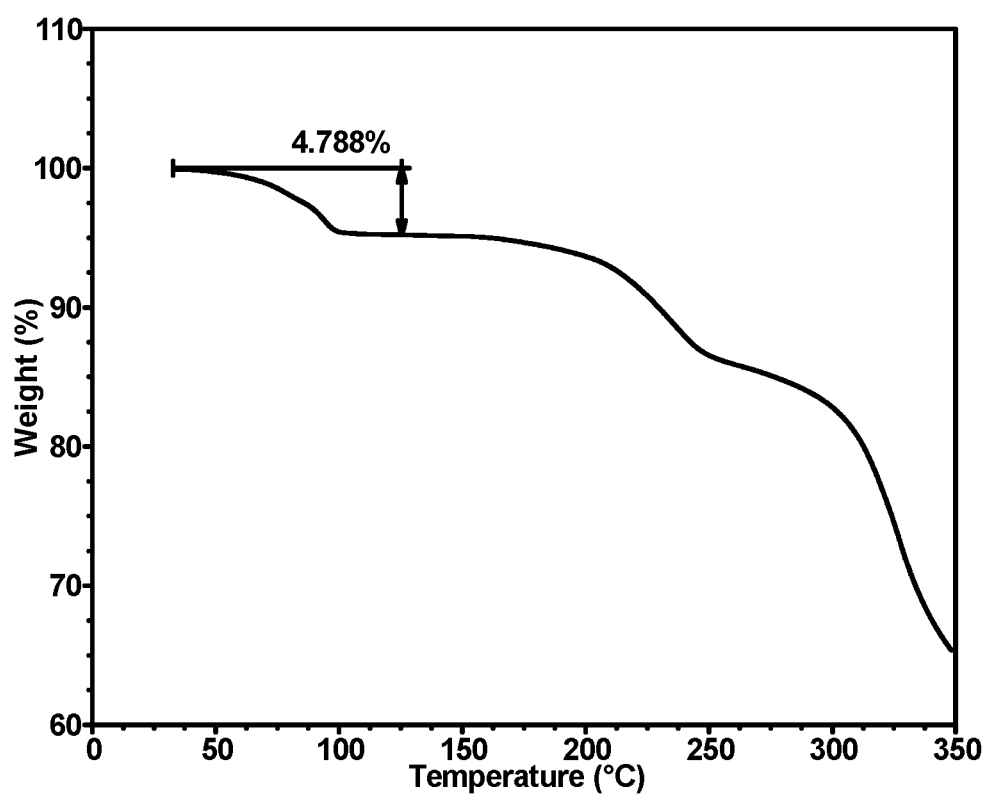
FIG. 23 shows a TGA thermogram of the Formula I tromethamine salt hydrate III.

In some embodiments, crystalline Formula I tromethamine salt hydrate III has at least one, at least two, or at least three of the following properties:

(a) an XRPD pattern substantially as shown in FIG. 21
(b) a DSC thermogram substantially as shown in FIG. 22
(c) a TGA thermogram substantially as shown in FIG. 23.

In some embodiments, crystalline Formula I tromethamine salt hydrate III has an XRPD pattern displaying at least two, at least three, at least four, at least five, at least six, at least seven, at least eight, or at least nine of the degree 2θ-reflections with the greatest intensity as the XRPD pattern substantially as shown in FIG. 21.

In certain embodiments, crystalline Formula I tromethamine salt hydrate III has an XRPD pattern comprising degree 2θ-reflections (±0.2 degrees 2θ) at 10.2, 16.0, and 23.2 degrees. In some embodiments, Formula I tromethamine salt hydrate III has an XRPD pattern comprising degree 2θ-reflections (±0.2 degrees 2θ) at 10.2, 16.0, and 23.2 degrees and one, two, or three of the degree 2θ-reflections (±0.2 degrees 2θ) at 9.1, 15.2, and 23.8 degrees. In some embodiments, Formula I tromethamine salt hydrate III has an XRPD pattern comprising degree 2θ-reflections (±0.2 degrees 2θ) at 10.2, 16.0, and 23.2 degrees and one, two, or three of the degree 2θ-reflections (±0.2 degrees 2θ) at 11.2, 12.3, 19.0, 21.6, and 26.1 degrees. In some embodiments, Formula I tromethamine salt hydrate III has an XRPD pattern comprising degree 2θ-reflections (±0.2 degrees 2θ) at 10.2, 16.0, 23.2, 9.1, 15.2, 23.8, 11.2, 12.3, 19.0, 21.6, and 26.1 degrees.

In some embodiments, Formula I tromethamine salt hydrate III has a differential scanning calorimetry thermogram having a broad endotherm with onset at about 82° C. In some embodiments, Formula I tromethamine salt hydrate III has a differential scanning calorimetry thermogram having an endotherm with onset at about 120° C. In some embodiments, Formula I tromethamine salt hydrate III has a differential scanning calorimetry thermogram having an exotherm with onset at about 154° C.

Formula I Tromethamine Salt Hydrate IV

Figure 24:
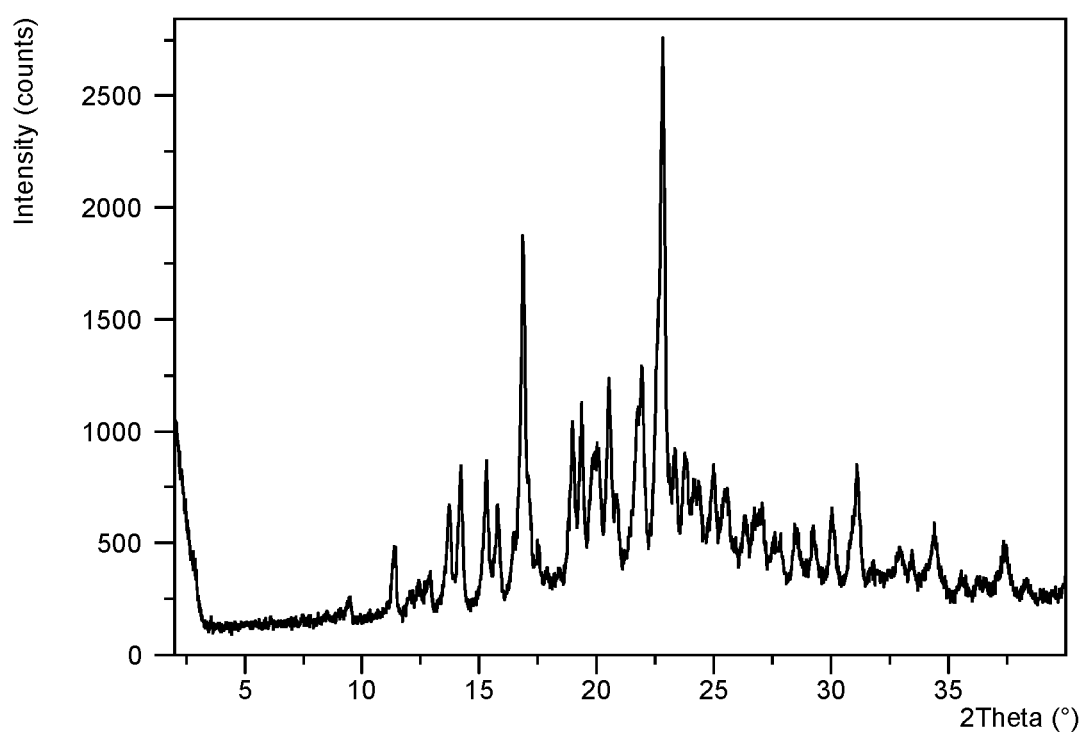
FIG. 24 shows an XRPD pattern of the Formula I tromethamine salt hydrate IV.
Figure 25:
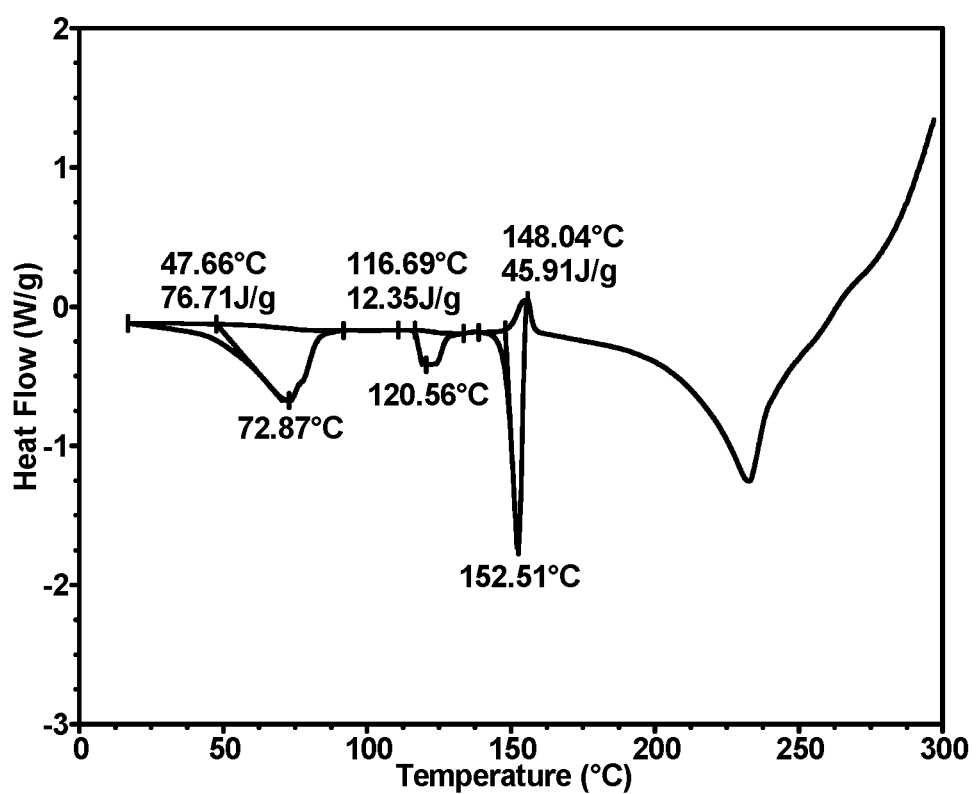
FIG. 25 shows a DSC thermogram of the Formula I tromethamine salt hydrate IV.

In some embodiments, provided herein is a crystalline compound of Formula I tromethamine salt hydrate IV (Formula I tromethamine salt hydrate IV), wherein the crystal structure exhibits an X-ray powder diffraction (XRPD) pattern substantially as shown in FIG. 24. Formula I tromethamine salt hydrate IV may exhibit a differential scanning calorimetry (DSC) thermogram substantially as shown in FIG. 25. Crystalline Formula I tromethamine salt hydrate IV may exhibit a thermogravimetric analysis (TGA) thermogram substantially as shown in FIG. 26.

In some embodiments of crystalline Formula I tromethamine salt hydrate IV, at least one, at least two, or all of the following (a)-(c) apply: (a) crystalline Formula I tromethamine salt hydrate IV has an XRPD pattern substantially as shown in FIG. 24; (b) crystalline Formula I tromethamine salt hydrate IV has a DSC thermogram substantially as shown in FIG. 25; (c) crystalline Formula I tromethamine salt hydrate IV has a TGA thermogram substantially as shown in FIG. 26.

Figure 26:
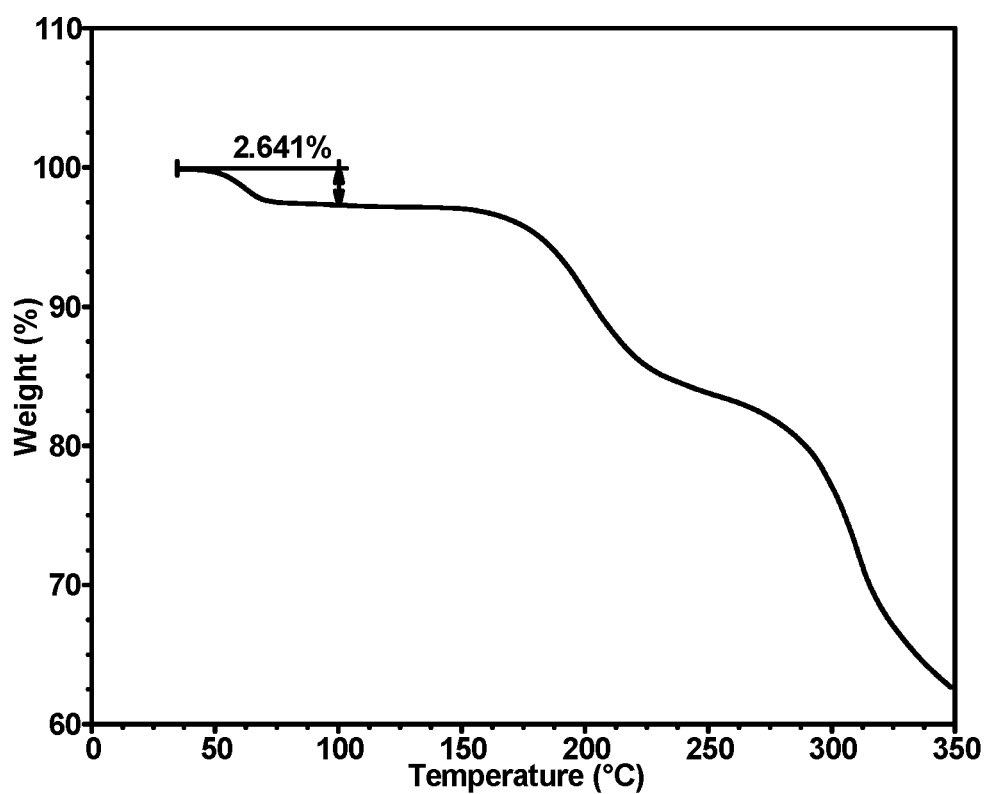
FIG. 26 shows a TGA thermogram of the Formula I tromethamine salt hydrate IV.

In some embodiments, crystalline Formula I tromethamine salt hydrate IV has at least one, at least two, or at least three of the following properties:

(a) an XRPD pattern substantially as shown in FIG. 24
(b) a DSC thermogram substantially as shown in FIG. 25
(c) a TGA thermogram substantially as shown in FIG. 26.

In some embodiments, crystalline Formula I tromethamine salt hydrate IV has an XRPD pattern displaying at least two, at least three, at least four, at least five, at least six, at least seven, at least eight, or at least nine of the degree 2θ-reflections with the greatest intensity as the XRPD pattern substantially as shown in FIG. 24.

In certain embodiments, crystalline Formula I tromethamine salt hydrate IV has an XRPD pattern comprising degree 2θ-reflections (±0.2 degrees 2θ) at 11.4, 16.9, and 22.8 degrees.

In some embodiments, Formula I tromethamine salt hydrate IV has an XRPD pattern comprising degree 2θ-reflections (±0.2 degrees 2θ) at 11.4, 16.9, and 22.8 degrees and one, two, or three of the degree 2θ-reflections (±0.2 degrees 2θ) at 14.2, 15.3, and 20.5 degrees.

In some embodiments, Formula I tromethamine salt hydrate IV has an XRPD pattern comprising degree 2θ-reflections (±0.2 degrees 2θ) at 11.4, 16.9, and 22.8 degrees and one, two, three, or four of the degree 2θ-reflections (±0.2 degrees 2θ) at 13.7, 15.8, 19.4, and 21.9 degrees.

In some embodiments, Formula I tromethamine salt hydrate IV has an XRPD pattern comprising degree 2θ-reflections (±0.2 degrees 2θ) at 11.4, 16.9, 22.8, 14.2, 15.3, 20.5, 13.7, 15.8, 19.4, and 21.9 degrees.

In some embodiments, Formula I tromethamine salt hydrate IV has a differential scanning calorimetry thermogram having a broad endotherm with onset at about 48° C. In some embodiments, Formula I tromethamine salt hydrate IV has a differential scanning calorimetry thermogram having an endotherm with onset at about 117° C. In some embodiments, Formula I tromethamine salt hydrate IV has a differential scanning calorimetry thermogram having an endotherm with onset at about 148° C.

Formula I Tromethamine Salt Methanol Solvate I

Figure 27:
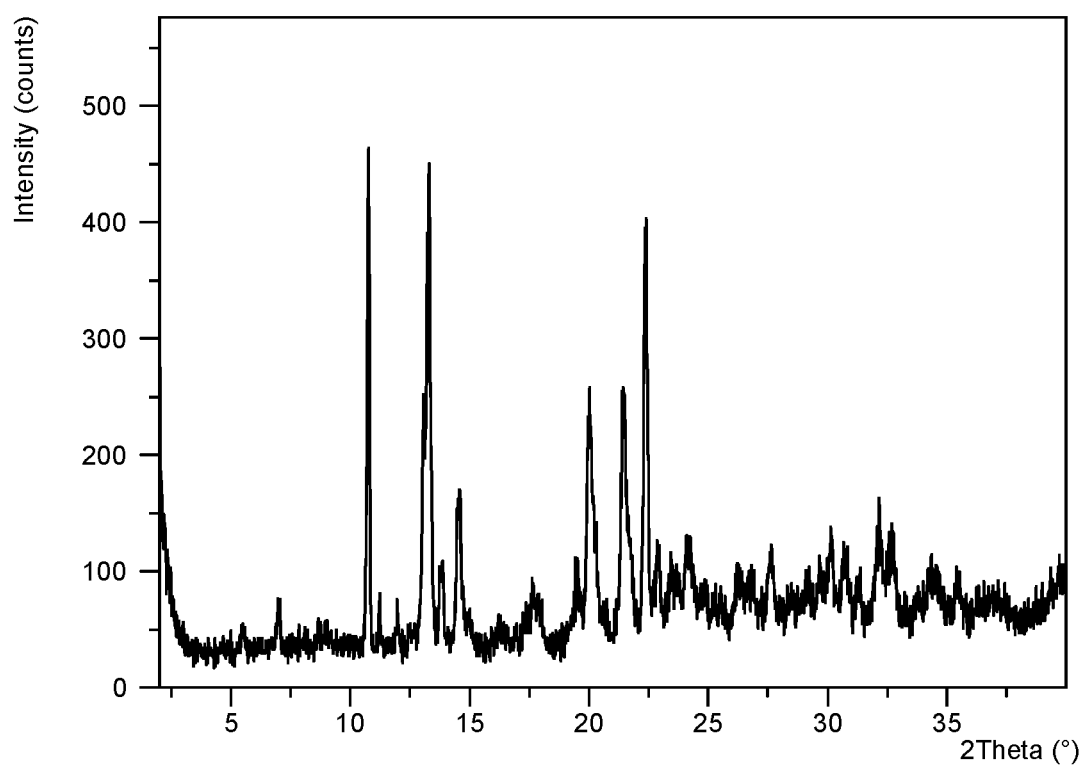
FIG. 27 shows an XRPD pattern of the Formula I tromethamine salt methanol solvate I.

In some embodiments, provided herein is a crystalline compound of Formula I tromethamine salt methanol solvate I (Formula I tromethamine salt methanol solvate I), wherein the crystal structure exhibits an X-ray powder diffraction (XRPD) pattern substantially as shown in FIG. 27.

In some embodiments, crystalline Formula I tromethamine salt methanol solvate I has an XRPD pattern displaying at least two, at least three, at least four, at least five, at least six, at least seven, at least eight, or at least nine of the degree 2θ-reflections with the greatest intensity as the XRPD pattern substantially as shown in FIG. 27.

In certain embodiments, crystalline Formula I tromethamine salt methanol solvate I has an XRPD pattern comprising degree 2θ-reflections (±0.2 degrees 2θ) at 10.8, 13.3, and 22.3 degrees.

In some embodiments, Formula I tromethamine salt methanol solvate I has an XRPD pattern comprising degree 2θ-reflections (±0.2 degrees 2θ) at 10.8, 13.3, and 22.3 degrees and one, two, or three of the degree 2θ-reflections (±0.2 degrees 2θ) at 14.5, 20.0, and 21.4 degrees.

In some embodiments, Formula I tromethamine salt methanol solvate I has an XRPD pattern comprising degree 2θ-reflections (±0.2 degrees 2θ) at 10.8, 13.3, 14.5, 20.0, 21.4, and 22.3 degrees.

Formula I Tromethamine Salt Methanol Solvate II

Figure 28:
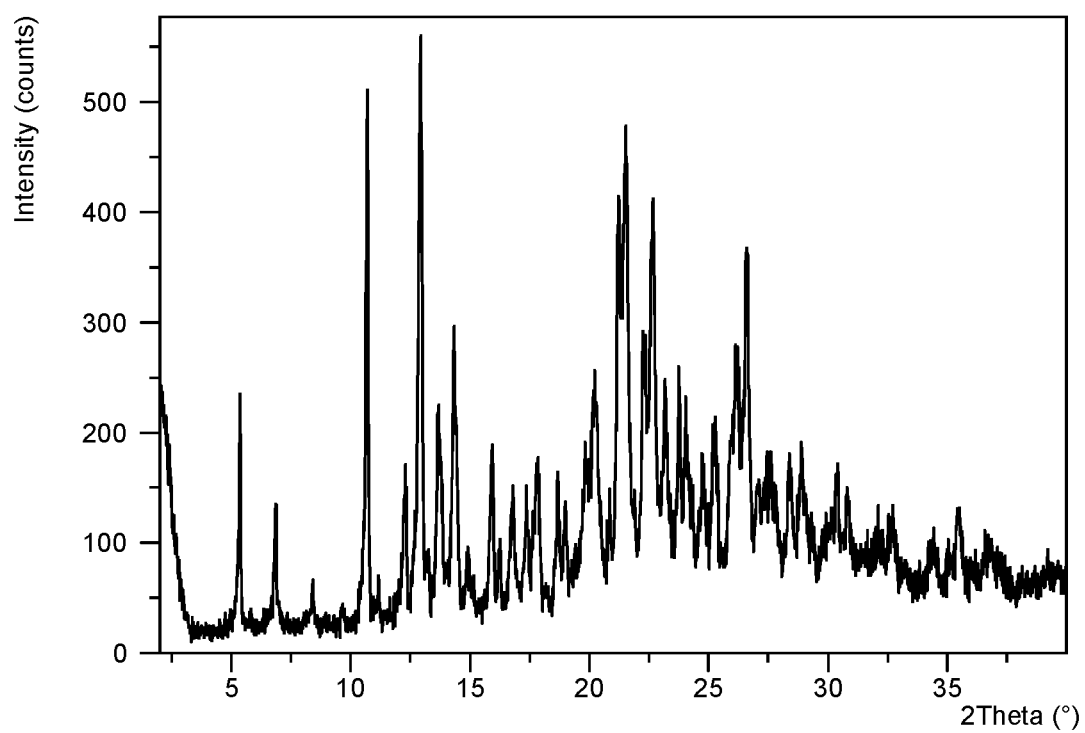
FIG. 28 shows an XRPD pattern of the Formula I tromethamine salt methanol solvate II.

In some embodiments, provided herein is a crystalline compound of Formula I tromethamine salt methanol solvate II (Formula I tromethamine salt methanol solvate II), wherein the crystal structure exhibits an X-ray powder diffraction (XRPD) pattern substantially as shown in FIG. 28.

In some embodiments, crystalline Formula I tromethamine salt methanol solvate II has an XRPD pattern displaying at least two, at least three, at least four, at least five, at least six, at least seven, at least eight, or at least nine of the degree 2θ-reflections with the greatest intensity as the XRPD pattern substantially as shown in FIG. 28.

In certain embodiments, crystalline Formula I tromethamine salt methanol solvate II has an XRPD pattern comprising degree 2θ-reflections (±0.2 degrees 2θ) at 5.4, 12.9, and 22.7 degrees. In some embodiments, Formula I tromethamine salt methanol solvate II has an XRPD pattern comprising degree 2θ-reflections (±0.2 degrees 2θ) at 5.4, 12.9, and 22.7 degrees and one, two, or three of the degree 2θ-reflections (±0.2 degrees 2θ) at 10.7, 14.3, and 15.9 degrees. In some embodiments, Formula I tromethamine salt methanol solvate II has an XRPD pattern comprising degree 2θ-reflections (±0.2 degrees 2θ) at 5.4, 12.9, and 22.7 degrees and one or two of the degree 2θ-reflections (±0.2 degrees 2θ) at 21.2 and 26.6 degrees. In some embodiments, Formula I tromethamine salt methanol solvate II has an XRPD pattern comprising degree 2θ-reflections (±0.2 degrees 2θ) at 5.4, 10.7, 12.9, 14.3, 15.9, 21.2, 22.7, and 26.6 degrees.

Formula I Tromethamine Salt Methanol Solvate III

Figure 29:
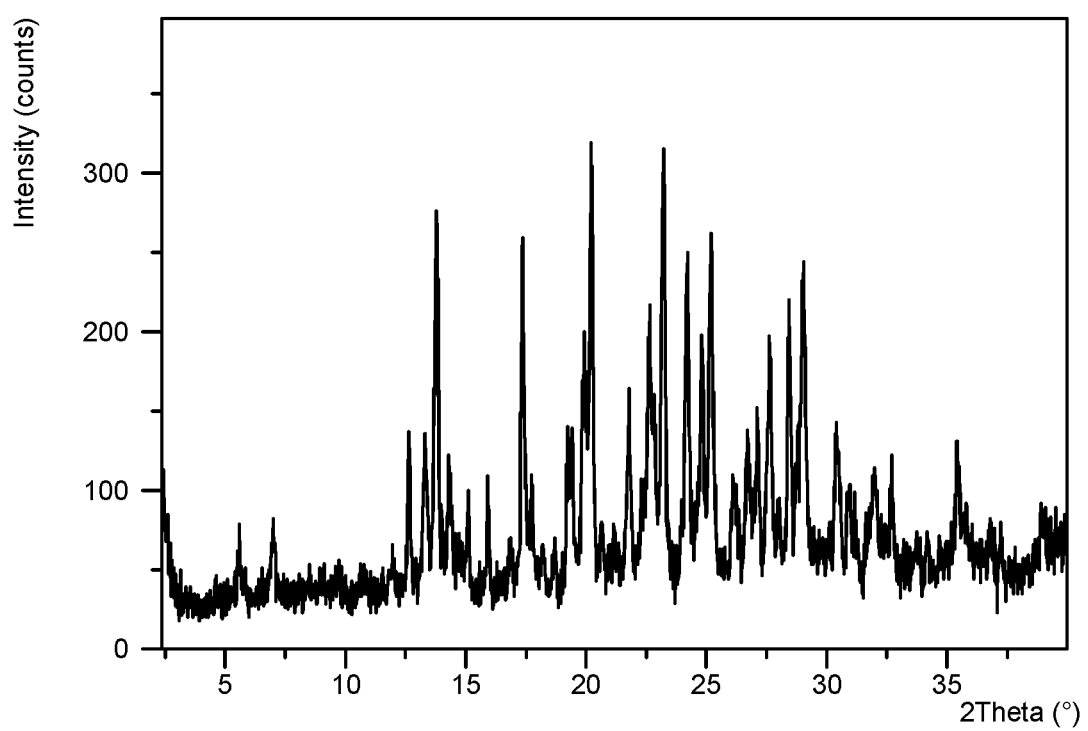
FIG. 29 shows an XRPD pattern of the Formula I tromethamine salt methanol solvate III.
Figure 30:
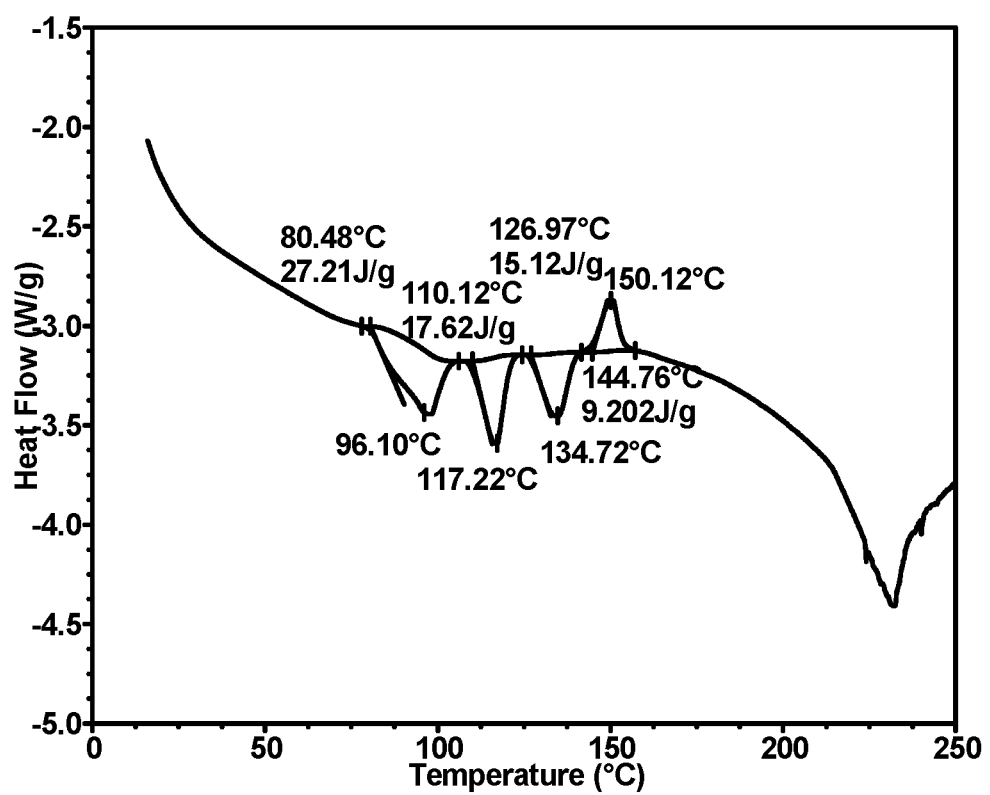
FIG. 30 shows a DSC thermogram of the Formula I tromethamine salt methanol solvate III.
Figure 31:
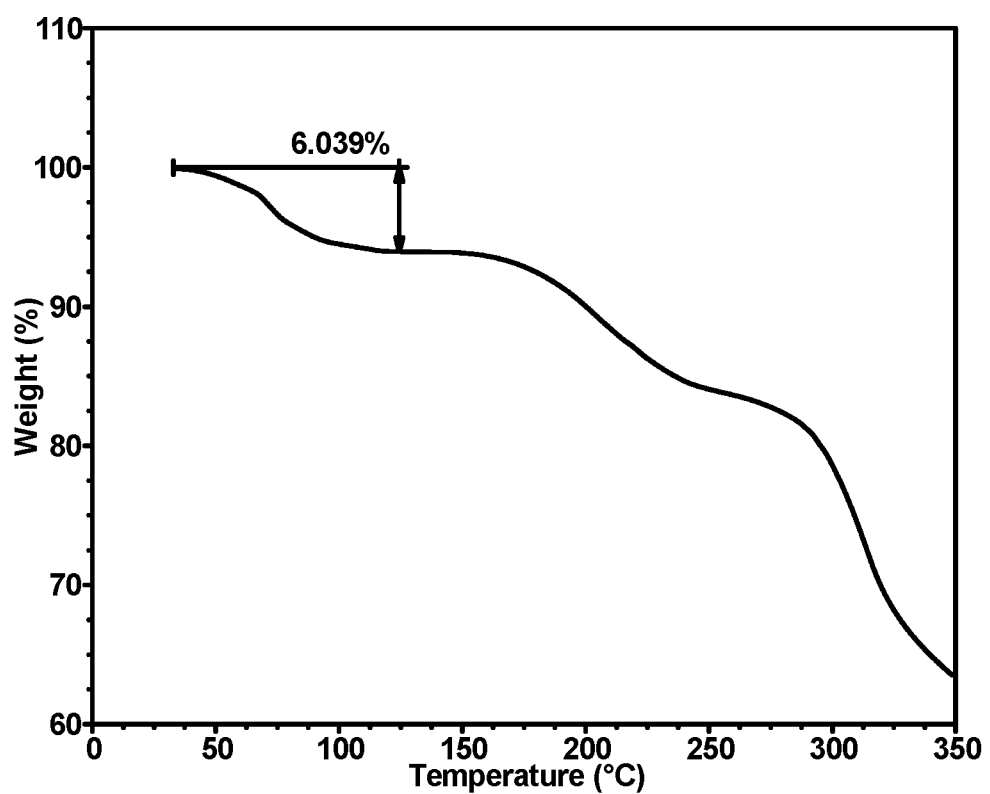
FIG. 31 shows a TGA thermogram of the Formula I tromethamine salt methanol solvate III.

In some embodiments, provided herein is a crystalline compound of Formula I tromethamine salt methanol solvate III (Formula I tromethamine salt methanol solvate III), wherein the crystal structure exhibits an X-ray powder diffraction (XRPD) pattern substantially as shown in FIG. 29. Formula I tromethamine salt methanol solvate III may exhibit a differential scanning calorimetry (DSC) thermogram substantially as shown in FIG. 30. Crystalline Formula I tromethamine salt methanol solvate III may exhibit a thermogravimetric analysis (TGA) thermogram substantially as shown in FIG. 31.

In some embodiments of crystalline Formula I tromethamine salt methanol solvate III at least one, at least two, or all of the following (a)-(c) apply: (a) crystalline Formula I tromethamine salt methanol solvate III has an XRPD pattern substantially as shown in FIG. 29; (b) crystalline Formula I tromethamine salt methanol solvate III has a DSC thermogram substantially as shown in FIG. 30; (c) crystalline Formula I tromethamine salt methanol solvate III has a TGA thermogram substantially as shown in FIG. 31.

In some embodiments, crystalline Formula I tromethamine salt methanol solvate III has at least one, at least two, or at least three of the following properties:
  (a) an XRPD pattern substantially as shown in FIG. 29
  (b) a DSC thermogram substantially as shown in FIG. 30
  (c) a TGA thermogram substantially as shown in FIG. 31.

In some embodiments, crystalline Formula I tromethamine salt methanol solvate III has an XRPD pattern displaying at least two, at least three, at least four, at least five, at least six, at least seven, at least eight, or at least nine of the degree 2θ-reflections with the greatest intensity as the XRPD pattern substantially as shown in FIG. 29.

In certain embodiments, crystalline Formula I tromethamine salt methanol solvate III has an XRPD pattern comprising degree 2θ-reflections (±0.2 degrees 2θ) at 12.6, 13.3, and 13.8 degrees.

In some embodiments, Formula I tromethamine salt methanol solvate III has an XRPD pattern comprising degree 2θ-reflections (±0.2 degrees 2θ) at 12.6, 13.3, and 13.8 degrees and one, two, or three of the degree 2θ-reflections (±0.2 degrees 2θ) at 14.3, 17.4, and 23.2 degrees.

In some embodiments, Formula I tromethamine salt methanol solvate III has an XRPD pattern comprising degree 2θ-reflections (±0.2 degrees 2θ) at 12.6, 13.3, and 13.8 degrees and one, two, or three of the degree 2θ-reflections (±0.2 degrees 2θ) at 20.2, 24.2, 25.2 and 29.1 degrees.

In some embodiments, Formula I tromethamine salt methanol solvate III has an XRPD pattern comprising degree 2θ-reflections (±0.2 degrees 2θ) at 12.6, 13.3, 13.8, 14.3, 17.4, 20.2, 23.2, 24.2, 25.2, and 29.1 degrees.

In some embodiments, Formula I tromethamine salt methanol solvate III has a differential scanning calorimetry thermogram having an endotherm with onset at about 80° C. In some embodiments, Formula I tromethamine salt methanol solvate III has a differential scanning calorimetry thermogram having an endotherm with onset at about 110° C. In some embodiments, Formula I tromethamine salt methanol solvate III has a differential scanning calorimetry thermogram having endotherm with onset at about 127° C. In some embodiments, Formula I tromethamine salt hydrate IV has a differential scanning calorimetry thermogram having an exotherm with onset at about 145° C.

Formula I Tromethamine Salt MTBE Solvate

Figure 32:
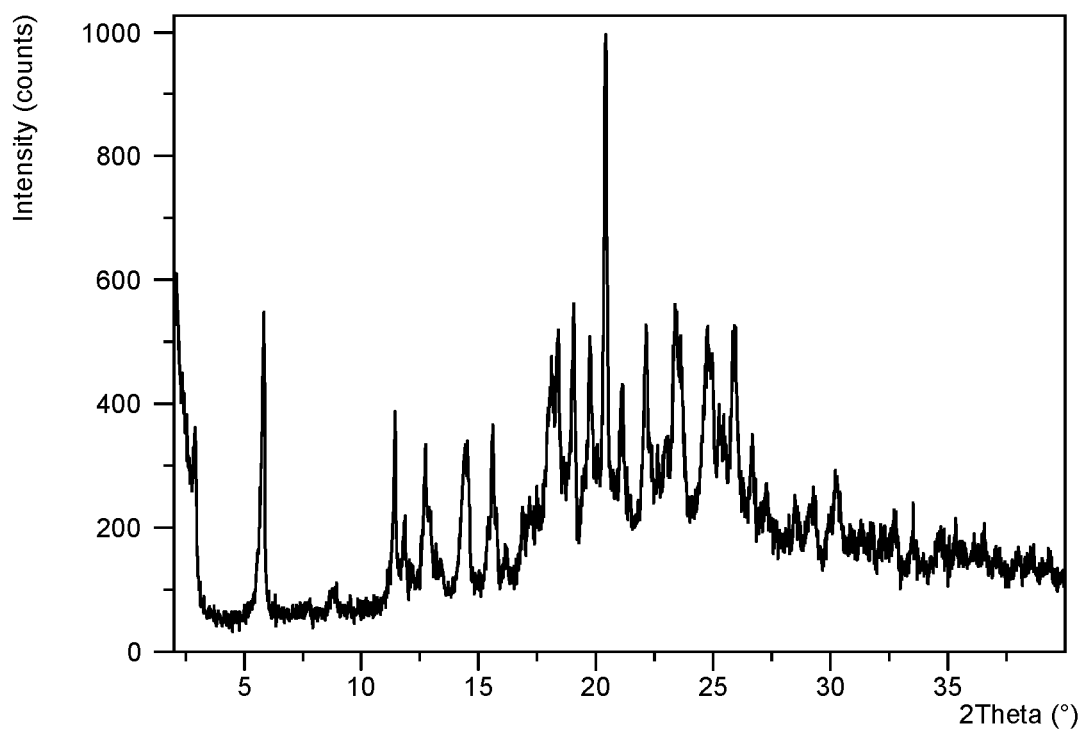
FIG. 32 shows an XRPD pattern of the Formula I tromethamine salt MTBE solvate.
Figure 33:
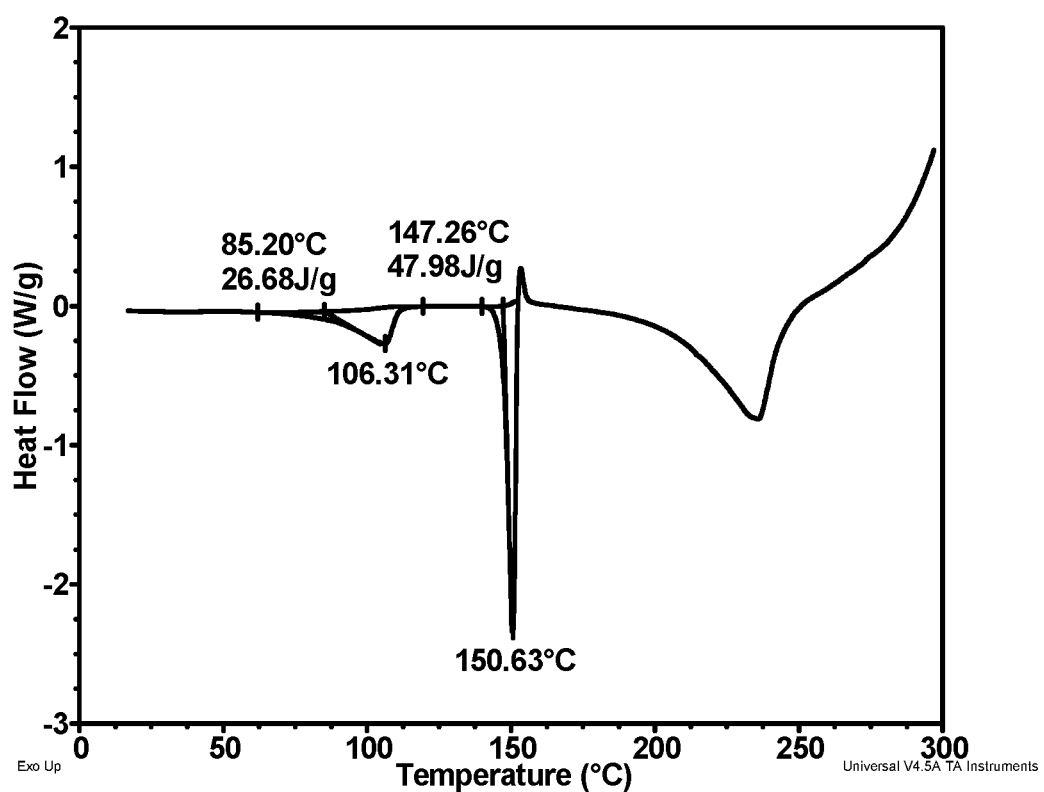
FIG. 33 shows a DSC thermogram of the Formula I tromethamine salt MTBE solvate.
Figure 34:
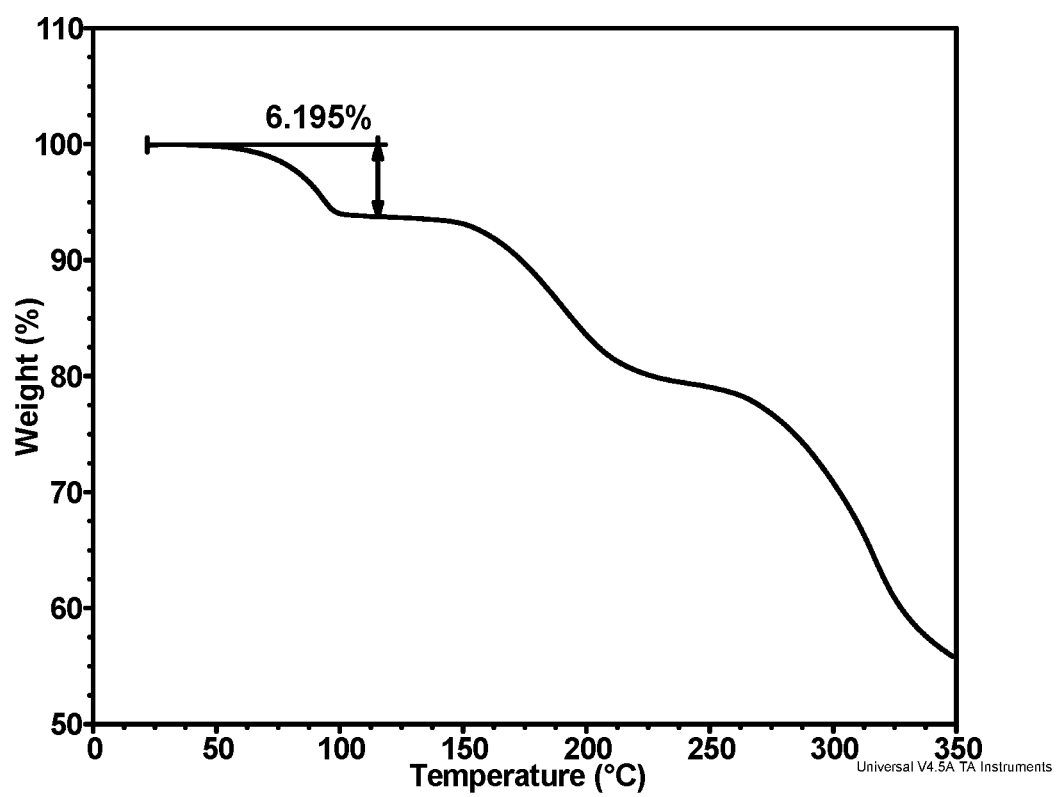
FIG. 34 shows a TGA thermogram of the Formula I tromethamine salt MTBE solvate.

In some embodiments, provided herein is a crystalline compound of Formula I tromethamine salt methyl tertiary-butyl ether (MTBE) solvate (Formula I tromethamine salt MTBE solvate), wherein the crystal structure exhibits an X-ray powder diffraction (XRPD) pattern substantially as shown in FIG. 32. Formula I tromethamine salt MTBE solvate may exhibit a differential scanning calorimetry (DSC) thermogram substantially as shown in FIG. 33. Crystalline Formula I tromethamine salt MTBE solvate may exhibit a thermogravimetric analysis (TGA) thermogram substantially as shown in FIG. 34.

In some embodiments of crystalline Formula I tromethamine salt MTBE solvate, at least one, at least two, or all of the following (a)-(c) apply: (a) crystalline Formula I tromethamine salt MTBE solvate has an XRPD pattern substantially as shown in FIG. 32; (b) crystalline Formula I tromethamine salt MTBE solvate has a DSC thermogram substantially as shown in FIG. 33; (c) crystalline Formula I tromethamine salt MTBE solvate has a TGA thermogram substantially as shown in FIG. 34.

In some embodiments, crystalline Formula I tromethamine salt MTBE solvate has at least one, at least two, or at least three of the following properties:
 (a) an XRPD pattern substantially as shown in FIG. 32
 (b) a DSC thermogram substantially as shown in FIG. 33
 (c) a TGA thermogram substantially as shown in FIG. 34.

In some embodiments, crystalline Formula I tromethamine salt MTBE solvate has an XRPD pattern displaying at least two, at least three, at least four, at least five, at least six, at least seven, at least eight, or at least nine of the degree 2θ-reflections with the greatest intensity as the XRPD pattern substantially as shown in FIG. 32.

In certain embodiments, crystalline Formula I tromethamine salt MTBE solvate has an XRPD pattern comprising degree 2θ-reflections (±0.2 degrees 2θ) at 5.8, 11.4, 15.6, and 20.4 degrees.

In some embodiments, Formula I tromethamine salt MTBE solvate has an XRPD pattern comprising degree 2θ-reflections (±0.2 degrees 2θ) at 5.8, 11.4, 15.6, and 20.4 degrees and one, two, three, or four of the degree 2θ-reflections (±0.2 degrees 2θ) at 14.5, 18.4, 23.4, and 25.9 degrees.

In some embodiments, Formula I tromethamine salt MTBE solvate has an XRPD pattern comprising degree 2θ-reflections (±0.2 degrees 2θ) at 5.8, 11.4, 15.6, and 20.4 degrees and one, two, or three of the degree 2θ-reflections (±0.2 degrees 2θ) at 12.7, 19.0, and 24.7 degrees.

In some embodiments, Formula I tromethamine salt MTBE solvate has an XRPD pattern comprising degree 2θ-reflections (±0.2 degrees 2θ) at 5.8, 11.4, 12.7, 14.5, 15.6, 18.4, 19.0, 20.4, 23.4, 24.7, and 25.9 degrees.

In some embodiments, Formula I tromethamine salt MTBE solvate has a differential scanning calorimetry thermogram having an endotherm with onset at about 85° C. In some embodiments, Formula I tromethamine salt MTBE solvate has a differential scanning calorimetry thermogram having endotherm with onset at about 147° C.

Formula I Tromethamine Amorphous

Figure 35:
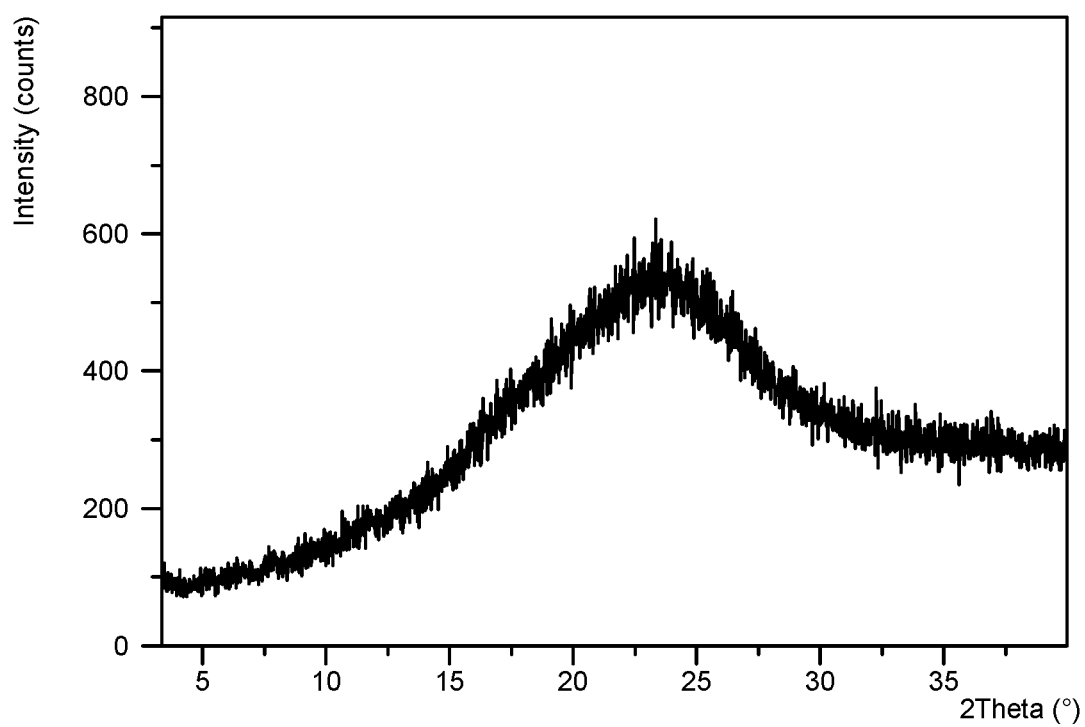
FIG. 35 shows an XRPD pattern of the Formula I tromethamine salt amorphous form.

In some embodiments, provided herein is a compound of Formula I tromethamine salt amorphous form (Formula I tromethamine amorphous form), wherein the solid form exhibits an X-ray powder diffraction (XRPD) pattern substantially as shown in FIG. 35.

Formula I Tromethamine Salt Ethanol Solvate

Figure 36:
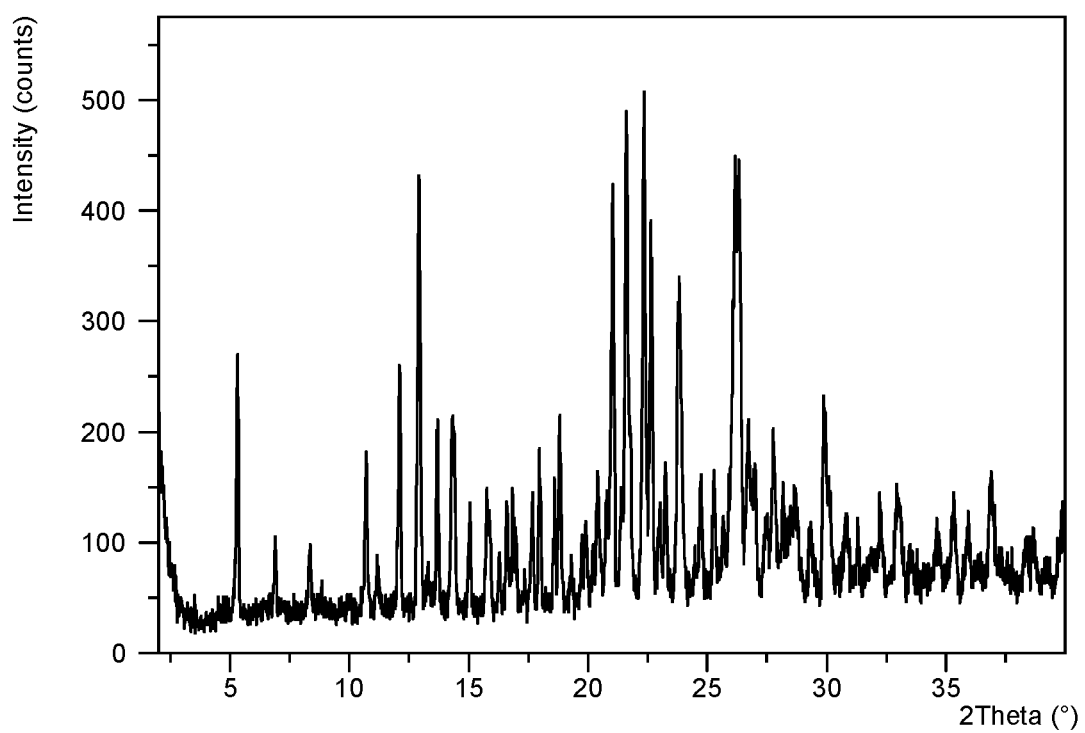
FIG. 36 shows an XRPD pattern of the Formula I tromethamine salt ethanol solvate.

In some embodiments, provided herein is a crystalline compound of Formula I tromethamine salt ethanol solvate (Formula I tromethamine salt ethanol solvate), wherein the crystal structure exhibits an X-ray powder diffraction (XRPD) pattern substantially as shown in FIG. 36.

In some embodiments, crystalline Formula I tromethamine salt ethanol solvate form has an XRPD pattern displaying at least two, at least three, at least four, at least five, at least six, at least seven, at least eight, or at least nine of the degree 2θ-reflections with the greatest intensity as the XRPD pattern substantially as shown in FIG. 36. In some embodiments, tromethamine salt ethanol solvate has four or more of the following characteristic peaks: 5.3, 10.7, 12.1, 12.9, 21.0, 21.6, 22.3, 22.6, 23.8, and 26.3° 2θ.

Formula I p-Toluenesulfonic Acid (p-TSA) Salt Form I

Figure 37:
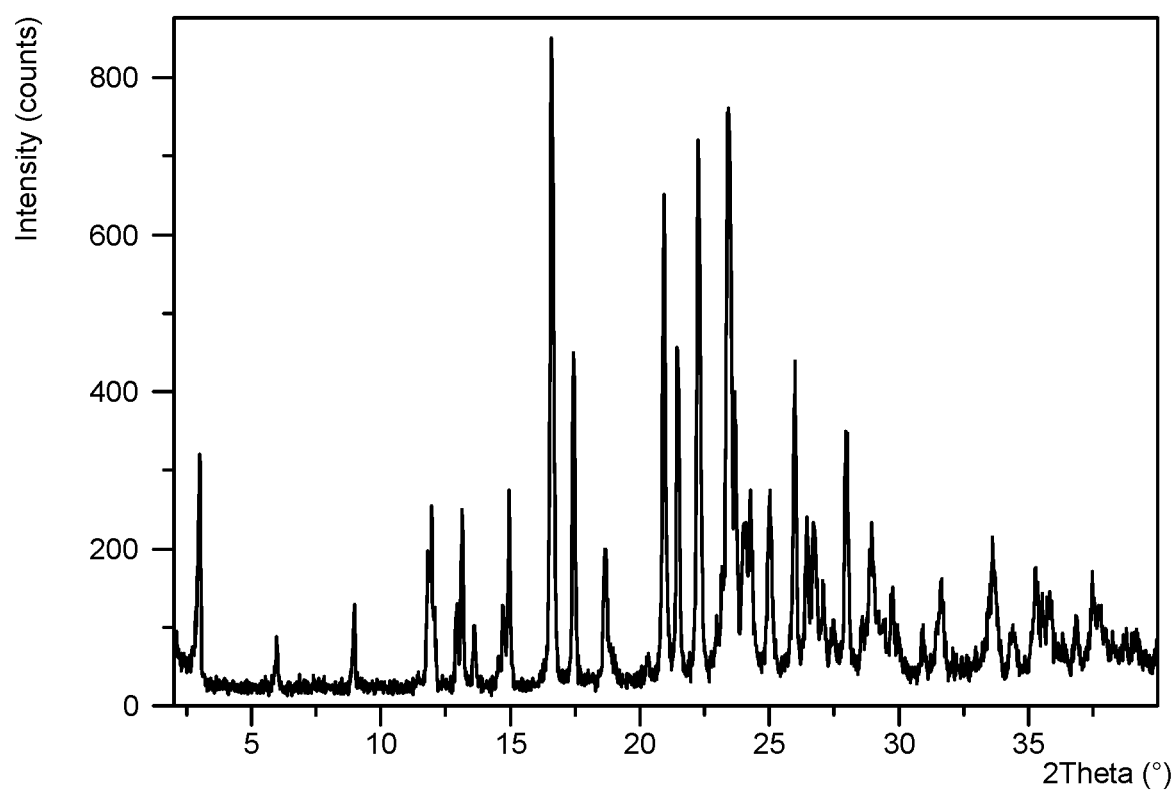
FIG. 37 shows an XRPD pattern of the Formula I p-toluenesulfonic acid salt Form I.
Figure 38:
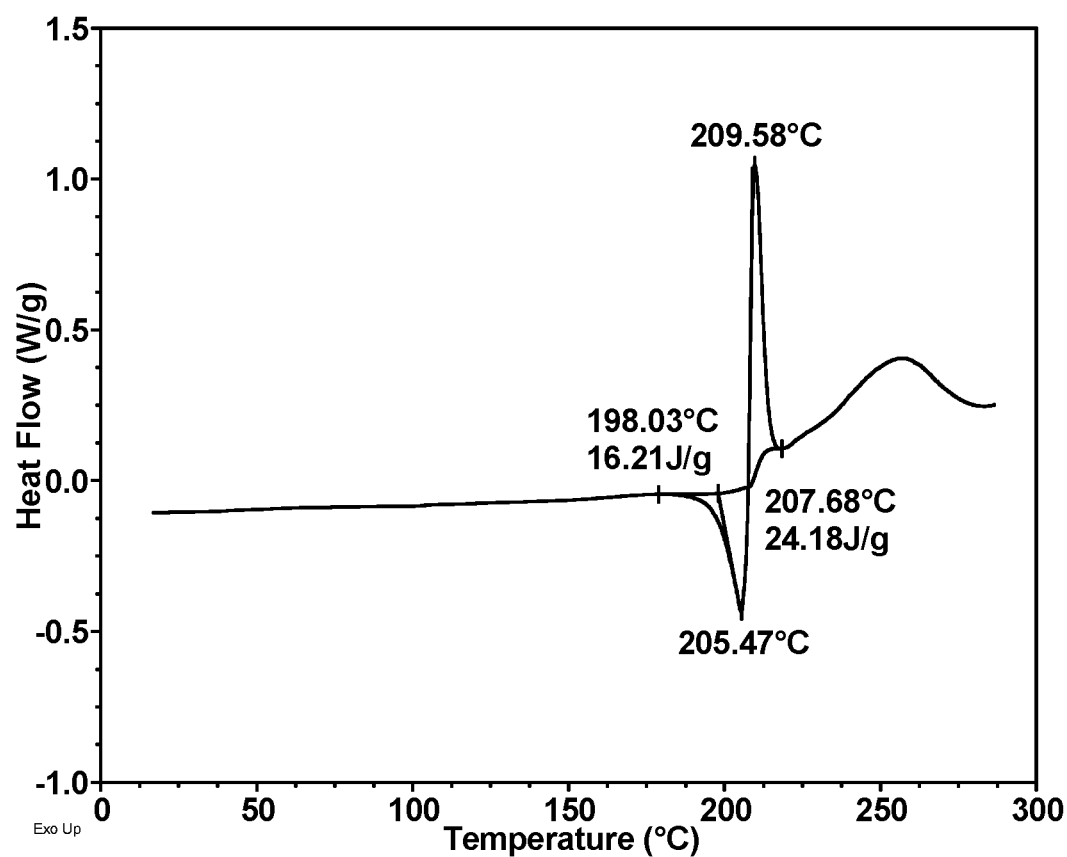
FIG. 38 shows a DSC thermogram of the Formula I p-toluenesulfonic acid salt Form I.
Figure 39:
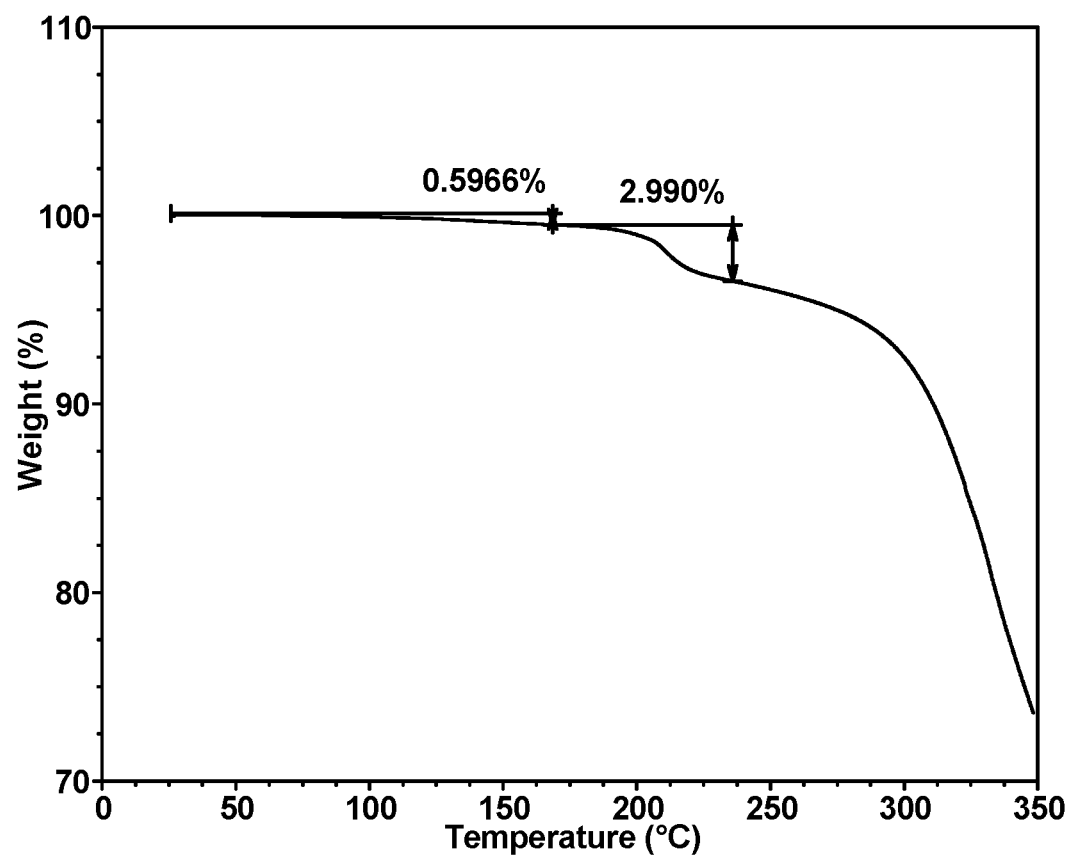
FIG. 39 shows a TGA thermogram of the Formula I p-toluenesulfonic acid salt Form I.

In some embodiments, provided herein is a crystalline compound of Formula I p-TSA salt Form I (Formula I p-TSA salt Form I), wherein the crystal structure exhibits an X-ray powder diffraction (XRPD) pattern substantially as shown in FIG. 37. Formula I p-TSA salt Form I may exhibit a differential scanning calorimetry (DSC) thermogram substantially as shown in FIG. 38. Crystalline Formula I p-TSA salt Form I may exhibit a thermogravimetric analysis (TGA) thermogram substantially as shown in FIG. 39.

In some embodiments of crystalline Formula I p-TSA salt Form I, at least one, at least two, or all of the following (a)-(c) apply: (a) crystalline Formula Ip-TSA salt Form I has an XRPD pattern substantially as shown in FIG. 37; (b) crystalline Formula I p-TSA salt Form I has a DSC thermogram substantially as shown in FIG. 38; (c) crystalline Formula I p-TSA salt Form I has a TGA thermogram substantially as shown in FIG. 39.

In some embodiments, crystalline Formula Ip-TSA salt Form I has at least one, at least two, or at least three of the following properties:
 (a) an XRPD pattern substantially as shown in FIG. 37
 (b) a DSC thermogram substantially as shown in FIG. 38
 (c) a TGA thermogram substantially as shown in FIG. 39.

In some embodiments, crystalline Formula Ip-TSA salt Form I has an XRPD pattern displaying at least two, at least three, at least four, at least five, at least six, at least seven, at least eight, or at least nine of the degree 2θ-reflections with the greatest intensity as the XRPD pattern substantially as shown in FIG. 37.

In certain embodiments, crystalline Formula I p-TSA salt Form I has an XRPD pattern comprising degree 2θ-reflections (±0.2 degrees 2θ) at 16.6, 20.9, 22.3, and 23.4 degrees.

In some embodiments, Formula I p-TSA salt Form I has an XRPD pattern comprising degree 2θ-reflections (±0.2 degrees 2θ) at 16.6, 20.9, 22.3, and 23.4 degrees and one, two, or three of the degree 2θ-reflections (±0.2 degrees 2θ) at 3.0, 13.1, and 21.5 degrees.

In some embodiments, Formula I p-TSA salt Form I has an XRPD pattern comprising degree 2θ-reflections (±0.2 degrees 2θ) at 16.6, 20.9, 22.3, and 23.4 degrees and one, two, or three of the degree 2θ-reflections (±0.2 degrees 2θ) at 9.0, 15.0, 17.5, and 26 degrees.

In some embodiments, Formula I p-TSA salt Form I has an XRPD pattern comprising degree 2θ-reflections (±0.2 degrees 2θ) at 16.6, 20.9, 22.3, 23.4, 3.0, 13.1, 21.5, 9.0, 15.0, 17.5, and 26 degrees.

In some embodiments, Formula I p-TSA salt Form I has a differential scanning calorimetry thermogram having an endotherm with onset at about 198° C. In some embodiments, Formula Ip-TSA salt Form I has a differential scanning calorimetry thermogram having an exotherm with onset at about 208° C.

Formula I p-Toluenesulfonic Acid (p-TSA) Salt Form II

Figure 40:
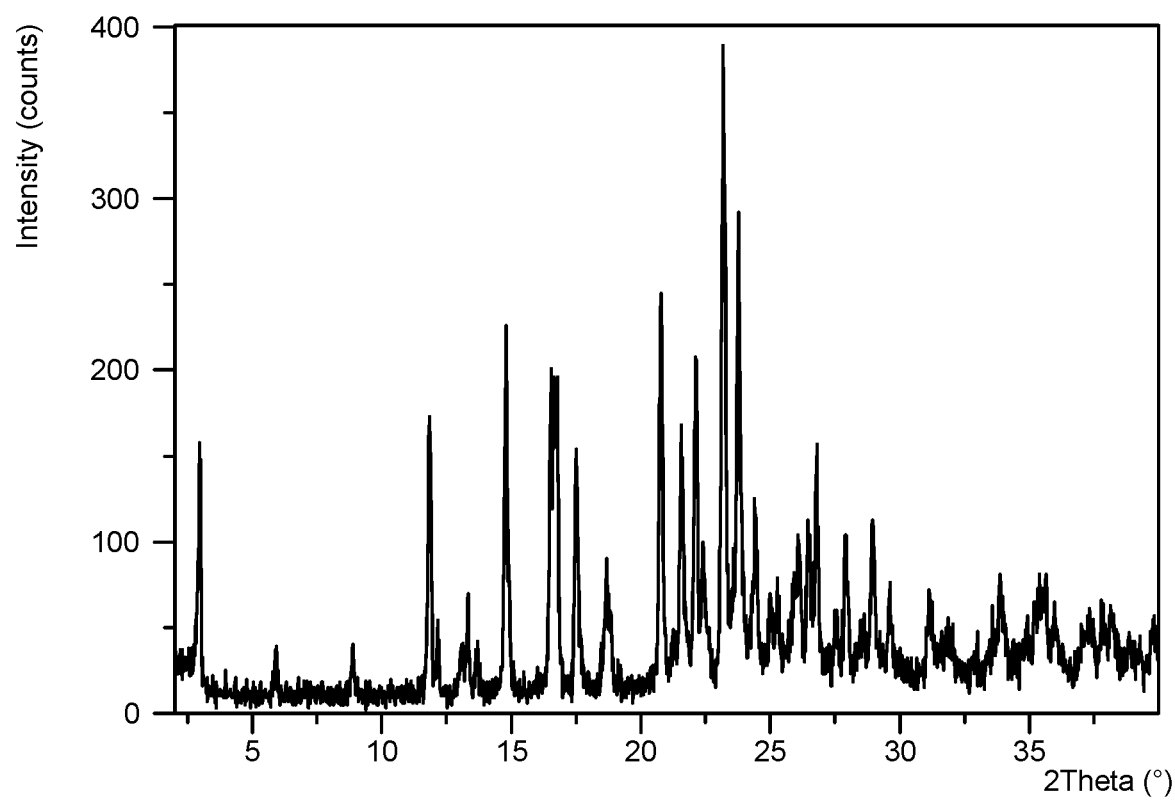
FIG. 40 shows an XRPD pattern of the Formula I p-toluenesulfonic acid salt Form II.
Figure 41:
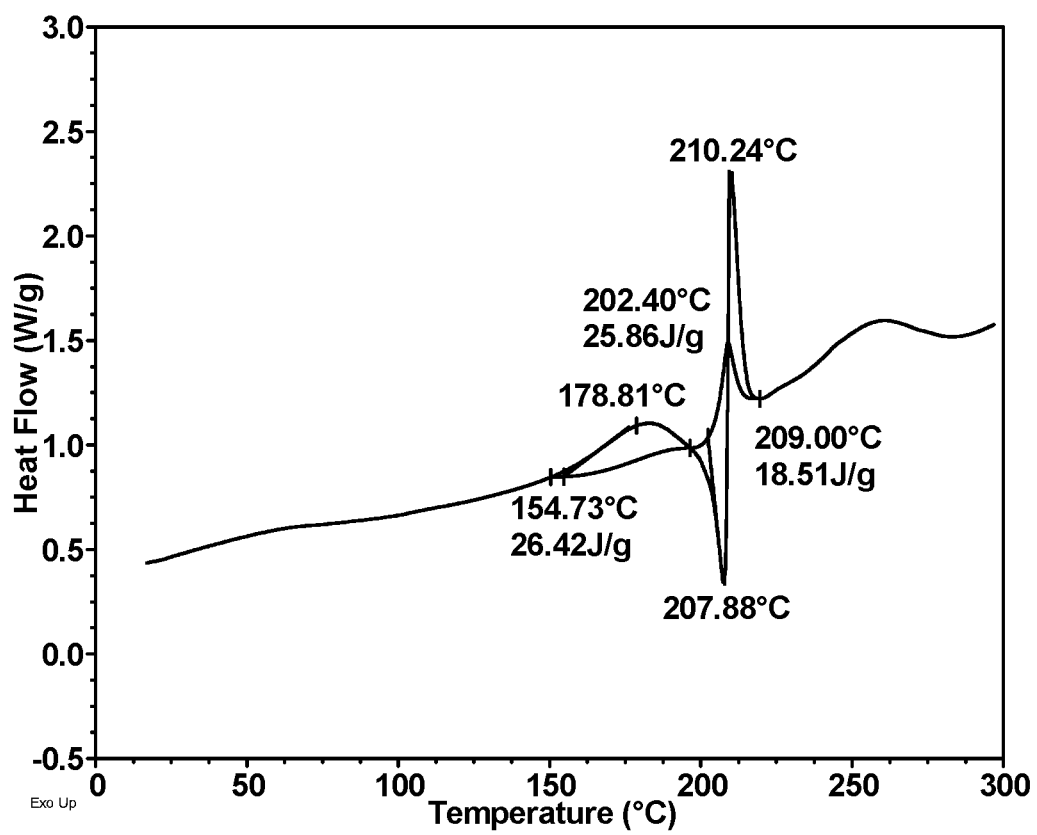
FIG. 41 shows a DSC thermogram of the Formula I p-toluenesulfonic acid salt Form II.
Figure 42:
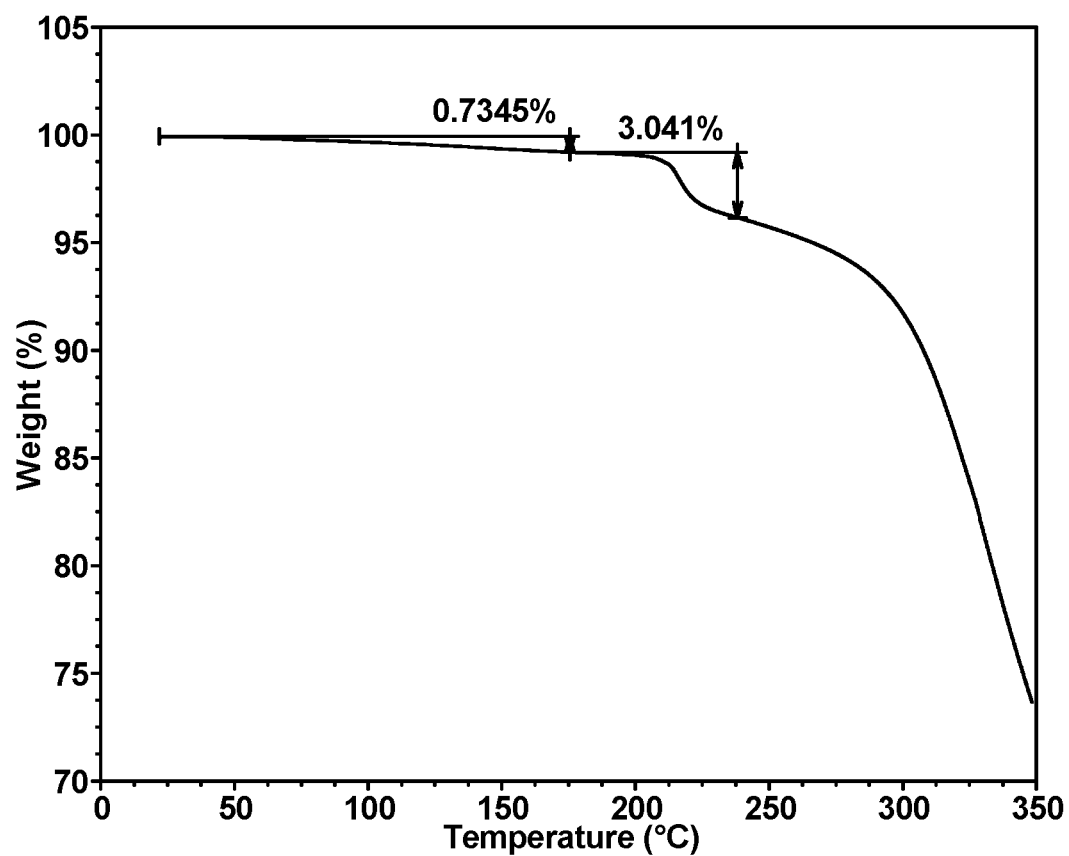
FIG. 42 shows a TGA thermogram of the Formula I p-toluenesulfonic acid salt Form II.

In some embodiments, provided herein is a crystalline compound of Formula I p-TSA salt Form II (Formula I p-TSA salt Form II), wherein the crystal structure exhibits an X-ray powder diffraction (XRPD) pattern substantially as shown in FIG. 40. Formula I p-TSA salt Form II may exhibit a differential scanning calorimetry (DSC) thermogram substantially as shown in FIG. 41. Crystalline Formula I p-TSA salt Form II may exhibit a thermogravimetric analysis (TGA) thermogram substantially as shown in FIG. 42.

In some embodiments of crystalline Formula I p-TSA salt Form II, at least one, at least two, or all of the following (a)-(c) apply: (a) crystalline Formula Ip-TSA salt Form II has an XRPD pattern substantially as shown in FIG. 40; (b) crystalline Formula I p-TSA salt Form II has a DSC thermogram substantially as shown in FIG. 41; (c) crystalline Formula I p-TSA salt Form II has a TGA thermogram substantially as shown in FIG. 42.

In some embodiments, crystalline Formula Ip-TSA salt Form II has at least one, at least two, or at least three of the following properties:
 (a) an XRPD pattern substantially as shown in FIG. 40
 (b) a DSC thermogram substantially as shown in FIG. 41
 (c) a TGA thermogram substantially as shown in FIG. 42.

In some embodiments, crystalline Formula Ip-TSA salt Form II has an XRPD pattern displaying at least two, at least three, at least four, at least five, at least six, at least seven, at least eight, or at least nine of the degree 2θ-reflections with the greatest intensity as the XRPD pattern substantially as shown in FIG. 40.

In certain embodiments, crystalline Formula I p-TSA salt Form II has an XRPD pattern comprising degree 2θ-reflections (±0.2 degrees 2θ) at 14.8, 20.8, 23.2, and 23.8 degrees.

In some embodiments, Formula I p-TSA salt Form II has an XRPD pattern comprising degree 2θ-reflections (±0.2 degrees 2θ) at 14.8, 20.8, 23.2, and 23.8 degrees and one, two, or three of the degree 2θ-reflections (±0.2 degrees 2θ) at 21.6, 22.1, and 24.4 degrees.

In some embodiments, Formula I p-TSA salt Form II has an XRPD pattern comprising degree 2θ-reflections (±0.2 degrees 2θ) at 14.8, 20.8, 23.2, and 23.8 degrees and one, two, or three of the degree 2θ-reflections (±0.2 degrees 2θ) at 3.0, 11.8, and 16.8 degrees.

In some embodiments, Formula I p-TSA salt Form I has an XRPD pattern comprising degree 2θ-reflections (±0.2 degrees 2θ) at 14.8, 20.8, 23.2, 23.8, 21.6, 22.1, 24.4, 3.0, 11.8, and 16.8 degrees.

In some embodiments, Formula I p-TSA salt Form II has a differential scanning calorimetry thermogram having an endotherm with onset at about 202° C. In some embodiments, Formula Ip-TSA salt Form II has a differential scanning calorimetry thermogram having an exotherm with onset at about 155° C. In some embodiments, Formula I p-TSA salt Form II has a differential scanning calorimetry thermogram having an exotherm onset at about 209° C.

Formula I p-Toluenesulfonic Acid (p-TSA) Salt Form III

Figure 43:
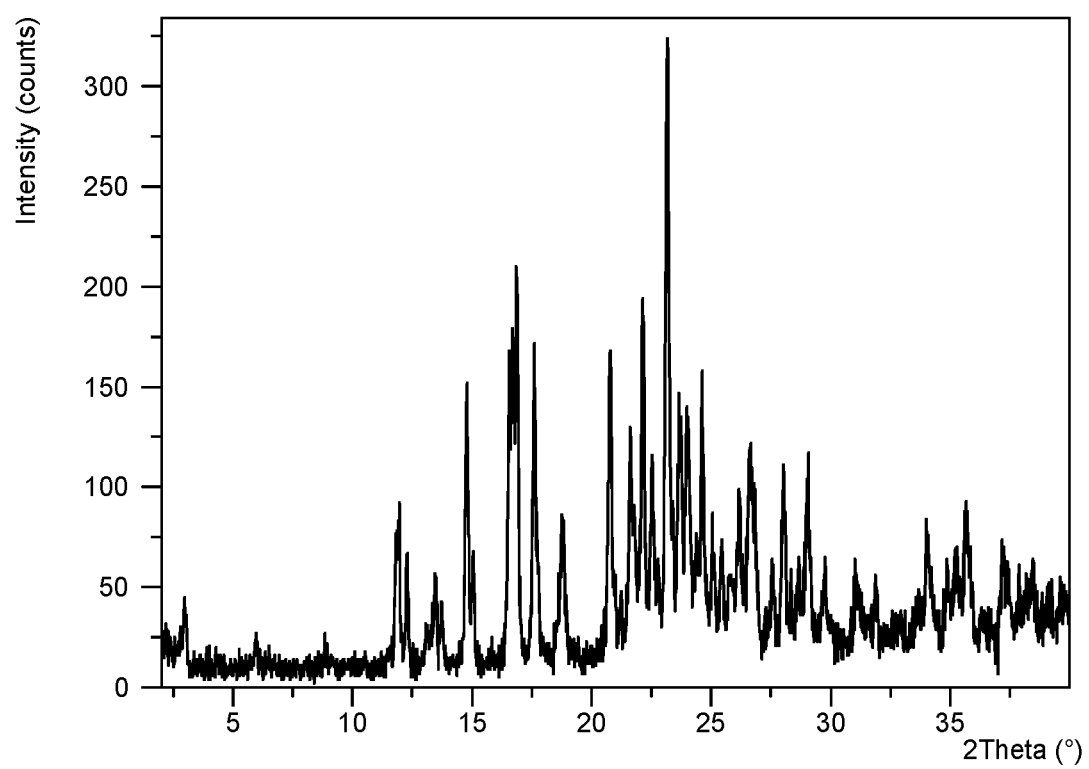
FIG. 43 shows an XRPD pattern of the Formula I p-toluenesulfonic acid salt Form III.
Figure 44:
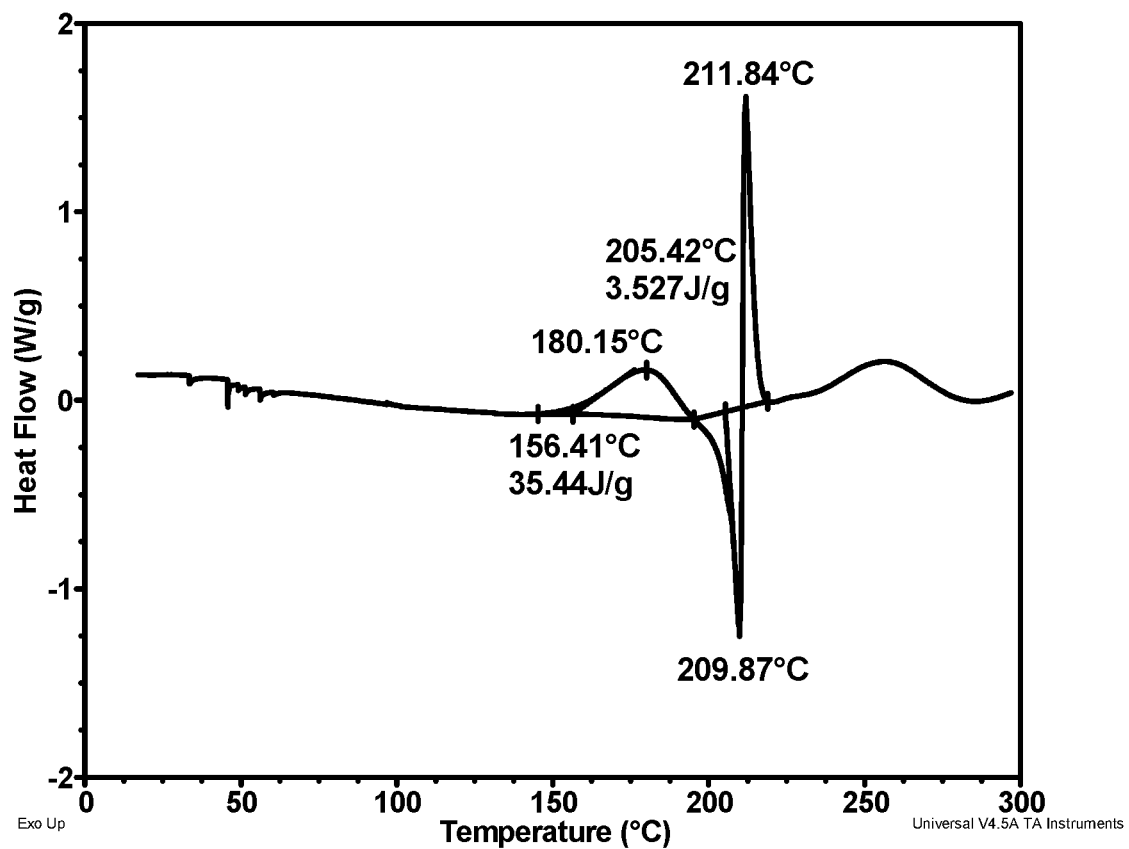
FIG. 44 shows a DSC thermogram of the Formula I p-toluenesulfonic acid salt Form III.
Figure 45:
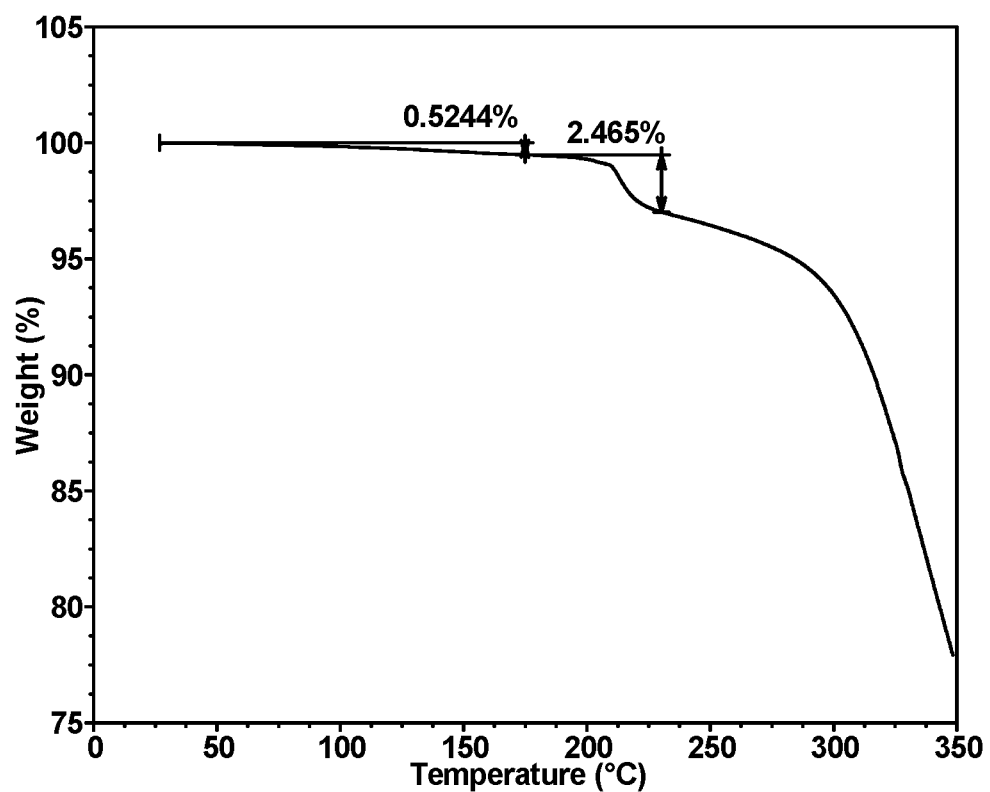
FIG. 45 shows a TGA thermogram of the Formula I p-toluenesulfonic acid salt Form III.

In some embodiments, provided herein is a crystalline compound of Formula I p-TSA salt Form III (Formula I p-TSA salt Form I), wherein the crystal structure exhibits an X-ray powder diffraction (XRPD) pattern substantially as shown in FIG. 43. Formula I p-TSA salt Form III may exhibit a differential scanning calorimetry (DSC) thermogram substantially as shown in FIG. 44. Crystalline Formula I p-TSA salt Form III may exhibit a thermogravimetric analysis (TGA) thermogram substantially as shown in FIG. 45.

In some embodiments of crystalline Formula I p-TSA salt Form III, at least one, at least two, or all of the following (a)-(c) apply: (a) crystalline Formula I p-TSA salt Form III has an XRPD pattern substantially as shown in FIG. 43; (b) crystalline Formula I p-TSA salt Form III has a DSC thermogram substantially as shown in FIG. 44; (c) crystalline Formula I p-TSA salt Form III has a TGA thermogram substantially as shown in FIG. 45.

In some embodiments, crystalline Formula Ip-TSA salt Form III has at least one, at least two, or at least three of the following properties:
 (a) an XRPD pattern substantially as shown in FIG. 43
 (b) a DSC thermogram substantially as shown in FIG. 44
 (c) a TGA thermogram substantially as shown in FIG. 45.

In some embodiments, crystalline Formula Ip-TSA salt Form III has an XRPD pattern displaying at least two, at least three, at least four, at least five, at least six, at least seven, at least eight, or at least nine of the degree 2θ-reflections with the greatest intensity as the XRPD pattern substantially as shown in FIG. 43.

In certain embodiments, crystalline Formula I p-TSA salt Form III has an XRPD pattern comprising degree 2θ-reflections (±0.2 degrees 2θ) at 11.9, 14.8, 16.9, and 23.2 degrees.

In some embodiments, Formula I p-TSA salt Form III has an XRPD pattern comprising degree 2θ-reflections (±0.2 degrees 2θ) at 11.9, 14.8, 16.9, and 23.2 degrees and one, two, or three of the degree 2θ-reflections (±0.2 degrees 2θ) at 17.6, 20.8, 22.1, and 24.6 degrees.

In some embodiments, Formula I p-TSA salt Form III has an XRPD pattern comprising degree 2θ-reflections (±0.2 degrees 2θ) at 11.9, 14.8, 16.9, and 23.2 degrees and one, two, or three of the degree 2θ-reflections (±0.2 degrees 2θ) at 12.3, 18.8, and 26.6 degrees.

In some embodiments, Formula I p-TSA salt Form I has an XRPD pattern comprising degree 2θ-reflections (±0.2 degrees 2θ) at 11.9, 14.8, 16.9, 23.2, 17.6, 20.8, 22.1, 24.6, 12.3, 18.8, and 26.6 degrees.

In some embodiments, Formula I p-TSA salt Form III has a differential scanning calorimetry thermogram having an exotherm with onset at about 156° C. In some embodiments, Formula I p-TSA salt Form III has a differential scanning calorimetry thermogram having endotherm with onset at about 205° C.

Formula I p-Toluenesulfonic Acid (p-TSA) Salt Hydrate

Figure 46:
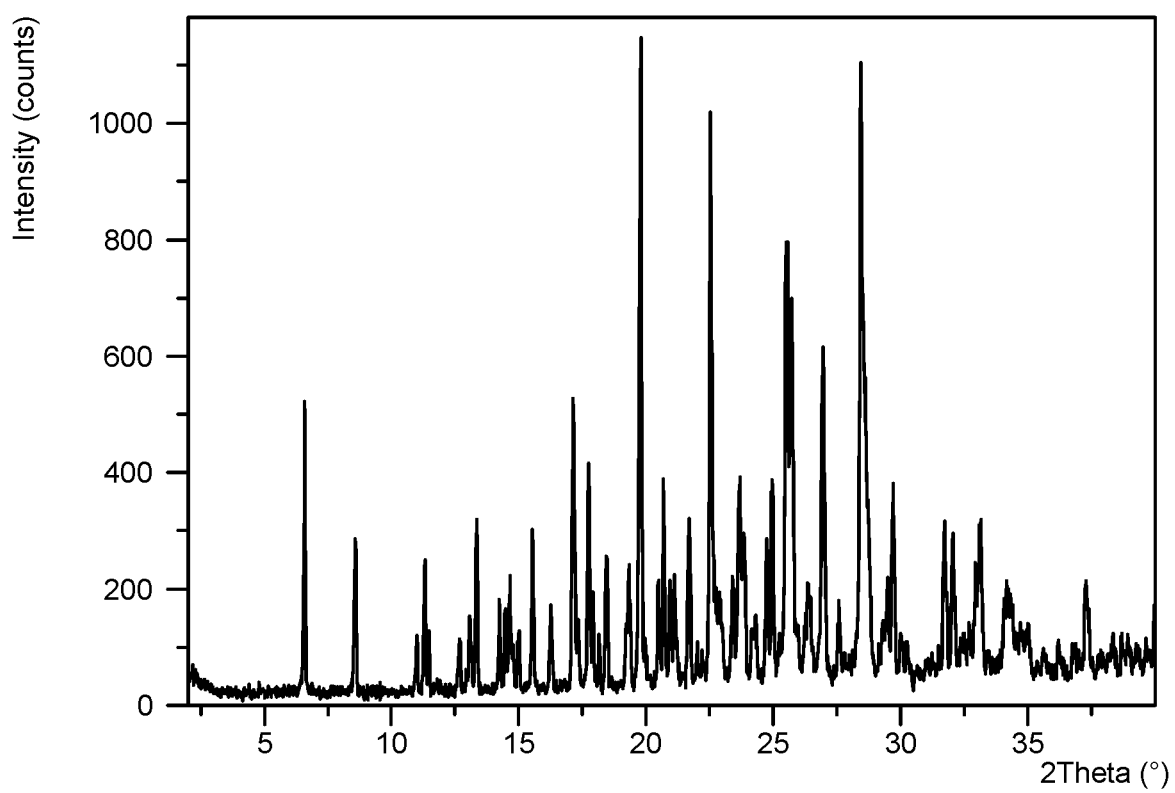
FIG. 46 shows an XRPD pattern of the Formula I p-toluenesulfonic acid salt hydrate.
Figure 47:
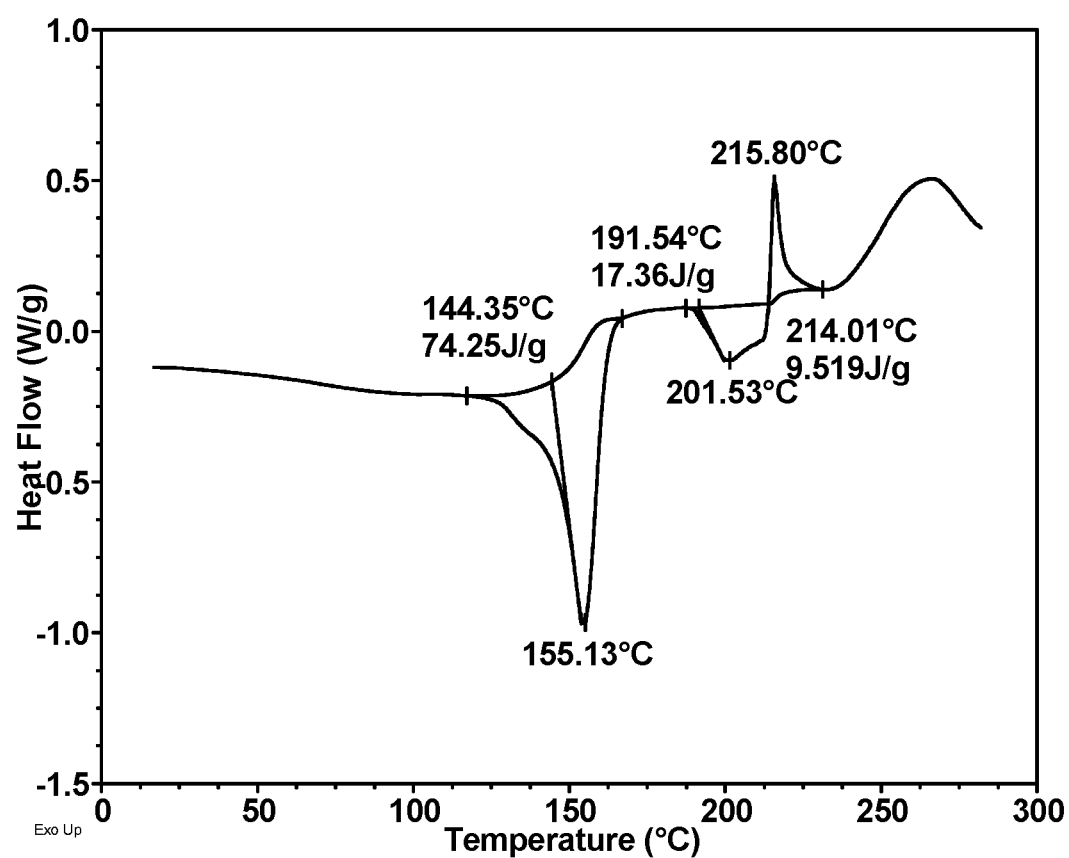
FIG. 47 shows a DSC thermogram of the Formula I p-toluenesulfonic acid salt hydrate.

In some embodiments, provided herein is a crystalline compound of Formula I p-TSA salt Form I (Formula I p-TSA salt hydrate), wherein the crystal structure exhibits an X-ray powder diffraction (XRPD) pattern substantially as shown in FIG. 46. Formula I p-TSA salt hydrate may exhibit a differential scanning calorimetry (DSC) thermogram substantially as shown in FIG. 47. Crystalline Formula I p-TSA salt hydrate may exhibit a thermogravimetric analysis (TGA) thermogram substantially as shown in FIG. 48.

In some embodiments of crystalline Formula I p-TSA salt hydrate, at least one, at least two, or all of the following (a)-(c) apply: (a) crystalline Formula Ip-TSA salt hydrate has an XRPD pattern substantially as shown in FIG. 46; (b) crystalline Formula I p-TSA salt hydrate has a DSC thermogram substantially as shown in FIG. 47; (c) crystalline Formula Ip-TSA salt hydrate has a TGA thermogram substantially as shown in FIG. 48.

Figure 48:
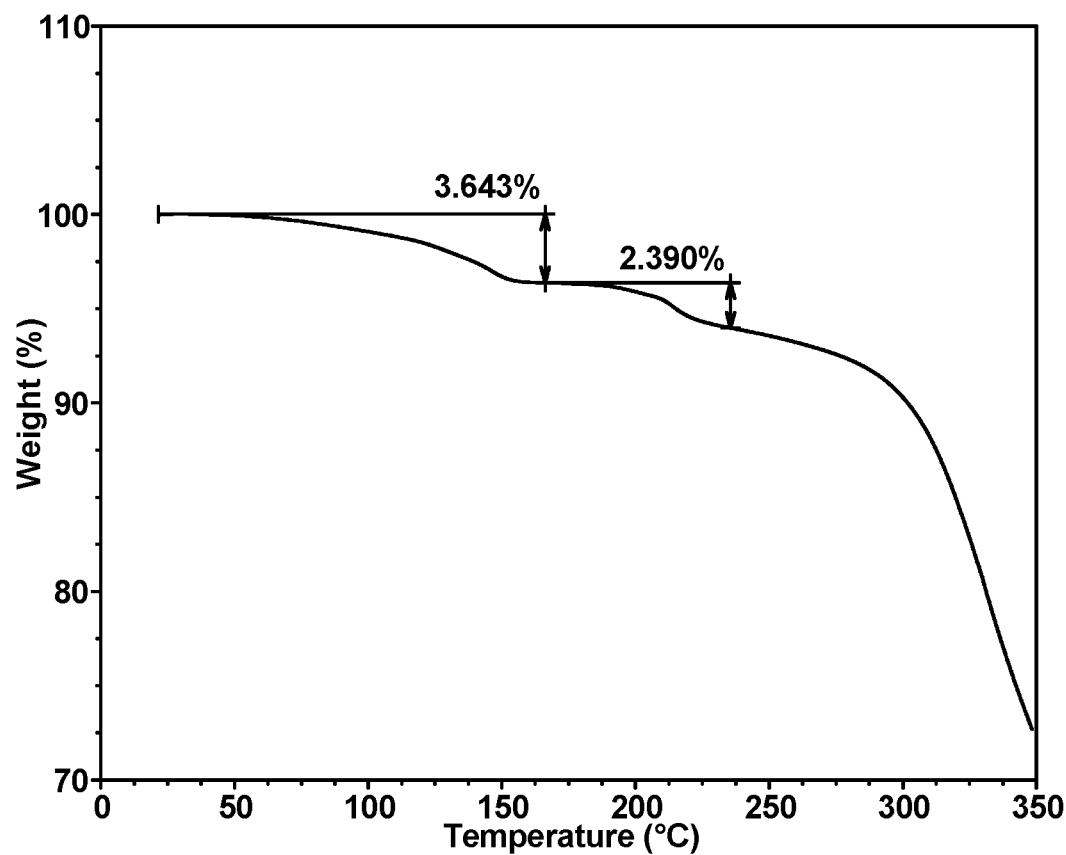
FIG. 48 shows a TGA thermogram of the Formula I p-toluenesulfonic acid salt hydrate.

In some embodiments, crystalline Formula Ip-TSA salt hydrate has at least one, at least two, or at least three of the following properties:

(a) an XRPD pattern substantially as shown in FIG. 46
(b) a DSC thermogram substantially as shown in FIG. 47
(c) a TGA thermogram substantially as shown in FIG. 48.

In some embodiments, crystalline Formula Ip-TSA salt hydrate has an XRPD pattern displaying at least two, at least three, at least four, at least five, at least six, at least seven, at least eight, or at least nine of the degree 2θ-reflections with the greatest intensity as the XRPD pattern substantially as shown in FIG. 46.

In certain embodiments, crystalline Formula I p-TSA salt hydrate has an XRPD pattern comprising degree 2θ-reflections (±0.2 degrees 2θ) at 6.6, 8.6, 19.8, and 25.5 degrees.

In some embodiments, Formula I p-TSA salt hydrate has an XRPD pattern comprising degree 2θ-reflections (±0.2 degrees 2θ) at 6.6, 8.6, 19.8, and 25.5 degrees and one, two, three, or four of the degree 2θ-reflections (±0.2 degrees 2θ) at 11.3, 17.1, 22.5, and 28.4 degrees.

In some embodiments, Formula I p-TSA salt hydrate has an XRPD pattern comprising degree 2θ-reflections (±0.2 degrees 2θ) at 6.6, 8.6, 19.8, and 25.5 degrees and one, two, or three of the degree 2θ-reflections (±0.2 degrees 2θ) 15.6, 17.7, and 26.9 degrees.

In some embodiments, Formula I p-TSA salt hydrate has an XRPD pattern comprising degree 2θ-reflections (±0.2 degrees 2θ) at 6.6, 8.6, 19.8, 25.5, 11.3, 17.1, 22.5, and 28.4, 15.6, 17.7, and 26.9 degrees.

In some embodiments, Formula I p-TSA salt hydrate has a differential scanning calorimetry thermogram having an endotherm with onset at about 144° C. In some embodiments, Formula I p-TSA salt hydrate has a differential scanning calorimetry thermogram having endotherm with onset at about 192° C. In some embodiments, Formula I p-TSA salt hydrate has a differential scanning calorimetry thermogram having an exotherm with onset at about 214° C.

Pharmaceutical Compositions

For the purposes of administration, in certain embodiments, the compounds described herein are administered as a raw chemical or are formulated as pharmaceutical compositions. Pharmaceutical compositions of the present disclosure can include a therapeutically effective amount of a compound of Formula I, and at least one pharmaceutically acceptable carrier and/or excipient. The compound of Formula I is present in the composition in an amount which is effective to treat a particular disease or condition of interest. The pharmaceutical compositions of the present disclosure may additionally comprise one or more other compounds as active ingredients, including for instance prodrugs, other nuclear receptor modulators, or other active pharmaceutical ingredients such as active pharmaceutical ingredients for use in treating liver disease, such as ACC inhibitors or ASK1 inhibitors. In some embodiments, the pharmaceutical compositions of the present disclosure additionally comprise an ACC inhibitor and an ASK1 inhibitor.

In some embodiments, a pharmaceutical composition includes Formula I zwitterion Form I; Formula I zwitterion Form II; Formula I hydrate; Formula I zwitterion amorphous; Formula I tromethamine salt Form I; Formula I tromethamine salt Form II; Formula I tromethamine salt hydrate I; Formula I tromethamine salt hydrate II; Formula I tromethamine salt hydrate III; Formula I tromethamine salt hydrate IV; Formula I tromethamine salt methanol solvate I; Formula I tromethamine salt methanol solvate II; Formula I tromethamine salt methanol solvate III; Formula I tromethamine salt MTBE solvate; Formula I tromethamine amorphous form; Formula I tromethamine salt ethanol solvate; Formula I p-toluenesulfonic acid salt Form I; Formula I p-toluenesulfonic acid salt Form II; Formula I p-toluenesulfonic acid salt Form III; and/or Formula I p-toluenesulfonic acid salt hydrate. In some embodiments, a pharmaceutical composition includes Formula I zwitterion Form I; Formula I zwitterion Form II; Formula I hydrate; Formula I zwitterion amorphous; Formula I tromethamine salt Form I; Formula I tromethamine salt Form II; Formula I tromethamine salt hydrate I; Formula I tromethamine salt hydrate II; Formula I tromethamine salt hydrate III; Formula I tromethamine salt hydrate IV; Formula I tromethamine salt methanol solvate I; Formula I tromethamine salt methanol solvate II; Formula I tromethamine salt methanol solvate III; Formula I tromethamine salt MTBE solvate; Formula I tromethamine amorphous form; Formula I tromethamine salt ethanol solvate; Formula I p-toluenesulfonic acid salt Form I; Formula I p-toluenesulfonic acid salt Form II; Formula I p-toluenesulfonic acid salt Form III; and/or Formula I p-toluenesulfonic acid salt hydrate and a pharmaceutically acceptable carrier.

In some embodiments, a pharmaceutical composition comprises a compound of Formula I (or zwitterion, hydrate, salt or solvate thereof), wherein at least 95% of Formula I is zwitterion Form I, and no more than 5%, 4%, 3%, 2% or 1% of other forms. In some embodiments, a pharmaceutical composition comprises a compound of Formula I (or zwitterion, hydrate, salt or solvate thereof), wherein at least 95% of Formula I is zwitterion Form II, and no more than 5%, 4%, 3%, 2% or 1% of other forms. In some embodiments, a pharmaceutical composition comprises a compound of Formula I (or zwitterion, hydrate, salt or solvate thereof), wherein at least 95% of Formula I is a hydrate, and no more than 5%, 4%, 3%, 2% or 1% of other forms. In some embodiments, a pharmaceutical composition comprises a compound of Formula I (or zwitterion, hydrate, salt or solvate thereof), wherein at least 95% of Formula I is Formula I zwitterion amorphous, and no more than 5%, 4%, 3%, 2% or 1% of other forms. In some embodiments, a pharmaceutical composition comprises a compound of Formula I (or zwitterion, hydrate, salt or solvate thereof), wherein at least 95% of Formula I is Formula I tromethamine salt Form I, and no more than 5%, 4%, 3%, 2% or 1% of other forms. In some embodiments, a pharmaceutical composition comprises a compound of Formula I (or zwitterion, hydrate, salt or solvate thereof), wherein at least 95% of Formula I is Formula I tromethamine salt Form II, and no more than 5%, 4%, 3%, 2% or 1% of other forms. In some embodiments, a pharmaceutical composition comprises a compound of Formula I (or zwitterion, hydrate, salt or solvate thereof), wherein at least 95% of Formula I is Formula I tromethamine salt hydrate I, and no more than 5%, 4%, 3%, 2% or 1% of other forms. In some embodiments, a pharmaceutical composition comprises a compound of Formula I (or zwitterion, hydrate, salt or solvate thereof), wherein at least 95% of Formula I is Formula I tromethamine salt hydrate II, and no more than 5%, 4%, 3%, 2% or 1% of other forms. In some embodiments, a pharmaceutical composition comprises a compound of Formula I (or zwitterion, hydrate, salt or solvate thereof), wherein at least 95% of Formula I is Formula I tromethamine salt hydrate III, and no more than 5%, 4%, 3%, 2% or 1% of other forms. In some embodiments, a pharmaceutical composition comprises a compound of Formula I (or zwitterion, hydrate, salt or solvate thereof), wherein at least 95% of Formula I is Formula I tromethamine salt hydrate IV, and no more than 5%, 4%, 3%, 2% or 1% of other forms. In some embodiments, a pharmaceutical composition comprises a compound of Formula I (or zwitterion, hydrate, salt or solvate thereof), wherein at least 95% of Formula I is Formula I tromethamine salt methanol solvate I, and no more than 5%, 4%, 3%, 2% or 1% of other forms. In some embodiments, a pharmaceutical composition comprises a compound of Formula I (or zwitterion, hydrate, salt or solvate thereof), wherein at least 95% of Formula I is Formula I tromethamine salt methanol solvate II, and no more than 5%, 4%, 3%, 2% or 1% of other forms. In some embodiments, a pharmaceutical composition comprises a compound of Formula I (or zwitterion, hydrate, salt or solvate thereof), wherein at least 95% of Formula I is Formula I tromethamine salt methanol solvate III, and no more than 5%, 4%, 3%, 2% or 1% of other forms. In some embodiments, a pharmaceutical composition comprises a compound of Formula I (or zwitterion, hydrate, salt or solvate thereof), wherein at least 95% of Formula I is Formula I tromethamine salt MTBE solvate, and no more than 5%, 4%, 3%, 2% or 1% of other forms. In some embodiments, a pharmaceutical composition comprises a compound of Formula I (or zwitterion, hydrate, salt or solvate thereof), wherein at least 95% of Formula I is Formula I tromethamine amorphous form, and no more than 5%, 4%, 3%, 2% or 1% of other forms. In some embodiments, a pharmaceutical composition comprises a compound of Formula I (or zwitterion, hydrate, salt or solvate thereof), wherein at least 95% of Formula I is Formula I tromethamine salt ethanol solvate, and no more than 5%, 4%, 3%, 2% or 1% of other forms. In some embodiments, a pharmaceutical composition comprises a compound of Formula I (or zwitterion, hydrate, salt or solvate thereof), wherein at least 95% of Formula I is Formula I p-toluenesulfonic acid salt Form I, and no more than 5%, 4%, 3%, 2% or 1% of other forms. In some embodiments, a pharmaceutical composition comprises a compound of Formula I (or zwitterion, hydrate, salt or solvate thereof), wherein at least 95% of Formula I is Formula I p-toluenesulfonic acid salt Form II, and no more than 5%, 4%, 3%, 2% or 1% of other forms. In some embodiments, a pharmaceutical composition comprises a compound of Formula I (or zwitterion, hydrate, salt or solvate thereof), wherein at least 95% of Formula I is Formula I p-toluenesulfonic acid salt Form III, and no more than 5%, 4%, 3%, 2% or 1% of other forms. In some embodiments, a pharmaceutical composition comprises a compound of Formula I (or zwitterion, hydrate, salt or solvate thereof), wherein at least 95% of Formula I is Formula I p-toluenesulfonic acid salt hydrate, and no more than 5%, 4%, 3%, 2% or 1% of other forms. In any of such embodiments, the pharmaceutical composition comprises a pharmaceutically acceptable carrier.

The activity of compounds of Formula I can be determined by one skilled in the art, for example, as described herein. Appropriate therapeutically effective concentrations and dosages can be readily determined by one skilled in the art.

In certain embodiments, the crystalline, salt, and/or solvate forms described herein may potentially exhibit improved properties. For example, in certain embodiments, the crystalline and/or salt forms described herein may potentially exhibit improved stability. Such improved stability could have a potentially beneficial impact on the manufacture of the compound of Formula I, such as for example offering the ability to store process intermediate for extended periods of time. Improved stability could also potentially benefit a composition or pharmaceutical composition of the compound of Formula I. In certain embodiments, the crystalline salt, and/or solvate forms described herein may also potentially result in improved yield of the compound of Formula I, or in an improvement of the quality of the compound of Formula I. In certain embodiments, the crystalline, salt, and/or solvate forms described herein may also exhibit improved pharmacokinetic properties and/or potentially improved bioavailability.

The compositions are suitable for oral, rectal, topical, parenteral (including subcutaneous, intramuscular, and intravenous), ocular (ophthalmic), pulmonary (nasal or buccal inhalation) or nasal administration, although the most suitable route in any given case will depend on the nature and severity of the conditions being treated and on the nature of the active ingredient. They may be conveniently presented in unit dosage form and prepared by any of the methods well-known in the art of pharmacy.

In practical use, the compounds of the present disclosure can be combined as the active ingredient in intimate admixture with a pharmaceutical carrier according to conventional pharmaceutical compounding techniques. The carrier may take a wide variety of forms depending on the form of preparation desired for administration, e.g., oral or parenteral (including intravenous). In preparing the compositions for oral dosage form, any of the usual pharmaceutical media may be employed, such as, for example, water, glycols, oils, alcohols, flavoring agents, preservatives, coloring agents and the like in the case of oral liquid preparations, such as, for example, suspensions, elixirs and solutions; or carriers such as starches, sugars, microcrystalline cellulose, diluents, granulating agents, lubricants, binders, disintegrating agents and the like in the case of oral solid preparations such as, for example, powders, hard and soft capsules and tablets, with the solid oral preparations being preferred over the liquid preparations.

Because of their ease of administration, tablets and capsules represent the most advantageous oral dosage unit form in which case solid pharmaceutical carriers are employed. If desired, tablets may be coated by standard aqueous or non-aqueous techniques. Such compositions and preparations should contain at least 0.1 percent of active compound. The percentage of active compound in these compositions may, of course, be varied and may conveniently be between about 2 percent to about 60 percent of the weight of the unit. The amount of active compound in such therapeutically useful compositions is such that an effective dosage will be obtained. The active compounds can also be administered intranasally as, for example, liquid drops or spray.

The tablets, pills, capsules, and the like may also contain a binder such as gum tragacanth, acacia, corn starch or gelatin; excipients such as dicalcium phosphate, microcrystalline cellulose, lactose monohydrate, mannitol or colloidal silicon dioxide; a disintegrating agent such as corn starch, potato starch, alginic acid, croscarmellose sodium or crospovidone; a lubricant such as magnesium stearate; and a sweetening agent such as sucrose, lactose or saccharin. When a dosage unit form is a capsule, it may contain, in addition to materials of the above type, a liquid carrier such as a fatty oil or pharmaceutical media, such as, for example, water, glycols (e.g., polyethylene glycol 400), or alcohols.

Various other materials may be present as coatings or to modify the physical form of the dosage unit. For instance, tablets may be coated with shellac, sugar, polyvinyl alcohol, polyethylene glycol 3350, titanium dioxide, talc, coloring agent, or combinations thereof. A syrup or elixir may contain, in addition to the active ingredient, sucrose as a sweetening agent, methyl and propylparabens as preservatives, a dye and a flavoring such as cherry or orange flavor.

The compounds of the present disclosure may also be administered parenterally. Solutions or suspensions of these active compounds can be prepared in water suitably mixed with an organic, an additive, or combinations thereof. Examples of organics include, but are not limited to, N-methyl pyrrolidone, dimethylsulfoxide, polyethylene glycols, and combinations thereof. Examples of additives include, but are not limited to, hydroxy-propylcellulose, polyvinylpyrrolidone, poloxamers, poly(lactic-co-glycolic acid), polysorbates, povidone, carboxymethylcellulose, and combinations thereof. Dispersions can also be prepared in glycerol, liquid polyethylene glycols and mixtures thereof in oils. Under ordinary conditions of storage and use, these preparations may contain a preservative to, for instance, prevent the growth of microorganisms. In some embodiments, the parenteral administration includes intravenous administration with formulations comprising solutions with a mixture of organics and aqueous media. In some embodiments, the intravenous administration is dosed as a 100% organic solution.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. For instance, the forms can be stable under the conditions of manufacture and storage. The forms can be preserved against the contaminating action of microorganisms such as bacteria and fungi (for instance, via use of preservatives). The carrier can be a solvent or dispersion medium containing, for example, water, ethanol, polyol (e.g., glycerol, propylene glycol and liquid polyethylene glycol), suitable mixtures thereof, and vegetable oils.

Any suitable route of administration may be employed for providing a mammal, especially a human, with an effective dose of a compound of the present disclosure. For example, oral, rectal, topical, parenteral, ocular, pulmonary, nasal, and the like may be employed. Dosage forms include tablets, troches, dispersions, suspensions, solutions, capsules, creams, ointments, aerosols, and the like. In some embodiments, compounds of the present disclosure are administered orally.

In some embodiments, the composition comprises a crystalline form of Formula I or a pharmaceutically acceptable salt thereof. In some embodiments, the composition includes a crystalline form of a zwitterion of the compound of Formula I. In some embodiments, the composition includes a crystalline form of a tromethamine salt of the compound of Formula I. In certain embodiments are provided compositions comprising a crystalline form as described herein, wherein the Formula I within the composition is substantially pure (i.e., substantially pure Formula I zwitterion Form I; Formula I zwitterion Form II; Formula I hydrate; Formula I zwitterion amorphous; Formula I tromethamine salt Form I; Formula I tromethamine salt Form II; Formula I tromethamine salt hydrate I; Formula I tromethamine salt hydrate II; Formula I tromethamine salt hydrate III; Formula I tromethamine salt hydrate IV; Formula I tromethamine salt methanol solvate I; Formula I tromethamine salt methanol solvate II; Formula I tromethamine salt methanol solvate III; Formula I tromethamine salt MTBE solvate; Formula I tromethamine amorphous form; Formula I tromethamine salt ethanol solvate; Formula I; Formula I p-toluenesulfonic acid salt Form I; Formula I p-toluenesulfonic acid salt Form II; Formula I p-toluenesulfonic acid salt Form III; or Formula I p-toluenesulfonic acid salt hydrate).

In particular embodiments of compositions comprising a crystalline form of Formula I or a pharmaceutically acceptable salt thereof, at least about 50%, at least about 60%, at least about 70%, at least about 80%, at least about 85%, at least about 90%, at least about 95%, at least about 96%, at least about 97%, at least about 98%, or at least about 99% of Formula I present in the composition is one of the crystalline forms disclosed herein. In certain embodiments, the composition includes at least about 50%, at least about 60%, at least about 70%, at least about 80%, at least about 85%, at least about 90%, at least about 95%, at least about 96%, at least about 97%, at least about 98%, or at least about 99% of one of the crystalline forms of Formula I.

In other embodiments of compositions comprising a crystalline form disclosed herein, less than about 50%, less than about 40%, less than about 30%, less than about 20%, less than about 10%, less than about 5%, less than about 4%, less than about 3%, less than about 2% or less than about 1% of Formula I present in the composition are other amorphous or crystal forms of Formula I and/or impurities.

In yet other embodiments of compositions comprising the crystalline forms disclosed herein, impurities make up less than about 5%, less than about 4%, less than about 3%, less than about 2% or less than about 1% of the total mass relative to the mass of the crystalline forms present. Impurities may, for example, include by-products from synthesizing Formula I, contaminants, degradation products, other crystalline forms, amorphous form, water, and solvents. In certain embodiments, impurities include by-products from the process of synthesizing Formula I. In certain embodiments, impurities include contaminants from the process of synthesizing Formula I. In certain embodiments, impurities include degradation products of Formula I. In certain embodiments, impurities include other crystalline forms of Formula I. In certain embodiments, impurities include other crystalline forms of Formula I and/or amorphous forms of Formula I. In certain embodiments, impurities include water or solvent. In certain embodiments of compositions comprising a crystalline form disclosed herein, impurities are selected from the group consisting of by-products from synthesizing Formula I, contaminants, degradation products, other crystalline forms, amorphous forms, water, solvents and combinations thereof.

Dosage

The effective dosage of active ingredient employed may vary depending on the particular compound employed, the mode of administration, the condition being treated and the severity of the condition being treated. Such dosage may be ascertained readily by a person skilled in the art.

When treating or preventing FXR mediated conditions for which compounds of the present disclosure are indicated, generally satisfactory results are obtained when the compounds of the present disclosure are administered at a daily dosage of from about 0.1 milligram to about 100 milligram per kilogram of animal body weight. In some embodiments, the compounds of the present disclosure are given as a single daily dose or in divided doses two to six times a day, or in sustained release form. For most large mammals, the total daily dosage can be from about 1 milligram to about 1000 milligrams. In the case of a 70 kg adult human, the total daily dose will generally be from about 7 milligrams to about 350 milligrams. This dosage regimen may be adjusted to provide the optimal therapeutic response. In some embodiments, the total daily dosage is from about 1 milligram to about 900 milligrams, about 10 milligrams to about 800 milligrams, about 20 milligrams to about 700 milligrams, about 30 milligrams to about 600 milligrams, about 40 milligrams to about 550 milligrams, or about 50 milligrams to about 400 milligrams. In some embodiments, the total daily dosage is from about 10 milligrams to about 50 milligrams, from about 20 milligrams to about 40 milligrams, from about 25 milligrams to about 35 milligrams, from about 50 milligrams to about 150 milligrams, from about 70 milligrams to about 130 milligrams, from about 80 milligrams to about 120 milligrams, from about 90 milligrams to about 100 milligrams, from about 1 milligram to about 150 milligrams, from about 1 milligram to about 75 milligrams, from about 1 milligram to about 50 milligrams, from about 25 milligrams to about 125 milligrams, from about 125 milligrams to about 275 milligrams, from about 275 milligrams to about 425 milligrams, from about 425 milligrams to about 575 milligrams, from about 575 milligrams to about 725 milligrams, from about 725 milligrams to about 875 milligrams, or from about 875 milligrams to about 1000 milligrams.

The compounds of the present application or the compositions thereof may be administered once, twice, three, or four times daily, using any suitable mode described above. Also, administration or treatment with the compounds may be continued for a number of days; for example, commonly treatment would continue for at least 7 days, 14 days, or 28 days, for one cycle of treatment. Treatment cycles are well known in cancer chemotherapy, and are frequently alternated with resting periods of about 1 to 28 days, commonly about 7 days or about 14 days, between cycles. In some embodiments, the treatment cycle is 30 days. The treatment cycles, in other embodiments, may also be continuous.

In a particular embodiment, the methods provided herein comprise administering to the subject an initial daily dose of about 1 mg to about 800 mg of a compound described herein and increasing the dose by increments until clinical efficacy is achieved. Increments of about 5, 10, 25, 30, 40, 50, or 100 mg can be used to increase the dose. The dosage can be increased daily, every other day, twice per week, once per week or once every 4 weeks.

Treatment Methods and Uses

"Treatment" or "treating" is an approach for obtaining beneficial or desired results including clinical results. Beneficial or desired clinical results may include one or more of the following: (a) inhibiting the disease or condition (e.g., decreasing one or more symptoms resulting from the disease or condition, and/or diminishing the extent of the disease or condition); (b) slowing or arresting the development of one or more clinical symptoms associated with the disease or condition (e.g., stabilizing the disease or condition, preventing or delaying the worsening or progression of the disease or condition, and/or preventing or delaying the spread (e.g., metastasis) of the disease or condition); and/or (c) relieving the disease, that is, causing the regression of clinical symptoms (e.g., ameliorating the disease state, providing partial or total remission of the disease or condition, enhancing effect of another medication, delaying the progression of the disease, increasing the quality of life, and/or prolonging survival.

The disclosure further relates to the use of said compounds for the treatment and/or prophylaxis of diseases and/or conditions through binding of said nuclear receptor by said compounds. Further the present disclosure relates to the use of said compounds for the preparation of a medicament for the treatment and/or prophylaxis of diseases and/or conditions through binding of said nuclear receptor by said compounds.

Also provided herein are methods of treating a patient having a FXR mediated condition. In some embodiments, the method includes administering a compound or composition disclosed herein. In some embodiments, a method of treating a patient having an FXR mediated condition includes administering a therapeutically effective amount of Formula I zwitterion Form I; Formula I zwitterion Form II; Formula I hydrate; Formula I zwitterion amorphous; Formula I tromethamine salt Form I; Formula I tromethamine salt Form II; Formula I tromethamine salt hydrate I; Formula I tromethamine salt hydrate II; Formula I tromethamine salt hydrate III; Formula I tromethamine salt hydrate IV; Formula I tromethamine salt methanol solvate I; Formula I tromethamine salt methanol solvate II; Formula I tromethamine salt methanol solvate III; Formula I tromethamine salt MTBE solvate; Formula I tromethamine amorphous form; Formula I tromethamine salt ethanol solvate; Formula I; Formula I p-toluenesulfonic acid salt Form I; Formula I p-toluenesulfonic acid salt Form II; Formula I p-toluenesulfonic acid salt Form III; and/or Formula I p-toluenesulfonic acid salt hydrate.

Also provided herein are methods of treating or preventing a disease or condition in a patient in need thereof, comprising administering a therapeutically effective amount of an FXR agonist, wherein the disease or condition is congenital hepatic fibrosis, and wherein the FXR agonist is a compound of Formula I

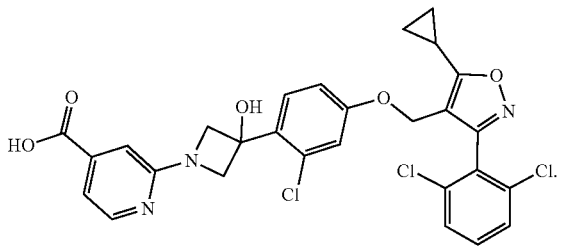

In some embodiments, a method of treating a patient having congenital hepatic fibrosis includes administering a compound of Formula I. In some embodiments, a method of treating a patient having congenital hepatic fibrosis includes administering a solid form of a compound of Formula I.

In some embodiments a compound or composition disclosed herein is provided for use in the treatment of a FXR mediated condition.

In some embodiments, a compound or composition disclosed herein is provided for the manufacture of a medicament for the treatment of a FXR mediated condition.

In some embodiments, the FXR mediated condition is: a chronic intrahepatic or some form of extrahepatic cholestatic condition; liver fibrosis; an obstructive inflammatory disorder of the liver; chronic inflammatory disorder of the liver; liver cirrhosis; liver steatosis or an associated syndrome; cholestatic or fibrotic effects that are associated with alcohol-induced cirrhosis or with viral-borne forms of hepatitis; liver failure or liver ischemia after major liver resection; chemotherapy associated steatohepatitis (CASH); acute liver failure; or Inflammatory Bowel Disease.

In some embodiments, the FXR mediated condition is a lipid and lipoprotein disorder; Type I Diabetes; Type II Diabetes; clinical complications of Type I and Type II Diabetes selected from the group consisting of diabetic nephropathy, diabetic neuropathy, diabetic retinopathy and other observed effects of clinically manifest long term Diabetes; Non-Alcoholic Fatty Liver Disease (NAFLD); Non-Alcoholic Steatohepatitis (NASH); obesity; a metabolic syndrome selected from the group consisting of combined conditions of dyslipidemia, diabetes and abnormally high body-mass index; acute myocardial infarction; acute stroke; or thrombosis which occurs as an endpoint of chronic obstructive atherosclerosis.

In some embodiments, the FXR mediated condition is: a non-malignant hyperproliferative disorder; and a malignant hyperproliferative disorder selected from the group consisting of hepatocellular carcinoma, colon adenoma, and polyposis; colon adenocarcinoma; breast cancer; pancreas adenocarcinoma; Barrett's esophagus; or other forms of neoplastic diseases of the gastrointestinal tract and the liver.

In some embodiments, the FXR mediated condition is Non-Alcoholic Steatohepatitis (NASH), primary sclerosing cholangitis (PSC), or primary biliary cirrhosis (PBC).

In some embodiments, the FXR mediated condition is congenital hepatic fibrosis.

In some embodiments, the present disclosure relates to the use of compounds and compositions disclosed herein in the preparation of a medicament for the prophylaxis and/or treatment of chronic intrahepatic or some forms of extrahepatic cholestatic conditions, of liver fibrosis, of acute intrahepatic cholestatic conditions, of obstructive or chronic inflammatory disorders that arise out of improper bile composition, of gastrointestinal conditions with a reduced uptake of dietary fat and fat-soluble dietary vitamins, of inflammatory bowel diseases, of lipid and lipoprotein disorders, of Type II Diabetes and clinical complications of Type I and Type II Diabetes, of conditions and diseases which result from chronic fatty and fibrotic degeneration of organs due to enforced lipid and specifically triglyceride accumulation and subsequent activation of profibrotic pathways, of obesity and metabolic syndrome (combined conditions of dyslipidemia, diabetes and abnormally high body-mass index), of acute myocardial infarction, of acute stroke, of thrombosis which occurs as an endpoint of chronic obstructive atherosclerosis, of persistent infections by intracellular bacteria or parasitic protozoa, of non-malignant hyperproliferative disorders, of malignant hyperproliferative disorders, of colon adenocarcinoma and hepatocellular carcinoma in particular, of liver steatosis and associated syndromes, of liver failure or liver malfunction as an outcome of chronic liver diseases or of surgical liver resection, of Hepatitis B infection, of Hepatitis C infection, of cholestatic and fibrotic effects that are associated with alcohol-induced cirrhosis or with viral-borne forms of hepatitis, and/or of congenital hepatic fibrosis.

Medicaments as referred to herein may be prepared by conventional processes, including the combination of a compound according to the present disclosure and a pharmaceutically acceptable carrier.

Kits

Provided herein are also kits that include a compound or composition described herein and suitable packaging. In one embodiment, a kit further includes instructions for use. In one aspect, a kit includes a crystalline form of the disclosure, or composition including a crystalline form of the disclosure and a label and/or instructions for use of the compounds in the treatment of the indications, including the diseases or conditions, described herein.

Provided herein are also articles of manufacture that include a compound or composition described herein in a suitable container. The container may be a vial, jar, ampoule, preloaded syringe, and intravenous bag.

Combination Therapy

In some embodiments, disclosed herein are oral dosage forms (e.g., tablets) comprising a novel crystalline forms of a compound of Formula I:

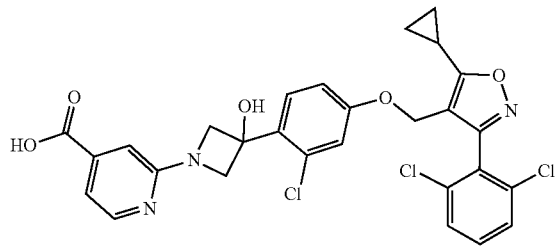

or a pharmaceutically acceptable salt thereof and at least one additional therapeutic agent. In some embodiments, the oral dosage forms disclosed herein comprise novel crystal forms Formula I or a pharmaceutically acceptable salt thereof and one, two, or three additional therapeutic agents.

In some embodiments, the therapeutic agent, or combination of therapeutic agents, are a(n) ACE inhibitor, Acetaldehyde dehydrogenase inhibitor, Acetyl CoA carboxylase inhibitor, Acetyl CoA carboxylase inhibitor, Diacylglycerol O acyltransferase 2 inhibitor, Adenosine A3 receptor agonist, Adiponectin receptor agonist, Aldehyde dehydrogenase 2 stimulator, AKT protein kinase inhibitor, AMP-activated protein kinases (AMPK), AMP kinase activator, ATP citrate lyase inhibitor, AMP activated protein kinase stimulator, Endothelial nitric oxide synthase stimulator, NAD-dependent deacetylase sirtuin-1 stimulator, Androgen receptor agonist, Amylin receptor agonist, Angiotensin II AT-1 receptor antagonist, Autophagy protein modulator, Autotaxin inhibitors, Axl tyrosine kinase receptor inhibitor, Bax protein stimulator, Bioactive lipid, Calcitonin agonist, Cannabinoid receptor modulator, Caspase inhibitor, Caspase-3 stimulator, Cathepsin inhibitor, Caveolin 1 inhibitor, CCR2 chemokine antagonist, CCR2 chemokine antagonist, Angiotensin II AT-1 receptor antagonist, CCR3 chemokine antagonist, CCR5 chemokine antagonist, CD3 antagonist, Chloride channel stimulator, CNR1 inhibitor, Cyclin D1 inhibitor, Cytochrome P450 7A1 inhibitor, DGAT1/2 inhibitor, Diacylglycerol O acyltransferase 1 inhibitor (DGAT1), Cytochrome P450 2E1 inhibitor (CYP2E1), CXCR4 chemokine antagonist, Dipeptidyl peptidase IV inhibitor, Endosialin modulator, Eotaxin ligand inhibitor, Extracellular matrix protein modulator, Famesoid X receptor agonist, Fatty acid synthase inhibitors, FGF1 receptor agonist, Fibroblast growth factor (FGF-15, FGF-19, FGF-21) ligands, Galectin-3 inhibitor, Glucagon receptor agonist, Glucagon-like peptide 1 agonist, G-protein coupled bile acid receptor 1 agonist, G-protein coupled receptor 84 antagonist, Hedgehog (Hh) modulator, Hepatitis C virus NS3 protease inhibitor, Hepatocyte nuclear factor 4 alpha modulator (HNF4A), Hepatocyte growth factor modulator, Histone deacetylase inhibitor, STAT-3 modulator, HMG CoA reductase inhibitor, Hypoxia inducible factor-2 alpha inhibitor, IL-10 agonist, IL-17 antagonist, Ileal sodium bile acid cotransporter inhibitor, Insulin sensitizer, Insulin ligand agonist, Insulin receptor agonist, integrin modulator, Integrin Antagonist, intereukin-1 receptor-associated kinase 4 (IRAK4) inhibitor, IL-6 receptor agonist, Jak2 tyrosine kinase inhibitor, Ketohexokinase (KHK) inhibitor, Klotho beta stimulator, 5-Lipoxygenase inhibitor, Lipoprotein lipase inhibitor, Liver X receptor, LPL gene stimulator, Lysophosphatidate-1 receptor antagonist, Lysyl oxidase homolog 2 inhibitor, Macrophage mannose receptor 1 modulator, Matrix metalloproteinases (MMPs) inhibitor, MEKK-5 protein kinase inhibitor, MCH receptor-1 antagonist, Membrane copper amine oxidase (VAP-1) inhibitor, Methionine aminopeptidase-2 inhibitor, Methyl CpG binding protein 2 modulator, MicroRNA-21 (miR-21) inhibitor, Mitochondrial uncoupler, Mixed lineage kinase-3 inhibitor, Myelin basic protein stimulator, NACHT LRR PYD domain protein 3 (NLRP3) inhibitor, NAD-dependent deacetylase sirtuin stimulator, NADPH oxidase inhibitor (NOX), Nicotinic acid receptor 1 agonist, P2Y13 purinoceptor stimulator, Nuclear receptor modulators, P2X7 purinoceptor modulator, PDE 3 inhibitor, PDE 4 inhibitor, PDE 5 inhibitor, PDGF receptor beta modulator, Phenylalanine hydroxylase stimulator, Phospholipase C inhibitor, PPAR alpha agonist, PPAR delta agonist, PPAR gamma agonist, Peptidyl-prolyl cis-trans isomerase A inhibitor, PPAR gamma modulator, Protease-activated receptor-2 antagonist, Protein kinase modulator, Rho associated protein kinase inhibitor, Snitrosoglutathione reductase (GSNOR) enzyme inhibitor, Sodium glucose transporter-2 inhibitor, SREBP transcription factor inhibitor, STAT-1 inhibitor, Stearoyl CoA desaturase-1 inhibitor, STK25 inhibitor, Suppressor of cytokine signalling-1 stimulator, Suppressor of cytokine signalling-3 stimulator, Transforming growth factor β (TGF-β), Transforming growth factor β activated Kinase 1 (TAK1), Thyroid hormone receptor beta agonist, TLR-4 antagonist, Transglutaminase inhibitor, Tyrosine kinase receptor modulator, GPCR modulator, nuclear hormone receptor modulator, WNT modulators, or YAP/TAZ modulator and Zonulin inhibitor.

Non-limiting examples of the one or more additional therapeutic agents include:

ACE inhibitors, such as enalapril;
Acetaldehyde dehydrogenase inhibitors, such as ADX-629;
Acetyl CoA carboxylase (ACC) inhibitors, such as NDI-010976 (firsocostat), DRM-01, gemcabene, PF-05175157, QLT-091382, PF-0522 1304;
Acetyl CoA carboxylase/Diacylglycerol O acyltransferase 2 inhibitors, such as PF-07055341;
Adenosine receptor agonists, such as CF-102 (namodenoson), CF-101, CF-502, CGS21680;
Adiponectin receptor agonists, such as ADP-355, ADP-399;
Aldehyde dehydrogenase 2 stimulators, such as FP-045;
Amylin/calcitonin receptor agonists, such as KBP-042, KBP-089;
AMP activated protein kinase stimulators, such as, PXL-770, 0-304;
AMP kinase activators/ATP citrate lyase inhibitors, such as bempedoic acid (ETC-1002, ESP-55016)
AMP activated protein kinase/Endothelial nitric oxide synthase/NAD-dependent deacetylase sirtuin-1 stimulators, such as NS-0200;
Androgen receptor agonists, such as LPCN-1144;
Angiotensin II AT-1 receptor antagonists, such as irbesartan; Angiopoietin-related protein-3 inhibitors, such as IONIS-ANGPTL3-LRx;
Autophagy protein modulators, such as A-2906;
Autotaxin inhibitors, such as PAT-505, PAT-048, GLPG-1690, X-165, PF-8380, AM-063, BBT-877;
Axl tyrosine kinase receptor inhibitors, such as bemcentinib (BGB-324, R-428);
Bax protein stimulators, such as CBL-514;
Bioactive lipids, such as DS-102;
Cannabinoid receptor modulators, such as namacizumab, GWP-42004, REV-200, CRB-4001;
Caspase inhibitors, such as emricasan;
Pan cathepsin B inhibitors, such as VBY-376;
Pan cathepsin inhibitors, such as VBY-825;
CCR2/CCR5 chemokine antagonists, such as cenicriviroc, maraviroc, CCX-872, WXSH-0213;
CCR2 chemokine antagonists, such as propagermanium;
CCR2 chemokine/Angiotensin II AT-1 receptor antagonists, such as DMX-200, DMX-250;
CCR3 chemokine antagonists, such as bertilimumab;
CD3 antagonists, such as NI-0401;
Chloride channel stimulators, such as cobiprostone;
CXCR4 chemokine antagonists, such as AD-214;
Diglyceride acyltransferase 2 (DGAT2) inhibitors, such as IONIS-DGAT2Rx, PF-06865571;
Diglyceride acyltransferase 1 (DGAT1) inhibitors, such as GSK-3008356;
Diacylglycerol O acyltransferase 1 (DGAT1)/Cytochrome P450 2E1 inhibitors (CYP2E1), such as SNP-610;
Dipeptidyl peptidase IV inhibitors, such as linagliptin, evogliptin;
Eotaxin ligand inhibitors, such as bertilimumab, CM-101;
Extracellular matrix protein modulators, such as CNX-024;
Farnesoid X receptor (FXR) agonists, such as AGN-242266, AGN-242256, EP-024297, RDX-023, BWL-200, AKN-083, EDP-305, GNF-5120, GS-9674, LMB-763, obeticholic acid, Px-102, Px-103, M790, M780, M450, M-480, (MET-409), PX20606, EYP-001, TERN-101, TC-100, INT-2228;
Farnesoid X receptor (FXR)/G-protein coupled bile acid receptor 1 (TGR5) agonists, such as INT-767;
Fatty acid synthase inhibitors, such as TVB-2640;
Fibroblast growth factor 19 (rhFGF19)/cytochrome P450 (CYP) 7A1 inhibitors, such as NGM-282;
Fibroblast growth factor 21 (FGF-21) ligand, such as BMS-986171, BIO089-100,
BMS-986036, B-1344;
Fibroblast growth factor 21 (FGF-21)/glucagon like peptide 1 (GLP-1) agonist, such as YH-25723 AKR-001;
Galectin-3 inhibitors, such as GR-MD-02, GB-1107;
Glucagon-like peptide 1 (GLP1R) agonists, such as AC-3174, liraglutide, cotadutide (MEDI-0382), SAR-425899, LY-3305677, HM-15211, YH-25723, YH-GLP1, RPC-8844, PB-718, semaglutide;
G-protein coupled bile acid receptor 1 (TGR5) agonists, such as RDX-009, INT-777;
Heat shock protein 47 (HSP47) inhibitors, such as ND-L02-s0201;
Histone deacetylase inhibitors/STAT-3 modulators, such as SFX-01;
HMG CoA reductase inhibitors, such as atorvastatin, fluvastatin, pitavastatin, pravastatin, rosuvastatin, simvastatin;
Hypoxia inducible factor-2 alpha inhibitors, such as PT-2567;
IL-10 agonists, such as peg-ilodecakin;
Ileal sodium bile acid cotransporter inhibitors, such as odevixibat (A-4250), volixibat potassium ethanolate hydrate (SHP-262), GSK2330672, CJ-14199, elobixibat (A-3309);
Insulin sensitizers, such as, KBP-042, MSDC-0602K, MSDC-5514, Px-102, RG-125 (AZD4076), VVP-100X, CB-4211, ETI-101;
Insulin ligand/dsInsulin receptor agonists, such as ORMD-0801;
Integrin antagonists, such as IDL-2965;
IL-6 receptor agonists, such as KM-2702;
Ketohexokinase (KHK) inhibitors, such as PF-06835919;

beta Klotho (KLB)-FGF1c agonists, such as MK-3655 (NGM-313);

5-Lipoxygenase inhibitors, such as tipelukast (MN-001), DS-102 (AF-102);

Lipoprotein lipase inhibitors, such as CAT-2003;

LPL gene stimulators, such as alipogene tiparvovec;

Liver X receptor (LXR) inhibitors, such as PX-L603, PX-L493, BMS-852927, T-0901317, GW-3965, SR-9238;

Lysophosphatidate-1 receptor antagonists, such as BMT-053011, UD-009 (CP-2090), AR-479, ITMN-10534, BMS-986020, KI-16198;

Lysyl oxidase homolog 2 inhibitors, such as simtuzumab, PXS-5382A (PXS-5338);

Macrophage mannose receptor 1 modulators, such as tilmanocept-Cy3 (technetium Tc 99 m tilmanocept);

Membrane copper amine oxidase (VAP-1) inhibitors, such as TERN-201;

MEKK-5 protein kinase (ASK-1) inhibitors, such as GS-4997, SRT-015, GS-444217, GST-HG-151;

MCH receptor-1 antagonists, such as CSTI-100 (ALB-127158);

Semicarbazide-Sensitive Amine Oxidase/Vascular Adhesion Protein-1 (SSAO/VAP-1) Inhibitors, such as PXS-4728A;

Methionine aminopeptidase-2 inhibitors, such as ZGN-1061, ZGN-839, ZN-1345;

Methyl CpG binding protein 2 modulators, such as mercaptamine;

Mineralocorticoid receptor antagonists (MCRA), such as MT-3995;

Mitochondrial uncouplers, such as 2,4-dinitrophenol;

Mixed lineage kinase-3 inhibitors, such as URMC-099-C;

Myelin basic protein stimulators, such as olesoxime;

Myeloperoxidase inhibitors, such as PF-06667272, AZM-198;

NADPH oxidase inhibitors, such as GKT-831, APX-311;

Nicotinic acid receptor 1 agonists, such as ARI-3037MO;

NACHT LRR PYD domain protein 3 (NLRP3) inhibitors, such as KDDF-201406-03, NBC-6, IFM-514, JT-194 (JT-349);

Nuclear receptor modulators, such as DUR-928 (DV-928);

P2X7 purinoceptor modulators, such as SGM-1019;

P2Y13 purinoceptor stimulators, such as CER-209;

PDE 3/4 inhibitors, such as tipelukast (MN-001);

PDE 5 inhibitors, such as sildenafil, MSTM-102;

PDGF receptor beta modulators, such as BOT-191, BOT-509;

Peptidyl-prolyl cis-trans isomerase inhibitors, such as CRV-431 (CPI-432-32), NVP-018, NV-556 (NVP-025);

Phenylalanine hydroxylase stimulators, such as HepaStem;

PPAR agonists, such as elafibranor (GFT-505), seladelpar lysine (MBX-8025), deuterated pioglitazone R-enantiomer, pioglitazone, DRX-065, saroglitazar, lanifibranor (IVA-337), CHS-131;

Protease-activated receptor-2 antagonists, such as PZ-235;

Protein kinase modulators, such as CNX-014;

Rho associated protein kinase (ROCK) inhibitors, such as REDX-10178 (REDX-10325), KD-025;

Snitrosoglutathione reductase (GSNOR) enzyme inhibitors, such as SL-891;

Sodium glucose transporter-2 (SGLT2) inhibitors, such as ipragliflozin, remogliflozin etabonate, ertugliflozin, dapagliflozin, tofogliflozin, sotagliflozin, Sodium glucose transporter-1/2 (SGLT 1/2) inhibitors, such as licogliflozin bis(prolinate);

SREBP transcription factor inhibitors, such as CAT-2003, MDV-4463;

Stearoyl CoA desaturase-1 inhibitors, such as aramchol;

Thyroid hormone receptor beta agonists, such as resmetirom (MGL-3196), MGL-3745, VK-2809;

TLR-2/TLR-4 antagonists, such as VB-201 (CI-201);

TLR-4 antagonists, such as JKB-121;

Tyrosine kinase receptor modulators, such as CNX-025;

GPCR modulators, such as CNX-023;

Nuclear hormone receptor modulators, such as Px-102;

Xanthine oxidase/Urate anion exchanger 1 (URAT1) inhibitors, such as RLBN-1001, RLBN-1127; and Zonulin Inhibitors, such as lorazotide acetate (INN-202).

In certain specific embodiments, the one or more additional therapeutic agents are selected from A-4250, AC-3174, acetylsalicylic acid, AK-20, alipogene tiparvovec, AMX-342, AN-3015, aramchol, ARI-3037MO, ASP-8232, AZD-2693, bertilimumab, Betaine anhydrous, BI-1467335, BMS-986036, BMS-986171, BMT-053011, BOT-191, BTT-1023, CAT-2003, cenicriviroc, CBW-511, CER-209, CF-102, CGS21680, CNX-014, CNX-023, CNX-024, CNX-025, cobiprostone, colesevelam, dapagliflozin, DCR-LIV1, deuterated pioglitazone R-enantiomer, 2,4-dinitrophenol, DRX-065, DS-102, DUR-928, EDP-305, elafibranor (GFT-505), emricasan, enalapril, ertugliflozin, evogliptin, F-351, fluasterone (ST-002), FT-4101, GKT-831, GNF-5120, GRI-0621, GR-MD-02, GS-300, GS-4997, GS-9674, HTD-1801, HST-202, HST-201, hydrochlorothiazide, icosabutate (PRC-4016), icosapent ethyl ester, IMM-124-E, INT-767, INV-240, IONIS-DGAT2Rx, ipragliflozin, Irbesarta, propagermanium, IVA-337, JKB-121, KB-GE-001, KBP-042, KD-025, M790, M780, M450, metformin, sildenafil, LC-280126, linagliptin, liraglutide, LJN-452, LM-011, LM-002 (CVI-LM-002), LMB-763, LYN-100, MBX-8025, MDV-4463, mercaptamine, MGL-3196, MGL-3745, MP-301, MSDC-0602K, namacizumab, NC-101, NDI-010976, ND-L02-s0201, NGM-282, NGM-313, NGM-386, NGM-395, NP-160, norursodeoxycholic acid, NVP-022, 0-304, obeticholic acid, 25HC3S, olesoxime, PAT-505, PAT-048, PB-4547, peg-ilodecakin, pioglitazone, pirfenidone, PRI-724, PX20606, Px-102, PX-L603, PX-L493, PXS-4728A, PZ-235, RDX-009, remogliflozin etabonate, RG-125 (AZD4076), RPI-500, saroglitazar, semaglutide, simtuzumab, solithromycin, sotagliflozin, statins (atorvastatin, fluvastatin, pitavastatin, pravastatin, rosuvastatin, simvastatin), TCM-606F, TEV-45478, TQA-3526, tipelukast (MN-001), TLY-012, TRX-318, TVB-2640, UD-009, ursodeoxycholic acid, VBY-376, VBY-825, VK-2809, vismodegib, volixibat potassium ethanolate hydrate (SHP-626), VVP-100X, WAV-301, WNT-974, XRx-117, ZGN-839, ZG-5216, ZSYM-008, ZYSM-007.

In some embodiments, methods and compositions include a therapeutically effective amount of an Apoptosis Signal-Regulating Kinase 1 (ASK1) inhibitor and a therapeutically effective amount of a Farnesoid X Receptor (FXR) agonist, wherein the FXR agonist is a solid form described herein.

In certain embodiments of the methods and pharmaceutical compositions disclosed herein, the ASK1 inhibitor is a compound of Formula II:

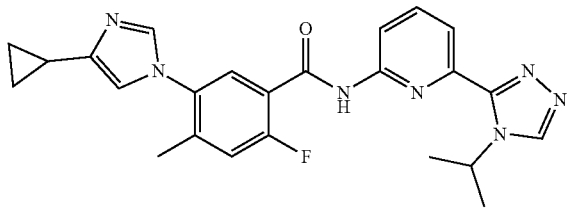

II or a pharmaceutically acceptable salt, a stereoisomer, a mixture of stereoisomers, or a tautomer thereof.

ASK1 inhibitors, such as the compound of Formula (II), can be synthesized and characterized using methods known to those of skill in the art, such as those described in U.S. 2007/0276050 U.S. 2011/0009410, and U.S. 2013/0197037.

In some embodiments, methods and compositions include a therapeutically effective amount of an Acetyl CoA Carboxylase inhibitor and a therapeutically effective amount of a Farnesoid X Receptor (FXR) agonist, wherein the FXR agonist is a solid form described herein.

Examples

Methods

Compounds of Formula I were synthesized according to known methods, such as those disclosed in U.S. Pat. No. 9,139,539.

X-Ray Powder Diffraction (XRPD)

XRPD patterns were collected on a PANanalytical XPERT-PRO diffractometer at ambient conditions under the following experimental settings: 45 KV, 40 mA, Kα1=1.5406 Å, scan range 2 to 40° 2 θ, step size 0.0084 or 0.0167° 2θ, measurement time: 5 min.

Some X-ray powder diffraction data were collected under ambient conditions on a Rigaku Miniflex 600 diffractometer using Cu K alpha (1.5406 Angstrom) radiation. Powder patterns were collected on a zero background holder with a 0.1 mm indent at a scan rate of 2 to 40° 2θ two theta at 2°2θ per min at 40 kV and 15 mA.

Differential Scanning Calorimetry (DSC)

DSC thermograms were collected on a TA Instruments Q2000 system equipped with a 50 position auto-sampler. The calibration for energy and temperature was carried out using certified indium. Typically 1-5 mg of each sample, in a pin-holed aluminum pan, was heated at 10° C./min from 25° C. to 300° C. A purge of dry nitrogen at 50 mL/min was maintained over the sample throughout the measurement. The onset of the melting endotherm was reported as the melting point.

Some DSC analyses were performed with a TA Discovery series DSC using a few milligrams of material in a Tzero aluminum pan sealed with a Tzero hermetic lid containing two pin holes. Samples were scanned at 10° C. per minute under 50 mL per minute of nitrogen flow.

Thermo-Gravimetric Analysis (TGA)

TGA thermograms were collected on a TA Instruments Q5000 system, equipped with a 25 position auto-sampler. Typically 1-5 mg of each sample was loaded onto a pre-tared aluminum pan and heated at 10° C./min from 25° C. to 350° C. A nitrogen purge at 25 mL/min was maintained over the sample throughout the measurement.

Some thermogravimetric analysis data were collected with a TA Discovery series TGA. A few milligrams of material were analyzed in an aluminum sample pan. The data was collected from room temperature to 300° C. with a 10 OC per minute scan rate.

Formula I Zwitterion Form I

Formula I zwitterion Form I is an unsolvated form. It was first obtained by crystallization of Formula I from EtOH at pH 3.5-4.0.

XRPD analysis was conducted. FIG. 1 shows an XRPD pattern of the zwitterionic compound of Formula I Form I. XRPD peaks were identified and are included in Table 1 below.

TABLE 1

| No. | Pos. [°2Th.] | Rel. Int. [%] |
|---|---|---|
| 1 | 3.4 | 15 |
| 2 | 6.7 | 100 |
| 3 | 9.9 | 11 |
| 4 | 12.3 | 35 |
| 5 | 12.9 | 6 |
| 6 | 13.3 | 52 |
| 7 | 14.1 | 16 |
| 8 | 15.3 | 29 |
| 9 | 16.2 | 71 |
| 10 | 16.6 | 85 |
| 11 | 17.1 | 18 |
| 12 | 17.6 | 31 |
| 13 | 18.5 | 16 |
| 14 | 20.0 | 73 |
| 15 | 21.1 | 7 |
| 16 | 22.4 | 65 |
| 17 | 23.2 | 28 |
| 18 | 23.9 | 18 |
| 19 | 24.7 | 28 |
| 20 | 26.6 | 77 |
| 21 | 28.0 | 21 |
| 22 | 31.1 | 6 |

DSC analysis was performed. FIG. 2 shows a DSC thermogram of the zwitterionic compound of Formula I Form I. The DSC analysis revealed an endotherm with onset at about 265° C., followed by an exotherm corresponding to decomposition.

TGA analysis was performed. FIG. 3 shows a TGA thermogram of the zwitterionic compound of Formula I Form I. The TGA analysis showed that solids lost about 0.9% weight below about 150° C.

Formula I Zwitterion Form II

Zwitterionic compound of Formula I Form II is an unsolvated form. It was obtained from crystallizations by dissolving Formula I zwitterion Form I in DMSO (4 volumes), followed by the addition of anti-solvent (40 volumes of IPAc, EtOAc, or MeCN) and stirring at room temperature. Formula I zwitterion Form II was also obtained after disproportionation of Formula I tromethamine salt in MeOH/water (0.4-0.6 water activity).

XRPD analysis was conducted. FIG. 4 shows an XRPD pattern of the zwitterionic compound of Formula I Form II. XRPD peaks were identified and are included in Table 2 below.

TABLE 2

| No. | Pos. [°2Th.] | Rel. Int. [%] |
|---|---|---|
| 1 | 7.3 | 51 |
| 2 | 12.5 | 8 |
| 3 | 13.6 | 6 |
| 4 | 14.5 | 36 |
| 5 | 15.7 | 14 |
| 6 | 17.0 | 5 |
| 7 | 17.5 | 18 |

TABLE 2-continued

| No. | Pos. [°2Th.] | Rel. Int. [%] |
|---|---|---|
| 8 | 18.1 | 73 |
| 9 | 20.2 | 19 |
| 10 | 21.1 | 21 |
| 11 | 21.7 | 22 |
| 12 | 22.6 | 10 |
| 13 | 23.2 | 7 |
| 14 | 24.1 | 100 |
| 15 | 25.0 | 34 |
| 16 | 25.4 | 34 |
| 17 | 26.0 | 8 |
| 18 | 27.6 | 11 |
| 19 | 28.2 | 5 |
| 20 | 29.1 | 33 |
| 21 | 29.4 | 16 |

DSC analysis was performed. FIG. 5 shows a DSC thermogram of the zwitterionic compound of Formula I Form II. As is shown, DSC afforded small endotherm with onset at about 135° C. and endotherm with onset at about 271° C., followed by exotherm corresponding to decomposition.

TGA analysis was performed. FIG. 6 shows a TGA thermogram of the zwitterionic compound of Formula I Form II. As indicated, solids lost about 0.7% weight below about 100° C. and about 1.1% weight at about 100-150° C.

Formula I Zwitterion Hydrate

Formula I zwitterion hydrate is a crystalline form. It was obtained from the slurry of Formula I tromethamine salt in water due to disproportionation of the salt.

XRPD analysis was conducted. FIG. 7 shows an XRPD pattern of the zwitterionic compound of Formula I hydrate. XRPD peaks were identified and are included in Table 3 below.

TABLE 3

| No. | Pos. [°2Th.] | Rel. Int. [%] |
|---|---|---|
| 1 | 10.2 | 47.6 |
| 2 | 10.8 | 15.7 |
| 3 | 12.1 | 13.8 |
| 4 | 14.5 | 12.1 |
| 5 | 15.4 | 53.1 |
| 6 | 16.4 | 31.6 |
| 7 | 17.9 | 28.4 |
| 8 | 19.7 | 63.0 |
| 9 | 20.5 | 19.2 |
| 10 | 21.7 | 40.4 |
| 11 | 23.1 | 100.0 |
| 12 | 25.0 | 46.9 |
| 13 | 25.8 | 56.1 |
| 14 | 26.4 | 51.0 |
| 15 | 27.9 | 19.4 |
| 16 | 30.7 | 23.0 |
| 17 | 34.0 | 20.3 |

DSC analysis was performed. FIG. 8 shows a DSC thermogram of the zwitterionic compound of Formula I hydrate. As can be seen, DSC afforded broad endotherm with onset at about 46° C., small exotherm with onset at about 157° C. and melting endotherm with onset about 268° C., followed by exotherm corresponding to decomposition.

TGA analysis was performed. FIG. 9 shows a TGA thermogram of the zwitterionic compound of Formula I hydrate. As is shown, solids lost about 2.4% weight below about 100° C. and about 1.1% weight at about 100-250° C.

Formula I Zwitterion Amorphous

Amorphous zwitterionic compound of Formula I was first obtained by ball milling Formula I (about 1.1 g) in stainless steel chamber containing stainless steel ball for about 5 min. Amorphous zwitterionic Formula I was also obtained using the following procedure: A reactor was charged with Formula I (1.0 equiv), water (20.0 V), and 50% NaOH (1.5 equiv), followed by stirring until dissolution was achieved. Then the reaction mixture was polish filtered, acidified with 1.0 M HCl (1.5 equiv), stirred for about 20 seconds, and filtered to isolate the resulting solids. Solids were washed with water (20V) and transferred to a nitrogen filled glove bag, followed by drying under nitrogen overnight.

XRPD analysis was conducted. FIG. 10 shows an XRPD pattern of the amorphous zwitterionic compound of Formula I.

Formula I Tromethamine Salt Form I

Formula I tromethamine salt (tris salt) Form I was obtained by drying Formula I tromethamine salt ethanol solvate (at 0% RH and 25° C.). Formula I tromethamine salt Form I was also obtained by drying of Formula I tromethamine salt hydrate I under vacuum at 50° C. Formula I tromethamine salt Form I was also obtained from drying Formula I tromethamine salt methanol solvate under vacuum at 50° C.

FIG. 11 shows an XRPD pattern of Formula I tromethamine salt Form I. XRPD peaks were identified as noted in Table 4 below.

TABLE 4

| No. | Pos. [°2Th.] | Rel. Int. [%] |
|---|---|---|
| 1 | 5.2 | 12 |
| 2 | 10.9 | 27 |
| 3 | 13.0 | 18 |
| 4 | 13.3 | 21 |
| 5 | 13.8 | 12 |
| 6 | 14.3 | 15 |
| 7 | 15.3 | 20 |
| 8 | 16.7 | 71 |
| 9 | 16.8 | 100 |
| 10 | 17.2 | 14 |
| 11 | 17.4 | 17 |
| 12 | 17.7 | 14 |
| 13 | 18.3 | 11 |
| 14 | 19.2 | 25 |
| 15 | 20.1 | 38 |
| 16 | 20.4 | 26 |
| 17 | 21.0 | 44 |
| 18 | 21.8 | 89 |
| 19 | 22.3 | 30 |
| 20 | 23.0 | 14 |
| 21 | 23.3 | 13 |
| 22 | 24.3 | 40 |
| 23 | 24.5 | 38 |
| 24 | 25.4 | 53 |
| 25 | 25.6 | 92 |
| 26 | 26.6 | 13 |
| 27 | 27.4 | 32 |
| 28 | 27.9 | 11 |
| 29 | 29.6 | 16 |
| 30 | 31.5 | 12 |
| 31 | 33.9 | 16 |

DSC analysis was performed. FIG. 12 shows a DSC thermogram of the Formula I tromethamine salt Form I. The melting onset is at about 129° C., followed by exotherm with onset at about 150° C. and decomposition.

TGA analysis was performed. FIG. 13 shows a TGA thermogram of the Formula I tromethamine salt Form I. As can be seen, the solids did not show any weight loss below about 150° C. prior to decomposition.

Formula I Tromethamine Salt Form II

Formula I tromethamine salt Form II was obtained by dehydrating Formula I tromethamine salt hydrate II at about 80-120° C., as well as after dehydration at 0% RH at 25° C. Formula I tromethamine salt Form II was also obtained by vacuum drying Formula I methanol solvate I, Formula I methanol solvate II, or Formula I methanol solvate III at about 50-80° C. Formula I tromethamine salt Form II is unsolvated form, which rapidly absorbs moisture at about >20% RH and converts to Formula I tromethamine salt hydrate II.

XRPD analysis was conducted. FIG. 14 shows an XRPD pattern of Formula I tromethamine salt Form II. XRPD peaks were identified as noted in Table 5 below.

TABLE 5

| No. | Pos. [°2Th.] | Rel. Int. [%] |
|---|---|---|
| 1 | 9.2 | 30 |
| 2 | 10.6 | 11 |
| 3 | 11.3 | 9 |
| 4 | 12.9 | 48 |
| 5 | 13.1 | 39 |
| 6 | 13.5 | 10 |
| 7 | 13.8 | 7 |
| 8 | 14.8 | 14 |
| 9 | 15.9 | 72 |
| 10 | 16.5 | 28 |
| 11 | 17.3 | 100 |
| 12 | 18.2 | 5 |
| 13 | 20.4 | 61 |
| 14 | 21.3 | 19 |
| 15 | 21.7 | 19 |
| 16 | 22.1 | 18 |
| 17 | 22.4 | 20 |
| 18 | 22.7 | 13 |
| 19 | 23.2 | 10 |
| 20 | 23.7 | 7 |
| 21 | 24.5 | 25 |
| 22 | 25.1 | 44 |
| 23 | 25.4 | 8 |
| 24 | 26.2 | 16 |
| 25 | 27.1 | 7 |
| 26 | 27.7 | 13 |
| 27 | 28.4 | 21 |

Formula I Tromethamine Salt Hydrate I

Formula I tromethamine salt hydrate I was obtained by equilibrating of Formula I tromethamine salt ethanol solvate at ambient conditions and at about 98% RH at about 20-25° C. Formula I tromethamine salt hydrate I was also obtained by equilibrating of Formula I tromethamine salt methanol solvate at ambient conditions and at about 98% RH at about 20-25° C. Formula I tromethamine salt hydrate I was also obtained by equilibrating of Formula I tromethamine salt form I at about 80-98% RH at about 20-25° C.

XRPD analysis was conducted. FIG. 15 shows an XRPD pattern of the Formula I tromethamine salt hydrate I. XRPD peaks were identified and are included in Table 6 below.

TABLE 6

| No. | Pos. [°2Th.] | Rel. Int. [%] |
|---|---|---|
| 1 | 5.9 | 13 |
| 2 | 7.1 | 12 |
| 3 | 9.8 | 13 |
| 4 | 12.7 | 19 |
| 5 | 13.9 | 67 |
| 6 | 14.1 | 20 |
| 7 | 14.5 | 16 |
| 8 | 15.2 | 14 |
| 9 | 16.0 | 11 |
| 10 | 17.4 | 39 |
| 11 | 17.8 | 21 |
| 12 | 18.7 | 13 |

TABLE 6-continued

| No. | Pos. [°2Th.] | Rel. Int. [%] |
|---|---|---|
| 13 | 20.0 | 47 |
| 14 | 20.3 | 62 |
| 15 | 20.7 | 11 |
| 16 | 21.9 | 37 |
| 17 | 22.7 | 35 |
| 18 | 23.3 | 100 |
| 19 | 24.2 | 31 |
| 20 | 24.9 | 23 |
| 21 | 25.3 | 53 |
| 22 | 26.3 | 16 |
| 23 | 26.7 | 16 |
| 24 | 27.2 | 23 |
| 25 | 27.8 | 38 |
| 26 | 28.5 | 31 |
| 27 | 29.1 | 33 |
| 28 | 30.6 | 26 |
| 29 | 32.3 | 15 |
| 30 | 35.5 | 22 |

DSC analysis was performed. FIG. 16 shows a DSC thermogram of the Formula I tromethamine salt hydrate I. The broad endotherm with onset at about 74° C. corresponds to the loss of water. The melting onset is at about 123° C., followed by exotherm with onset at about 145° C. and decomposition. After dehydration at about 100° C., Formula I tromethamine salt hydrate I converts to an unsolvated Formula I tromethamine salt Form I.

TGA analysis was performed. FIG. 17 shows a TGA thermogram of the Formula I tromethamine salt hydrate I. The solids lost about 6.2% weight below about 100° C., which corresponds to about 2.4 equivalents of water.

Formula I Tromethamine Salt Hydrate II

Formula I tromethamine salt hydrate II was obtained by slurrying Formula I tromethamine salt ethanol solvate and Formula I tromethamine salt Form I in acetonitrile at ambient conditions by moisture adsorption from the air (at >10% RH). Formula I tromethamine salt hydrate II was also obtained by equilibrating of Formula I tromethamine salt form II at ambient conditions.

XRPD analysis was conducted. FIG. 18 shows an XRPD pattern of the Formula I tromethamine salt hydrate II. XRPD peaks were identified and are included in Table 7 below.

TABLE 7

| No. | Pos. [°2Th.] | Rel. Int. [%] |
|---|---|---|
| 1 | 9.0 | 21 |
| 2 | 10.5 | 58 |
| 3 | 13.1 | 12 |
| 4 | 13.4 | 21 |
| 5 | 15.1 | 10 |
| 6 | 16.1 | 100 |
| 7 | 16.4 | 19 |
| 8 | 17.2 | 59 |
| 9 | 18.8 | 56 |
| 10 | 20.1 | 41 |
| 11 | 20.4 | 12 |
| 12 | 20.9 | 17 |
| 13 | 21.5 | 91 |
| 14 | 22.1 | 11 |
| 15 | 22.7 | 30 |
| 16 | 23.4 | 38 |
| 17 | 23.8 | 32 |
| 18 | 24.5 | 22 |
| 19 | 24.9 | 52 |
| 20 | 25.6 | 11 |
| 21 | 26.0 | 18 |
| 22 | 26.2 | 28 |
| 23 | 26.9 | 60 |
| 24 | 27.5 | 13 |

TABLE 7-continued

| No. | Pos. [°2Th.] | Rel. Int. [%] |
|---|---|---|
| 25 | 28.0 | 17 |
| 26 | 28.5 | 22 |

DSC analysis was performed. FIG. 19 shows a DSC thermogram of the Formula I tromethamine salt hydrate II. The broad endotherm with onset at about 48° C. corresponds to the loss of water. The melting onset is at about 130° C., followed by exotherm and decomposition. After dehydration at about 80° C., Formula I tromethamine salt hydrate II converts to an unsolvated form, Formula I tromethamine salt Form II.

TGA analysis was performed. FIG. 20 shows a TGA thermogram of the Formula I tromethamine salt hydrate II. The solids lost about 4.3% weight below about 100° C., which corresponds to about 1.8 equivalents of water.

Formula I Tromethamine Salt Hydrate III

Formula I tromethamine salt hydrate III was obtained by charging a 20 mL vial with 220 mg of Formula I and about 1.1 eq Tris (50 mg) and 6 mL of MeCN/10% water. The slurry was stirred at about 50° C. overnight, followed by stirring at room temperature for about 3 days. Isolated solids were washed with 2 mL acetonitrile and dried under vacuum at about 40° C. overnight.

XRPD analysis was conducted. FIG. 21 shows an XRPD pattern of the Formula I tromethamine salt hydrate III. XRPD peaks were identified and are included in Table 8 below.

TABLE 8

| No. | Pos. [°2Th.] | Rel. Int. [%] |
|---|---|---|
| 1 | 9.1 | 27 |
| 2 | 10.2 | 100 |
| 3 | 11.2 | 17 |
| 4 | 12.3 | 18 |
| 5 | 15.0 | 29 |
| 6 | 15.2 | 35 |
| 7 | 15.5 | 19 |
| 8 | 16.0 | 60 |
| 9 | 16.3 | 21 |
| 10 | 16.9 | 23 |
| 11 | 18.0 | 15 |
| 12 | 18.3 | 18 |
| 13 | 19.0 | 32 |
| 14 | 19.2 | 24 |
| 15 | 20.0 | 26 |
| 16 | 21.6 | 43 |
| 17 | 22.6 | 17 |
| 18 | 23.2 | 50 |
| 19 | 23.8 | 71 |
| 20 | 24.1 | 55 |
| 21 | 24.3 | 20 |
| 22 | 24.7 | 46 |
| 23 | 26.1 | 95 |
| 24 | 26.7 | 61 |
| 25 | 28.5 | 19 |
| 26 | 28.8 | 30 |

DSC analysis was performed. FIG. 22 shows a DSC thermogram of the Formula I tromethamine salt hydrate III. The broad endotherm at about 20-110° C. with onset at about 82° C. corresponds to the loss of water. The melting onset is at about 120° C., followed by exotherm with onset at about 154° C. and decomposition.

TGA analysis was performed. FIG. 23 shows a TGA thermogram of the Formula I tromethamine salt hydrate III. The solids lost about 4.8% weight below about 125° C., which corresponds to about 2 equivalents of water.

Formula I Tromethamine Salt Hydrate IV

Formula I tromethamine salt hydrate IV was obtained by combining Formula I tromethamine salt Form I with acetone, DCM and toluene and equilibrating the solids obtained at ambient conditions.

XRPD analysis was conducted. FIG. 24 shows an XRPD pattern of the Formula I tromethamine salt hydrate IV. XRPD peaks were identified and are included in Table 9 below.

TABLE 9

| No. | Pos. [°2Th.] | Rel. Int. [%] |
|---|---|---|
| 1 | 11.4 | 10 |
| 2 | 13.7 | 17 |
| 3 | 14.2 | 27 |
| 4 | 15.3 | 27 |
| 5 | 15.8 | 18 |
| 6 | 16.9 | 69 |
| 7 | 19.0 | 28 |
| 8 | 19.4 | 30 |
| 9 | 19.8 | 21 |
| 10 | 20.0 | 24 |
| 11 | 20.5 | 38 |
| 12 | 20.9 | 13 |
| 13 | 21.7 | 26 |
| 14 | 21.9 | 36 |
| 15 | 22.8 | 100 |
| 16 | 23.3 | 16 |
| 17 | 23.8 | 14 |
| 18 | 24.4 | 10 |
| 19 | 25.0 | 12 |
| 20 | 25.5 | 10 |
| 21 | 27.1 | 11 |
| 22 | 30.0 | 12 |
| 23 | 31.1 | 22 |
| 24 | 34.4 | 11 |

DSC analysis was performed. FIG. 25 shows a DSC thermogram of the Formula I tromethamine salt hydrate IV. The broad endotherm at about 20-90° C. with onset at about 48° C. corresponds to the loss of water, followed by small endotherm with onset at about 117° C. The melting onset is at about 148° C., followed by exotherm and decomposition.

TGA analysis was performed. FIG. 26 shows a TGA thermogram of the Formula I tromethamine salt hydrate IV. The solids lost about 2.6% weight below about 100° C., which corresponds to about 1 equivalent of water.

Formula I Tromethamine Salt Methanol Solvate I

Formula I tromethamine salt methanol solvate I was obtained by charging a 100 mL jacketed reactor with 6 g of Formula I, about 1.1 equivalent Tris (1.36 g) and 60 mL of MeOH. The slurry was stirred at about 50° C. overnight to afford very large particles of MeOH solvate I, which was confirmed by single crystal x-ray analysis. Single crystal x-ray analysis showed two molecules of methanol per one molecule of Formula I tromethamine salt. Formula I tromethamine salt methanol solvate I loses methanol very rapidly at ambient conditions and converts to tromethamine salt methanol solvate III, which further converts to tromethamine salt hydrate I. Formula I tromethamine salt methanol solvate I also converted to methanol solvate II in THF and MTBE slurries. Formula I tromethamine salt methanol solvate I was also obtained by equilibration of Formula I tromethamine salt form I, Formula I tromethamine salt hydrate I, Formula I tromethamine salt hydrate II, Formula I tromethamine salt hydrate III, Formula I tromethamine salt hydrate IV, Formula I tromethamine salt methanol solvate II, Formula I tromethamine salt methanol solvate III, Formula I tromethamine salt ethanol solvate, and Formula I tromethamine salt MTBE solvate in up to 10% water/MeOH mixtures at ambient conditions.

XRPD analysis was conducted. FIG. 27 shows an XRPD pattern of the Formula I tromethamine salt methanol solvate I. XRPD peaks were identified and are included in Table 10 below.

TABLE 10

| No. | Pos. [°2Th.] | Rel. Int. [%] |
|---|---|---|
| 1 | 7.0 | 10 |
| 2 | 10.8 | 100 |
| 3 | 13.0 | 44 |
| 4 | 13.3 | 93 |
| 5 | 13.9 | 16 |
| 6 | 14.5 | 31 |
| 7 | 19.5 | 15 |
| 8 | 20.0 | 50 |
| 9 | 21.4 | 49 |
| 10 | 22.3 | 73 |
| 11 | 22.9 | 14 |
| 12 | 24.1 | 14 |
| 13 | 27.6 | 12 |
| 14 | 30.1 | 13 |
| 15 | 30.7 | 10 |
| 16 | 32.2 | 19 |
| 17 | 32.7 | 16 |

Formula I Tromethamine Salt Methanol Solvate II

Formula I tromethamine salt methanol solvate II was obtained from the slurry of Formula I tromethamine MeOH solvate I in THF, as described above. It was also obtained from the Formula I tromethamine salt formation in MeOH/MTBE and MeOH/5% water/MTBE.

XRPD analysis was conducted. FIG. 28 shows an XRPD pattern of the Formula I tromethamine salt methanol solvate II. XRPD peaks were identified and are included in Table 11 below.

TABLE 11

| No. | Pos. [°2Th.] | Rel. Int. [%] |
|---|---|---|
| 1 | 5.4 | 40 |
| 2 | 6.9 | 21 |
| 3 | 10.7 | 94 |
| 4 | 12.3 | 21 |
| 5 | 12.9 | 100 |
| 6 | 13.7 | 34 |
| 7 | 14.3 | 48 |
| 8 | 15.9 | 23 |
| 9 | 16.8 | 19 |
| 10 | 17.4 | 17 |
| 11 | 17.8 | 24 |
| 12 | 18.7 | 19 |
| 13 | 19.0 | 14 |
| 14 | 20.3 | 27 |
| 15 | 21.2 | 62 |
| 16 | 21.6 | 69 |
| 17 | 22.3 | 36 |
| 18 | 22.7 | 62 |
| 19 | 23.2 | 27 |
| 20 | 23.7 | 27 |
| 21 | 24.0 | 22 |
| 22 | 24.8 | 15 |
| 23 | 25.3 | 17 |
| 24 | 26.2 | 30 |
| 25 | 26.6 | 50 |
| 26 | 28.4 | 16 |
| 27 | 28.9 | 16 |
| 28 | 30.4 | 15 |

Formula I Tromethamine Salt Methanol Solvate III

Formula I tromethamine salt methanol solvate III was obtained by equilibrating Formula I tromethamine salt methanol solvate I for about 5-10 minutes at ambient conditions. It was also obtained by equilibrating Formula I tromethamine salt methanol solvate II for about 5-10 min at ambient conditions. Tromethamine methanol solvate III fully converted to Formula I tromethamine salt hydrate I at ambient conditions within about 1 hour (depending on % RH).

XRPD analysis was conducted. FIG. 29 shows an XRPD pattern of the Formula I tromethamine salt methanol solvate III. XRPD peaks were identified and are included in Table 12 below.

TABLE 12

| No. | Pos. [°2Th.] | Rel. Int. [%] |
|---|---|---|
| 1 | 5.6 | 11 |
| 2 | 7.1 | 13 |
| 3 | 12.6 | 33 |
| 4 | 13.3 | 35 |
| 5 | 13.8 | 84 |
| 6 | 14.3 | 26 |
| 7 | 15.1 | 19 |
| 8 | 15.9 | 25 |
| 9 | 17.4 | 83 |
| 10 | 17.7 | 23 |
| 11 | 19.2 | 30 |
| 12 | 19.9 | 47 |
| 13 | 20.2 | 95 |
| 14 | 21.8 | 33 |
| 15 | 22.6 | 56 |
| 16 | 23.2 | 100 |
| 17 | 24.2 | 75 |
| 18 | 24.8 | 52 |
| 19 | 25.2 | 73 |
| 20 | 26.1 | 16 |
| 21 | 26.7 | 28 |
| 22 | 27.1 | 30 |
| 23 | 27.6 | 49 |
| 24 | 28.4 | 52 |
| 25 | 29.1 | 58 |
| 26 | 30.4 | 26 |
| 27 | 30.9 | 13 |
| 28 | 32.0 | 17 |
| 29 | 32.7 | 19 |
| 30 | 35.4 | 27 |

DSC analysis was performed. FIG. 30 shows a DSC thermogram of the Formula I tromethamine salt methanol solvate III. Two endotherms with onsets at about 80 and 110° C. were observed. These may correspond to the loss of methanol and water. The melting onset is at about 127° C., followed by exotherm with onset at about 145° C. and decomposition. After the desolvation, Formula I tromethamine methanol solvate III converted to an unsolvated form-Formula I tromethamine salt Form I.

TGA analysis was performed. FIG. 31 shows a TGA thermogram of the Formula I tromethamine salt methanol solvate III. The solids lost about 6.0% weight below about 120° C. Karl Fischer (KF) analysis showed about 1.1% water. $^1$H NMR analysis was performed, and the resultant spectrum showed about 1.1 equivalent of methanol which corresponds to about 4.7 wt %.

Formula I Tromethamine Salt MTBE Solvate

Formula I tromethamine salt MTBE solvate was obtained by slurrying Formula I tromethamine salt Form I (50 mg) in MTBE (1 mL) at 50° C. The wet solids were analyzed by XRPD. The MTBE solvate converted to disordered material at ambient conditions and after vacuum drying at 50° C.

XRPD analysis was conducted. FIG. 32 shows an XRPD pattern of the Formula I tromethamine salt MTBE solvate. XRPD peaks were identified and are included in Table 13 below.

TABLE 13

| No. | Pos. [°2Th.] | Rel. Int. [%] |
|---|---|---|
| 1 | 5.8 | 61 |
| 2 | 11.4 | 37 |
| 3 | 11.8 | 14 |
| 4 | 12.7 | 30 |
| 5 | 14.5 | 25 |
| 6 | 15.6 | 30 |
| 7 | 16.9 | 10 |
| 8 | 18.1 | 34 |
| 9 | 18.4 | 40 |
| 10 | 19.0 | 44 |
| 11 | 19.7 | 36 |
| 12 | 20.4 | 100 |
| 13 | 21.1 | 29 |
| 14 | 22.1 | 35 |
| 15 | 23.4 | 41 |
| 16 | 24.7 | 37 |
| 17 | 25.9 | 38 |
| 18 | 26.7 | 16 |
| 19 | 29.3 | 11 |
| 20 | 30.3 | 13 |

DSC analysis was performed. FIG. 33 shows a DSC thermogram of the Formula I tromethamine salt MTBE solvate. The broad endotherm with onset at about 85° C. corresponds to the loss of solvent. The melting onset is at about 147° C., followed by exotherm and decomposition.

TGA analysis was performed. FIG. 34 shows a TGA thermogram of the Formula I tromethamine salt MTBE solvate. The solids showed about 6.2% weight loss below about 120° C. corresponding to about 0.5 equivalents of MTBE.

Formula I Tromethamine Salt Amorphous

Formula I tromethamine salt amorphous form was obtained by Formula I tromethamine salt (about 0.89 mg) in about 5 mL of THF at high temperature (about 65° C.), followed by fast evaporation on rotary evaporator at about 40° C. (bath temperature) to obtain foam, and then drying under vacuum at about 50° C. for about 2 hours.

XRPD analysis was conducted. FIG. 35 shows an XRPD pattern of the Formula I tromethamine salt amorphous form.

Formula I Tromethamine Salt Ethanol Solvate

Formula I tromethamine salt ethanol solvate was obtained by charging a 4 mL vial with 52.5 mg of zwitterionic Formula I, about 1.1 equivalent Tris (12 mg) and 1 mL of ethanol. The slurry was stirred at about 50° C. for about 5 hours and at room temperature overnight. The sample of wet solids was analyzed by XRPD and afforded unique XRPD pattern of ethanol solvate, which converted to Formula I tromethamine salt hydrate I at ambient conditions.

XRPD analysis was conducted. FIG. 36 shows an XRPD pattern of the Formula I tromethamine salt ethanol solvate. XRPD peaks were obtained and are depicted in Table 14 below.

TABLE 14

| No. | Pos. [°2Th.] | Rel. Int. [%] |
|---|---|---|
| 1 | 5.3 | 53 |
| 2 | 10.7 | 34 |
| 3 | 12.1 | 52 |
| 4 | 12.9 | 93 |
| 5 | 13.7 | 39 |
| 6 | 14.3 | 39 |
| 7 | 15.1 | 22 |
| 8 | 15.8 | 22 |
| 9 | 16.6 | 21 |
| 10 | 16.9 | 21 |

TABLE 14-continued

| No. | Pos. [°2Th.] | Rel. Int. [%] |
|---|---|---|
| 11 | 18.0 | 31 |
| 12 | 18.8 | 40 |
| 13 | 20.4 | 22 |
| 14 | 21.0 | 83 |
| 15 | 21.6 | 100 |
| 16 | 22.3 | 97 |
| 17 | 22.6 | 67 |
| 18 | 23.2 | 22 |
| 19 | 23.8 | 56 |
| 20 | 24.7 | 22 |
| 21 | 25.3 | 23 |
| 22 | 26.1 | 79 |
| 23 | 26.3 | 88 |
| 24 | 26.7 | 31 |
| 25 | 27.0 | 24 |
| 26 | 27.8 | 31 |
| 27 | 28.2 | 21 |
| 28 | 28.7 | 19 |
| 29 | 29.9 | 34 |
| 30 | 36.9 | 21 |

Formula Ip-TSA Salt Form I

Formula I p-TSA salt Form I was obtained by dissolving 52.7 mg Formula I Form I with 1.1 eq. of p-toluenesulfonic acid monohydrate (18.8 mg) in 1 mL EtOH at 50° C., followed by cooling to room temperature and stirring at this temperature for about 16 hours. Formula I p-TSA salt Form I was also obtained using a similar procedure in following solvents: THF, MeTHF, MeCN, IPAc, IPA, EtOAc. Formula I p-TSA salt Form I was also made from Formula I Form I in MeCN/water or EtOH/water mixtures (9:1 or 8:2) with NaOH (1.1 equiv) and p-toluenesulfonic acid monohydrate (2.2 equiv) or from Formula I tromethamine salt Form I in MeCN/water or EtOH/water mixtures (9:1 or 8:2) with NaOH (1.1 equiv) and p-toluenesulfonic acid monohydrate (3.2 equiv). Formula Ip-TSA salt Form I was also prepared by slurrying Formula I p-TSA salt hydrate in MeCN at 20, 35, 55 and 70° C.

XRPD analysis was conducted. FIG. 37 shows an XRPD pattern of the Formula I p-TSA salt Form I. XRPD peaks were identified and are included in Table 15 below.

TABLE 15

| No. | Pos. [°2Th.] | Rel. Int. [%] |
|---|---|---|
| 1 | 3.0 | 38.3 |
| 2 | 9.0 | 14.1 |
| 3 | 11.8 | 23.2 |
| 4 | 12.0 | 29.4 |
| 5 | 13.1 | 28.6 |
| 6 | 15.0 | 32.9 |
| 7 | 16.6 | 100.0 |
| 8 | 17.5 | 55.0 |
| 9 | 18.7 | 21.0 |
| 10 | 20.9 | 78.8 |
| 11 | 21.5 | 54.7 |
| 12 | 22.3 | 86.5 |
| 13 | 23.4 | 91.1 |
| 14 | 23.5 | 78.6 |
| 15 | 23.7 | 43.1 |
| 16 | 24.0 | 19.8 |
| 17 | 24.3 | 28.9 |
| 18 | 25.0 | 28.1 |
| 19 | 26.0 | 49.7 |
| 20 | 26.4 | 25.3 |
| 21 | 26.7 | 23.1 |
| 22 | 28.0 | 38.6 |
| 23 | 28.9 | 18.3 |
| 24 | 33.7 | 18.2 |

DSC analysis was performed. FIG. 38 shows a DSC thermogram of the Formula I p-TSA salt Form I. DSC afforded melting endotherm with onset at about 198° C., followed by exotherm with onset at about 208° C. and decomposition.

TGA analysis was performed. FIG. 39 shows a TGA thermogram of the Formula I p-TSA salt Form I. The solids lost about 0.6% weight below about 170° C. and about 3.0% weight at about 170-235° C., which corresponds to the loss of water due to decomposition Formula Ip-TSA Salt Form II Formula I p-TSA salt Form II was obtained by stirring of Formula I p-TSA salt Form I for 3 weeks at room temperature in the following solvents: MeCN, MeOH, EtOH, IPA, acetone, MEK, MIBK, THF, MeTHF, EtOAc, IPAc, MTBE, toluene, and heptane XRPD analysis was conducted. FIG. 40 shows an XRPD pattern of the Formula I p-TSA salt Form II. XRPD peaks were identified and are included in Table 16 below.

TABLE 16

| No. | Pos. [°2Th.] | Rel. Int. [%] |
|---|---|---|
| 1 | 3.0 | 41.3 |
| 2 | 11.8 | 49.8 |
| 3 | 14.8 | 61.7 |
| 4 | 16.5 | 51.4 |
| 5 | 16.8 | 54.6 |
| 6 | 17.5 | 40.8 |
| 7 | 18.7 | 20.0 |
| 8 | 20.8 | 66.7 |
| 9 | 21.6 | 41.3 |
| 10 | 22.1 | 54.1 |
| 11 | 22.4 | 19.3 |
| 12 | 23.2 | 100.0 |
| 13 | 23.8 | 70.7 |
| 14 | 24.4 | 23.4 |
| 15 | 26.1 | 17.8 |
| 16 | 26.5 | 18.2 |
| 17 | 26.8 | 29.6 |
| 18 | 27.9 | 19.3 |
| 19 | 29.0 | 24.8 |

DSC analysis was performed. FIG. 41 shows a DSC thermogram of the Formula I p-TSA salt Form II. DSC afforded broad exotherm with onset at about 155° C., melting endotherm with onset at about 202° C., followed by exotherm with onset at about 209° C. and decomposition.

TGA analysis was performed. FIG. 42 shows a TGA thermogram of the Formula I p-TSA salt Form II. The solids lost about 0.7% weight below about 175° C. and about 3.0% weight at about 175-238° C., which corresponds to the loss of water due to decomposition.

Formula Ip-TSA Salt Form III

Formula I p-TSA salt Form III was obtained by stirring of Formula I p-TSA salt Form I obtained after stirring of Formula I p-TSA salt Form I for about 3 weeks at room temperature in the following solvents: EtOAc, toluene, and in MeCN/water (with 0.6, 0.7, and 0.95 water activity).

XRPD analysis was conducted. FIG. 43 shows an XRPD pattern of the Formula I p-TSA salt Form III. XRPD peaks were identified and are included in Table 17 below.

TABLE 17

| No. | Pos. [°2Th.] | Rel. Int. [%] |
|---|---|---|
| 1 | 11.9 | 22.6 |
| 2 | 12.3 | 19.0 |
| 3 | 13.5 | 15.1 |

TABLE 17-continued

| No. | Pos. [°2Th.] | Rel. Int. [%] |
|---|---|---|
| 4 | 14.8 | 46.5 |
| 5 | 15.0 | 18.2 |
| 6 | 16.6 | 48.8 |
| 7 | 16.9 | 67.8 |
| 8 | 17.6 | 54.6 |
| 9 | 18.8 | 24.0 |
| 10 | 20.8 | 51.4 |
| 11 | 21.6 | 32.0 |
| 12 | 22.1 | 55.5 |
| 13 | 22.5 | 26.7 |
| 14 | 23.2 | 100.0 |
| 15 | 23.7 | 34.8 |
| 16 | 24.0 | 31.1 |
| 17 | 24.6 | 32.7 |
| 18 | 26.2 | 21.6 |
| 19 | 26.6 | 28.8 |
| 20 | 28.0 | 26.4 |
| 21 | 29.1 | 24.8 |
| 22 | 34.0 | 16.0 |
| 23 | 35.7 | 19.2 |

DSC analysis was performed. FIG. 44 shows a DSC thermogram of the Formula I p-TSA salt Form III. DSC afforded broad exotherm with onset at about 156° C., melting endotherm with onset at about 205° C., followed by immediate exotherm and decomposition.

TGA analysis was performed. FIG. 45 shows a TGA thermogram of the Formula I p-TSA salt Form III. The solids lost about 0.5% weight below about 175° C. and about 2.5% weight at about 175-235° C., which corresponds to the loss of water due to decomposition Formula I p-TSA Salt Hydrate Formula I p-TSA salt hydrate was obtained by stirring Formula I tromethamine salt in water with 2 equivalents of p-toluenesulfonic acid monohydrate at 50° C. and at room temperature. Formula I p-TSA salt hydrate was also obtained from competition slurries of Formula I p-TSA salt Form I and hydrate in MeCN/water mixtures at 70° C. with >0.4 water activity. Formula I p-TSA salt hydrate was also prepared from Formula I Form I with or without p-TSA salt hydrate seeds in MeCN/water mixtures (9:1 or 8:2) with NaOH (1.1 equiv) andp-toluenesulfonic acid monohydrate (2.2 equiv) or from Formula I tromethamine salt Form I in MeCN/water mixtures (9:1 or 8:2) with NaOH (1.1 equiv) and p-toluenesulfonic acid monohydrate (3.2 equiv).

XRPD analysis was conducted. FIG. 46 shows an XRPD pattern of the Formula I p-TSA salt hydrate. XRPD peaks were identified and are included in Table 18 below.

TABLE 18

| No. | Pos. [°2Th.] | Rel. Int. [%] |
|---|---|---|
| 1 | 6.6 | 43.5 |
| 2 | 8.6 | 23.4 |
| 3 | 11.3 | 19.7 |
| 4 | 13.3 | 26.0 |
| 5 | 15.6 | 24.0 |
| 6 | 17.1 | 43.2 |
| 7 | 17.7 | 32.0 |
| 8 | 18.4 | 20.2 |
| 9 | 19.8 | 100.0 |
| 10 | 20.7 | 29.4 |
| 11 | 21.7 | 22.4 |
| 12 | 22.5 | 85.4 |
| 13 | 23.7 | 31.1 |
| 14 | 23.9 | 20.9 |
| 15 | 24.7 | 19.9 |
| 16 | 24.9 | 28.6 |
| 17 | 25.5 | 65.0 |

TABLE 18-continued

| No. | Pos. [°2Th.] | Rel. Int. [%] |
|---|---|---|
| 18 | 25.7 | 57.9 |
| 19 | 26.9 | 46.7 |
| 20 | 28.4 | 93.0 |
| 21 | 29.7 | 26.9 |
| 22 | 31.7 | 20.8 |
| 23 | 32.0 | 19.0 |
| 24 | 33.1 | 20.2 |

DSC analysis was performed. FIG. 47 shows a DSC thermogram of the Formula I p-TSA salt hydrate. DSC afforded broad endotherm with onset at about 144° C., followed by broad melting endotherm with onset at about 192° C., exotherm with onset at about 214° C., and decomposition.

TGA analysis was performed. FIG. 48 shows a TGA thermogram of the Formula I p-TSA salt hydrate. The solids lost about 3.6% weight below about 166° C. and about 2.4% weight at about 166-236° C., which corresponds to the loss of water due to decomposition.

Unless otherwise defined, all technical and scientific terms used herein have the same meaning as commonly understood by one of ordinary skill in the art to which this disclosure belongs.

Thus, it should be understood that although the present disclosure has been specifically disclosed by preferred embodiments and optional features, modification, improvement and variation of the disclosures embodied therein herein disclosed may be resorted to by those skilled in the art, and that such modifications, improvements and variations are considered to be within the scope of this disclosure. The materials, methods, and examples provided here are representative of preferred embodiments, are exemplary, and are not intended as limitations on the scope of the disclosure.

The disclosure has been described broadly and generically herein. Each of the narrower species and subgeneric groupings falling within the generic disclosure also form part of the disclosure. This includes the generic description of the disclosure with a proviso or negative limitation removing any subject matter from the genus, regardless of whether or not the excised material is specifically recited herein.

In addition, where features or aspects of the disclosure are described in terms of Markush groups, those skilled in the art will recognize that the disclosure is also thereby described in terms of any individual member or subgroup of members of the Markush group.

It is to be understood that while the disclosure has been described in conjunction with the above embodiments, that the foregoing description and examples are intended to illustrate and not limit the scope of the disclosure. Other aspects, advantages and modifications within the scope of the disclosure will be apparent to those skilled in the art to which the disclosure pertains.

What is claimed is:

1. A solid form tromethamine salt of a compound, having the following formula:

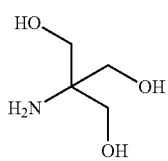

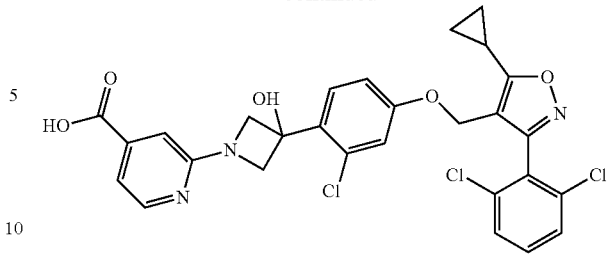

wherein the solid form is tromethamine salt Form I characterized by an X-ray diffraction pattern having 2θ-reflections at 5.2, 16.8, and 25.6 degrees 2θ, plus or minus 0.2 degrees 2θ.

2. The solid form of claim 1, characterized by an X-ray diffraction pattern further comprising 2θ-reflections at 10.9, 15.3, and 21.8 degrees 2θ, plus or minus 0.2 degrees 2θ.

3. The solid form of claim 1, characterized by an X-ray diffraction pattern further comprising 2θ-reflections at 13.3, 20.1, 20.4, 21.0, and 24.3 degrees 2θ, plus or minus 0.2 degrees 2θ.

4. The solid form of claim 1, having a differential scanning calorimetry thermogram comprising an endotherm with onset at about 129° C.

5. A solid form tromethamine salt of a compound having the following formula:

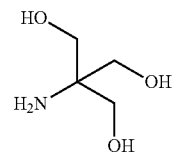

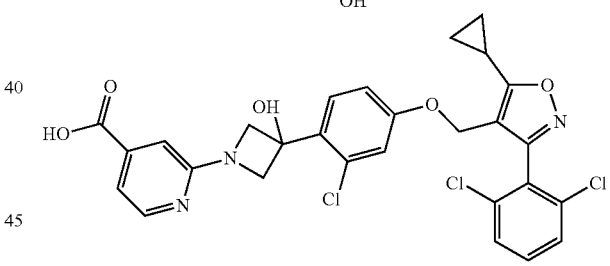

wherein the solid form is tromethamine salt Form II characterized by an X-ray diffraction pattern having 2θ-reflections at 9.2, 15.9, and 17.3 degrees 2θ, plus or minus 0.2 degrees 2θ.

6. The solid form of claim 5, characterized by an X-ray diffraction pattern further comprising 2θ-reflections at 12.9, 20.4, 24.5, and 25.1 degrees 2θ, plus or minus 0.2 degrees 2θ.

7. A solid form tromethamine salt of a compound having the following formula:

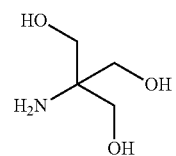

-continued

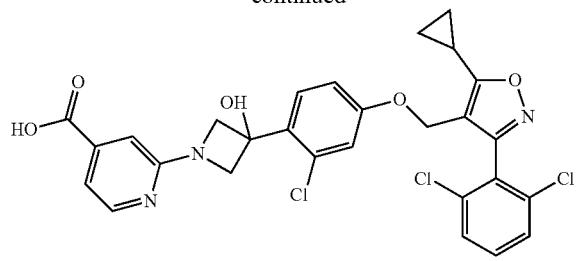

wherein the solid form is tromethamine salt hydrate I characterized by an X-ray diffraction pattern having 2θ-reflections at 5.9, 13.9, 23.3 degrees 2θ, plus or minus 0.2 degrees 2θ.

8. The solid form of claim 7, characterized by an X-ray diffraction pattern further comprising 2θ-reflections at 7.1, 12.7, and 20.3 degrees 2θ, plus or minus 0.2 degrees 2θ.

9. The solid form of claim 7, characterized by an X-ray diffraction pattern further comprising 2θ-reflections at 9.8, 17.4, 22.7, and 25.3 degrees 2θ, plus or minus 0.2 degrees 2θ.

10. The solid form of claim 7, having a differential scanning calorimetry thermogram comprising an endotherm with onset at about 74° C., an endotherm with onset at about 123° C., and an exotherm with onset at about 145° C.

11. A solid form tromethamine salt of a compound having the following formula:

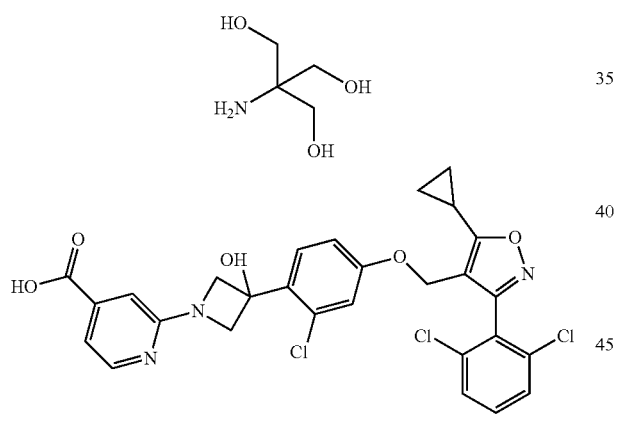

wherein the solid form is tromethamine salt hydrate II characterized by an X-ray diffraction pattern having 2θ-reflections at 10.5, 16.1, and 21.5 degrees 2θ, plus or minus 0.2 degrees 2θ.

12. The solid form of claim 11, characterized by an X-ray diffraction pattern further comprising 2θ-reflections at 9.0, 17.2, and 18.8 degrees 2θ, plus or minus 0.2 degrees 2θ.

13. The solid form of claim 11, characterized by an X-ray diffraction pattern further comprising 2θ-reflections at 13.4, 20.1, 24.9, and 26.9 degrees 2θ, plus or minus 0.2 degrees 2θ.

14. The solid form of claim 11, having a differential scanning calorimetry thermogram comprising an endotherm with onset at about 48° C. and an endotherm with onset at about 130° C.

15. A solid form tromethamine salt of a compound having the following formula:

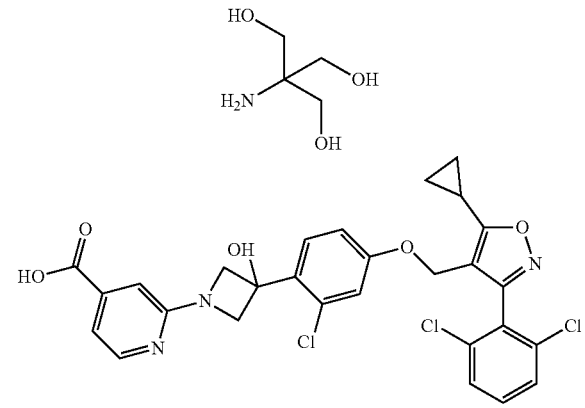

wherein the solid form is tromethamine salt hydrate III characterized by an X-ray diffraction pattern having 2θ-reflections at 10.2, 16.0, and 23.2 degrees 2θ, plus or minus 0.2 degrees 2θ.

16. The solid form of claim 15, characterized by an X-ray diffraction pattern further comprising 2θ-reflections at 9.1, 15.2, and 23.8 degrees 2θ, plus or minus 0.2 degrees 2θ.

17. The solid form of claim 15, characterized by an X-ray diffraction pattern further comprising 2θ-reflections at 11.2, 12.3, 19.0, 21.6, and 26.1 degrees 2θ, plus or minus 0.2 degrees 2θ.

18. The solid form of claim 15, having a differential scanning calorimetry thermogram comprising an endotherm with onset at about 82° C., an endotherm with onset at about 120° C., and an exotherm with onset at about 154° C.

19. A solid form tromethamine salt of a compound having the following formula:

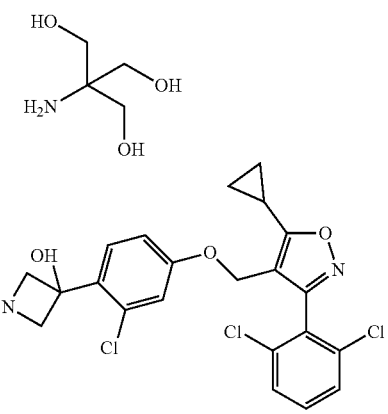

wherein the solid form is tromethamine salt hydrate IV characterized by an X-ray diffraction pattern having 2θ-reflections at 11.4, 16.9, and 22.8 degrees 2θ, plus or minus 0.2 degrees 2θ.

20. The solid form of claim 19, characterized by an X-ray diffraction pattern further comprising 2θ-reflections at 14.2, 15.3, and 20.5 degrees 2θ, plus or minus 0.2 degrees 2θ.

21. The solid form of claim 19, characterized by an X-ray diffraction pattern further comprising 2θ-reflections at 13.7, 15.8, 19.4, and 21.9 degrees 2θ, plus or minus 0.2 degrees 2θ.

22. The solid form of claim 19, having a differential scanning calorimetry thermogram comprising an endotherm with onset at about 48° C., an endotherm with onset at about 117° C. and an endotherm with onset at about 148° C.

23. A solid form tromethamine salt of a compound having the following formula:

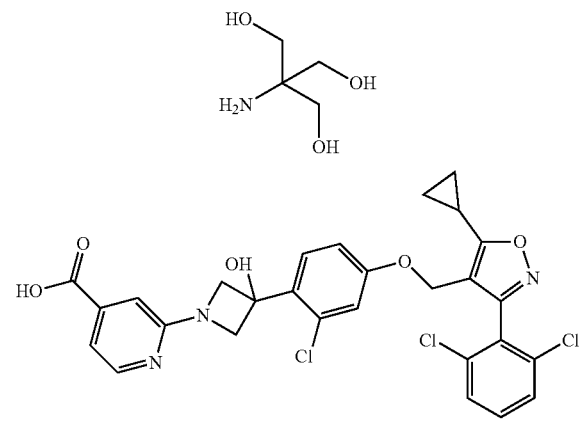

wherein the solid form is tromethamine salt methanol solvate I characterized by an X-ray diffraction pattern having 2θ-reflections at 10.8, 13.3, and 22.3 degrees 2θ, plus or minus 0.2 degrees 2θ.

24. The solid form of claim 23, characterized by an X-ray diffraction pattern further comprising 2θ-reflections at 14.5, 20.0, and 21.4 degrees 2θ, plus or minus 0.2 degrees 2θ.

25. A solid form tromethamine salt of a compound having the following formula:

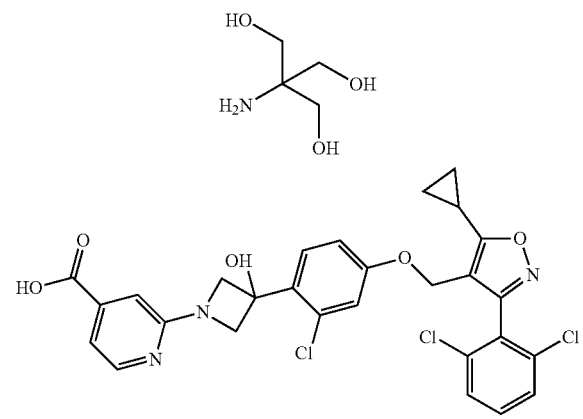

wherein the solid form is tromethamine salt methanol solvate II characterized by an X-ray diffraction pattern having 2θ-reflections at 5.4, 12.9, and 22.7 degrees 2θ, plus or minus 0.2 degrees 2θ.

26. The solid form of claim 25, characterized by an X-ray diffraction pattern further comprising 2θ-reflections at 10.7, 14.3, and 15.9 degrees 2θ, plus or minus 0.2 degrees 2θ.

27. The solid form of claim 25, characterized by an X-ray diffraction pattern further comprising 2θ-reflections at 21.2, and 26.6 degrees 2θ, plus or minus 0.2 degrees 2θ.

28. A solid form tromethamine salt of a compound having the following formula:

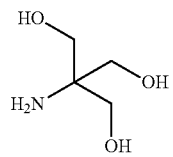
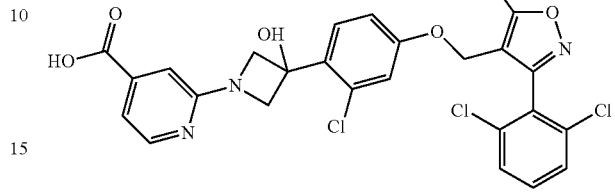

wherein the solid form is tromethamine salt methanol solvate III characterized by an X-ray diffraction pattern having 2θ-reflections at 12.6, 13.3, and 13.8 degrees 2θ, plus or minus 0.2 degrees 2θ.

29. The solid form of claim 28, characterized by an X-ray diffraction pattern further comprising 2θ-reflections at 14.3, 17.4, and 23.2 degrees 2θ, plus or minus 0.2 degrees 2θ.

30. The solid form of claim 28, characterized by an X-ray diffraction pattern further comprising 2θ-reflections at 20.2, 24.2, 25.2, and 29.1 degrees 2θ, plus or minus 0.2 degrees 2θ.

31. The solid form of claim 28, having a differential scanning calorimetry thermogram comprising an endotherm with onset at about 80° C., an endotherm with onset at about 110° C., an endotherm with onset at about 127° C., and an exotherm with onset at about 145° C.

32. A solid form tromethamine salt of a compound having the following formula:

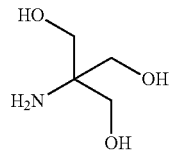

wherein the solid form is MTBE solvate characterized by an X-ray diffraction pattern having 2θ-reflections at 5.8, 11.4, 15.6, and 20.4 degrees 2θ, plus or minus 0.2 degrees 2θ.

33. The solid form of claim 32, characterized by an X-ray diffraction pattern further comprising 2θ-reflections at 14.5, 18.4, 23.4, and 25.9 degrees 2θ, plus or minus 0.2 degrees 2θ.

34. The solid form of claim 32, characterized by an X-ray diffraction pattern further comprising 2θ-reflections at 12.7, 19.0, and 24.7 degrees 2θ, plus or minus 0.2 degrees 2θ.

35. The solid form of claim 32, having a differential scanning calorimetry thermogram comprising an endotherm with onset at about 85° C. and an endotherm with onset at about 147° C.

36. A solid form of claim 1, tromethamine salt of a compound having the following formula:

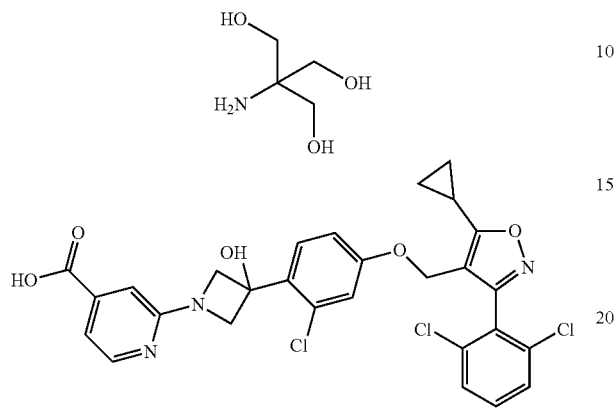

wherein the solid form is tromethamine salt amorphous having an X-ray diffraction pattern substantially as shown in FIG. 35.

* * * * *